(12) United States Patent
Ignjatovic et al.

(10) Patent No.: US 7,449,556 B2
(45) Date of Patent: Nov. 11, 2008

(54) RECOMBINANT ANTIBODIES AGAINST INFECTIOUS BURSAL DISEASE VIRUS (IBDV)

(75) Inventors: Jagodina Ignjatovic, Highton (AU); Stephen Prowse, Torquay (AU); Hans G. Heine, Clifton Springs (AU); Sandra I. Sapats, Manifold Heights (AU)

(73) Assignee: Commonwealth Scientific and Industrial Organisation, Campbell (AU)

( * ) Notice: Subject to any disclaimer, the term of this patent is extended or adjusted under 35 U.S.C. 154(b) by 304 days.

(21) Appl. No.: 10/479,670

(22) PCT Filed: Jun. 5, 2002

(86) PCT No.: PCT/AU02/00729

§ 371 (c)(1),
(2), (4) Date: Feb. 25, 2004

(87) PCT Pub. No.: WO02/098921

PCT Pub. Date: Dec. 12, 2002

(65) Prior Publication Data

US 2004/0141980 A1    Jul. 22, 2004

(30) Foreign Application Priority Data

Jun. 5, 2001    (AU)    .................... PR5468

(51) Int. Cl.
*A61K 39/00* (2006.01)
*C12N 15/00* (2006.01)
(52) U.S. Cl. .............. 530/388.2; 530/388.15; 530/388.1; 424/139.1; 424/142.1; 424/130.1
(58) Field of Classification Search ................ None
See application file for complete search history.

(56) References Cited

U.S. PATENT DOCUMENTS

| 3,773,919 | A |   | 11/1973 | Boswell et al. |
| 4,485,045 | A |   | 11/1984 | Regen |
| 4,544,545 | A |   | 10/1985 | Ryan et al. |
| 5,252,479 | A |   | 10/1993 | Srivastava |
| 5,605,827 | A |   | 2/1997 | Jackwood et al. |
| 6,528,063 | B2 | * | 3/2003 | Stram et al. ............ 424/204.1 |

FOREIGN PATENT DOCUMENTS

| DE | 32 18 121 | 11/1983 |
| EP | 0 036 676 | 9/1981 |
| EP | 0 052 322 | 5/1982 |
| EP | 0 058 481 | 8/1982 |
| EP | 0 073 657 | 3/1983 |
| EP | 0 088 046 | 9/1983 |
| EP | 0 102 324 | 3/1984 |
| EP | 0 133 988 | 3/1985 |
| EP | 0 142 641 | 5/1985 |
| EP | 0 143 949 | 12/1985 |
| JP | 60-7934 | 1/1985 |
| WO | WO 90/15140 | 12/1990 |
| WO | WO 91/16925 | 11/1991 |
| WO | WO 93/07282 | 4/1993 |
| WO | WO 01/62907 | 2/2001 |

OTHER PUBLICATIONS

Eterradossi et al. Modified activity of a VP2-located neutralizing epitope on various vaccine, pathogenic and hypervirulent strains of infectious bursal disease virus. (1997) Archives in Virology, 142, pp. 255-270.*

Clarkson et al. Making antibody fragments using phage displey libraries. (1991) Nature vol. 352, pp. 624-628.*

Rudikoff et al. Single amino acid substitution altering antigen-binding specificity. PNAS, 1982, vol. 79, p. 1979-1983.*

Panka et al. Variable region framework differences result in decreased or increased affinity of variant anti-digoxin antibodies, PNAS, 1988, vol. 85, p. 3080-3084.*

Sambrook et al. *Molecular Cloning: A Laboratory Manual, 2nd Ed.* vols. 1-3, (1989).

(Continued)

*Primary Examiner*—Bruce Campell
*Assistant Examiner*—Agnieszka Boesen
(74) *Attorney, Agent, or Firm*—Merchant & Gould P.C.

(57) ABSTRACT

The purpose of this project was to isolate recombinant antibodies for diagnosis of very virulent infectious bursal disease virus (vvIBDV) in fixed tissues. Phage-displayed recombinant antibodies, comprised of the single chain variable fragment (scFv), were investigated. A previously made recombinant antibody library generated against vvIBDV was selected and screened for recombinant antibodies that reacted against vvIBDV in ELISA. A new library was constructed fom chickens immunized with fixed vvIBDV and also screened for recombinant antibodies against vvIBDV. Also, a previously identified recombinant antibody, known to react well with vvIBDV, was used to replace either the Vh or Vl gene with corresponding fragments from a new library. The Vh and Vl antibody genes were initially amplified effectively by PCR. No new recombinant antibody clones were isolated from the libraries generated against vvIBDV. However, exchanging the Vh or Vl genes from a known recombinant antibody with genes from a new library showed that the heavy chain was essential when binding to vvBDV. Light chains could be exchanged without loss of activity, but when heavy chains were exchanged, all activity was lost. The light chains were found to create new binding properties when combined with the essential heavy chain. The recombinant antibody clones were sequenced, analyszd and characterize.

22 Claims, 42 Drawing Sheets

OTHER PUBLICATIONS

Maniatis et al. In *Molecular Cloning: A Laboratory Manual.*, pp. 280-281 (1989).

Voller et al. (Ed.) Immunoassays for the 80's. University Park, pp. 205-288, 325-360, 457-479 (1981).

Hunter et al. "Preparation of iodine-131 labelled human growth hormone of high specific activity". *Nature*, vol. 144, pp. 495 (1962).

David et al. "Protein iodination with solid state lactoperoxidase". *Biochemistry*, vol. 13, No. 55, pp. 1014-1021 (1974).

Pain et al. "Preparation of protein a-peroxidase monoconjucate using a heterobifunctional reagent, and its use in enzyme immunoassays". *Journal of Immunological Methods*, vol. 40, pp. 219-230 (1981).

Nygren. "Conjugation of horseradish peroxidase to fab fragments with different homobifunctional and heterobifunctional cross-linking reagents". *The Journal of Histochemistry and Cytocheimistry*, vol. 30, No. 5, pp. 407-412 (1982).

Work (Ed.) *Laboratory Techniques in Biochemistry and Molecular Biology*, vol. 6, (1978).

Hood et al. *Immunology*, 2nd Ed. pp. 384 (1984).

Osol (Ed.) Remington's Pharmaceutical Sciences, 16th Ed.cpp. 1355, 1369, 1378 (1980).

Langer. "Controlled release of macromolecules". *Chemtech*, vol. 12, pp. 98-105 (1982).

Langer et al. "Biocompatibility of polymeric delivery systems for macromolecules". *Journal of Biomedical Materials Research*, vol. 15, pp. 267-277 (1981).

Sidman et al. "Controlled release of macromolecules and pharmaceuticals from synthetic polypeptides based on glutamic acid". *Biopolymers*, vol. 22, pp. 547-556 (1983).

Eppstein et al. "Biological activity of liposome-encapsulated murine interferon γ is mediated by a cell membrane receptor". *Proc. Natl. Acad. Sci., USA*, vol. 82, pp. 3688-3692 (Jun. 1985).

Hwang et al. "Hepatic uptake and degradation of unilamellar sphingomyelin/choloesterol liposomes: a kinetic study". *Proc. Natl. Acad. Sci., USA*, vol. 77, No. 7, pp. 4080-4084 (Jul. 1980).

Glover (Ed.) DNA Cloning, vol. 1. pp. 101-133, 151-163 (1985).

McCafferty et al. (Eds.) *Antibody Engineering*. pp. 253-268 (1996).

Firth. "Occurrence of an infectious bursal syndrome within an Australian poultry flock". *Australian Veterinary Journal*, vol. 50, pp. 128-130 (1974).

Brown et al. "VP2 sequences of recent European 'very virulent' isolates of infectious bursal disease virus are closely related to each other but are distinct from those of 'classical' strains". *Journal of General Virology*, vol. 75, pp. 675-680 (1994).

Sapats et al. "Antigenic and sequence heterogeneity of infectious bursal disease virus strains isolated in Australia". *Arch Virol*, vol. 145, pp. 773-785 (2000).

Ignjatovic et al. "Confirmation of the existence of two distinct genetic groups of infectious bursal disease virus in Australia". *Australian Veterinary Journal*, vol. 80, No. 11, (Nov. 2002).

Bayliss et al. "A comparison of the sequences of segment A of four infectious bursal disease virus strains and identification of a variable region in VP2". *Journal of General Virology*, vol. 71, pp. 1303-1312 (1990).

Heine et al. "Sequence analysis and expression of the host-protective immunogen VP2 of a variant strain of infectious bursal disease virus which can circumvent vaccination with standard type I strains". *Journal of General Virology*, vol. 72, pp. 1835-1843 (1991).
Eterradossi et al. "Modified activity of a VP2-located neutralizing epitope on various vaccine, pathogenic and hypervirulent strains of infectious bursal disease virus". *Arch Virol*, vol. 142, pp. 255-270 (1997).
Parede et al. "Characterization of infectious bursal disease virus isolates from Indonesia indicates the existence of very virulent strains with unique genetic changes". *Avian Pathology*, vol. 32, No. 5, pp. 511-518 (2003).
Griffiths et al. "Human anti-self antibodies with high specificity from phage display libraries". *The EMBO Journal*, vol. 12, No. 2, pp. 725-734 (1993).
Thompson et al. "The CLUSTAL_X windows interface: flexible strategies for multiple sequence alignment aided by quality analysis tools". *Nucleic Acids Research*, vol. 25, No. 24, pp. 4876-4882 (1997).
Fahey et al. "Virus-neutralizing and passively protective monoclonal antibodies to infectious bursal disease virus of chickens". *Avian Diseases*, vol. 35, pp. 365-373 (1991).
Whitfill et al. "Determination of optimum formulation of a novel infectious bursal disease (IBDV) vaccine constructed by mixing bursal disease antibody with IBDV". *Avian Diseases*, vol. 39, pp. 687-699 (1995).
Haddad et al. "Efficacy of a novel infectious bursal disease virus immune complex vaccine in broiler chickens". *Avian Diseases*, vol. 41, pp. 822-889 (1997).
Jeurissen et al. "The working mechanism of an immune complex vaccine that protects chickens against infectious bursal disease". *Immunology*, vol. 95, pp. 494-500 (1998).
Sapats et al. "Antigenic and sequence heterogeneity of infectious bursal disease virus strains isolated in Australia." *Archives of Virologoy* (2000) vol. 145, No. 4. 2000. pp. 773-785.
Gao et al., 1999, IUBMB Life, 48(5):513-517.
DeNardo et al., 1999, Clin. Cancer Res., 5:3213s-3218s.
Zhou et al., 1999, Chin. J. Biotechnol., 15(1):29-35 (shown as Medline PMID 10668132 on the International Search Report).
International Search Report, Jun. 2002.

* cited by examiner

Figure.1 pCANTAB 5E

```
    SfiI                                              NotI
GCG GCC CAG CCG GCC ------//------insert------//---- GCG GCC GCA
CGC CGG GTC GGC CGG                                  CGC CGG CGT
 A   A   Q   P   A                                    A   A   A
``` pCANTAB-AscI

```
         SfiI                   NcoI        AscI                            XbaI                    EcoRV        NotI
GCG GCC CAG CCG GCC ATG GGG CGC GCC GGG CGC GCC GTC TAG AGC TAA GAT ATC GCG GCC GCA
CGC CGG GTC GGC CGG TAC CCC GCG CGG CCC GCG CGG CAG ATC TCG ATT CTA TAG CGC CGG CGT
 A   A   Q   P   A   M   G   R   A   G   R   A   V  End  S  End  D   I   A   A   A
``` pCANTAB-SmaI

```
         SfiI                   NcoI        AscI                            PstI        XbaI             SmaI        SalI                    EcoRV
GCG GCC CAG CCG GCC ATG GGG CGC GCC GGG CGC GCC ACT GCA GCT CTA GAT CCC GGG TCG ACA GAT ATC AGT GCG GCC GCA
CGC CGG GTC GGC CGG TAC CCC GCG CGG CCC GCG CGG TGA CGT CGA GAT CTA GGG CCC AGC TGT CTA TAG TCA CGC CGG CGT
 A   A   Q   P   A   M   G   R   A   G   R   A   T   A   A   L   D   P   G   S   T   D   I   S   A   A   A
```

Figure.1 (Cont.)

pCANTAB-link

```
     SfiI            NcoI              AscI                   PstI         XbaI
     ―――――           ――――              ――――                   ――――         ――――
GCG GCC CAG CCG GCC ATG GGG CGC GCC ACT GCA GCT CTA GAT GGT GGA GGC GGT TCA GGC GGA
CGC CGG GTC GGC CGG TAC CCC GCG CGG TGA CGT CGA GAT CTA CCA CCT CCG CCA AGT CCG CCT
 A   A   Q   P   A   M   G   R   A   T   A   A   L   D   G   G   G   G   S   G   G
                                                        EcoRV            NotI
                                                        ―――――            ――――
GGT GGC TCT GGC GGT GGC GGG TCG ACA GAT ATC AGT GCG GCC GCA
CCA CCG AGA CCG CCA CCG CCC AGC TGT CTA TAG TCA CGC CGG CGT
 G   G   S   G   G   G   G   S   T   D   I   S   A   A   A
                    SalI
                    ――――
```

Figure 3A:

Nucleotide sequence for $V_H$ (SEQ ID NO:1).

GCCGTGACGTTGGACGAGTCCGGGGGCGGCCTCCAGACGCCCGGAGGAACGCTCAGC
CTCGTCTGCAAGGCCTCCGGGTTCACCTTCAGCAGTTATCAGATGAACTGGTTGCGC
CAGGCTCCCGGCAAGGGGCTGGAGTGGGTCGGTGTTATTAGCACCCGTGGCAGTAGC
ACAGCATACGGGGCGGCGGTGAAGGGCCGTGCCACCATCTCGAGGGACAACGGGCAG
AGCACAGTGAGGCTGCAGCTGAACAGCCTCAGGACTGAGGACACCGCCACCTACTAC
TGCGCCAAAGCTGGTTATGCTTGTGGTTGGAGTGTTGGTTGTATCGACGCATGGGGC
CACGGGACCGAAGTCATCGTCTCCTCTAGAT

Nucleotide sequence for $V_H$ (SEQ ID NO:2).

GCCGTGACGTTGGACGAGTCCGGGGGCGGCCTCCAGACGCCCGGAGGAACGCTCAGC
CTCGTCTGCAAGGCCTCCGGGTTCACCTTCAGCAGTTATCAGATGAACTGGTTGCGC
CAGGCTCCCGGCAAGGGGCTGGAGTGGGTCGGTGTTATTAGCACCCGTGGCAGTAGC
ACAGCATACGGGGCGGCGGTGAAGGGCCGTGCCACCATCTCGAGGGACAACGGGCAG
AGCACAGTGAGGCTGCAGCTGAACAGCCTCAGGACTGAGGACACCGCCACCTACTAC
TGCGCCAAAGCTGGTTATGCTTGTGGTTGGAGTGTTGGTTGTATCGACGCATGGGGC
CACGGGACCGAAGTCATCGTCTCCTCC

Nucleotide sequence for $V_H$ (SEQ ID NO:3).

GCCGTGACGTTGGACGAGTCCGGGGGCGGCCTCCAGACGCCCGGAGGAGCACTCAGC
CTCGTCTGCAAGGGCTCCGGGTTCACCTTCAGCAGTTACAACATGGGTTGGGTGCGA
CAGGCGCCCGGCAAGGGGCTGGAATTCGTCGCAGCTATTAGCAACACTGGTAGATAC
ACAGGCTACGGGTCGGCGGTGAAGGGCCGTGCCACCATCTCGAGGGACAACGGGCAG
AGCACAGTGAGGCTGCAGCTGAACAACCTCAGGGCTGAGGACACCGCCACCTACTAC
TGCGCCAAAACTGCTGGTTACTATGGTTGGAATACTGCTAGTGATATCGACGCATGG
GGCCACGGGACCGAAGTCATCGTCTCCTCTAGAT

Nucleotide sequence for $V_H$ (SEQ ID NO:4).

GCCGTGACGTTGGACGAGTCCGGGGGTGGCCTCCAGACGCCCGGAAGAGCGCTCAGC
CTCGTCTGCAAGGGCTCCGGGTTCACCCTCAGCAGTTACAACATGGGTTGGGTGCGA
CAGGCGCCCGGCAAGGGGCTGGAATTCGTCGCAGCTATTAGCAACACTGGTAGATAC
ACAGGCTACGGGTCGGCGGTGAAGGGCCGTGCCACCATCTCGAGGGACAACGGGCAG
AGCACAGTGAGGCTGCAGCTGAACAACCTCAGGGCTGAGGACACCGCACCTACTAC
TGCGCCAAAACTGCTGGTTACTATGGTTGGAATACTGCTAGTGATATCGACGCATGG
GGCCACGGGACCGAAGTCATCGTCTCCTCTAGAT

Figure 3B:

Nucleotide sequence for V$_H$ (SEQ ID NO:5).

GCCGTGACGTTGGACGAGTCCGGGGGCGGCCTCCAGACGCCCGGAAGAGCGCTCAGC
CTCGTCTGCAAGGCCTCCGGGTTCTCTATCAGCGGTTACAACATGGGTTGGGTGCGA
CAGGCGCCCGGCAAGGGGCTGGAGTTCGTCGCTGGTATTGGCAACACTGGTAGATAC
ACAGGATACGGGGCGGCGGTGAAGGGCCGTGCCACCATCTCGAGGGACAACGGGCAG
AGCACAGTGAGGCTGCAGCTGAACAACCTCAGGGCTGAGGACACCGGCATCTACTAC
TGCGCCAAAGGTGCTAGTCATTACTGTTGGGATGTTGGTTGTAGTAATATTGCTGGT
AGTATCGACGCATGGGGCCACGGGACCGAAGTCATCGTCTCCTCTCTAGAT

Nucleotide sequence for V$_H$ (SEQ ID NO:6).

GCCGTGACGTTGGACGAGTCCGGGGGCGGCCTCCAGACGCCCGGAAGAGCGCTCAGC
CTCGTCTGCAAGGCCTCCGGGTTCACCTTCAGGAGTTACAACATGGCCTGGGTGCGA
CAGGCGCCCGGCAAGGGGCTGGAGTTCGTCGCTGAAATTAGCGGCACTGGTAGTACC
ACAAACTACGCGCCGGCGGTGAAGGGCCGTGCCACCATCTCGAGGGACAACGGGCAG
AGCACAGTGAGGCTGCAGCTGAACAACCTCAGGGCTGAGGACACCGGCACCTACTTC
TGCGCCAAAGCTGCTGGTGCTTACTGTGCTTGGAGTGGTTGTACTGCTGGTAGCATC
GACGCATGGGGCCACGGGACCGAAGTCATCGTCTCCTCTCTAGAT

Nucleotide sequence for V$_H$ (SEQ ID NO:7).

GCCGTGACGTTGGACGAGTCCGGGGGCGGCCTCCAGACGCCCAGAGGACGGCTCCGC
CTCGTCTGCAAGGCCTCCGGGTTCACCTTCAGCAGTTACGAGATGGGTTGGGTGCGA
CAGGCGCCCGGCAAGGGGCTGGAGTGGGTCGCTGGTATTGGCGGCAGTGGTAGTGGC
TCAGCATACGGGTCGGCGGTGAAGGGCCGTGCCACCATCTCGAGGGACAACGGGCAG
AGCACCGTGAGGCTGCAGCTGAACAACCTCAGGGCTGAGGACACCGGCACCTACTAT
TGCGCCAAAAGTACTACAAAATGTAGTTACTGCTGGTATGGTGCTACTGCTGGTAGT
ATCGACGCATGGGGCCACGGGGCCGAAGTCATCGTCTCCTCTCTAGAT

Nucleotide sequence for V$_H$ (SEQ ID NO:8).

GCCGTGACGTTGGACGAGTCCGGGGGCGGCCTCCAGACGCCCAGAGGACGGCTCCGC
CTCGTCTGCAAGGCCTCCGGGTTCGACTTCAGCAGTTACGAGATGGGTTGGGTGCGA
CAGGCGCCCGGCAAGGGGCTGGAGTGGGTCGCTGGTATTGGCGGCAGTGGTAGTGGC
TCAGCATACGGGCCGGCGGTGAAGGGCCGTGCCACCATCACGAGGGACAATGGGCAG
AGCACAGTGAGGCTGCAGCTGAACAACCTCAGGGCTGAGGACACCGGCACCTACTAC
TGCGCCAAAAGTACTACAAGATGTAGTTTCTGTTGGTATGGTGCTACTGCTGGTAGC
ATCGACGCATGGGGCCACGGGGCCGAAGTCATCGTCTCCTCTCTAGAT

Figure 3C:

Nucleotide sequence for V$_H$ (SEQ ID NO:9).

GCCGTGACGTTGGACGAGTCCGGGGGCGGCCTCCAGACGCCCAGAGGACGGCTCCGC
CTCGTCTGCAAGGCCTCCGGGTTCACCTTCAGCAGTTACGAGATGGGTTGGGTGCGA
CAGGCGCCCGGCAAGGGGCTGGAGTGGGTCGCTGGTATTGGCGGCAGCGGTAGTGGC
TCAGCATACGGGTCGGCGGTGAAGGGCCGTGCCACCATCTCGAGGGACAACGGGCAG
AGCACCGTGAGGCTGCAGCTGAACAACCTCAGGGCTGAGGACACCGGCACCTACTAT
TGCGCCAAAAGTACTACAAAATGTAATCACTGTTGGTATGGTGCAACTGCTGGTAGC
ATCGACGCATGGGGCCACGGGACCGAAGTCATCGTCTCCTCTCTAGAT

Nucleotide sequence for V$_H$ (SEQ ID NO:10).

GCCGTGACGTTGGACGAGTCCGGGGGCGGCCTCCATACGCCCGGAGGAGCGCTCAGG
CTCGTCTGCAAGGCCTCCGGGTTCTCCATCAGCAGTTATGGCATGGGTTGGGTGCGA
CAGGCGCCCGGCAAGGGGCTGGAGTGGGTCGCTCGTATTGGCAGTGGTGCTAGTGGC
ACAGCATACGGGTCGGCGGTGAAGGGCCGTGCCACCATCTCGAGGGACAACGGGCAG
AGCACAGTGAGGCTGCAGCTGAACAACCTCAGGGCTGACGACACCGGCACCTACTAC
TGCGCCAAAAGTGCTGGTGCTTACTGTTGGTATGCTGGTTGTCCTAGTAGCATCGAC
GCATGGGGCCACGGGGCCGAAGTCATCGTCTCCTCTCTAGAT

Nucleotide sequence for V$_H$ (SEQ ID NO:11).

GCCGTGACTCTTGACGAGTCCGGGGGCGGACTCCAGACGCCCGGAGGAGCGCTCAGG
CTTGTATGCAAGGCATCCGGGTTCTCCATCAGCAGTTATGGCATGGGTTGGGTGCGA
CAGGCGCCCGGCAAGGGGCTGGAGTGGGTCGCTCGTATTGGCAGCGGTGCTAGTGGC
ACAGCATACGGGTCGACGGTGAAGGGCCGTGCCACCATCTCGAGGGACAACGGACAG
AGCACAGTGAGGTTGCAGCTGAACAACCTCAGGACTGAGGACACCGGCACCTACTAC
TGCGCCAAAACTGCTGGTGCTTACTGCTGGTATGCTGGTTGTCCTAGTAGCATCGAC
GCATGGGGCCACGGGACCGAAGTCATCGTCTCCTCTTTAGAT

Nucleotide sequence for V$_H$ (SEQ ID NO:12).

GCCGTGACGTTGGACGAGTCCGGGGGCGGCCTCCAGACGCCCGGCAAGGGGCTCAGC
CTCGTCTGCAAGGCCTCCGGGTTCTCCCTCAATAGTTATGGTATGGGTTGGGTGCGA
CAGGCGCCCGGCAAGGGGCTGGAGTGGGTCGCTCGTATTGGCAGCGGTGCTAGTGGC
ACTGCCTACGGGTCGGCGGTGAAGGGCCGTGCCACCATCTCGAGGGACAACGGGCAG
AGTATAGTGAGGCTGCAGCTGAACGACCTCAGGGCTGAGGACACCGCCACCTACTAC
TGCGCCAAAACTGCTGGTGCTTACTGTTGGTATGCTGGTTGTCCTAGTAGCATCGAC
GCATGGGGCCACGGGACCGAAGTCATCGTCTCCTCTCTAGAT

Figure 3D:

Nucleotide sequence for V$_H$ (SEQ ID NO:13).

GCCGTGACGTTGGACGAGTCCGGGGGCGGCCTCCAGACGCCCGGCAAGGGGCTCAGC
CTCGTCTGCAAGGCCTCCGGGTTTACCTTCACTAGTTATGGCATGGGTTGGGTGCGA
CAGGCGCCCGGCAAGGGGCTGGAGTGGGTCGCTCGTATTGGCAGCGGTGCTAGTGGC
ACTGCCTACGCGACAGCGGTGAAGGGCCGTGCCACCATCTCGAGGGACAACGGGCAG
AGCACAGTGAGGCTGCAGCTGAACGACCTCAGGGCTGAGGACACCGCCACCTACTAC
TGCGCCAAAACTGCTGGTGCTTACTGTTGGTATGCTGGTTGTCCTAGTAGCATCGAC
GCATGGGGCCACGGGACCGAAGTCATCGTCTCCTCTCTAGAT

Nucleotide sequence for V$_H$ (SEQ ID NO:14).

GCCGTGACGTTGGACGAGTCCGGGGGCGGCCTCCAGACGCCCGGAAGAGCGCTCAGC
CTCGTCTGCAAGGCCTCCGGGTTCACCTTCAGCAGTTACGCCATGAACTGGGTGCGA
CAGGCGCCCGGCAAGGGGCTGGAGTTCGTCGCTGAAATTAGCGGCAGTGGTAGATAC
ACATACTACGCGCCGGCGGTGAAGGGCCGTGCCACCATCTCGAGGGACAACGGGCAG
AGCACAGTAAGCCTGCAGCTGAACAACCTCAGGGCTGAGGACACCGCCACCTACTAC
TGCGCCAAAACTGCTGATAGCTGTCGTTACGGTTGTAGTGCTGATCGTATCGACGCA
TGGGGCCACGGGACCGAAGTCATCGTCTCCTCTCTAGAT

Nucleotide sequence for V$_H$ (SEQ ID NO:15).

GCCGTGACGTTGGACGAATCCGGGGGCGGCCTCCAGACGCCCGGAGGAGCGCTCAGC
CTCGTCTGCAAGGCCTCCGGGTTCACCTTCAGCAGTTACGCCATAAACTGGGTGCGA
CAGGCGCCCGGCAAGGGGCTGGAGTTCGTCGCTGAAATTAGCGGCAGTGGTAGATAC
GTATACTACGCGCCGGCGGTGCAGGGCCGTGCCACCATCTCGAGGGACAACGGGCAG
AGCACAGTGAGGCTGCAGCTGAACAACCTCAGGGCTGAGGACACCGGCACCTACTAC
TGCGCCAAAACTGCTGATAGTTGTAGATACGGTTGTAATGCTGATCGTATCGACGCA
TGGGGCCGCGGGACCGAAGTCATCGTCTCCTCTCTAGAT

Nucleotide sequence for V$_H$ (SEQ ID NO:16).

GCCGTGACGTTGGACGAGTCCGGGGGCGGCCTCCAGACGCCCGGAGGAGCGCTCAGC
CTCGTCTGCAAGGGCTCCGGGTTCACCTTCAGCAGCCATGGCATGTTCTGGGTGCGA
CAGGCGCCCGGCAAGGGGCTGGAATACGTCGCTCAAATTAGCGGCAGTGGTAGATTA
ACAAACTACGGGCCGGCGGTGAAGGGCCGTGCCACCATCTCGAGGGACAACGGGCAG
AGCACAGTGAGGCTGCAGCTGAACAACCTCAGGGCTGAGGACACCGGCACCTACTAC
TGCGCCAAAACTGCCGTTAATTGTAGATACGGTTGTGCAGGTGATAATATCGACGCA
TGGGGCCACGGGACCGAAGTCATCGTCTCCTCTCTAGAT

Figure 3E:

Nucleotide sequence for V_H (SEQ ID NO:17).

```
GCCGTGACGTTGGACGAGTCCGGGGGCGGCCTCCAGACGCCCGGAGGAGGGCTCAGC
CTCGTCTGCAAGGCCTCCGGGTTCACCTTCAGCAGTTACGGCATGGGTTGGGTGCGA
CAGGCGCCCGGCAAAGGGCTGGAATGGGTCGCTGAGATTAGCGGCAGTGGTCGATAC
ACAGGATATGGGCCGGCGGTGCAGGGCCGTGCCACCATCTCGAGGGACAACGGGCAG
AGCACAGTGAGGCTGCAGCTGAGCGACCTCAGGGCTGAGGACACCGGCACCTACTAC
TGCGCCAAAGCTACAGCTAGCTGTACTTACGGTTGTACTCCTTATACTGGTGAAATC
GACGCATGGGGCCACGGGACCGAAGTCATCGTCTCCTCTCTAGAT
```

Nucleotide sequence for V_H (SEQ ID NO:18).

```
GCCGTGACGTTGGACGAGTCCGGGGGCGGCCTCCAGACGCCCGGAGGAGCGCTCAGC
CTCGTCTGCAAGGCCTCCGGGTTCACCTTCAGCAGTTACGGCATGCAGTGGGTGCGC
CAGGCGCCCGGCAAGGGGCTGGAGTGGGTCGCGGGTATTAGTGGTAGTGGTAGAGGC
ACATGGTACGCGCCGGCGGTGAAGGGCCGTGCCACCATCTCGAGGGACAACGGGCAG
AGCACAGTGAGGCTGCAGCTGAACAACCTCAGGGCTGAGGACACCGGCACCTACTAC
TGCGCCAAAGCTGCTGGTAGTGATACTTACGGTAGTACTGGTGATAATATCGACGCA
TGGGGCCACGGGACCGAAGTCATCGTCTCCTCTCTAGAT
```

Nucleotide sequence for V_H (SEQ ID NO:19).

```
GCCGTGACGTTGGACGAGTCCGGGGGCGGCCTCCAGACGCCCGGAGGAACGCTCAGC
CTCGTCTGCAAGGGCTCCGGGTTCACCTTCAGCGATTATGGCATGGGTTGGATGCGG
CAGGCGCCCGGCAAGGGGCTGGAATACGTCGCTGAAATCAGCAGCAGTGGTAGATAC
ACAAACTACGGGCCGGCGGTGAAGGGCCGTGCCACCATCTCGAGGGACAACGGGCAG
AGCACAGTGAGGCTGCAGCTGAACAACCTCAGGGCTGAGGACACCGGCACCTACTAC
TGCGCCAAAGCTGCTGGTAGGGGTTACTATGGTTGGAGTGCTGGTACCATCGACGCA
TGGGGCCACGGGACCGAAGTCATCGTCTCCTCTCTAGAT
```

Nucleotide sequence for V_H (SEQ ID NO:20).

```
GCCGTGACGTTGGACGAGTCCGGGGGCGGCCTCCAGACGCCCGGAGGAACGCTCAGC
CTCGTCTGCAAGGCCTCCGGGTTCACTTTCAGCAGTTATGGCATGGGATGGATGCGA
CAGGCGCCCGGCAAGGGGCTCGAATACGTCGCTGAAAGCAGCAGCAGTGGTAGATAC
ACAAACTACGGGCCGGCGGTGAAGGGCCGTGCCACCATCTCGAGGGACAACGGGCAG
AGCACAGTGAGGCTGCAGCTGAACAACCTCAGGGCTGAGGACACCGGCACCTACTAC
TGCGCCAAAGCTGCTGGTAGTGGTTACTATGGTTGGAGTGCTGGTAGCATCGACGCA
TGGGGCCACGGGACCGAAGTCATCGTCTCCTCTCTAGAT
```

Figure 3F:

Nucleotide sequence for V$_H$ (SEQ ID NO:21).

GCCGTGACGTTGGACGAGTCCGGGGGCGGCCTCCAGACGCCCGGAGGAACGCTCAGC
CTCGTCTGCAAGGCCTCCGGGTTCACCTTCAGCAGCTTCAACATATTCTGGGTGCGA
CAGGCGCCCGGCAAGGGGCTGGAATTCGTCGCAGCTATTAACAAGGATGGTAGTTTC
ACACACTACGGGTCGGCGGTGAAGGGCCGTGCCACCATCTCGAGGGACAACGGGCAG
AGCACATTGAGGCTGCAGCTGAACGACCTCGGGGCTGAGGACGCCGGCACCTACTTC
TGCGCCAGAAGTCCTGGTGGTTTTAGTTGTGCTGGTGGTTGGTGCGGTGCTTATGCT
GATGGCATCGACGCATGGGGCCACGGGACCGAAGTCATCATCTCCTCTCTAGAT

Nucleotide sequence for V$_H$ (SEQ ID NO:22).

GCCGTGACGTTGGACGAGTCCGGGGGCGGCCTCCAGACGCCCGGAGGAGGGCTCAGC
CTCGTCTGCAAGGGCTCCGGGTTCGACTTCAGCAGTTACAACATGTTCTGGGTGCGA
CAGGCGCCCGGCAAGGGGCTGGAGTTCGTCGCAGCTATTAGCAGCACTGGTAGTTAC
ACACACTACGGGCCGGCGGTGAAGGGCCGTGCCACCATCTCGAGGGACAACGGGCAG
AGCACAGTGAGGCTGCAGCTGAACAACCTCAGGGCTGAGGACACCGCCATCTACTAC
TGCGCCAGAAGTCCTGGTGGTTTTAGTTGTGCTGGTGGTTGGTGTGGTGGTTATGCT
GATAGCATCGACGCATGGGGCCACGGGACCGAAGTCATCGTCTCCTCTCTAGAT

Nucleotide sequence for V$_H$ (SEQ ID NO:23).

GCCGTGACGTTGGACGAGTCCGGGGGCGGCCTCCAGACGCCCGGAGGAACGCTCAGC
CTCGTCTGCAAGGCCTCCGGGTTCACCTTCAGCAGCTTCAACATGCAGTGGGTGCGA
CAGGCGCCCGGCAAGGGGCTGGAGTTCGTCGCGGGTATTGACAATATTGGTAGAAAA
ACATCATATGGGTCGGCGGTGAAGGGCCGTGCCACCATCTCGAGGGACAACGGGCAG
AGCACAGTGAGGCTGCAGCTGAATAACCTCAGGGCCGAGGACACCGCCACCTACTTC
TGCGCCAAAGGTGCTGGGAGTAGTGCTTACAGTTGTGCTTTTTGTTATCCTGGTTGG
ATCGACGCATGGGGCCACGGGACCGAAGTCATCGTCTCCTCTCTAGAT

Nucleotide sequence for V$_H$ (SEQ ID NO:24).

GCCGTGACGTTGGACGAGTCCGGGGGCGGCCTCCAGACGCCCGGAGGAGCGCTCAGC
CTCGTCTGCAAGGCCTCCGGGTTCACCTTCAGCAGCCATGGCATGGGTTGGGTGCGA
CAGGCGCCCGGCAAGGGGCTGGAGTGGGTCGCTGGTATTGAGAATGATGGTAGTATA
ACAGGCTACGGGGCGGCGGTGAAGGGCCGTGCCACCATCTCGAGGGACAACGGGCAG
AGCACAGTGAGGCTGCAGCTGAACAACCTCAGGGCTGAGGACACCGGCACCTACTTC
TGCGCCAAACGCAGTGGTAGTGGTTGTTGTAATGCTTACGCTATCGACGCATGGGGC
CACGGGACCGAAGTCATCGTCTCCTCTCTAGAT

Figure 3G:

Nucleotide sequence for V$_H$ (SEQ ID NO:25).

GCCGTGACGTTGGACGAGTCCGGGGGCGGCCTCCAGACGCCCGGAGGAGGGCTCAGC
CTCGTCTGCAAGGCCTCCGGGTTCACCTTCAGCAGTTACGCCATGTACTGGGTGCGA
CAGACGCCCGGCAAGGGGCTGGAGTTCGTCGCCGGTATTGACAGCGGTGATGGTAGA
TACTCAAAATACGGGCCGGCGGTGGATGGCCGTGCCACCATGTCGAGGGACAACGGG
CAGAGCACAGTGAGGCTGCAGCTGAACGACCTCAGGGCTGAGGACTCCGGCACCTAC
TACTGCGCCAAGGGTGCAGTAACTGGTTACTGTGGTTGGAATGCTTGCACTGTTGCT
AACATCGACACATGGGGCCACGGGACCGAAGTCATCGTCTCCTCTCTAGAT

Nucleotide sequence for V$_H$ (SEQ ID NO:26).

GCCGTGACGTTGGACGAGTCCGGGGGCGGCCTCCAGACGCCCGGAGGAGGGCTCAGC
CTCGTCTGCAAGGCCTCCGGGTTCTCCTTCAGCAGTTATTCCATGCAGTGGGTGCGA
CAGGCGCCCGGCAAGGGGCTGGACTGGGTCGCTGGTATTAGTGGCACTGGTAGACAC
AGAAACTACGGGTCGGCGGTGGAGGGCCGTGCCACCATCTCGAGGGACAACGGGCAG
AGTACAGTGAGGCTGCAGCTGGACAACCTCAGGGCTGAGGACACCGGCACCTACTAC
TGCGCCAGAGCTCCTTGTACTGGTTGTGGTTGGAGTGCCGGTAGCATCGACGCATGG
GGCCACGGGACCGAAGTCATCGTCTCCTCTCTAGAT

Nucleotide sequence for V$_H$ (SEQ ID NO:27).

GCCGTGACGTTGGACGAGTCCGGGGGCGGCCTCCAGACGCCCGGAGGAGGGCTCAGC
CTCGTCTGCAAGGCCTCCGGGTTCACCTTCAGCAGTTATCAGATGCACTGGATACGA
CAGGCTCCCGGCAAGGGGCTGGAGTGGGTCGGTGTTATTAGCAGCAGAGGTAGTAGC
ACAAACTACGGGGCTGCGGTGAAGGGCCGTGCCACCATCTCGAGGGACAACGGGCAG
AGCACAGTGAGGCTGCAACTGAACAACCTCAGGGCTGAGGACACCGCCACCTACTAC
TGCGCCAAAAGTGGTTATGCTTGTGGTTGGAGTGGTGGTTGTATCGACGCATGGGGC
CACGGGACCGAAGTCATCGTCTCCTCTCTAGAT

Nucleotide sequence for V$_H$ (SEQ ID NO:28).

GCCGTGACGTTGGACGAGTCCGGGGGCGGCCTCCAGGCGCCCGGAGGAGGGCTCAGC
CTCGTCTGCAAGGCCTCCGGGTTCACCTTCAGCAGCCATGGCATGGGCTGGGTGCGA
CAGGCACCCGGCAAGGGGCTGGAATACGTCGCGAGTATTAGCACCAGAGGTAGTAGC
ACATACTACGGGGCGGCGGTGAAGGGCCGTGCCACCATCTCGAGGGACAACGGGCAG
AGCACAGTGAGGCTGCAGCTGAACAACCTCAGGGCTGAGGACACCGCCACCTACTAC
TGCGCCAAAACTGGTTATGCATGTAGTTATAGTTATCATACTGCCTGTATCGACGCA
TGGGGCCACGGGACCGAAGTCATCGTCTCCTCTCTAGAT

Figure 3H:

Nucleotide sequence for V_H (SEQ ID NO:29).

GCCGTGACGTTGGACGAGTCCGGGGGCGGCCTCCAGACGCCCGGAGGAGCGCTCAGC
CTCGTCTGCAAGGCCTCCGGGTTCACCTTCAGGAGTCATCAGATGTTCTGGGTGCGA
CAGGCTCCCGGCAAGGGGCTGGAATACGTCGGTCAAATTACCACCAGGGGTACTACT
ACATATTACGGGGCGGCGGTGACGGGCCGCGCCACCATCTCGAGGGACAACGGGCAG
AACACAGTGAGGCTGCAGCTAAACAACCTCAGGGCTGAGGACACCGGCACCTACTTC
TGCGCCAAAGCTGCTTACGGTTATAGTTATGTTAGTACCATCGACGCATGGGGCCAC
GGGACCGAAGTCATCGTCTCCTCTAGAT

Nucleotide sequence for V_H (SEQ ID NO:30).

GCCGTGACGTTGGACGAGTCCGGGGGCGGCCTCCAGACGCCCGGAGGAGGGCTCAGC
CTCGTCTGCAGGGCCTCCGGGTTCATCTTCAGCAGTCATCCCATGGTGTGGGTGCGA
CAGGCGCCCGGCAAGGGGCTGGAATGGGTCGCAGCAATTACCACAAGAGGTACTAGC
GCATACTACGGGCCGGCGGTGAAGGGCCGTGCCACCATCTCGAGGGACAACGGGCAG
AGCACAGTGAGGCTGCAGCTGAACAGCCTCAGGGCTGAGGACACCGGCACCTACTAC
TGCGCCAGAAGTGGTTATGGTTACACTGGTAGTGATGCTGGTAACATCGACACATGG
GGCCACGGGACCGAAGTCATCGTCTCCTCTAGAT

Nucleotide sequence for V_H (SEQ ID NO:31).

GCCGTGACGTTGGACGAGTCCGGGGGCGGCCTCCAGACGCCCGGAGGAGCGCTCAGC
CTCGTCTGCAAGGCCTCCGGGTTCGCCTTCAGCAGATACGCCATGAACTGGGTGCGA
CAGGCGCCCGGCAAGGGGCTGGAGTGGGTCGCGGGTGTCAGAAATGTTGGGAGTAGC
ACAAACTACGCGCCGGCAGTGAAGGGCCGTGCCACCATCTCGAGGGACAACGGGCAG
AGCACACTGAGGCTGCAGCTGAACAACCTCAGGGCTGAGGACACCGGCATCTACTAC
TGCGCCAAAGCTGCCGGTAGTGGTTACTGTGCTTGGTGGGCTGATGCTTTGACTTGT
GGTGGTTATAAGACTCATGACATCGACGCATGGGGCCACGGGACCGAAGTCATCGTC
TCCTCTCTAGAT

Nucleotide sequence for V_H (SEQ ID NO:32).

GCCGTGACGTTGGACGAGTCCGGGGGCGGCCTCCAGACGCCCGGAGGAGCGCTCAGC
CTCGTCTGCAAGGCCTCCGGGTTCACCTTCAGCAGTTATGGCATGGGCTGGGTGCGA
CAGGCGCCTGGCAAAGGGCTGGAATGGGTCGCTGGTATTGACAACATTGGTAGATAC
ACAAACTACGGGCCGGCGGTGAAGGGCCGTGCCACCATCTCGAGGGACAACGGGCAG
AGCACAGTGAGGCTGCAGCTGAACAACCTCAGGGCTGAGGACACCGCCACCTACTAC
TGCGCCAAATCTGCTGCTAGTGGTAGTTGGTCCTATTACGGTACTGGTTGGATCGAC
GGATGGGGCCACGGGACCGAAGTCATCGTCTCCTCTAGAT

Figure 3I:

Nucleotide sequence for V$_H$ (SEQ ID NO:33).

GCCGTGACGTTGGACGAGTCCGGGGGCGGCCTCCAGACGCCCGGAGGAGCGCTCAGC
CTCGTCTGCAAGGCCTCCGGGTTCACCTTCGCCATTTATGCCATGCACTGGGTGCGA
CAGGCGCCCGACAAGGGGCTGGAGTTCGTCGCTGGTATTAGCAGTGATGGTAGTAGG
ACGAAATACGGGGCTGCGGTGAAGGGCCGTGCCACCATGTCGAGGGACAACGGGCAG
AGCACAGTGAGGCTGCAGCTGAACAACCTCAGGACTGAGGACACCGCCACCTACTTC
TGCGCCAAAACTGCTGGTAGTTGGAGTCGCTATAATGGTCTTCATTCTAATATCGAC
ACATGGGGCCACGGGACCGAAGTCATCGTCTCCTCTAGAT

Nucleotide sequence for V$_H$ (SEQ ID NO:34).

GCCGTGACGTTGGACGAGTCCGGGGGCGGCCTCCAGACGCCCGGAGGAGGGCTCAGC
CTCGTCTGCAAGGCCTCCGGGTTCACCTTCACCGATTATGGCATGGGCTGGATGCGA
CAGGCACCCGGGAAGGGGCTGGAATACGTCGTTGGTATTAGCAACACTGGTAGATAC
ACATACTACGGGTCGGCGGTGAAGGGCCGTGCCACCATCTCAAGGGACAACGGGCAG
AGCACAGTGAGGCTGCAGCTGAACAACCTCAGGGCTGAGGACACCGCCACCTACTAC
TGCGCCAAATCTGCTGGGAGTTGGTGGCATTATACTGGTGCTGATAATATCGACGCA
TGGGGCCACGGGACCGAAGTCATCGTCTCCTCTAGAT

Nucleotide sequence for V$_H$ (SEQ ID NO:35).

GCCGTGACGTTGGACGAGTCCGGGGGCGGCCTCCAGACGCCCGGAGGAGGGCTCAGC
CTCGTCTGCAAGGCCTCCGGGTTCACCTTCAGCAGTTACGCCATGAACTGGGTGCGA
CAGGCGCCCGGCAAGGGGCTGGAGTGGGTCGCCAGTATTAACAGTGCTGGTAGTTAC
ACACACTACGGGTCGGCGGTGAAGGGCCGTGCCACCATCTCAAGGGACAACGGGCAG
AGCACAGTGAGGCTGCAGCTGAACAACCTCAGGGCTGAGGACACCGGCACCTACTAC
TGCGCCAGAGGAGGTGGTGGTTGTGGTATTTGGAGTTGTGGTTCTTATGCTGGTGAA
ATCGACGCATGGGGCCACGGGACCGAAGTCATCGTCTCCTCC

Figure 3J:

Nucleotide sequence for V$_L$ (SEQ ID NO:36).

ACAGCGCTGACTCAGCCGTCCTCGGTGTCAGCGAACCCGGGAGAAACCGTCGAGATC
ACCTGCTCCGGGGATACCACCTACTATGGCTGGTACCAGCAGAAGGCACCTGGCAGT
GCCCCTGTCACTCTGATCTATGACAACACCAACAGACCCTCGGACATCCCTTCACGA
TTCTCCGGTTCCAGATCCGGCTCCACAGCCACATTAACCATCACTGGGGTCCAAGCC
GAGGACGAGGCTGTCTATTTCTGTGGGAGTGCAGACACCAGTGGTTATGCTGGTATA
TTTGGGGCCGGGACAACCCTGACCGTCCTAGGTGCGGCCGCA

Nucleotide sequence for V$_L$ (SEQ ID NO:37).

ACAGCGCTGACTCAGCCGTCCTCGGTGTCAGCGAACCCGGGAGAAACCGTCGAGATC
ACCTGCTCCGGGGGTAGTGGCAGCTACTATGGCTGGTACCAGCAGAAGCCACCTGGC
AGTGCCCCTGTCACTGTGATCTATAACAACAACAACAGACCCTCGGACATCCCTTCA
CGATTCTCCGGTTCCAGATCCGGCTCCACAGCCACATTAACCATCACTGGGGTCCAA
GCCGACGACGAGGCTGTCTATTTCTGTGGGAGTGAAGACAGCACAGGATATGTTGGT
ATATTTGGGGCCGGGACAACCCTGACCGTCCTAGGTGCGGCCGCA

Nucleotide sequence for V$_L$ (SEQ ID NO:38).

ACAGCGCTGACTCAGCTGTCCTCGGTGTCAGCGAACCCGGGAGAAACCGTCGAGATC
ACCTGCTCCGGGGATAGCAGCTACTATGGCTGGTATCAGCAGAAGGCACCTGGCAGT
GCCCCTGTCACTCTGATCTATGACAACACCAACAGACCCTCGGACATCTCTTCACGA
TTCTCCGGTTCCAAATCCGGCTCCACAGCCACATTAACCATCACTGGGGTCCAAGCC
GACGACGAGGCTGTCTATTACTGTGGGAGTGCAGGCAGCAGCCATGTTGGTATGTTT
GGGGCCGGGACAACCCTGACCGTCCTAGGTGCGGCCGCA

Nucleotide sequence for V$_L$ (SEQ ID NO:39).

ACAGCGCTGACTCAGCCGTCCTCGGTGTCAGCGAACCCGGGAGAAACCGTCGAGATC
ACCTGCTCCGGGGATAGCAGCTACTATGGCTGGTATCAGCAGAAGGCACCTGGCAGT
GCCCCTGTCACTCTGATCTATGACAACACCAACAGACCCTCGGACATCTCTTCACGA
TTCTCCGGTTCCAAATCCGGCTCCACAGCCACATTAACCATCACTGGGGTCCAAGCC
GACGACGAGGCTGTCTATTACTGTGGGAGTGCAGGCAGCAGCCATGTTGGTATGTTT
GGGGCCGGGACAACCCTGACCGTCCTAGGTGCGGCCGCA

Nucleotide sequence for V$_L$ (SEQ ID NO:40).

ACAGCGCTGACTCAGCCGTCCTCGGTGTCGGCAAACCTGGGAGGAACCGTCAAGATC
ACCTGCTCCGGGGATAGCAGCTACTATGGTTGGTACCAGCAGAAGGCACCTGGCAGT
GCCCCTGTCACTGTAATCTATGACAACACCAACAGACCCTCGGGTATCCCTTCACGA
TTCTCCGGTTCCAAATCCGGCTCCACAGCCACATTAACCATCACTGGGGTCCGAGCC
GACGACGAGGCTGTCTATTACTGTGGGAATACAGACAGCAGTGGTGCTATATTTGGG
GCCGGGACAACCCTGACCGTCCTAGGTGCGGCCGCA

Figure 3K:

Nucleotide sequence for V$_L$ (SEQ ID NO:41).

ACAGCGCTGACTCAGCCGTCCTCGGTGTCAGCGAACCCGGGAGAAACCGTCAAGATC
ACCTGCTCCGGGGGTAGCAACAACTATGGCTGGTACCAGCAGAAGTCTCCTGGCAGT
GCCCCTGTCACTCTGATCTATGACAACACCAACAGACCCTCGAACATCCCTTCACGA
TTTTCCGGTTCCAAATCCGGCTCCACAGCCACATTAACCATCACTGGGGTCCAAGCC
GACGACGAGGCTGTCTATTACTGTGGGAGTGCAGACAGCAGTAGTACTGGTATATTT
GGGGCCGGGACAACCCTGACCGTCCTAGGTGCGGCCGCA

Nucleotide sequence for V$_L$ (SEQ ID NO:42).

ACAGCGCTGACTCAGCCGTCCTCGGTGTCAGCAAACCCGGGAGAAACCGTCAAGATC
ACCTGCTCCGGGGGTAGTGGCAGCTACTATGGCTGGTACCAGCAGAAGTCTCCTGGC
AGTGCCCCTGTCACTCTGATCTATGACAACGACAAGAGACCCTCGGGCATCCCTTCA
CGATTCTCCGGTTCCACATCTGGCTCCACGGGCACATTAACCATCACTGGGGTCCAA
GCCGAGGACGAGGCTGTCTATTATTGTGGGAGCAGGGACAGCAGCTATGTTGGTATG
TTTGGGGCCGGGACAACCCTGACCGTCCTAGGTGCGGCCGCA

Nucleotide sequence for V$_L$ (SEQ ID NO:43).

ACAGCGCTGACTCAGCCGTCCTCGGTGTCAGCAAATCCAGGAGAAACCGTCAAGATC
ACCTGCTCCGGGGGTTACAACTACTATGGCTGGTACCAGCAGAAGTCACCTGGCAGT
GTCCCTGTCACTCTGATCTATGACAACACCAACAGACCCTCGAACATCCCTTCACGA
TTCTCCGGTTCCACATCTGGCTCCACAGGCACATTAACCATCACTGGGGTCCAAGCC
GACGACGAGGCTGTCTATTTCTGTGGGAGTGCAGACAGCAGCAGCACTAGTGCTTCA
TTTGGGGCCGGGACAACCCTGACCGTCCTAGGTGCGGCCGCA

Nucleotide sequence for V$_L$ (SEQ ID NO:44).

ACAGCGCTGACTCAGCCGTCCTCGGTGTCAGCGAACCCGGGAGGAACCGTCAAGCTC
ACCTGCTCCGGGGATAGCAGCTACTATGGCTGGTACCATCAGAAGTCTCCTGGCAGT
GCCCCTGTCACTGTGATCTATGACAACACCAACAGACCCTCGAACATCCCTTCACGA
TTCTCCGGTTCCCTATCCGGCTCCACAGCCACATTAACCATCACTGGGGTCCAAGCC
GAGGACGAGGCTGTCTATTACTGTGGGAGTGAAGACAACACCAGTACTGCTGCATTT
GGGGCCGGGACAACCCTGACCGTCCTAGGTGCGGCCGCA

Nucleotide sequence for V$_L$ (SEQ ID NO:45).

ACAGCGCTGACTCAGCCGTCCTCGGTGTCAGCGAACCCGGGAGAAACCGTCAAGATC
ACCTGCTCCGGGGATAGCACCTACTATGGCTGGTACCAGCAGAAGGCACCTGGCAGT
GCCCCTGTCACTCTGATCTATGACAACACCAACAGACCCTCGAACATCCCTTCACGA
TTCTCCGGTTCCCTATCTGGCTCCACAGCCACATTAACCATCACTGGGGTCCAAGCC
GAGGACGAGGCTGTCTATTTCTGTGGGGGTGCAGACAGCAGCAGTGCTGCTTCATTT
GGGGCCGGGACAGCCCTGACCGTCCTAGGTGCGGCCGCA

Figure 3L:

Nucleotide sequence for $V_L$ (SEQ ID NO:46).

ACAGCGCTGACTCAACCGTCCTCGGTGTCAGCAAACCTGGGAGGAACCGTCGAGATC
ACCTGCTCCGGGAGTAGTGGCAGCTACTATGGCTGGTACCAGCAGAAGGCACCTGGC
AGTGCCCCTGTCACTCTGATCTATGACAACACCAACAGACCCTCAGACATCCCTTCA
CGATTCTCCGGTTCCAAATCCGGCTCCACAGCCACATTAACCATCACTGGGGTCCGA
GCCGAGGACGAGGCTGTCTATTACTGTGGAAGTGCCGACAGCAGCAGTAGTGAAGCT
GCATTTGGGGCCGGGACAACCCTGACCGTCCTAGGTGCGGCCGCA

Nucleotide sequence for $V_L$ (SEQ ID NO:47).

ACAGCGCTGACTCAGCCGTCCTCGGTGTCAGCGAACCCGGGAGAAACCGTCGAGATC
ACCTGCTCCGGGGGTGGCAGCAGCTATGGCTGGTACCAGCAGAAGTCTCCTGGCAGT
GCCCCTGTCACTGTGATCTATGACAACACCAACAGACCCTCGAACATCCCTTCACGA
TTCTCCGGTTCCCTATCCGGCTCCGCAAACACGTTAACCATCACTGGGGTCCAAGCC
GACGACGAGGCTGTCTATTACTGTGGGAGTGGAGACAGCAGTGCTGCTTATGTTCCT
ATATTTGGGGCCGGGACAACCCTGACCGTCCTAGGTGCGGCCGCA

Nucleotide sequence for $V_L$ (SEQ ID NO:48).

ACAGCGCTGACTCAGCCGTCCTCGGTGTCAGCAAACCCGGGAGAAACCGTCGAGATC
ACCTGCAGTGGAGGTATCGGCCACTATGGCTGGTACCAGCAGAAGGCACCTGGCAGT
GCCCCTGTCACTGTGATTTATGATAGCAGCAGCAGACCCTCGGACATCCCTTCACGA
TTCTCCGGTTCCAAATCCGGCTCCACGGGCACATTAACCATCACTGGGGTCCAAGCC
GACGACGAGGCTGTCTATTACTGTGGGAGTGGAGGCAGCAATGGTGCTGGTATATTT
GGGGCCGGGACAACCCTGACCGTCCTAGGTGCGGCCGCA

Nucleotide sequence for $V_L$ (SEQ ID NO:49).

ACAGCGCTGACTCAGCCGTCCTCGGTGTCAGCAAACCCAGGAGAAACCGTCAAGATC
ACCTGCTCCGGGGATGGGAGCAGCTATGGCTGGTATCAGCAGAAGTCACCTGGCAGT
GCCCCTGTCACTGTGATCTATGACAGCACCAACAGACCCTGGGACATCCCTTCACGA
TTCTCCGGTTCCAAATCCGGCTCCACGGGCACATTAACCATCACTGGGGTCCAAGCC
GAGGACGAGGCTGTCTATTTCTGTGGGACTACAGACAGCACCAGTGCTGCTATATTT
GGGGCCGGGACAACCCTGACCGTCCTAGGTGCGGCCGCA

Nucleotide sequence for $V_L$ (SEQ ID NO:50).

ACAGCGCTGACTCAGCCGTCCTCGGTGTCAGCGAACCCGGGAGAAACCGTCAAGATC
ACCTGCTCCGGGGGTGGTAGCAGCAGCTACTATGGCTGGTACCAGCAGAAGGCACCT
GGCAGTGCCCCTGTCACTGTGATCTATGACAACACCAACAGACCCTCGGGCATCCCT
TCACGATTTTCCGGTTCCAAATCCGGCTCCACAGCCACATTAACCATCACTGGGGTC
CAAGCCGACGACGAGGCTGTCTATTACTGTGGTGGTGGGAGTGCAGACAGCAGTGGT
GCTGGTATATTTGGGGCCGGGACAACCCTGACCGTCCTAGGTGCGGCCGCA

Figure 3M:

Nucleotide sequence for V_L (SEQ ID NO:51).

ACAGCGCTGACTCAGCCGTCCTCGGTGTCAGCAAACCCGGGAGAAACCGTCGTGATC
ACCTGCTCCGGGGATACCTATACTTATGGCTGGTATCAGCAGAAGTCACCTGGCAGT
GCCCCTGTCACTGTGATCTATGCTAACACCAACAGACCCTCGGACATCCCTTCACGA
TTCTCCGGTTCTGGATCCGGCTCCACAGCCACATTAACCATCACTGGGGTCCAAGCC
GAGGACGAGGCTGTCTATTACTGTGGTGGCTGGGACAGCAGTGCTGGTTATTCTGGT
ATATTTGGGGCCGGGACAACCCTGACCGTCCTAGGTGCGGCCGCA

Nucleotide sequence for V_L (SEQ ID NO:52).

ACAGCGCTGACTCAGCCGTCCTCGGTGTCAGCGAACCCGGGAGAAACCGTCGAGATC
ACCTGCTCCGGGGATAGCAGCTACTATGGCTGGTATCAGCAGAAGTCACCTGGCAGT
GCCCCTGTCACTGTGATCTATAACAACGACAACAGACCCTCGGACATCCCTTCACGA
TTCTCCGGTTCCAGATCCGGCTCCACAAACACATTAACCATCACTGGGGTCCAAGCC
GACGACGAGGCTGTCTATTACTGTGGGAGTGCAGACAGCAGTACTGATGGTATATTT
GGGGCCGGGACAACCCTGACCGTCCTAGGTGCGGCCGCA

Nucleotide sequence for V_L (SEQ ID NO:53).

ACAGCGCTGACTCAGCCGTCCTCGGTGTCAGCGAACCCGGGAGAAACCGTCGAGATC
ACCTGCTCCGGGGGTAGCAACAACTATGGCTGGTTCCAGCAGAAGTCTCCTGGCAGT
GCCCCTGTCACTGTGATCTATGACAACACCAACAGACCCTCGGACATCCCTTCACGA
TTCTCCGGTTCCACATCCGGCTCCACAAGCACATTAACCATCACTGGGGTCCAAGCC
GACGACGAGGCTGTCTATTTCTGTGGGAGTGCAGACACCAACTATGATTTTATATTT
GGGGCCGGGACAACCCTGACCGTCCTAGGTGCGGCCGCA

Nucleotide sequence for V_L (SEQ ID NO:54).

ACAGCGCTGACTCAGCCGTCCTCGGTGTCAGCAAACCCGGGAGAAACCGTCGAGATC
ACCTGCTCTGGGGGTCACTATAGCTACGGCTGGTTCCAGCAGAAGGCACCTGGCAGT
GCCCCTGTCACTGTGATCTATAGGAACGACAAGAGACCCTCGGGCATCCCTTCACGA
TTCTCCGGTTCCCTATCCGGCTCCACGGGCACATTAACCATCACTGGGGTCCAAGCC
GACGACGAGGCTGTCTACTACTGTGGGAGTGCAGACAGCAGCTATGTTGCTATATTT
GGGGCCGGGACAACCCTGACCGTCCTAGGTGCGGCCGCA

Nucleotide sequence for V_L (SEQ ID NO:55).

ACAGCGCTGACTCAGCCGTCCTCGGTGTCAGCAAACCTGGGAGGAACCGTCGAGATC
ACCTGCTCTGGGAGGAACCGTCACTATAGTTACGGCTGGTTCCAGCAGAAGGCACCT
GGCAGTGCCCTTGTCACTGTGATCTATAGCAACAACAAGAGACCCTCGGACATCCCT
TCACGATTCTCCGGTTCCCTATCCGGCTCCACAAACACATTAACCATCACTGGGGTC
CAAGCCGACGACGAGGCTGTCTATTACTGCGGGAGTGCAGACAGCAGCAATGTTGCT
ATATTTGGGGCCGGGACAACCCTGACCGTCCTAGGTGCGGCCGCA

Figure 3N:

Nucleotide sequence for V$_L$ (SEQ ID NO:56).

ACAGCGCTGACTCAACCGTCCTCGGTGTCAGCAAACCTGGGAGGAACCGTCGAGATC
ACCTGCTCCGGGGGTCACTATTCCTACGGCTGGTTCCAGCAGAAGGCACCTGGCAGT
GCCCCTGTCACTGTGATCTATAGGAACGACAAGAGACCCTCGGACATCCCTTCACGA
TTCTCCGGTTCCCTATCCGGCTCCACGGGCACATTAACCATCACTGGGGTCCAAGCC
GACGACGAGGCTGTCTATTTCTGTGGGAGTGCAGACAGCACCTATGTTGGTATATTT
GGGGCCGGGACAACCCTGACCGTCCTAGGTGCGGCCGCA

Nucleotide sequence for V$_L$ (SEQ ID NO:57).

ACAGCGCTGACTCAGCCGTCCTCGGTGTCAGCAAACCTGGGAGGAACCGTCGAGATC
ACCTGCTCCGGGGGTAGTGGCAGCTATGGCTGGTATCAGCAGAAGTCACCTGGCAGT
GCCCCTGTCACTGTGATCTATGCTAACACCAACAGACCCTCGGACATCCCTTCACGA
TTCTCCGGTTCCACATCTGGCTCCACGGGCACATTAACCATCACTGGGGTCCAAGCC
GACGACGAGGCTGTCTATTTCTGTGGGAGCTACGACAGCAGTAATACTGCTGGTATA
TTTGGGGCCGGGACAACCCTGACCGTCCTAGGTGCGGCCGCA

Nucleotide sequence for V$_L$ (SEQ ID NO:58).

ACAGCGCTGACTCAGCCGTCCTCGGTGTCAGCAAACCCGGGAGAAACCGTCAAGATC
ACCTGCTCCGGGGGTGGCAGCTATGCTGGAAGTTACTATTATGGCTGGTATCAGCAA
AAGGCATCTGGCAGTGCCCCTGTCACTGTGATCTATAGCAACGACAAGAGACCCTCG
GACATCCCTTCACGATTCTCCGGTTCCACATCCGGCTCCACGGGCACATTAACCATC
ACTGGGGTCCAAGCCGACGACGAGGCTGTCTATTACTGTGGGAGCTGGGACAGCAGC
AGTTATGATGGTATATTTGGAGCCGGAACAACCCTGACCGTCCTAGGTGCGGCCGCA

Nucleotide sequence for V$_L$ (SEQ ID NO:59).

ACAGCGCTGACTCAGCCGTCCTCGGTGTCAGCGAACCCGGGAGAAACCGTCGAGATC
ACCTGCTCCGGGGGCAACTATGGCTGGTATAGCTGGCACCAGCAGAAGTCTCCTGGC
AGTGCCCCTGTCACTCTGATCTATGAAAACAACAAGAGACTCTCGGACATCCCTTCA
CGATTCTCCGGTTCCAAATCCGGCTCCACAGCCACATTAACCATCACTGGGGTCCAA
GCCGAGGACGAGGCTGTCTATTTCTGTGGGAGTACAGACAGCAGCTATGTTGGTATA
TTTGGGGCCGGGACAACCCTGACCGTCCTAGGTGCGGCCGCA

Nucleotide sequence for V$_L$ (SEQ ID NO:60).

ACAGCGCTGACTCAGCCGTCCTCGGTGTCAGCAAACCCGGGAGAAACCGTCAAGATC
ACCTGCTCCGGGGGTAGCAGCAGCTATAGGTATGGCTGGTACCAGCAGAAGTCTCCT
GGCAGTGCCCCTGTCACTCTGATCTATGCTAACACCAACAGACCCTCAAACATCCCT
TCACGATTCTCCGGTTCCAAATCTGGCTCCACACACATTAACCATCACTGGGGTC
CAAGCCGACGACGAGGCTGTCTATTACTGTGGGAGTGCAGACAGCAGCTATGTTGGT
ATATTTGGGGCCGGGACAACCCTGACCGTCCTAGGTGCGGCCGCA

Figure 3O:

Nucleotide sequence for V$_L$ (SEQ ID NO:61).

ACAGCGCTGACTCAGCCGTCCTCGGTGTCAGCGAACCCGGGAGAAACCGTCAAGATC
ACCTGCTCCGGGGGTGGCAGCAGCTATGGCTGGTACCAGCAGAAGGCACCTGGCAGT
GCCCCTGTCACTGTGATCTATGGTAACACCAACAGACCCTCGAACATCCCTTCACGA
TTTTCCGGTTCCAAATCCGGCTCCACAGCCACATTAACCATCACTGGGGTCCAAGCC
GACGACGAGGCTGTCTATTTCTGTGGGAGTGCAGACAGCAGCGGGGCCGGGACAACC
CTGACCGTCCTAGGTGCGGCCGCA

Nucleotide sequence for V$_L$ (SEQ ID NO:62).

GCGCTGACTCAGCCGTCCTCGGTGTCAGCAAACCCGGGAGGAACCGTCAAGATCACC
TGCTCCGGGAGTAGTGGCAACTATGGCTGGTATCAGCAGAAGTCTCCTGGTAGTGCC
CTTGTCACTGTGATCTATAGCAACGACAAGAGACCCTCAGACATCCCTTCACGATTC
TCCGGTTCCAAATCCGGCTCCACGGGCACATTAACCATCACTGGGGTCCAAGCCGAC
GACGAGGCTGTCTATTTCTGTGGGAGTGAAGACAGCAGCAGTATTGGTGATGGTATA
TTTGGGGCCGGGACAACCCTGACCGTCCTAGGTGCGGCCGCA

Nucleotide sequence for V$_L$ (SEQ ID NO:63).

ACAGCGCTGACTCAGCCGTCCTCGGTGTCAGCAAACCTGGGAGGAACCGTCAAGATC
ACCTGCTCCGGGGGTAGCAACAACTATGGCTGGTTCCAGCAGAAGTCACCTGGCAGT
GCCCCTGTCACTGTGATCTATAGCAACAACCAGAGACCCTCGAACATCCCTTCACGA
TTCTCCGGTTCCAAATCCGGCTCCACGGGCACATTAACCATCACTGGGGTCCAAGCC
GACGACGAGGCTGTCTATTACTGTGGGAGTGGAGACAGCAGCTATATTGGTATATTT
GGGGCCGGGACAACCCTGACCGTCCTAGGTGCGGCCGCA

Nucleotide sequence for V$_L$ (SEQ ID NO:64).

ACAGCGCTGACTCAGCCGTCCTCGGTGTCAGCAAACCTGGGAGGAACCGTCGAGATC
ACCTGCTCCGGGAGTAGTGGCAGCTATGGCTGGTATCAGCAGAAGTCTCCTGACAGT
GCCCCTGTCAGTGTGATCTATAGCACCAACCAGAGACCCTCGAACATCCCTTCACGA
TTCTCCGGTTCCAAATCCGGCTCCACAGCCACATTAACCATCACTGGGGTCCAAGCC
GACGACGAGGCTGTCTATTACTGTGGGAGCTACGAAGACAGTAGCAATACTATTGGG
GCCGGGACAACCCTGACCGTCCTAGGTGCGGCCGCA

Nucleotide sequence for V$_L$ (SEQ ID NO:65).

ACAGCGCTGACTCAGCCGTCCTCGGTGTCAGCGAACCCGGGAGAAACCGTCAAGATC
ACCTGCTCCGGGGGTAGTGGCAACTATGGCTGGTATCAGCAGAAGGCACCTGGCAGT
GCCCCTGTCACTGTGATCTCTGGTAGTACCCTGAGACCCTCGGACATCCCTTCACGA
TTCTCCGGTTCCAAATCCGGCTCCACGGGCACATTAACCATCACTGGGGTCCAAGCC
GAGGACGAGGCTGTTTATTTCTGTGGGAGTGCAGACAGCAGCTATGCTGGTATATTT
GGGGCCGGGACAACCCTGACCGTCCTAGGTGCGGCCGCA

Figure 3P:

Nucleotide sequence for V$_L$ (SEQ ID NO:66).

ACAGCGCTGACTCAGCCGTCCTCGGTGTCAGCAAACCCGGGAGAAACCGTCAAGATC
ACCTGCTCCGGGGGTAGCAATTACTACTATGGCTGGTACCAGCAGAAGTCTCCTGGC
AGTGCCCCTGTCACTGTGATCTATGCTAACACCAACAGACCCTCGGACATCCCTTCA
CGATTCTCCGGTTCCCTATCCGGCTCCACAGCCACATTAACCATCACTGGGGTCCAA
GCCGACGACGAGGCTGTCTACTACTGTGGGAGTGCAGACAGCAGCACTTATGCTGGT
ATATTTGGGGCCGGGACAACCCTGACCGTCCTAGGTGCGGCCGCA

Nucleotide sequence for V$_L$ (SEQ ID NO:67).

ACAGCGCTGACTCAGCCGTCCTCGGTGTCAGCAAACCCGGGAGAAACCGTCAAGATC
ACCTGTTCCGGGGGAAGCAACAACTGGTATAGCTGGCACCAGCAGAAGTCTCCTGGC
AGTGCCCCTGTCACTGTGATCTATAACAACGACAAGAGACCCTCGGACATCCCTTCA
CGATTCTCCGGTTTCACATCTGGCTCCACAAGCACATTAACCATCACTGGGGTCCAA
GCCGACGACGAGGCTGTCTATTTCTGTGGTGGCTGGGACAGTAGTAGTCGTGCCGGT
ATATTTGGGGCCGGGACAACCCTGACCGTCCTAGGTGCGGCCGCA

Nucleotide sequence for V$_L$ (SEQ ID NO:68).

ACAGCGCTGACTCAACCGTCCTCGGTGTCAGCAAACCCGGGAGAAACCGTCAAGATC
ACCTGCTCCGGGGGCAACAGCGGCTATGGCTGGTACCAGCAGAAGTCACCTGGCAGT
GCCCCTGTCACTGTGATCTATAGCAACGACAAGAGACCCTCGGACATCCCTTCACGA
TTCTCCGGTGCCCTATCCGGCTCCACAGCCACATTAACCATCACTGGGGTCCGAGCC
GAGGACGAGGCTGTCTATTACTGTGGGAGTGGAGACAGCAGTGGTTCTGTATTTGGG
GCCGGGACAACCCTGACCGTCCTAGGTGCGGCCGCA

Nucleotide sequence for V$_L$ (SEQ ID NO:69).

ACAGCGCTGACTCAGCCGTCCTCGGTGTCAGCGAACCCGGGAGAAACCGTCGAGATC
ACCTGCTCCGGGGATAGCAGCAGCAACTATGGCTGGTACCAGCAGAAGTCTCCTGGC
AGTGCCCCTGTCACTCTGATCTACTATGATGATGAGAGACCCTCGGGCATCCCTTCA
CGATTCTCCGGTTCCAAATCCGGCTCCACAGCCACATTAACCATTACTGGGGTCCAA
GCCGACGACGAGGCTGTCTATTACTGTGGGAGCTACGACAGCAGTACTGGTATATTT
GGGGCCGGGACAACCCTGACCGTCCTAGGTGCGGCCGCA

Nucleotide sequence for V$_L$ (SEQ ID NO:70).

ACAGCGCTGACTCAGCCGTCCTCGGTGTCAGCAAACCCAGGAGAAACCGTCGAGATC
ACCTGCTCCGGGGGTGGTAGCAGCAGCTACTATGGCTGGTACCAGCAGAAGTCTCCT
GGCAGTGCCCCTGTCACTGTAATCTATGAGAACACCAACAGACCCTCGGACATCCCT
TCACGATTCTCCGGTTCCAAATCCGGCTCCACAGCCACATTAACCATCACTGGAGTC
CAAGCCGAGGACGAGGCTGTCTATTACTGTGGGAGTGGAGACAGCAACACTTATAAT
GGTATATTTGGGGCCGGGACAACCCTGACCGTCCTAGGTGCGGCCGCA

Figure 3Q:

Nucleotide sequence for $V_L$ (SEQ ID NO:71).

ACAGCGCTGACTCAACCGTCCTCGGTGTCAGCAAACCCGGGAAAAACCGTCGAGATC
ACCTGCTCCGGGGGTAGTGGCAGCTACGGCTGGTATCAGCAGAAGTCACCTGGCAGT
GCCCCTGTCACTGTGATCTACTGGGATGACAAGAGACCCTCGGGCATCCCTTCACGA
TTCTCCGGTTCCGAGTCCGGCTCCACAGCCACATTAACCATCACTGGGGTCCAAGCC
GAGGACGAGGCTGTCTATTACTGTGGGAGTGCAGACAGCAGTGGTGCTATATTTGGG
GCCGGGACAACCCTGACCGTCCTAGGTGCGGCCGCA

Nucleotide sequence for $V_L$ (SEQ ID NO:72).

ACAGCGCTGACTCAGCCGTCCTCGGTGTCAGCAAACCTGGGAGGAACCGTCAAGATC
ACCTGCTCCGGGAGTAGTGGCAGCTATGGCTGGTACCGGCAGAAGGCACCTGGCAGT
GCCCCTGTCACTGTGATCTATAGCAACGACAAGAGACCCTCGGACATCCCTTCACGA
TTCTCCGGTTCCGCATCCGGCTCCACAGCCACATTAACCATCACTGGGGTCCAAGCC
GAGGACGAGGCTGTCTATTTCTGTGGTGGCTACGACGGCAGCAGTTATGTTGGTATA
TTTGGGGCCGGGACAACCCTGACCGTCCTAGGTGCGGCCGCA

Nucleotide sequence for $V_L$ (SEQ ID NO:73).

ACAGCGCTGACTCAGCCGTCCTCGGTGTCAGCAAACCCGGGAGAAACCGTCAAGATC
ACCTGCTCTGGGGGTAGTGGCTATGGTTATGGCTGGTATCAGCAGAAGTCTCCTGGC
AGTGCCCCTGTCACTGTGATCTATCAGAACGACAAGAGACCCTCGAACATCCCTTCA
CGATTCTCCGGTTCTGGATCCGGCTCCACAGGCACATTAACCATCACTGGGGTCCAA
GTCGAGGACGAGGCTGTCTATTACTGTGGGACTGCAGACAGCAGCTATGTTGGTGAT
GCTGGTATATTTGGGGCCGGGACAACCCTGACCGTCCTAGGTGCGGCCGCA

Nucleotide sequence for $V_L$ (SEQ ID NO:74).

ACAGCGCTGACTCAGCCGTCCTCGGTGTCAGCAAACCCAGGAGAAACCGTCAAGATC
ACCTGCTCCGGGGGTAGCAGTGGCAGGTATGGCTGGTATCAGCAGAAGTCACCTGGC
AGTGCCCCTGTCACTGTGATCTATTACAACGACAAGAGACCCTCGGACATCCCTTCA
CGATTCTCCGGCTCCCTACCCGGCTCCACAGCCACATTAACCATCACTGGGGTCCAA
GTCGAAGACGAGGCTGTCTATTTCTGTGGGAGTGCAGACAGCACTGCTGGTATATTT
GGGGCCGGGACAACCCTGACCGTCCTAGGTGCGGCCGCA

Nucleotide sequence for $V_L$ (SEQ ID NO:75).

ACAGCGCTGACTCAGCCGTCCTCGGTGTCAGCAAACCTGGGAGGAACCGTCAAGATC
ACCTGCTCCGGGGGTTACAGTGGCTATGGTTATGGCTGGTATCAGCAGAAGTCACCT
GGCAGTGCCCCTGTCACTTTGATCTATAATGGCAATAACAGACCCTCGGACATCCCT
TCACGATTCTCCGGTTCTGGATCTGGCTCCACAAACACATTAACCATCACTGGGGTC
CAAGTCGAGGACGAGGCTATCTATTTCTGTGGGAGTGCAGACAGCAGCAGTATTGCT
GTATTTGGGGCCGGGACAACCCTGACCGTCCTAGGTGCGGCCGCA

Figure 3R:

Nucleotide sequence for $V_L$ (SEQ ID NO:76).

ACAGCGCTGACTCAGCCGTCCTCGGTGTCAGCGAACCCGGGAGAAACCGTCGAGATC
ACCTGCTCCGGGGGTAGGAAGTACTATGGCTGGTACCAGCAGAAGTCTCCTGGCAGT
GCCCCTGTCACTCTGATCTATAGCAACGACAAGAGACCCTCGGACATCCCTTCACGA
TTCTCCGGTTCCAAATCCGGCTCCACAGCCACATTAACCATCACTGGGGTCCAAGTC
GACGACGAGGCTGTCTATTACTGTGGGAGTGCAGACACCAGCAGCAGTGAAGCTGCA
TTTGGGGCCGGGACAACCCTGACCGTCCTAGGTGCGGCCGCA

Nucleotide sequence for $V_L$ (SEQ ID NO:77).

GCGCTGACTCAGCCGGCCTCGGTGTCAGCAAACCTGGGAGAAACCGTCAAGATCACC
TGCTCCGGGGGTGGTAGCTATGCTGGAAGTTACTATTATGGCTGGTATCAGCAGAAG
TCTCCTGGCAGTGCCCCTGTCACTGTGATCTATGACAACACCAACAGACCCTCGAAC
ATCCCTTCACGATTCTCCGGTTCCAAATCCGGCCCCACAGCCACATTAACCATCACT
GGGGTCCAAGTCGACGACGAGGCTGTCTATTATTGTGGGAGCATGGACAGCAGTAGT
GGTGGCGGTATATTTGGGGCCGGGACAACCCTGACCGTCCTAGGTGCGGCCGCA

Figure 4A

Deduced amino acid sequence for $V_H$ (SEQ ID NO:78).

AVTLDESGGGLQTPGGTLSLVCKASGFTFSSYQMNWLRQAPGKGLEWVGVISTRGSS
TAYGAAVKGRATISRDNGRSTVRLQLNSLRTEDTATYYCAKAGYACGWSVGCIDAWG
HGTEVIVSSLD

Deduced amino acid sequence for $V_H$ (SEQ ID NO:79).

AVTLDESGGGLQTPGGTLSLVCKASGFTFSSYQMNWLRQAPGKGLEWVGVISTRGSS
TAYGAAVKGRATISRDNGQSTVRLQLNSLRTEDTATYYCAKAGYACGWSVGCIDAWG
HGTEVIVSS

Deduced amino acid sequence for $V_H$ (SEQ ID NO:80).

AVTLDESGGGLQTPGGALSLVCKGSGFTFSSYNMGWVRQAPGKGLEFVAAISNTGRY
TGYGSAVKGRATISRDNGQSTVRLQLNNLRAEDTATYYCAKTAGYYGWNTASDIDAW
GHGTEVIVSSLD

Deduced amino acid sequence for $V_H$ (SEQ ID NO:81).

AVTLDESGGGLQTPGRALSLVCKGSGFTLSSYNMGWVRQAPGKGLEFVAAISNTGRY
TGYGSAVKGRATISRDNGQSTVRLQLNNLRAEDTGTYYCAKTAGYYGWNTASDIDAW
GHGTEVIVSSLD

Deduced amino acid sequence for $V_H$ (SEQ ID NO:82).

AVTLDESGGGLQTPGRALSLVCKASGFSISGYNMGWVRQAPGKGLEFVAGIGNTGRY
TGYGAAVKGRATISRDNGQSTVRLQLNNLRAEDTGIYYCAKGASHYCWDVGCSNIAG
SIDAWGHGTEVIVSSLD

Deduced amino acid sequence for $V_H$ (SEQ ID NO:83).

AVTLDESGGGLQTPGRALSLVCKASGFTFRSYNMAWVRQAPGKGLEFVAEISGTGST
TNYAPAVKGRATISRDNGQSTVRLQLNNLRAEDTGTYFCAKAAGAYCAWSGCTAGSI
DAWGHGTEVIVSSLD

Deduced amino acid sequence for $V_H$ (SEQ ID NO:84).

AVTLDESGGGLQTPRGRLRLVCKASGFTFSSYEMGWVRQAPGKGLEWVAGIGGSGSG
SAYGSAVKGRATISRDNGQSTVRLQLNNLRAEDTGTYYCAKSTTKCSYCWYGATAGS
IDAWGHGAEVIVSSLD

Deduced amino acid sequence for $V_H$ (SEQ ID NO:85).

AVTLDESGGGLQTPRGRLRLVCKASGFDFSSYEMGWVRQAPGKGLEWVAGIGGSGSG
SAYGPAVKGRATITRDNGQSTVRLQLNNLRAEDTGTYYCAKSTTRCSFCWYGATAGS
IDAWGHGAEVIVSSLD

Figure 4B

Deduced amino acid sequence for V$_H$ (SEQ ID NO:86).

AVTLDESGGGLQTPRGRLRLVCKASGFTFSSYEMGWVRQAPGKGLEWVAGIGGSGSGSAYGS
AVKGRATISRDNGQSTVRLQLNNLRAEDTGTYYCAKSTTKCNHCWYGATAGSIDAWGHGTEV
IVSSLD

Deduced amino acid sequence for V$_H$ (SEQ ID NO:87).

AVTLDESGGGLHTPGGALRLVCKASGFSISSYGMGWVRQAPGKGLEWVARIGSGASGTAYGS
AVKGRATISRDNGQSTVRLQLNNLRADDTGTYYCAKSAGAYCWYAGCPSSIDAWGHGAEVIV
SSLD

Deduced amino acid sequence for V$_H$ (SEQ ID NO:88).

AVTLDESGGGLQTPGGALRLVCKASGFSISSYGMGWVRQAPGKGLEWVARIGSGASGTAYGS
TVKGRATISRDNGQSTVRLQLNNLRTEDTGTYYCAKTAGAYCWYAGCPSSIDAWGHGTEVIV
SSLD

Deduced amino acid sequence for V$_H$ (SEQ ID NO:89).

AVTLDESGGGLQTPGKGLSLVCKASGFSLNSYGMGWVRQAPGKGLEWVARIGSGASGTAYGS
AVKGRATISRDNGQSIVRLQLNDLRAEDTATYYCAKTAGAYCWYAGCPSSIDAWGHGTEVIV
SSLD

Deduced amino acid sequence for V$_H$ (SEQ ID NO:90).

AVTLDESGGGLQTPGKGLSLVCKASGFTFTSYGMGWVRQAPGKGLEWVARIGSGASGTAYAT
AVKGRATISRDNGQSTVRLQLNDLRAEDTATYYCAKTAGAYCWYAGCPSSIDAWGHGTEVIV
SSLD

Deduced amino acid sequence for V$_H$ (SEQ ID NO:91).

AVTLDESGGGLQTPGRALSLVCKASGFTFSSYAMNWVRQAPGKGLEFVAEISGSGRYTYYAP
AVKGRATISRDNGQSTVSLQLNNLRAEDTATYYCAKTADSCRYGCSADRIDAWGHGTEVIVS
SLD

Deduced amino acid sequence for V$_H$ (SEQ ID NO:92).

AVTLDESGGGLQTPGGALSLVCKASGFTFSSYAINWVRQAPGKGLEFVAEISGSGRYVYYAP
AVQGRATISRDNGQSTVRLQLNNLRAEDTGTYYCAKTADSCRYGCNADRIDAWGRGTEVIVS
SLD

Deduced amino acid sequence for V$_H$ (SEQ ID NO:93).

AVTLDESGGGLQTPGGALSLVCKGSGFTFSSHGMFWVRQAPGKGLEYVAQISGSGRLTNYGP
AVKGRATISRDNGQSTVRLQLNNLRAEDTGTYYCAKTAVNCRYGCAGDNIDAWGHGTEVIVS
SLD

Figure 4C

Deduced amino acid sequence for V$_H$ (SEQ ID NO:94).

AVTLDESGGGLQTPGGGLSLVCKASGFTFSSYGMGWVRQAPGKGLEWVAEISGSGRY
TGYGPAVQGRATISRDNGQSTVRLQLSDLRAEDTGTYYCAKATASCTYGCTPYTGEI
DAWGHGTEVIVSSLD

Deduced amino acid sequence for V$_H$ (SEQ ID NO:95).

AVTLDESGGGLQTPGGALSLVCKASGFTFSSYGMQWVRQAPGKGLEWVAGISGSGRG
TWYAPAVKGRATISRDNGQSTVRLQLNNLRAEDTGTYYCAKAAGSDTYGSTGDNIDA
WGHGTEVIVSSLD

Deduced amino acid sequence for V$_H$ (SEQ ID NO:96).

AVTLDESGGGLQTPGGTLSLVCKGSGFTFSDYGMGWMRQAPGKGLEYVAEISSSGRY
TNYGPAVKGRATISRDNGQSTVRLQLNNLRAEDTGTYYCAKAAGRGYYGWSAGTIDA
WGHGTEVIVSSLD

Deduced amino acid sequence for V$_H$ (SEQ ID NO:97).

AVTLDESGGGLQTPGGTLSLVCKASGFTFSSYGMGWMRQAPGKGLEYVAESSSSGRY
TNYGPAVKGRATISRDNGQSTVRLQLNNLRAEDTGTYYCAKAAGSGYYGWSAGSIDA
WGHGTEVIVSSLD

Deduced amino acid sequence for V$_H$ (SEQ ID NO:98).

AVTLDESGGGLQTPGGTLSLVCKASGFTFSSFNIFWVRQAPGKGLEFVAAINKDGSF
THYGSAVKGRATISRDNGQSTLRLQLNDLGAEDAGTYFCARSPGGFSCAGGWCGAYA
DGIDAWGHGTEVIISSLD

Deduced amino acid sequence for V$_H$ (SEQ ID NO:99).

AVTLDESGGGLQTPGGGLSLVCKGSGFDFSSYNMFWVRQAPGKGLEFVAAISSTGSY
THYGPAVKGRATISRDNGQSTVRLQLNNLRAEDTAIYYCARSPGGFSCAGGWCGGYA
DSIDAWGHGTEVIVSSLD

Deduced amino acid sequence for V$_H$ (SEQ ID NO:100).

AVTLDESGGGLQTPGGTLSLVCKASGFTFSSFNMQWVRQAPGKGLEFVAGIDNIGRK
TSYGSAVKGRATISRDNGQSTVRLQLNNLRAEDTATYFCAKGAGSSAYSCAFCYPGW
IDAWGHGTEVIVSSLD

Deduced amino acid sequence for V$_H$ (SEQ ID NO:101).

AVTLDESGGGLQTPGGALSLVCKASGFTFSSHGMGWVRQAPGKGLEWVAGIENDGSI
TGYGAAVKGRATISRDNGQSTVRLQLNNLRAEDTGTYFCAKRSGSGCCNAYAIDAWG
HGTEVIVSSLD

Figure 4D

Deduced amino acid sequence for V$_H$ (SEQ ID NO:102).

AVTLDESGGGLQTPGGGLSLVCKASGFTFSSYAMYWVRQTPGKGLEFVAGIDSGDGR
YSKYGPAVDGRATMSRDNGQSTVRLQLNDLRAEDSGTYYCAKGAVTGYCGWNACTVA
NIDTWGHGTEVIVSSLD

Deduced amino acid sequence for V$_H$ (SEQ ID NO:103).

AVTLDESGGGLQTPGGGLSLVCKASGFSFSSYSMQWVRQAPGKGLDWVAGISGTGRH
RNYGSAVEGRATISRDNGQSTVRLQLDNLRAEDTGTYYCARAPCTGCGWSAGSIDAW
GHGTEVIVSSLD

Deduced amino acid sequence for V$_H$ (SEQ ID NO:104).

AVTLDESGGGLQTPGGGLSLVCKASGFTFSSYQMHWIRQAPGKGLEWVGVISSRGSS
TNYGAAVKGRATISRDNGQSTVRLQLNNLRAEDTATYYCAKSGYACGWSGGCIDAWG
HGTEVIVSSLD

Deduced amino acid sequence for V$_H$ (SEQ ID NO:105).

AVTLDESGGGLQAPGGGLSLVCKASGFTFSSHGMGWVRQAPGKGLEYVASISTRGSS
TYYGAAVKGRATISRDNGQSTVRLQLNNLRAEDTATYYCAKTGYACSYSYHTACIDA
WGHGTEVIVSSLD

Deduced amino acid sequence for V$_H$ (SEQ ID NO:106).

AVTLDESGGGLQTPGGALSLVCKASGFTFRSHQMFWVRQAPGKGLEYVGQITTRGTT
TYYGAAVTGRATISRDNGQNTVRLQLNNLRAEDTGTYFCAKAAYGYSYVSTIDAWGH
GTEVIVSSLD

Deduced amino acid sequence for V$_H$ (SEQ ID NO:107).

AVTLDESGGGLQTPGGGLSLVCRASGFIFSSHPMVWVRQAPGKGLEWVAAITTRGTS
AYYGPAVKGRATISRDNGQSTVRLQLNSLRAEDTGTYYCARSGYGYTGSDAGNIDTW
GHGTEVIVSSLD

Deduced amino acid sequence for V$_H$ (SEQ ID NO:108).

AVTLDESGGGLQTPGGALSLVCKASGFAFSRYAMNWVRQAPGKGLEWVAGVRNVGSS
TNYAPAVKGRATISRDNGQSTLRLQLNNLRAEDTGIYYCAKAAGSGYCAWWADALTC
GGYKTHDIDAWGHGTEVIVSSLD

Deduced amino acid sequence for V$_H$ (SEQ ID NO:109).

AVTLDESGGGLQTPGGALSLVCKASGFTFSSYGMGWVRQAPGKGLEWVAGIDNIGRY
TNYGPAVKGRATISRDNGQSTVRLQLNNLRAEDTATYYCAKSAASGSWSYYGTGWID
GWGHGTEVIVSSLD

Figure 4E

Deduced amino acid sequence for $V_H$ (SEQ ID NO:110).
AVTLDESGGGLQTPGGALSLVCKASGFTFAIYAMHWVRQAPDKGLEFVAGISSDGSR
TKYGAAVKGRATMSRDNGQSTVRLQLNNLRTEDTATYFCAKTAGSWSRYNGLHSNID
TWGHGTEVIVSSLD Deduced amino acid sequence for $V_H$ (SEQ ID NO:111).
AVTLDESGGGLQTPGGGLSLVCKASGFTFTDYGMGWMRQAPGKGLEYVVGISNTGRY
TYYGSAVKGRATISRDNGQSTVRLQLNNLRAEDTATYYCAKSAGSWWHYTGADNIDA
WGHGTEVIVSSLD Deduced amino acid sequence for $V_H$ (SEQ ID NO:112).
AVTLDESGGGLQTPGGGLSLVCKASGFTFSSYAMNWVRQAPGKGLEWVASINSAGSY
THYGSAVKGRATISRDNGQSTVRLQLNNLRAEDTGTYYCARGGGGCGIWSCGSYAGE
IDAWGHGTEVIVSS

Figure 4F

Deduced amino acid sequence for V$_L$ (SEQ ID NO:113).

TALTQPSSVSANPGETVEITCSGDTTYYGWYQQKAPGSAPVTLIYDNTNRPSDIPSR
FSGSRSGSTATLTITGVQAEDEAVYFCGSADTSGYAGIFGAGTTLTVLGAAA

Deduced amino acid sequence for V$_L$ (SEQ ID NO:114).

TALTQPSSVSANPGETVEITCSGGSGSYYGWYQQKPPGSAPVTVIYNNNNRPSDIPS
RFSGSRSGSTATLTITGVQADDEAVYFCGSEDSTGYVGIFGAGTTLTVLGAAA

Deduced amino acid sequence for V$_L$ (SEQ ID NO:115).

TALTQLSSVSANPGETVEITCSGDSSYYGWYQQKAPGSAPVTLIYDNTNRPSDISSR
FSGSKSGSTATLTITGVQADDEAVYYCGSAGSSHVGMFGAGTTLTVLGAAA

Deduced amino acid sequence for V$_L$ (SEQ ID NO:116).

TALTQPSSVSANPGETVEITCSGDSSYYGWYQQKAPGSAPVTLIYDNTNRPSDISSR
FSGSKSGSTATLTITGVQADDEAVYYCGSAGSSHVGMFGAGTTLTVLGAAA

Deduced amino acid sequence for V$_L$ (SEQ ID NO:117).

TALTQPSSVSANLGGTVKITCSGDSSYYGWYQQKAPGSAPVTVIYDNTNRPSGIPSR
FSGSKSGSTATLTITGVRADDEAVYYCGNTDSSGAIFGAGTTLTVLGAAA

Deduced amino acid sequence for V$_L$ (SEQ ID NO:118).

TALTQPSSVSANPGETVKITCSGGSNNYGWYQQKSPGSAPVTLIYDNTNRPSNIPSR
FSGSKSGSTATLTITGVQADDEAVYYCGSADSSTGIFGAGTTLTVLGAAA

Deduced amino acid sequence for V$_L$ (SEQ ID NO:119).

TALTQPSSVSANPGETVKITCSGGSGSYYGWYQQKSPGSAPVTLIYDNDKRPSGIPS
RFSGSTSGSTGTLTITGVQAEDEAVYYCGSRDSSYVGMFGAGTTLTVLGAAA

Deduced amino acid sequence for V$_L$ (SEQ ID NO:120).

TALTQPSSVSANPGETVKITCSGGYNYYGWYQQKSPGSVPVTLIYDNTNRPSNIPSR
FSGSTSGSTGTLTITGVQADDEAVYFCGSADSSSTSASFGAGTTLTVLGAAA

Deduced amino acid sequence for V$_L$ (SEQ ID NO:121).

TALTQPSSVSANPGGTVKLTCSGDSSYYGWYHQKSPGSAPVTVIYDNTNRPSNIPSR
FSGSLSGSTATLTITGVQAEDEAVYYCGSEDNTSTAAFGAGTTLTVLGAAA

Figure 4G

Deduced amino acid sequence for V<sub>L</sub> (SEQ ID NO:122).

TALTQPSSVSANPGETVKITCSGDSTYYGWYQQKAPGSAPVTLIYDNTNRPSNIPSR
FSGSLSGSTATLTITGVQAEDEAVYFCGGADSSSAASFGAGTALTVLGAAA

Deduced amino acid sequence for V<sub>L</sub> (SEQ ID NO:123).

TALTQPSSVSANLGGTVEITCSGSSGSYYGWYQQKAPGSAPVTLIYDNTNRPSDIPS
RFSGSKSGSTATLTITGVRAEDEAVYYCGSADSSSSEAAFGAGTTLTVLGAAA

Deduced amino acid sequence for V<sub>L</sub> (SEQ ID NO:124).

TALTQPSSVSANPGETVEITCSGGGSSYGWYQQKSPGSAPVTVIYDNTNRPSNIPSR
FSGSLSGSANTLTITGVQADDEAVYYCGSGDSSAAYVPIFGAGTTLTVLGAAA

Deduced amino acid sequence for V<sub>L</sub> (SEQ ID NO:125).

TALTQPSSVSANPGETVEITCSGGIGHYGWYQQKAPGSAPVTVIYDSSSRPSDIPSR
FSGSKSGSTGTLTITGVQADDEAVYYCGSGGSNGAGIFGAGTTLTVLGAAA

Deduced amino acid sequence for V<sub>L</sub> (SEQ ID NO:126).

TALTQPSSVSANPGETVKITCSGDGSSYGWYQQKSPGSAPVTVIYDSTNRPWDIPSR
FSGSKSGSTGTLTITGVQAEDEAVYFCGTTDSTSAAIFGAGTTLTVLGAAA

Deduced amino acid sequence for V<sub>L</sub> (SEQ ID NO:127).

TALTQPSSVSANPGETVKITCSGGGSSSYYGWYQQKAPGSAPVTVIYDNTNRPSGIP
SRFSGSKSGSTATLTITGVQADDEAVYYCGGGSADSSGAGIFGAGTTLTVLGAAA

Deduced amino acid sequence for V<sub>L</sub> (SEQ ID NO:128).

TALTQPSSVSANPGETVVITCSGDTYTYGWYQQKSPGSAPVTVIYANTNRPSDIPSR
FSGSGSGSTATLTITGVQAEDEAVYYCGGWDSSAGYSGIFGAGTTLTVLGAAA

Deduced amino acid sequence for V<sub>L</sub> (SEQ ID NO:129).

TALTQPSSVSANPGETVEITCSGDSSYYGWYQQKSPGSAPVTVIYNNDNRPSDIPSR
FSGSRSGSTNTLTITGVQADDEAVYYCGSADSSTDGIFGAGTTLTVLGAAA

Deduced amino acid sequence for V<sub>L</sub> (SEQ ID NO:130).

TALTQPSSVSANPGETVEITCSGGSNNYGWFQQKSPGSAPVTVIYDNTNRPSDIPSR
FSGSTSGSTSTLTITGVQADDEAVYFCGSADTNYDFIFGAGTTLTVLGAAA

Figure 4H

Deduced amino acid sequence for $V_L$ (SEQ ID NO:131).

TALTQPSSVSANPGETVEITCSGGHYSYGWFQQKAPGSAPVTVIYRNDKRPSGIPSR
FSGSLSGSTGTLTITGVQADDEAVYYCGSADSSYVAIFGAGTTLTVLGAAA

Deduced amino acid sequence for $V_L$ (SEQ ID NO:132).

TALTQPSSVSANLGGTVEITCSGRNRHYSYGWFQQKAPGSALVTVIYSNNKRPSDIP
SRFSGSLSGSTNTLTITGVQADDEAVYYCGSADSSNVAIFGAGTTLTVLGAAA

Deduced amino acid sequence for $V_L$ (SEQ ID NO:133).

TALTQPSSVSANLGGTVEITCSGGHYSYGWFQQKAPGSAPVTVIYRNDKRPSDIPSR
FSGSLSGSTGTLTITGVQADDEAVYFCGSADSTYVGIFGAGTTLTVLGAAA

Deduced amino acid sequence for $V_L$ (SEQ ID NO:134).

TALTQPSSVSANPGGTVEITCSGGSGSYGWYQQKSPGSAPVTVIYANTNRPSDIPSR
FSGSTSGSTGTLTITGVQADDEAVYFCGSYDSSNTAGIFGAGTTLTVLGAAA

Deduced amino acid sequence for $V_L$ (SEQ ID NO:135).

TALTQPSSVSANPGETVKITCSGGGSYAGSYYYGWYQQKASGSAPVTVIYSNDKRPS
DIPSRFSGSTSGSTGTLTITGVQADDEAVYYCGSWDSSSYDGIFGAGTTLTVLGAAA

Deduced amino acid sequence for $V_L$ (SEQ ID NO:136).

TALTQPSSVSANPGETVEITCSGGNYGWYSWHQQKSPGSAPVTLIYENNKRLSDIPS
RFSGSKSGSTATLTITGVQAEDEAVYFCGSTDSSYVGIFGAGTTLTVLGAAA

Deduced amino acid sequence for $V_L$ (SEQ ID NO:137).

TALTQPSSVSANPGETVKNTCSGGSSSYRYGWYQQKSPGSAPVTLIYANTNRPSNIP
SRFSGSKSGSTHTLTITGVQADDEAVYYCGSADSSYVGIFGAGTTLTVLGAAA

Deduced amino acid sequence for $V_L$ (SEQ ID NO:138).

TALTQPSSVSANPGETVKITCSGGGSSYGWYQQKAPGSAPVTVIYGNTNRPSNIPSR
FSGSKSGSTATLTITGVQADDEAVYFCGSADSSGAGTTLTVLGAAA

Deduced amino acid sequence for $V_L$ (SEQ ID NO:139).

ALTQPSSVSANPGGTVKITCSGSSGNYGWYQQKSPGSALVTVIYSNDKRPSDIPSRF
SGSKSGSTGTLTITGVQADDEAVYFCGSEDSSSIGDGIFGAGTTLTVLGAAA

Figure 4I

Deduced amino acid sequence for $V_L$ (SEQ ID NO:140).

TALTQPSSVSANLGGTVKITCSGGSNNYGWFQQKSPGSAPVTVIYSNNQRPSNIPSR
FSGSKSGSTGTLTITGVQADDEAVYYCGSGDSSYIGIFGAGTTLTVLGAAA

Deduced amino acid sequence for $V_L$ (SEQ ID NO:141).

TALTQPSSVSANLGGTVEITCSGSSGSYGWYQQKSPDSAPVSVIYSTNQRPSNIPSR
FSGSKSGSTATLTITGVQADDEAVYYCGSYEDSSNTIGAGTTLTVLGAAA

Deduced amino acid sequence for $V_L$ (SEQ ID NO:142).

TALTQPSSVSANPGETVKITCSGGSGNYGWYQQKAPGSAPVTVISGSTLRPSDIPSR
FSGSKSGSTGTLTITGVQAEDEAVYFCGSADSSYAGIFGAGTTLTVLGAAA

Deduced amino acid sequence for $V_L$ (SEQ ID NO:143).

TALTQPSSVSANPGETVKITCSGGSNYYYGWYQQKSPGSAPVTVIYANTNRPSDIPS
RFSGSLSGSTATLTITGVQADDEAVYYCGSADSSTYAGIFGAGTTLTVLGAAA

Deduced amino acid sequence for $V_L$ (SEQ ID NO:144).

TALTQPSSVSANPGETVKITCSGGSNNWYSWHQQKSPGSAPVTVIYNNDKRPSDIPS
RFSGFTSGSTSTLTITGVQADDEAVYFCGGWDSSSRAGIFGAGTTLTVLGAAA

Deduced amino acid sequence for $V_L$ (SEQ ID NO:145).

TALTQPSSVSANPGETVKITCSGGNSGYGWYQQKSPGSAPVTVIYSNDKRPSDIPSR
FSGALSGSTATLTITGVRAEDEAVYYCGSGDSSGSVFGAGTTLTVLGAAA

Deduced amino acid sequence for $V_L$ (SEQ ID NO:146).

TALTQPSSVSANPGETVEITCSGDSSSNYGWYQQKSPGSAPVTLIYYDDERPSGIPS
RFSGSKSGSTATLTITGVQADDEAVYYCGSYDSSTGIFGAGTTLTVLGAAA

Deduced amino acid sequence for $V_L$ (SEQ ID NO:147).

TALTQPSSVSANPGETVEITCSGGGSSSYYGWYQQKSPGSAPVTVIYENTNRPSDIP
SRFSGSKSGSTATLTITGVQAEDEAVYYCGSGDSNTYNGIFGAGTTLTVLGAAA

Deduced amino acid sequence for $V_L$ (SEQ ID NO:148).

TALTQPSSVSANPGKTVEITCSGGSGSYGWYQQKSPGSAPVTVIYWDDKRPSGIPSR
FSGSESGSTATLTITGVQAEDEAVYYCGSADSSGAIFGAGTTLTVLGAAA

Figure 4J

Deduced amino acid sequence for $V_L$ (SEQ ID NO:149).

TALTQPSSVSANLGGTVKITCSGSSGSYGWYRQKAPGSAPVTVIYSNDKRPSDIPSR
FSGSASGSTATLTITGVQAEDEAVYFCGGYDGSSYVGIFGAGTTLTVLGAAA

Deduced amino acid sequence for $V_L$ (SEQ ID NO:150).

TALTQPSSVSANPGETVKITCSGGSGYGYGWYQQKSPGSAPVTVIYQNDKRPSNIPS
RFSGSGSGSTGTLTITGVQVEDEAVYYCGTADSSYVGDAGIFGAGTTLTVLGAAA

Deduced amino acid sequence for $V_L$ (SEQ ID NO:151).

TALTQPSSVSANPGETVKITCSGGSSGRYGWYQQKSPGSAPVTVIYYNDKRPSDIPS
RFSGSLPGSTATLTITGVQVEDEAVYFCGSADSTAGIFGAGTTLTVLGAAA

Deduced amino acid sequence for $V_L$ (SEQ ID NO:152).

TALTQPSSVSANLGGTVKITCSGGYSGYGYGWYQQKSPGSAPVTLIYNGNNRPSDIP
SRFSGSGSGSTNTLTITGVQVEDEAIYFCGSADSSSIAVFGAGTTLTVLGAAA

Deduced amino acid sequence for $V_L$ (SEQ ID NO:153).

TALTQPSSVSANPGETVEITCSGGRKYYGWYQQKSPGSAPVTLIYSNDKRPSDIPSR
FSGSKSGSTATLTITGVQVDDEAVYYCGSADTSSSEAAFGAGTTLTVLGAAA

Deduced amino acid sequence for $V_L$ (SEQ ID NO:154).

ALTQPASVSANLGETVKITCSGGGSYAGSYYYGWYQQKSPGSAPVTVIYDNTNRPSN
IPSRFSGSKSGPTATLTITGVQVDDEAVYYCGSMDSSSGGGIFGAGTTLTVLGAAA

Figure 5: Alignment of deduced amino acid sequences of chicken recombinant antibodies CRAb 0 to CRAb 176.

RECOMBINANT ANTIBODIES AGAINST INFECTIOUS BURSAL DISEASE VIRUS (IBDV)

FIELD OF THE INVENTION

The present invention relates to the field of recombinant antibodies, and more particularly to the generation and screening of recombinant antibodies generated against infectious bursal disease virus (IBDV). The present invention also provides neutralising antibodies against IBDV and various means by which a wide range of IBDV recombinant antibody-based therapeutics, prophylactics and diagnostic reagents may be developed.

BACKGROUND

Infectious bursal disease virus (IBDV) belongs to the Birnaviridae family. It causes a highly contagious immunosuppressive disease in chickens by depleting B cell populations within the Bursa of Fabricius.

The IBDV virion consists of a double stranded RNA genome in a non-enveloped icosahedral capsid. The capsid contains two major structural proteins, VP3 and VP2. Virus neutralizing antibodies have been shown to recognise a conformational epitope located in the hypervariable region of VP2, between amino acid residues 206 and 350. Thus, the VP2 protein is an important target for immunodetection and immunoprophylaxis studies.

A large number of IBDV strains have been identified throughout the world and grouped according to their relative pathogenicity and antigenicity. Three major groups have been identified: (i) classical strains, (ii) very virulent types (vvIBDV) capable of causing up to 70% mortality and (iii) antigenic variants. In Australia both classical and variant field strains of IBDV have been identified which are genetically distinct from overseas strains. Australian classical strains are similar to vaccine strains such as 002/73 and V877 both antigenically and by nucleotide sequencing. Australian variants, however, are quite distinct both at the antigenic and genetic level forming a distinct group of viruses that are unrelated to variants isolated in other countries such as the USA.

The ability to differentiate and treat infection caused by IBDV strains is a major concern to the poultry industry worldwide, as effective control of this devastating disease relies on the administration of different vaccine strains. In many countries both accidental incursion of IBDV strains from neighbouring countries and the absence of a test for establishing whether outbreaks in the field are due to vaccine breaks or circulating field strains are also major problems.

Differentiation of IBDV strains is currently largely based upon using either monoclonal antibodies directed against the major neutralising protein of the virus (VP2) or by nucleotide sequencing of the VP2 gene. Monoclonal antibodies generated against the VP2 and VP3 gene product have perhaps played the most significant role in detecting and differentiating IBDV strains and several VP2 and VP3 specific monoclonal antibodies have been developed.

Testing with monoclonal antibodies is generally quicker and significantly cheaper than other prior art technologies, however, monoclonal antibodies are limited in terms of their differentiation. Furthermore, a major drawback of using monoclonal antibodies as immunodiagnostics or immunotherapeutic reagents lies in the cost and time required for production, screening and maintenance of hybridoma cell lines. In addition, an anti-antibody response is often induced when monoclonal antibodies are administered in a heterologous species, thus compromising their effectiveness.

Thus, there is currently a need for improved diagnostic and or therapeutic agents effective against IBDV. In particular there is a need for diagnostics that are capable of differentiating IBDV strains, that might be used to track the incursion of exotic strains of IBDV into a particular country and or for differentiating IBDV strains very similar to vaccine IBDV strains from circulating field strains. In addition, there is a need to differentiate between an immune response induced by IBDV vaccines from that induced by field strains. There is also strong demand for new therapeutics capable of combating this devastating disease.

SUMMARY OF THE INVENTION

The present invention provides at least a recombinant antibody fragment against IBDV. More particularly, the recombinant antibody fragment will have specificity for an IBDV antigenic determinant and comprise a variable region having a heavy chain ($V_H$) region and or a light chain ($V_L$) region.

The subject invention also provides polynucleotides encoding specific recombinant antibody fragments as described herein. In preferred form of the invention it provides nucleic acid molecules encoding $V_H$ or $V_L$ regions or single chain antibody fragments comprising $V_H$ and $V_L$ regions linked together via a linker.

The present invention also provides a process for identifying recombinant antibody fragments, which process comprises the steps:

(i) Amplifying nucleotide sequences comprising $V_H$ and $V_L$ chains from lymphocytes from a host which has been caused to produce antibodies against at least IBDV or an IBDV polypeptide or a fragment thereof;

(ii) Generating a library comprising amplified nucleotide sequences from step (i), which library is capable of being screened to identify $V_H$ and or $V_L$ regions reactive with at least IBDV or an IBDV polypeptide or a fragment thereof; and (iii) Screening said library and selecting at least a recombinant antibody fragment that has an affinity for IBDV or an IBDV polypeptide or a fragment thereof.

Such a method is particularly useful for identifying recombinant IBDV antibodies that may serve as immunodiagnostic and or immunotherapeutic agents that may for example serve as candidate antagonists of IBDV biological activity.

The isolation of recombinant antibodies from the host infected with IBDV has the advantage that a degree of certainty is associated with the immunological specificity of the generated antibodies. When antibodies are produced and amplified in one animal species that is not a natural target (eg a mouse system) different from the animal species that is a natural target of infection (eg a chicken) with a virus, antibody presentation is dependant on the first host species immune system and the way in which antigen is presented in that system. Potentially there are many antigenic determinants that may not be recognised by the first animal species that are recognised by the immune system of the natural target species. The method of the present invention seeks to capitalise on this aspect of antigen presentation in that antibodies produced by the method of the invention are derived from the infected-natural host animal, rather than an artificially infected species, which is not a natural target of a virus. Amplification of the antibodies is then achieved by recombinant molecular biology techniques therein assuring that immunological specificity within the selected antibody population is not diluted or indeed lost as perhaps may happen when foreign (different) animal species are used to produce said antibodies.

Recombinant IBDV antibodies capable of distinguishing IBDV strains can be selected by comparing the observed activity when such antibodies are brought in contact with the stains in the presence of a control system. Using differences in the observed activity it is possible to identify recombinant IBDV antibodies which are either desired for the ability to identify particular IBDV strains or in the alternate case those which are not able to identify these strains.

The invention also provides a method for detecting the presence of IBDV in a sample comprising contacting said sample with a recombinant IBDV antibody which specifically binds to an IBDV antigen, comprising a variable region having a heavy chain region and a light chain region, and determining binding of said antibody to IBDV antigen in said sample as a determination of IBDV infection in said sample.

Further the invention provides therapeutic, pharmaceutical or diagnostic compositions comprising a recombinant antibody fragment according to the invention, in combination with a pharmaceutically acceptable excipient, diluent or carrier.

BRIEF DESCRIPTION OF DRAWINGS

The Figures are described as follows:

FIG. 1: Sequence and restriction sites of the multiple cloning regions of pCANTAB 5E and derived plasmids pCANTAB-Ascl, pCANTAB-Smal and pCANTAB-link

FIG. 3: (FIGS. 3A to I) Nucleotide sequence of the variable regions of the heavy chain (SEQ ID NOS: 1-35) and (FIG. 3J to R) (light chain (SEQ ID NOS 36-77) genes of scFV clones.

FIG. 4: Deduced amino acid sequences of the variable regions of the heavy (FIG. 4A to E) and light chain (FIG. 4F to J) of scFv clones.

FIG. 5: Alignment of the deduced amino acid sequences of CRAbs. Only those amino acids that differ from the consensus sequence are shown, while identical amino acids are shown by dots and the absence of corresponding residues is shown by dashes. Complementarity regions are shown underlined while the linker sequence $(Gly_4Ser)_3$ is shown in bold. CRAb34 and CRAb0 were obtained by cloning of scFv's into pCANTAB 5E while the remaining CRAbs were obtained by sequential cloning of VH and VL genes into pCANTAB-link vector.

FIG. 6: Reactivity of CRAb34 with a panel of IBDV strains in ELISA.

FIG. 11: Partial neutralization of BursvacL vaccine with various CRAbs in 2-week-old specific pathogen-free chickens

DETAILED DESCRIPTION OF THE INVENTION

General

Figure 2:
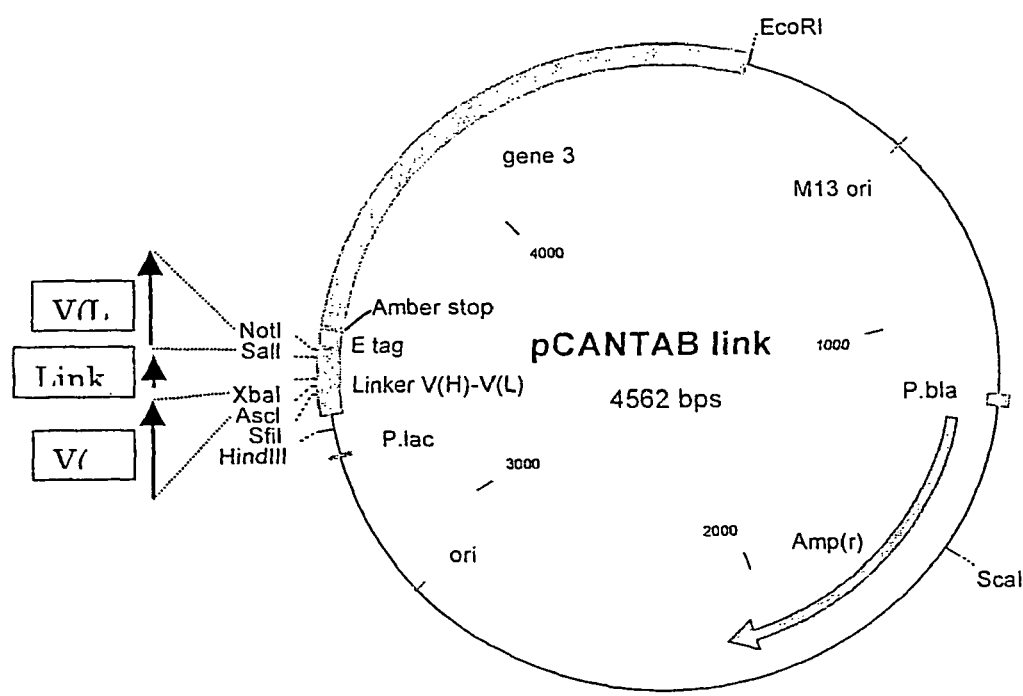
FIG. 2: Plasmid map pCANTAB-link.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively, and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

Sequence identity numbers (SEQ ID NO:) containing nucleotide and amino acid sequence information included in this specification are collected at the end of the description and have been prepared using the programme Patentin Version 3.1. Each nucleotide or amino acid sequence is identified in the sequence listing by the numeric indicator <210> followed by the sequence identifier (e.g. <210>1, <210>2, etc.). The length, type of sequence and source organism for each nucleotide or amino acid sequence are indicated by information provided in the numeric indicator fields <211>, <212> and <213>, respectively. Nucleotide and amino acid sequences referred to in the specification are defined by the information provided in numeric indicator field <400> followed by the sequence identifier (e.g. <400>1, <400>2, etc.).

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

As used herein the term "derived" and "derived from" shall be taken to indicate that a specific integer may be obtained from a particular source albeit not necessarily directly from that source.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Description

The present invention provides novel, recombinant antibody fragments specific for IBDV. The invention also provides methods for the production of these antibody fragments as well as methods for their use in the diagnosis and treatment of IBDV disease.

The term "recombinant antibody fragment" is used herein to denote any antibody fragment produced using recombinant DNA or in vitro protein synthesis techniques, and excludes monoclonal antibodies produced by traditional monoclonal antibody techniques. Preferably, such fragments are initially derived from nucleotide sequences encoding heavy and light chain variable regions produced in B-lymphocytes from a host that has been caused to produce antibodies against at least IBDV or an IBDV polypeptide or a fragment thereof.

The term "antibody" as used herein, unless indicated otherwise, is used broadly to refer to, for example, Fv fragments, single-chain Fv fragments (scFv), Fab' fragments, and F(ab')2 fragments, diabodies, individual $V_L$ chains, individual $V_H$ chains, chimeric fusions between $V_H$ and or $V_L$ chains and other molecules, and the like.

Recombinant antibody fragments including substitutions, deletions and modifications within the scope of the present invention include those antibodies that have binding affinity for at least an IBDV strain. In most instances such antibodies will recognise more than, one IBDV strain, however, where binding is specific to a single IBDV strain that recombinant antibody fragment may provide a means to differentially identify that strain. Preferably, the recombinant antibody fragments are capable of binding one or more of the group selected from: Australian IBDV strain 002/73; vaccine strain V877; classical field strains 06/95, K3, M4, R1, T4, N1/99, N2/99, A-1 or Y-5; variant field strains 01/94, 02/95, 03/95, 04/95 or 08/95; classical overseas strains 52/70 and 1/68; variant strain E and vvIBDV strain CS88.

Recombinant antibody fragments according to the invention may be derived from any host that has been caused to produce antibodies against IBDV or an IBDV polypeptide or fragment thereof. Preferably, that host is of avian origin. Even more preferably the host is a fowl such as for example, chickens, turkeys, guinea fowls, ducks, and geese. In the present disclosure the invention is described in terms of recombinant antibody fragments derived from domestic fowl and in particular chickens. It should be appreciated however that the scope of the disclosure is not so limited and hence the invention may apply to any avian species that succumbs to IBDV.

The isolation of recombinant antibody fragments from domestic fowl has the advantage that the antibody fragments are obtained from a normal host for IBDV. In addition, deriving recombinant antibody fragments from domestic fowls offer technical advantages over antibodies from other mammalian hosts like mice as the variable region genes in domestic fowl are flanked by constant regions and can easily be amplified using techniques such as polymerase chain reaction (PCR), using a single primer set.

IBDV Related Recombinant Antibody Polypeptide Fragments

It should be appreciated that the IBDV related recombinant antibody fragment(s) described herein can take a variety of forms. Preferably the recombinant antibody fragment(s) are Fv fragments, scFv or Fab' fragments that have an affinity for IBDV.

According to the invention the $V_H$ domain and the $V_L$ domain within the recombinant antibody fragment may be linked in a single chain to produce a single chain Fv fragment or bound by one or more covalent bonds such as disulphide bonds. Where the recombinant antibody fragment is prepared as an scFv fragment, the $V_H$ domain and the $V_L$ domain are preferably linked by a short peptide spacer (usually 15-20 amino acids long) that is introduced at the genetic level during the construction of the scFv. Linkage of $V_H$ and $V_L$ regions may be achieved by any method known in the art. For example, a synthetic linker such as a flexible glycine-serine linker may be used. An example of a linker that is illustrated in the Examples herein is $(Gly_4Ser)_3$.

In a highly preferred form of the invention the recombinant antibody fragments comprise: a $V_H$ region selected from the group consisting of SEQ ID NOS:78 to 112, or a homologue of any one of these sequences and or a $V_L$ region selected from the group consisting of SEQ ID NOS:113 to 154, or a homologue of any one of these sequences.

A homologous sequence is taken to include an amino acid sequence which is at least 60, 70, 80 or 90% identical, preferably at least 95 or 98% identical at the amino acid level over at least 20, 50 or 100 amino acids against which that sequence is compared and will possess IBDV related immunological properties. Homology should typically be considered with respect to those regions of the sequence known to be essential for the function of the protein rather than nonessential neighbouring sequences. Thus, for example, homology comparisons are preferably made over $V_H$ and $V_L$ chain regions and more particularly over those regions of the $V_H$ and $V_L$ chains that are essential for antigen binding.

Although homology can also be considered in terms of similarity (i.e. amino acid residues having similar chemical properties/functions), in the context of the present invention it is preferred to express homology in terms of sequence identity. Homology comparisons can be conducted by eye, or more usually, with the aid of readily available sequence comparison programs. These commercially available computer programs can calculate % homology between two or more sequences.

It will be appreciated that any $V_H$ may be linked to any $V_L$ region. By pairing different $V_H$ and $V_L$ regions to produce recombinant antibody fragments it is possible to change the immunological profile of these fragments. Thus, when referring to the sequences exemplified in this application any of SEQ ID NOS:1 to 35 may be linked to any of SEQ ID NOS:36 to 77. Preferably, however, the sequences are linked via a synthetic linker like $(Gly_4Ser)_3$ in the following order:

SEQ ID NO:1 linked to SEQ ID NO:60; [SEQ ID NO:155 (CRAb19)]
SEQ ID NO:1 linked to SEQ ID NO:61; [SEQ ID NO:156 (CRAb 83)]
SEQ ID NO:1 linked to SEQ ID NO:63; [SEQ ID NO:157 (CRAb 03)]
SEQ ID NO:1 linked to SEQ ID NO:64; [SEQ ID NO:158 (CRAb 24)]
SEQ ID NO:1 linked to SEQ ID NO:65; [SEQ ID NO:159 (CRAb 15)]
SEQ ID NO:1 linked to SEQ ID NO:66; [SEQ ID NO:160 (CRAb 05)]
SEQ ID NO:1 linked to SEQ ID NO: 67; [SEQ ID NO:161 (CRAb 33)]
SEQ ID NO:1 linked to SEQ ID NO: 68; [SEQ ID NO:162 (CRAb 96)]
SEQ ID NO:2 linked to SEQ ID NO: 62; [SEQ ID NO:163 (CRAb 34)]
SEQ ID NO:3 linked to SEQ ID NO: 36; [SEQ ID NO:164 (CRAb 18)]
SEQ ID NO:4 linked to SEQ ID NO. 37; [SEQ ID NO:165 (CRAb 37)]
SEQ ID NO:5 linked to SEQ ID NO: 38; [SEQ ID NO:166 (CRAb 32)]
SEQ ID NO:6 linked to SEQ ID NO: 39; [SEQ ID NO:167 (CRAb 66)]

SEQ ID NO:7 linked to SEQ ID NO: 40; [SEQ ID NO:168 (CRAb 04)]
SEQ ID NO:8 linked to SEQ ID NO; 41; [SEQ ID NO:169 (CRAb 62)]
SEQ ID NO:9 linked to SEQ ID NO: 42; [SEQ ID NO:170 (CRAb 45)]
SEQ ID NO:10 linked to SEQ ID NO: 43; [SEQ ID NO:171 (CRAb 149)]
SEQ ID NO:11 linked to SEQ ID NO: 44; [SEQ ID NO:172 (CRAb 154)]
SEQ ID NO:12 linked to SEQ ID NO:45; [SEQ ID NO:173 (CRAb 151)]
SEQ ID NO:13 linked to SEQ ID NO: 46; [SEQ ID NO:174 (CRAb 176)]
SEQ ID NO:14 linked to SEQ ID NO: 47; [SEQ ID NO:175 (CRAb 28)]
SEQ ID NO:15 linked to SEQ ID NO: 48; [SEQ ID NO:176 (CRAb 88)]
SEQ ID NO:16 linked to SEQ ID NO: 49; [SEQ ID NO:177 (CRAb 29)]
SEQ ID NO:17 linked to SEQ ID NO: 50; [SEQ ID NO:178 (CRAb 50)]
SEQ ID NO:18 linked to SEQ ID NO: 51; [SEQ ID NO:179 (CRAb 38)]
SEQ ID NO:19 linked to SEQ ID NO: 52; [SEQ ID NO:180 (CRAb 30)]
SEQ ID NO:20 linked to SEQ ID NO: 53; [SEQ ID NO:181 (CRAb 39)]
SEQ ID NO:21 linked to SEQ ID NO: 54; [SEQ ID NO:182 (CRAb 27)]
SEQ ID NO:22 linked to SEQ ID NO: 55; [SEQ ID NO:183 (CRAb 35)]
SEQ ID NO:23 linked to SEQ ID NO: 56; [SEQ ID NO:184 (CRAb 174)]
SEQ ID NO:24 linked to SEQ ID NO: 57; [SEQ ID NO:185 (CRAb 26)]
SEQ ID NO:25 linked to SEQ ID NO: 58; [SEQ ID NO:186 (CRAb 7)]
SEQ ID NO:26 linked to SEQ ID NO: 59; [SEQ ID NO:187 (CRAb 12)]
SEQ ID NO:27 linked to SEQ ID NO: 69; [SEQ ID NO:188 (CRAb 23)]
SEQ ID NO:28 linked to SEQ ID NO: 70; [SEQ ID NO:189 (CRAb 22)]
SEQ ID NO:29 linked to SEQ ID NO: 71; [SEQ ID NO:190 (CRAb 52)]
SEQ ID NO:30 linked to SEQ ID NO: 72; [SEQ ID NO:191 (CRAb 08)]
SEQ ID NO:31 linked to SEQ ID NO: 73; [SEQ ID NO:192 (CRAb 11)]
SEQ ID NO:32 linked to SEQ ID NO: 74; [SEQ ID NO:193 (CRAb 21)]
SEQ ID NO:33 linked to SEQ ID NO: 75; [SEQ ID NO:194 (CRAb 9)]
SEQ ID NO:34 linked to SEQ ID NO: 76; [SEQ ID NO:195 (CRAb 20)]
SEQ ID NO:35 linked to SEQ ID NO: 77; [SEQ ID NO:196 (CRAb 0)]

In a highly preferred form of the invention the recombinant antibody fragment is selected from the group comprising: SEQ ID NO:155 to SEQ ID NO:196, or is a homologue of any one of these sequences.

It will be appreciated that the amino acid sequences for $V_H$ and $V_L$ regions described herein may also be modified in any manner or form that does not extinguish and more preferably substantially alter the affinity of $V_H$ and $V_L$ regions to an IBDV antigen. Such modifications may be naturally and non-naturally occurring. By way of example, the modifications may include, deletions, additions, substitutions, glycosylations, acetylations, phosphorylations, and the like. Examples of amino acid sequence substitution modifications that may be made to recombinant antibody fragments include: (a) one or more aspartic acid residues is substituted with glutamic acid; (b) one or more isoleucine residues is substituted with leucine; (c) one or more glycine or valine residues is substituted with alanine; (d) one or more arginine residues is substituted with histidine; or (e) one or more tyrosine or phenylalanine residues is substituted with tryptophan.

Recombinant antibody fragments in lacking glycosylation and the regions comprising the binding sites for complement and Fc-receptors, also lack the natural effector function associated with these regions. Several strategies have been developed to reintroduce these natural effector functions into recombinant antibodies, e.g. the generation of bi-specific antibody fragments for recruitment of effector molecules and cells. For example, IBDV related recombinant antibody fragments may be fused with polypeptide sequences expressing different effector functions, like toxins, enzymes, cytokines, reporter genes (for diagnostic and imaging applications) and the like. Such fragments are not only useful for IBDV diagnosis, but find much greater applications in IBDV immunotherapy and gene therapy. For IBDV therapy, an advantage of recombinant antibody fragments is their small size (the size of a scFv is only about 25 kD), facilitating tissue penetration, bio-distribution and blood clearance. However, it has been shown that somewhat larger fragments (50-80 kD) show in some cases even better pharmacokinetics and that di- or multivalent fragments increase the functional affinity and thereby tissue targeting. Recombinant antibody fragments can furthermore be easily used as building blocks for genetic engineering of new effector mechanisms, affinity maturation, and humanisation.

Therefore, according to another embodiment in the invention the recombinant antibody fragments described may be conjugated with, or attached to other antibodies (or parts thereof) such as monoclonal antibodies. These other antibodies may be reactive with other markers (epitopes) characteristic for the disease against which the antibodies of the invention are directed or may have different specificities chosen, for example, to recruit fragments or cells of the animals immune system to the diseased cells. The antibodies of the invention (or parts thereof) may be linked to such antibodies by conventional chemical or by molecular biological methods.

According to a further aspect of the invention there is provided a multivalent monospecific recombinant antibody fragment comprising two, three, four or more single chain antibody fragments or fragments thereof bound to each other by a connecting structure which protein is not a natural immunoglobulin, each of said recombinant antibody, fragments or fragments having a specificity for an IBDV epitope said protein being optionally conjugated with an effector or reporter fragment.

IBDV Related Recombinant Antibody Polynucleotide Sequences

Determination of the amino acid sequence for a recombinant antibody fragment will reveal information about the likely nucleotide sequence encoding that fragment. Using that information the nucleotide sequence for the recombinant fragment may be obtained. Once the nucleotide sequence for a recombinant antibody fragment has been identified its DNA sequences may be synthesised completely or in part using standard oligonucleotide synthesis techniques. Site-directed mutagenesis and polymerase chain reaction (PCR) techniques may be used as appropriate to modify and or amplify such sequences.

Thus, the subject invention provides also polynucleotides encoding specific recombinant antibody fragments as described herein. The subject polypeptides may be encoded by a wide variety of sequences because of the degeneracy of the genetic code. A person of ordinary skill in the art may readily change a given polynucleotide sequence encoding an IBDV specific antibody into a different polynucleotide encoding the same IBDV specific antibody embodiment. The polynucleotide sequence encoding the antibody may be varied to take into account factors affecting expression such as codon frequency, RNA secondary structure, and the like.

According to the invention there is provided a nucleic acid fragment encoding an isolated recombinant antibody fragment or an allelic variant or analogue or fragments thereof, which is capable of specifically binding IBDV. Specifically provided are DNA molecules encoding $V_H$ or $V_L$ regions or single chain antibody fragments comprising $V_H$ and $V_L$ regions linked together via a linker. Most preferably, the nucleotide sequences are selected from the group consisting of: (a) DNA molecules set out in SEQ ID NOS:1 to 77 or fragments thereof; (b) DNA molecules that hybridise to the DNA molecules defined in (a) or hybridisable fragments thereof; and (c) DNA molecules that encode expression for the amino acid sequence encoded by any of the foregoing DNA molecules.

Preferred DNA molecules according to the invention include DNA molecules comprising the sequence set out in SEQ ID NOS:1 to 77 or fragments thereof as well as nucleic acid sequences that are substantially homologous to these sequences.

A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced there from.

An "isolated" or "substantially pure" nucleic acid (e.g., an RNA, DNA or a mixed polymer) is one which is substantially separated from other cellular components which naturally accompany a native animal sequence or protein, e.g., ribosomes, polymerases, many other animal genome sequences and proteins. The term embraces a nucleic acid sequence or protein that has been removed from its naturally occurring environment, and includes recombinant or cloned DNA isolates and chemically synthesized analogues or analogues biologically synthesized by heterologous systems.

A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

Alternatively, substantial homology or (identity) exists when a nucleic acid or fragment thereof will hybridise to another nucleic acid (or a complementary strand thereof) under selective hybridisation conditions, to a strand, or to its complement. Selectivity of hybridisation exists when hybridisation that is substantially more selective than total lack of specificity occurs. Typically, selective hybridisation will occur when there is at least about 55% identity over a stretch of at least about 14 nucleotides, preferably at least about 65%, more preferably at least about 75%, and most preferably at least about 90%. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Thus, polynucleotides of the invention preferably have at least 75%, more preferably at least 85%, more preferably at least 90% homology to the sequences shown in the sequence listings herein. More preferably there is at least 95%, more preferably at least 98%, homology. Nucleotide homology comparisons may be conducted as described below for polypeptides. A preferred sequence comparison program is the GCG Wisconsin Bestfit program. The default scoring matrix has a match value of 10 for each identical nucleotide and −9 for each mismatch. The default gap creation penalty is −50 and the default gap extension penalty is −3 for each nucleotide.

In the context of the present invention, a homologous sequence is taken to include a nucleotide sequence which is at least 60, 70, 80 or 90% identical, preferably at least 95 or 98% identical at the amino acid level over at least 20, 50, 100, 200, or 300 nucleotides with the nucleotides sequences set out in SEQ ID NOS: 1 to 77.

Generally, the shorter the length of the polynucleotide, the greater the homology required to obtain selective hybridisation. Consequently, where a polynucleotide of the invention consists of less than about 30 nucleotides, it is preferred that the % identity is greater than 75%, preferably greater than 90% or 95% compared with the recombinant antibody fragment nucleotide sequences set out in the sequence listings herein. Conversely, where a polynucleotide of the invention consists of, for example, greater than 50 or 100 nucleotides, the % identity compared with the nucleotide sequences set out in the sequence listings herein may be lower, for example greater than 50%, preferably greater than 60 or 75%.

Nucleic acid hybridisation will be affected by such conditions as salt concentration, temperature, or organic solvents, in addition to the base composition, length of the complementary strands, and the number of nucleotide base mismatches between the hybridising nucleic acids, as will be readily appreciated by those skilled in the art. Stringent temperature conditions will generally include temperatures in excess of 30 degrees C., typically in excess of 37 degrees C., and preferably in excess of 45 degrees C. Stringent salt conditions will ordinarily be less than 1000 mM, typically less than 500 mM, and preferably less than 200 mM. However, the combination of parameters is much more important than the measure of any single parameter. An example of stringent hybridisation conditions is 65° C. and 0.1×SSC (1×SSC=0.15 M NaCl, 0.015 M sodium citrate pH 7.0).

The "polynucleotide" of this invention include RNA, cDNA, genomic DNA, synthetic forms, and mixed polymers, both sense and antisense strands, and may be chemically or biochemically modified or may contain non-natural or derivatised nucleotide bases, as will be readily appreciated by those skilled in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of anyone of SEQ ID NOS:1 to 77. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered, e.g., by deletion, substitution or insertion.

A "Recombinant nucleic acid" is a nucleic acid that is not naturally occurring, or which is made by the artificial combination of two otherwise separated segments of sequence. This artificial combination is often accomplished by either chemical syntheses means, or by the artificial manipulation of isolated segments of nucleic acids, by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

cDNA or genomic libraries generated from lymphocytes caused to be infected with IBDV may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source that is abundant in mRNA for the desired proteins. Phage libraries are normally preferred, but other types of libraries may be used. Clones of a library are spread onto plates, transferred to a substrate for screening, denatured and probed for the presence of desired sequences.

Techniques for nucleic acid manipulation are described generally, for example, in Sambrook et al., (1989) "Molecular Cloning: a laboratory, manual". Sambrook, J., Fritsch, E. F. and Maniatis, T. (eds) (1989). Coldspring Harbour Laboratory Press, Coldspring Harbour, N.Y. or Ausubel et al., (1992) "Current Protocols in Molecular Biology". Ausubel, F. M., Brent, R., Kingston, R. E., Moore, D. D., Seidman, J. G., Smith, J. G. and Struhl, K. (1987). John Wiley and Sons, NY. Reagents useful in applying such techniques, such as restriction enzymes and the like, are widely known in the art and commercially available from such vendors as New England BioLabs, Boehringer Mannheim, Amersham, Promega Biotec, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

Portions of the polynucleotide sequence having at least about eight nucleotides, usually at least about 15 nucleotides, and fewer than about 6 kb, usually fewer than about 1.0 kb, from a polynucleotide sequence encoding IBDV related antibody recombinant fragments are preferred as probes. The probes may also be used to determine whether mRNA encoding antibody recombinant fragments is present in a cell or tissue and whether the genomic organisation of the constituent parts of the antibody recombinant fragments are deleted or otherwise damaged.

In further aspects, the invention also includes cloning and expression vectors containing these DNA sequences, host cells transformed with these DNA sequences and processes for producing the heavy or light chains and antibody fragments comprising expressing these DNA sequences in a transformed host cell.

Identification of Recombinant IBDV Antibodies

According to a further aspect the invention provides a process for identifying recombinant antibody fragments, which process comprises the steps:
(i) Amplifying nucleotide sequences comprising $V_H$ and $V_L$ chains from lymphocytes from a host which has been caused to produce antibodies against at least IBDV or an IBDV polypeptide or a fragment thereof;
(ii) Generating a library comprising amplified nucleotide sequences from step (i), which library is capable of being screened to identify $V_H$ and or $V_L$ regions reactive with at least IBDV or an IBDV polypeptide or a fragment thereof; and
(iii) Screening said library and selecting at least a recombinant antibody fragment that has an affinity for IBDV or an IBDV polypeptide or a fragment thereof.

According to this method nucleotide sequences encoding $V_H$ and $V_L$ region fragments are derived from B-lymphocytes from a host, which has been caused to produce antibodies against at least IBDV or an IBDV polypeptide or a fragment thereof. Selecting such nucleotide sequences and using them to generate recombinant antibody fragments generates a level of certainty that the $V_H$ and $V_L$ chains will be specific for the IBDV agent that provoked the antibody production in the B-lymphocyte. Moreover, by selecting B-lymphocytes infected with a particular virus as the source for nucleotide sequences for generating recombinant antibody fragments, problems attendant with differential antigen presentation and hence differential immune responses between different animal species may be ameliorated.

Any system capable of generating a library comprising amplified nucleotide sequences from step (i), which library is capable of being screened to identify $V_H$ and $V_L$ chains reactive with at least IBDV or an IBDV polypeptide or a fragment thereof may be used in the described method. Preferably, phage display technology is used to generate and screen the library such technology.

Phage displayed recombinant antibody libraries offer a number of advantages over other systems in that they allow expression of conformational epitopes and enable the use of strong selection procedures for the isolation of strain specific antibodies. The isolation of IBDV specific recombinant antibody fragments from chickens has the advantage of obtaining antibodies from the normal host. In addition, they offer technical advantages over antibodies from other mammalian hosts like mouse as the V region genes in chickens are flanked by constant regions and can easily be amplified by PCR using a single primer set. Large libraries of diverse antibody combining sites can be expressed in E. coli by bacteriophage and can be easily screened.

Phage display is a technique for the expression or 'display' of a peptide or protein on the surface of a filamentous phage. This is accomplished by the insertion of a gene or gene fragment in a phage surface protein gene. Provided that the reading frame is correct and that the insert does not interfere with the essential functions of the surface protein, the insert will result in a fusion protein on the phage surface. If the peptide is well exposed on the phage surface it will be available to act as a ligand, enzyme, immunogen or otherwise actively participate in a biochemical process. The insertion of random oligonucleotide sequences such as those derived from B-lymphocytes from a host, which has been caused to produce antibodies against at least IBDV or an IBDV polypeptide or a fragment thereof, provides a means of constructing extensive peptide libraries that may be screened to select peptides with specific affinities or activities against IBDV molecules.

Separation of phage particles expressing different peptide inserts in the phage surface protein may be accomplished by any method known in the art. One such method of affinity selection is a method called panning. This strategy allows one to test a myriad of structures for optimal function without detailed information about the relationship between the function and the structure.

Filamentous phage are ideal as in vitro selection vehicles because they have small genomes in which large libraries, consisting of a number of different genes or gene fragments, are easily constructed. The viral particles (virions) are stable to potential elution conditions such as low pH and they accumulate to high titers ($10^{12}$ $ml^{-1}$) so that every clone in a gene library can be well represented. Some commonly used phage particles are M13, fd, and f1. The phage have ten different genes of which the two that have been used in phage display are gene III (gill) and gene VIII (gVIII). Gene III encodes a protein at the proximal end of the phage, protein III (pIII). Protein III is required for infection of *E. coli* and binds to the end of the pili of the bacteria. Gene VIII encodes a major coat protein, protein VIII (pVIII), and is therefore present in approximately 2700 copies in comparison with gene III that is present in 3-5 copies depending on the phage used.

Phage display technology can be performed in two different ways, polyvalent phage display and monovalent phage display. In both methods the insertion is usually done near the amino-terminal end between the amino- and carboxy-terminal domains. In polyvalent phage display, small foreign DNA fragments are inserted into the phage surface protein gene. In this method the peptide is expressed in multiple copies on the phage produced, i.e. the peptide is expressed in all copies of the gene product. In polyvalent display the fusion using pIII cannot have a too large insert since it will affect the infectivity of the phage. Fusion using pVIII is even more limited by the size of the insert, since larger peptides than 6-10 amino acids will probably interfere with the packaging process. For monovalent phage display, the gene fusion is constructed in a phagemid where DNA fragments of varying sizes are inserted in the phage surface protein gene. A phagemid is a plasmid with the intergenic sequence from the phage that is used and the phage origin of replication, but it lacks all other phage genes and can therefore not give rise to new phage. The intergenic sequence contains the packing sequence used for phage construction. The virions are produced after infection of the cells harbouring the phagemid with a helper phage. The helper phage provide for those functions and genes the phagemid lacks and also contains the wild type gene for the surface protein. The helper phage is packaging-deficient, meaning that the intergenic region of the genome is not as efficient as in the phagemid. The phagemid is then transferred into a bacterial host (eg *E. coli*). Selection by antibiotic resistance will result in only bacteria that have acquired the phagemid growing. The number of clones that are required to cover the whole genome is dependent of the size of the gene insert. While the helper phage supplies wild-type protein in large excess, only approximately 10% of the phagemid population will display one copy of the fusion protein. This system removes the problem of a protein fusion affecting the phage packing properties and functions in the case where all of the proteins have an insertion. Insertion of the amber stop codon TAG is commonly interposed between the foreign gene and the gene used for the fusion. The stop codon is suppressed in suitable strains to allow phage production and allows for easy production of soluble protein by transfer to a non-suppressor strain.

According to a highly preferred form of the method described herein the library is generated using a phagemid system. The efficacy of such a system is largely dependant on the phagemid vector selected and used. Numerous phagemid vectors are commercially available: Amersham Pharmacia Biotech, Sweden; Maxim Biotech, USA; Mediators Diagnostika, Austria; Mobitec, Germany; New England Biolabs, USA; Stratagene, USA. Desirably, however, the selected vector enables the direct sequential ligation of heavy and or light chain nucleotide sequences. By using such a vector, a higher diversity of recombinant antibodies may be generated.

A particularly preferred phagemid vector that may be used in the described method is pCANTAB-link. This vector is based on pCANTAB 5E. However, it encodes a polypeptide linker region (Gly4Ser)3 flanked by two multiple cloning regions. PCR fragments for $V_H$ or $V_L$ can be sequentially ligated into unique restriction sites upstream (SfiI, NcoI, AscI, PstI and XbaI) or downstream (SalI, EcoRV and NotI) of the linker. This vector eliminates the inefficient and problematic PCR assembly step, replacing it with sequential ligation of $V_H$ and $V_L$ chains directly into the vector. Using this vector much higher diversities of recombinant antibody scFv libraries can be generated by sequential ligation of $V_H$ and $V_L$ PCR fragments into pCANTAB-link vector than by using pCANTAB 5E. The presence of unique restriction sites between the polypeptide linker and the variable fragments also offers the option for easy downstream modifications of libraries/clones such as convenient shuffling of $V_H$ and $V_L$ fragments or the exchange of different polypeptide linkers (for generation of diabodies etc.). The vector can be used for the construction of scFv libraries of any animal species.

Advantages of the highly efficient pCANTAB-link vector for libraries of high diversity compared with pCANTAB 5E may be summarised as follows:

(i) Compatible with PCANTAB 5E system.

(ii) Option of two different cloning strategies:

(a) either direct sequential ligation of $V_H$ and $V_L$ PCR fragments (b) or ligation of PCR assembly products (used like pCANTAB 5E).

(iii) Contains additional unique restriction enzyme sites for subcloning and screening.

(iv) Contains region for polypeptide linker $(G_4S)_3$ (vector without linker is also available).

(v) Facilitates easy replacement of different polypeptide linkers or shuffling of $V_H$ and $V_L$ chains to generate new combinatorial libraries.

(vi) Can be used to construct scFv libraries of any species.

Therefore in a preferred form of the above method the recombinant IBDV antibody fragment is identified according to the following method:

(i) Lymphocytes are obtained from the spleen of chickens immunised against an infectious bursal disease strain;
(ii) mRNA is extracted from those Lymphocytes and transcribed into cDNA;
(iii) $V_H$ and $V_L$ chain genes are then amplified and purified;
(iv) Purified $V_H$ and $V_L$ chains are then joined together via the use of a synthetic linker to yield scFv fragments;
(v) The scFv fragments are then cloned into an expression vector and transformed into a suitable host;
(vi) With the aid of a helper phage, recombinant phage specific for IBDV are selected by panning against a plate coated with IBDV antigens; and
(vii) Phage specific for IBDV antigens are eluted off and grown up individually.

In an even more preferred form of the invention, steps (iv) and (v) are combined and a pCANTAB-link vector is used as the expression vector. Thus Purified $V_H$ and $V_L$ chains are ligated directly into a pCANTAB-link vector which contains a synthetic linker to yield scFv fragments. The vector is then transformed into a suitable host.

After, the nucleotide sequences of $V_H$ and $V_L$ chains are cloned into the vector a library of recombinant antibody fragments is generated. Techniques for inserting such vectors into cells are conventional, for example, transformation, electroporation, protoplast fusion and transfection are examples of well-known methods. The host cells that may be used for this step in the method may be bacterial (for example *E. coli*), fungi, algae, mammalian cells or any other prokaryote or eukaryotic cell. Desirably the host cell is *E. coli*.

The recombinant antibody fragments of interest can be selected by techniques known to persons skilled in the art. Such techniques include those based on affinity interaction. Standard procedures use either antigens coated directly or indirectly (e.g using streptavidin) onto plastic surfaces (plates or immunotubes) or antigens that are biotinylated and coupled to strepavidin-coated paramagnetic beads. Selections can be carried out with whole cells or even living organisms. Usually, the antigens are incubated with phage display libraries and specifically bound phage are eluted after each round. Desirably, the antibody of interest is detected by the technique of panning, which is known to persons skilled in the art.

Preparation of Recombinant or Chemically Synthesized IBDV Related Recombinant Antibody Nucleic Acids; Vectors, Transformation, Host Cells Once the amino acid constitution for a recombinant antibody fragment is known, that fragment may be reproduced by any means known in the recombinant DNA art. It should be appreciated that one of the significant advantages of using recombinant antibody fragments over traditional antibody preparation techniques is that such antibodies can be produced in large volume using standard protein production techniques.

Any IBDV related recombinant antibody nucleic acid specimen, in purified or non-purified form, can be utilised as the starting nucleic acid or acids for the preparation of recombinant antibody fragment(s).

Functional gene fragments utilised herein may be extracted as mRNA from any tissue sample, such as blood, tissue material (eg B lymphocytes) and the like and converted to cDNA by reverse transcription by a variety of techniques such as that described by Maniatis, et. al. in Molecular Cloning: A Laboratory Manual, Cold Spring Harbor, N.Y., p 280-281, 1982). If the extracted sample has not been purified, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

PCR is one such process that may be used to amplify IBDV related recombinant antibody gene sequences. This technique may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilised. In addition, a DNA-RNA hybrid that contains one strand of each may be utilised. A mixture of nucleic acids may also be employed, or the nucleic acids produced in a previous amplification reaction described herein, using the same or different primers may be so utilised.

The specific nucleic acid sequence to be amplified, i.e., the polymorphic gene sequence, may be a fraction of a larger molecule or can be present initially as a discrete molecule, so that the specific sequence constitutes the entire nucleic acid. It is not necessary that the sequence to be amplified is present initially in a pure form; it may be a minor fraction of a complex mixture, such as contained in whole human DNA.

A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Large amounts of the polynucleotides of the present invention may also be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eucaryotic cell. Usually the polynucleotide constructs will be suitable for replication in a unicellular host, such as yeast or bacteria, but may also be intended for introduction to (with and without integration within the genome) cultured mammalian or plant or other eucaryotic cell lines.

Polynucleotides of the invention may be incorporated into a recombinant replicable vector for introduction into a prokaryotic or eucaryotic host. Such vectors may typically comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, which allow the protein to cross and/or lodge in cell membranes, and thus attain its functional topology, or be secreted from the cell. For example, a recombinant antibody fragment may be expressed with a bacterial leader sequence at the N-terminus capable of driving export of the protein to the periplasmic space. There, the various domains of the recombinant antibody molecules may fold into functionally active proteins.

Such vectors may be prepared by means of standard recombinant techniques well known in the art and discussed, for example, in Sambrook et al., 1989 supra or Ausubel et al. 1992 supra.

An appropriate promoter and other necessary vector sequences will be selected so as to be functional in the host. Examples of workable combinations of cell lines and expression vectors are described in Sambrook et al., 1989 or Ausubel et al., 1992. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 or promoters derived from murine Moloney leukaemia virus, mouse tumour virus, avian sarcoma viruses, adenovirus II, bovine papilloma virus or polyoma. In addition, the construct may be joined to an amplifable gene (e.g., DHFR) so that multiple copies of the gene may be made. For appropriate enhancer and other expression control sequences.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that a) confer resistance to antibiotics or other toxic substances, e.g. ampicillin, neomycin, methotrexate, etc.; b) complement auxotrophic deficiencies, or supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection, or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. The introduction of the polynucleotides into the host cell by any method known in the art, including, inter alia, those described above, will be referred to herein as "transformation." The cells into which have been introduced nucleic acids described above are meant to also include the progeny of such cells.

Thus the present invention provides host cells transformed or transfected with a nucleic acid molecule of the invention. Preferred host cells include bacteria, yeast, mammalian cells, plant cells, insect cells, and human cells in tissue culture. Illustratively, such host cells are selected from the group consisting of E. coli Pseudomonas, Bacillus, Streptomyces, yeast, CHO, R1.1, B-W, L-M, COS 1. COS 7, BSC1, BSC40, BMT10, and Sf9 cells.

Also provided are mammalian cells containing an IBDV antibody polypeptide encoding DNA sequence and modified in vitro to permit higher expression of IBDV related antibody polypeptides by means of a homologous recombinational event.

The general methods for construction of the vector of the invention, transfection of cells to produce the host cell of the invention, culture of cells to produce the antibody of the invention are all conventional molecular biology methods. Likewise, once produced, the recombinant antibody fragments of the invention may be purified by standard procedures of the art, including cross-flow filtration, ammonium sulphate precipitation, affinity column chromatography, gel electrophoresis and the like.

Thus, the present invention also provides methods for preparing an IBDV related antibody polypeptide comprising: (a) culturing a cell as described above under conditions that provide for expression of the IBDV related antibody polypeptide; and (b) recovering the expressed IBDV related antibody polypeptide. This procedure can also be accompanied by the steps of: (c) chromatographing the polypeptide using any suitable means known in the art; and (d) purifying the polypeptide by for example gel filtration.

The present invention also provides for host cells transformed with two or more expression vectors of the invention, the first vector containing an operon encoding a $V_H$ chain derived polypeptide and the second containing an operon encoding a $V_L$ chain derived polypeptide. The two vectors may contain different selectable markers but, with the exception of the $V_H$ and $V_L$ chain coding sequences, are preferably identical. This procedure provides for equal expression of $V_H$ and $V_L$ chain polypeptides. Alternatively, a single vector may be used which encodes both $V_H$ and $V_L$ chain polypeptides. The coding sequences for the $V_H$ and $V_L$ chains may comprise cDNA or genomic DNA or both. In a preferred embodiment of this aspect of the invention at both vectors provide leader sequences capable of directing the expressed proteins out of the cell, most preferably into the periplasm where disulphide bond formations may occur.

Many uses for antibodies, which have been produced using the disclosed methods, are contemplated, including diagnostic and therapeutic uses.

Diagnostic Use and Detection of IBDV

The present invention also provides the above antibody fragments, detectably labeled, as described below, for use in diagnostic methods for in vitro or in vivo detection of IBDV.

(i) IBDV Related Recombinant Antibody Polypeptide Fragments

The recombinant antibody fragments of the present invention may be employed in any known antibody associated assay method. For example, the recombinant antibody fragments of the present invention are useful for immunoassays that detect or quantitate IBDV in a sample. For example they may be employed in competitive binding assays, direct and indirect sandwich assays, or immunoprecipitation assays and immunohistochemistry assays.

An immunoassay for IBDV will typically comprise incubating a biological sample in the presence of a detectably labeled recombinant antibody fragment capable of binding to IBDV and detecting the labeled antibody which is bound in a sample. Various clinical immunoassay procedures are described in Immunoassays for the 80s, A. Voller eds, University Park, 1981.

Thus in an embodiment of the diagnostic uses of IBDV related recombinant antibody fragments, the antibody fragment or a biological sample may be added to nitrocellulose, or other solid support that is capable of immobilizing cells, cell particles or soluble proteins. The support may then be washed with suitable buffers followed by treatment with the detectably labeled recombinant antibody fragment. The solid phase support may then be washed with the buffer a second time to remove unbound antibody fragments. The amount of bound label on said solid support may then be detected by conventional means.

By "solid phase support" or "carrier" is intended any support capable of binding antigen or antibodies. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to IBDV or. Thus, the support configuration may be spherical, as in a bead, or cylindrical, as in the inside surface of a test tube, or the external surface of a rod.

Alternatively, the surface may be flat such as a sheet, test strip, etc. Preferred supports include polystyrene beads. Those skilled in the art will know many other suitable carriers for binding recombinant antibody fragments or antigen, or will be able to ascertain the same by use of routine experimentation.

For diagnostic applications, the recombinant antibody fragment typically will be labelled directly or indirectly with a detectable moiety. The detectable moiety can be any one, which is capable of producing, either directly or indirectly, a detectable signal. Any method known in the art for separately conjugating the antibody to the detectable moiety may be employed, including those methods described by Hunter et al., Nature 144:945 (1962); David et al., Biochemistry 13:1014 (1974); Pain et al., J. Immunol. Meth. 40:219 (1981); and Nygren, J. Histochem. and Cytochem. 30:407 (1982).

The recombinant antibody fragment can be fused to a short immunogenic peptide sequence which is detected by an antibody directed against it.

Enzymes which can be used to detectably label the IBDV-specific antibodies of the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the recombinant antibody fragments, it is possible to detect IBDV through the use of a radioimmunoassay (RIA) (see, for example, Work, T. S., et al., Laboratory Techniques and Biochemisty in Molecular Biology, North Holland Publishing Company, N.Y. (1978). The radioactive isotope can be detected by such means as the use of a gamma counter or a scintillation counter or by autoradiography. Isotopes which are particularly useful for the purpose of the present invention are: $^3$H, $^{14}$C, $^{32}$P, $^{35}$S, $^{125}$I or $^{131}$I and preferably, $^{125}$I.

It is also possible to label the recombinant antibody fragments with a fluorescent compound. When the fluorescent labeled recombinant antibody fragment is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, 2-phthaldehyde and fluorescamine.

The recombinant antibody fragments can also be detectably labeled using fluorescence-emitting metals such as $^{152}$Eu, or others of the lanthanide series. These metals can be attached to the MF-specific antibody using such metal chelating groups as diethylenetriaminepentaacetic acid or ethylenediamine-tetraacetic acid.

The recombinant antibodies also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are isoluminol, theromatic acridinium ester, imidazole, acridinii salt and oxalate ester.

Likewise, a bioluminescent compound may be used to label the recombinant antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the recombinant antibody may be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards.

For the purposes of the present invention, IBDV which is detected by the above assays may be present in a biological sample. Any sample containing IBDV can be used. Preferably, the sample is a tissue extract or homogenate, allantoic fluid, or any biological fluid such as, for example, blood, serum, lymph, urine, inflammatory exudate, cerebrospinal fluid, and the like and fixed tissue (like in formalin fixed and paraffin embedded blocks) and tissue impression smears. However, the invention is not limited to assays using only these samples, it being possible for one of ordinary skill in the art to determine suitable conditions which allow the use of other samples.

In situ detection may be accomplished by removing a histological specimen from a patient, and providing the combination of labeled antibodies of the present invention to such a specimen. The antibody (or fragment) is preferably provided by applying or by overlaying the labeled antibody (or fragment) to a biological sample.

Therefore according to an embodiment of the invention there is provided a method for detecting presence of IBDV in a sample comprising contacting said sample with a recombinant antibody fragment which specifically binds to an IBDV antigen, comprising a $V_H$ region and a $V_L$ region, said $V_H$ region having an amino acid sequence selected from the group consisting of SEQ ID NOS:76 to 112, and said $V_L$ region having an amino acid sequence selected from the group consisting of SEQ ID NOS:113 to 154, and determining binding of said recombinant antibody fragments to IBDV antigen in said sample as a determination of IBDV presence in said sample.

It will be appreciated that by varying the $V_H$ and $V_L$ regions employed in the antibody fragments it is possible to alter the affinity and hence possible use to which said antibodies may be put. For example, SEQ ID NOS:157 to SEQ ID NOS:195 show varying degrees of specificity for IBDV strains. Thus different fragments may be employed in differing diagnostic applications. In particular, SEQ ID NOS:159, 160, 187, 195, 158, 167, 156, 162, 171, 172, 173, 184 and 174 (CRAb's 15, 5, 12, 20, 24, 66, 83, 96, 149, 151, 154, 174 and 176) are reactive with all most all or all IBDV strains tested in the Examples. Such fragments may be employed to identify the presence of IBDV in a sample. Phage antibody like CRAb 20 (SEQ ID NOS:195), that react strongly with denatured IBDV samples may be used as diagnostic reagents on fixed and/or denatured diagnostic samples such as in immunohistochemistry of fixed infected tissue and in protein blotting applications. Further, SEQ ID NOS:192 and 163 (CRAb's 11 & 34) are only reactive with Australian IBDV strains tested in the Examples. Such fragments might be used to differentiate Australian IBDV strains from IBDV strains from closely related countries. Further, SEQ ID NO:176 (CRAb 88) is only reactive with very virulent IBDV strains such as CS88 tested in the Example and such fragments might be used to differentiate very virulent IBDV strains from all other IBDV strains.

The recombinant antibodies, for example such as described in the example herein SEQ ID NO:155 to SEQ ID NO:196 can be packaged into diagnostic kits. Diagnostic kits include the recombinant antibodies which may be labelled; alternatively, the recombinant antibodies may be unlabeled and the ingredients for labelling may be included in the kit. The kit may also contain other suitably packaged reagents and materials needed for the particular antigen or antibody detection, for example, standards, as well as instructions for conducting the test. Recombinant antibody fragments are also useful for the affinity purification of IBDV from recombinant cell culture or natural sources.

(ii) IBDV Related Recombinant Antibody Polynucleotide Fragments

Polynucleotides encoding recombinant antibody fragments may also be used to provide diagnostic analysis. For example, allele specific oligonucleotide primers derived from IBDV related recombinant antibody gene sequences, particular those gene sequences encoding IBDV neutralising recombinant antibodies described herein may be useful in determining whether an animal is at risk of suffering from an IBDV ailment. Alternatively by detecting changes in the transcription of and or translation of polynucleotide sequences described herein it will be possible to identify whether a particular host is suffering from a particular IBDV ailment. Therefore through the use of such a procedure, it is possible to determine not only the presence of IBDV but also the distribution of IBDV in the examined tissue.

According to one detection system recombinant antibody polynucleotides may be identified using PCR related technologies. Many different PCR related technologies suitable for such use are known in the field. Such methodologies are broadly described in Ausubel, F., Brent, R., Kingston, R. E., Moore, D. D., Seidman, J. G., Smith, J. A., Struhl, K. *Current protocols in molecular biology*. Greene Publishing Associates/Wiley Intersciences, New York and are incorporated herein by reference.

Primers used in any diagnostic assays derived from the present invention should be of sufficient length and appropriate sequence to provide initiation of polymerisation. Environmental conditions conducive to synthesis include the presence of nucleoside triphosphates and an agent for polymerisation, such as DNA polymerase, and a suitable temperature and pH.

Primers are preferably single stranded for maximum efficiency in amplification, but may be double stranded. If double stranded, primers may be first treated to separate the strands before being used to prepare extension products. Primers should be sufficiently long to prime the synthesis of extension products in the presence of the inducing agent for polymerisation. The exact length of a primer will depend on many factors, including temperature, buffer, and nucleotide composition. Oligonucleotide primers will typically contain 12-20 or more nucleotides, although they may contain fewer nucleotides.

The deoxyribonucleotide triphosphates dATP, dCTP, dGTP and dTTP are added to the synthesis mixture, either separately or together with the primers, in adequate amounts and the resulting solution is heated to about 90-100° C. from about 1 to 10 minutes, preferably from 1 to 4 minutes. After this heating period, the solution is allowed to cool, which is preferable for, the primer hybridisation.

To the cooled mixture is added an appropriate agent for effecting the primer extension reaction (called herein "agent for polymerisation"), and the reaction is allowed to occur under conditions known in the art. The agent for polymerisation may also be added together with the other reagents if it is heat stable. This synthesis (or amplification) reaction may occur at room temperature up to a temperature above which the agent for polymerisation no longer functions. Thus, for example, if DNA polymerase is used as the agent, the temperature is generally no greater than about 40° C. Most conveniently the reaction occurs at room temperature.

Some other useful diagnostic techniques for detecting the presence of particular fragments and or mutations to the fragment genes that encode recombinant antibody fragments of particular interest include, but are not limited to: 1) allele-specific PCR; 2) single stranded conformation analysis (SSCA); 3) denaturing gradient gel electrophoresis (DGGE); 4) RNase protection assays; 5) the use of proteins which recognize nucleotide mismatches, such as the *E. coli* mutS protein; 6) allele-specific oligonucleotides (ASOs); and 7) fluorescent in situ hybridisation (FISH). Other approaches based on the detection of mismatches between the two complementary DNA strands include clamped denaturing gel electrophoresis (CDGE), heteroduplex analysis (HA) and chemical mismatch cleavage (CMC).

In addition to the above methods recombinant antibody fragment genes and mutants thereof may be detected using conventional probe technology. Using the disclosed portions of the isolated IBDV related recombinant antibody polynucleotide fragments as a basis oligomers of approximately 8 nucleotides or more can be prepared, either by excision or synthetically, which hybridise with the IBDV related recombinant antibody polynucleotides.

The probes for IBDV related recombinant antibody polynucleotides (natural or derived) are a preferably of a length which allows the detection of these unique sequences. While 6-8 nucleotides may be a workable length, sequences of 10-12 nucleotides are preferred, and about 20 nucleotides would be optimal. Preferably, these sequences will derive from regions which lack heterogeneity. These probes can be prepared using routine methods, including automated oligonucleotide synthetic methods.

For use as probes, complete complementarity is desirable, though it may be unnecessary as the length of the fragment is increased. For use of such probes as diagnostics, the biological sample to be analysed is treated, if desired, to extract the nucleic acids contained therein. The resulting nucleic acid from the sample may be subjected to gel electrophoresis or other size separation techniques; alternatively, the nucleic acid sample may be dot blotted without size separation.

When probes are used to detect the presence of the target sequences, the biological sample to be analysed, such as tissue homogenate, may be treated, if desired, to extract the nucleic acids. The sample nucleic acid may be prepared in various ways to facilitate detection of the target sequence; e.g. denaturation, restriction digestion, electrophoresis or dot blotting. The targeted region of the sample nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Sample nucleic acid and probe are incubated under conditions that promote stable hybrid formation of the target sequence in the probe with the putative targeted sequence in the sample. The region of the probes that is used to bind to the sample can be made completely complementary to the targeted region. Therefore, high stringency conditions are desirable in order to prevent false positives. However, conditions of high stringency may be used only if the probes are complementary to regions of the chromosome that are unique in the genome. The stringency of hybridisation is determined by a number of factors during hybridisation and during the washing procedure, including temperature, ionic strength, base composition, probe length, and concentration of formamide. Under certain circumstances, the formation of higher order hybrids, such as triplexes, quadraplexes, etc., may be desired to provide the means of detecting target sequences.

Detection, if any, of the resulting hybrid is usually accomplished by the use of labelled probes. Alternatively, the probe may be unlabeled, but may be detectable by specific binding with a ligand that is labelled, either directly or indirectly. Suitable labels, and methods for labelling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labelled moiety.

Two detection methodologies that are particularly effective, work on the principle that a small ligand (such as digoxigenin, biotin, or the like) is attached to a nucleic acid probe capable of specifically binding IBDV related antibody polynucleotides. The small ligand is then detected. In one example, the small ligand attached to the nucleic acid probe might be specifically recognized by an antibody-enzyme conjugate. For example, digoxigenin may be attached to the nucleic acid probe. Hybridisation is then detected by an antibody-alkaline phosphatase conjugate that turns over a chemiluminescent substrate. In a second example, the small ligand may be recognized by a second ligand-enzyme conjugate that is capable of specifically complexing to the first ligand. A well-known example is the biotin-avidin type of interactions.

It is also contemplated within the scope of this invention that the nucleic acid probe assays of this invention will employ a cocktail of nucleic acid probes capable of detecting IBDV related antibody polynucleotides. Thus, in one example to detect the presence of IBDV related antibody polynucleotides in a cell sample, more than one probe complementary to IBDV related antibody polynucleotides is employed and in particular the number of different probes is alternatively 2, 3, or 5 different nucleic acid probe sequences. In another example, to detect the presence of mutations in the IBDV related antibody polynucleotides gene sequence in an animal, more than one probe complementary to IBDV related antibody polynucleotides is employed where the cocktail includes probes capable of binding to an allele-specific mutation identified in populations of animals with alterations in IBDV related antibody polynucleotides. In this embodiment, any number of probes can be used, and will preferably include probes corresponding to the major gene mutations identified as predisposing an animal to the IBDV infection.

In a highly preferred embodiment, screening techniques based on hybridisation to probes, particularly a plurality of probes that correspond to allele-specific mutations use probes immobilized to solid substrates as described above, for example in the form of DNA arrays on silicon substrates (DNA chips).

The probes or primers described herein can be packaged into diagnostic kits. Diagnostic kits include the probe DNA, which may be labelled; alternatively, the probe DNA may be unlabeled and the ingredients for labelling may be included in the kit. The kit may also contain other suitably packaged reagents and materials needed for the particular hybridisation protocol, for example, standards, as well as instructions for conducting the test.

Therapeutic Use

The present invention also provides therapeutic, pharmaceutical or prophylactic compositions, which may take any suitable form, for administration to an animal to treat that animal against IBDV related ailments. It also provides methods for the administration of the antibodies fragments, either labelled or unlabelled, to an animal.

According to the invention the therapeutic, pharmaceutical or prophylactic composition will preferably comprise at least a recombinant antibody fragment as described herein and a pharmaceutically acceptable carrier. While any of the described fragments that have a binding affinity for IBDV or a IBDV polypeptide or fragment thereof may be used in the compositions, preferably the fragment will possess a property which facilitates inhibition or neutralization of IBDV. Most preferably the fragment will possess the capacity to neutralise virus infection. As an example of a highly preferred form of the invention the fragment is identified by SEQ ID NOS:157, 160, 191, 194, 192, 159, 195, 189, 188, 158, 161, 163, 190, 156, 162, 172 and 184 (CRAbs 3, 5, 8, 9, 11, 15, 20, 22, 23, 24, 33, 34, 52, 83, 96, 154 and 174) each of which display an inhibition or neutralisation ability for IBDV infection.

Where the recombinant antibody fragment(s) is to be administered to a an animal it is preferably in a form suitable for administration e.g. by injection or infusion, for example by bolus injection or continuous infusion. Where the product is for injection or infusion, it may take the form of a suspension, solution or emulsion in an oily or aqueous vehicle and it may contain adjuvants and or formulatory agents such as acceptable carriers, excipients or stabilizers.

The term "adjuvant" refers to a compound or mixture that enhances the immune response to an antigen. An adjuvant can serve as a tissue depot that slowly releases the immunogen and also as a lymphoid system activator that nonspecifically enhances the immune response [Hood et al., in Immunology, p. 384, Second Ed., Benjamin/Cummings, Menlo Park, Calif. (1984)].

Acceptable carriers, excipients or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA, sugar alcohols such as mannitol or sorbitol;

salt-forming counterions such as sodium; and/or nonionic surfactants such as Tween, Pluronics or polyethylene glycol (PEG).

Therapeutic formulations of the recombinant antibody fragments may be prepared for by mixing the recombinant antibody fragments having the desired degree of purity with optional physiologically acceptable carriers, excipients, or stabilizers (Remington's Pharmaceutical Sciences, 16th edition, Osol, A., Ed., [1980]), in the form of lyophilised cake or aqueous solutions.

The recombinant antibody fragments may also be administered either as individual therapeutic agents or in combination with other therapeutic agents. For example the recombinant antibody fragments of this invention my be utilized in combination with other monoclonal antibodies or other antibody fragments and regions or with lymphokines or hemopoietic growth factors, etc., which serve to increase the number or activity of effector cells which interact with the antibodies.

An example of therapeutic application of recombinant antibodies is when the recombinant antibody is complexed with either live vaccine, or virus. Such CRAb.IBDV complex for example can be given to chickens (or any other host) as an alternative vaccination approach by variety of means. Recombinant antibodies can also be complexed with an antigen such a peptide or protein or a whole inactivated virus, or other biologically active molecules. Such CRAb.antigen complex for example can be administered to animals to induce higher immune responses; or for delivery to a particular site to achieve a variable biological effect.

The fragments may also be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, supra.

The fragments to be used for in vivo administration must be sterile. This is readily accomplished by filtration through sterile filtration membranes, prior to or following lyophilization and reconstitution. The fragments ordinarily will be stored in lyophilized form or in solution.

Therapeutic fragment compositions generally are placed into a container having a sterile access port, for example, an intravenous solution bag or vial having a stopper pierce-able by a hypodermic injection needle.

The route of fragment administration will accord with known methods, e.g., injection or infusion by intravenous, intraperitoneal, intracerebral, intramuscular, intraocular, intraarterial, or intralesional routes, or by sustained release systems as noted below. The fragments may also be administered continuously by infusion or by bolus injection.

Suitable examples of sustained-release preparations include semi-permeable matrices of solid hydrophobic polymers containing the protein, which matrices are in the form of shaped articles, e.g., films, or microcapsules. Examples of sustained-release matrices include polyesters, hydrogels [e.g., poly(2-hydroxyethyl-methacrylate) as described by Langer et al., J. Biomed. Mater. Res. 15:167-277 (1981) and Langer, Chem. Tech. 12:98-105 (1982) or poly(vinylalcohol)], polylactides (U.S. Pat. No. 3,773,919, EP 58,481), copolymers of L-glutamic acid and gamma ethyl-L-glutamate (Sidman et al., Biopolymers 22:547-556 [1983]), non-degradable ethylene-vinyl acetate (Langer et al., supra), degradable lactic acid-glycolic acid copolymers such as the LUPRON DEPOT.TM. (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for antibody stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release fragment compositions also include liposomally entrapped fragments. Liposomes containing the antibody are prepared by methods known per se: DE 3,218, 121; Epstein et al., Proc. Natl. Acad. Sci. USA 82:3688-3692 (1985); Hwang et al., Proc. Nat. Acad. Sci. USA 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal antibody therapy.

An effective amount of antibody to be employed therapeutically will depend, for example, upon the therapeutic objectives, the route of administration, and the condition of the animal. Accordingly, it will be necessary for the therapist to titer the dosage and modify the route of administration as required to obtain the optimal therapeutic effect. A typical daily dosage might range from about 1 mg/kg to up to 10 mg/kg or more, depending on the factors mentioned above. Typically, the clinician will administer fragments until a dosage is reached that achieves the desired effect. The progress of this therapy is easily monitored by conventional assays.

The present invention further provides the use of a polypeptide or polynucleotide of the invention, which polypeptide or polynucleotide is, or encode, biologically active in gene therapy. Thus the invention provides a method of treating a IBDV disease which method comprises administering to said cells a functional recombinant antibody polypeptide or polynucleotide encoding said polypeptide fragment to suppress IBDV proliferation in a host.

Thus a recombinant antibody fragment polynucleotide sequence may be introduced into the cell or host (or live animal) in a vector or as naked DNA such that the polynucleotide sequence remains extrachromosomal. In such a situation, the polynucleotide sequence will be expressed by the cell from the extrachromosomal location. If a polynucleotide sequence is introduced and expressed in a cell carrying a mutant IBDV related antibody encoding polynucleotide sequence, the polynucleotide sequence should encode an IBDV related antibody protein that is capable of disturbing IBDV proliferation. More preferred is the situation where the wild-type polynucleotide sequence is introduced into the mutant cell in such a way that it recombines with the endogenous mutant polynucleotide sequence present in the cell. Such recombination requires a double recombination event that results in the correction of the polynucleotide sequence mutation.

Vectors for introduction of genes both for recombination and for extrachromosomal maintenance are known in the art, and any suitable vector may be used. However, replication-incompetent retroviral vectors have proved safe and effective in recent trials and most of the approved human gene therapy trials to date rely on retroviral vectors. Thus it is preferred to use retroviral vectors, such as lentiviral vectors, comprising a polynucleotide of the invention and capable of expressing a polypeptide of the invention. Other viral vector systems include adenoviral vectors and herpes virus vectors.

Methods for introducing DNA into cells such as electroporation, calcium phosphate co-precipitation and viral transduction are known in the art, and the choice of method is within the competence of the person skilled in the art. A further gene transfer technique that has been approved by the FDA is the transfer of plasmid DNA in liposomes. Suitable liposome compositions include Lipofectin™.

Gene therapy would be carried out according to generally accepted methods. Cells from an animal would be first analysed by the diagnostic methods described above, to ascertain the production of IBDV related recombinant antibody fragment in a host. A virus or plasmid vector (see further details below), containing a copy of an IBDV related recombinant antibody fragment polynucleotide sequence linked to expression control elements and capable of replicating inside preferably a lymphocyte, is prepared. Suitable vectors are known, such as disclosed in U.S. Pat. No. 5,252,479 and PCT published application WO 93/07282. The vector is then injected into the patient, either locally or systemically. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, e.g., SV40, adenovirus, vaccinia virus, adeno-associated virus, herpesviruses including HSV and EBV, and retroviruses of avian, murine, and human origin. Most gene therapy protocols have been based on disabled murine retroviruses.

Nonviral gene transfer methods known in the art include chemical techniques such as calcium phosphate co-precipitation; mechanical techniques, for example microinjection; membrane fusion-mediated transfer via liposomes; and direct DNA uptake and receptor-mediated DNA transfer. Viral-mediated gene transfer can be combined with direct in vivo gene transfer using liposome delivery, allowing one to specifically direct the viral vectors to the cells of interest Alternatively, the retroviral vector producer cell line can be injected into the lymphocytes. Injection of producer cells would then provide a continuous source of vector particles.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalisation, and degradation of the endosome before the coupled DNA is damaged.

Liposome/DNA complexes have been shown to be capable of mediating direct in vivo gene transfer. While in standard liposome preparations the gene transfer process is non-specific, localised in vivo uptake and expression have been reported in some tumour deposits, for example, following direct in situ administration.

Best Mode(s) for Carrying Out the Invention

Further features of the present invention are more fully described in the following non-limiting Figures, Tables and Example. It is to be understood, however, that this description is included solely for the purposes of exemplifying the present invention. It should not be understood in any way as a restriction on the broad description of the invention as set out above.

EXAMPLE

Methods of molecular biology that are not explicitly described in the following examples are reported in the literature and are known by those skilled in the art.

General texts that described conventional molecular biology, microbiology, and recombinant DNA techniques within the skill of the art, included, for example: Sambrook et al., *Molecular Cloning: A Laboratory Manual*, Second Edition, Cold Spring Harbor Laboratory Press, Cold Spring Harbor, N.Y. (1989); Glover ed., *DNA Cloning: A Practical Approach*, Volumes I and II, MRL Press, Ltd., Oxford, U.K. (1985); and Ausubel, F., Brent, R., Kingston, R. E., Moore, D. D., Seidman, J. G., Smith, J. A., Struhl, K. Current protocols in molecular biology. Greene Publishing Associates/Wiley Interscience, New York. McCafferty, J., Hoogenboom, H. R. and Chiswell, D. J. (eds.), Antibody engineering, a practical approach (1996), Oxford University Press.

Virus Strains

Australian IBDV strain 002/73 described by Firth (1974), *Australian Veterinary Journal* 50; 128-130, and vvIBDV strain CS88 [Brown, M.D., et al (1994), *J. Gen Virol.* 75, 675-680)] were used for hyper-immunization of chickens and for ELISA. Additional Australian IBDV strains used for ELISA included vaccine strain V877, nine classical field strains (06195, K3, M4, R1, T4, A-1, Y-5, N1/99, N2/99) and variant field strains (H-1, 01/94, 02/95, 03/95, 04/95 and 08/95) [Sapats and Ignjatovic (2000) *Archives of Virology* 145; 773-785; Ignjatovic and Sapats; submitted for publication]. Overseas strains used included classical strains 52/70, 1/68, DV86 AND APHIS; variant strains E, A, GLS AND Ga, and very virulent strains CS88, DV8, UK661, VB849, 99006, 89163, 91168, 94432, Tsik94, Indo1, Indo6 and Indo10 [Bayliss, C. D. et al (1990) *J. Gen. Virol.* 71, 1303-1312; Heine, H. G., et al. (1991). *J. Gen. Virol* 72, 1835-1843; Eterradossi et al, (1997) *Arch Virol* 142, 255-270; Parede et al, submitted for publication].

Immunisation of Chickens

Four three-week-old specific pathogen free (SPF) chickens were immunized with Australian vaccine strain 002/73 or vvIBDV strain CS88, as previously described [Sapats and Ignjatovic, (2000) *Archives of Virology* 145; 773-785]. Chickens were boosted two weeks later by intramuscular injection with 0.5 ml of inactivated preparation of 002/73 or CS88 (diluted 1/10 using PBS and emulsified with an equal volume of Freunds Incomplete Adjuvant). Four weeks post secondary immunization, chickens were euthanased and spleens removed for purification of lymphocytes. Titres of immune sera were determined by ELISA.

Preparation of mRNA and cDNA

Spleens from immunized chickens (ELISA antibody titres≧200,000) were minced through a stainless steel mesh screen with cold PBS and layered onto an equal volume of Histopaque (Sigma). White blood cells were separated by centrifugation for 20 minutes at 700×g and mRNA extracted from $2.4\times10^9$ cells using QuickPrep mRNA Purification kit (Pharmacia).

Approximately 8 μg of mRNA was used to produce randomly primed cDNA (total volume 100 μl) using a cDNA synthesis kit (Boehringer Mannheim).

PCR Amplification of Heavy and Light Chain Variable Domain Genes

PCR reactions were set up in a total volume of 100 μl containing 5 μl of cDNA, 10 μl of 10×Pfu buffer (Stratagene), 1 μl dNTPs (25 mM each), 2 μl (6 ng) of each oligonucleotide: HF & HR for the heavy chain variable region (VH) or LF & LR for the light chain variable region (VL) (Table 1). After chilling the tubes on ice, 2 μl of cloned PFU was added (Stratagene) and reactions were cycled 30 times for 45 sec at 94° C., 45 sec at 50° C. and 2 min at 72° C. In the final cycle, the extension time at 72° C. was increased to 10 min. Amplifications were repeated five times each and the final VH and VL products were pooled respectively. VL and VH products of approximately 350 bp and 390 bp were gel purified using a gel extraction kit (Qiagen).

TABLE 1

Sequences of oligonucleotides used for construction of libraries and improved phagmid vectors. Restriction enzyme sites used for cloning are shown underlined.

| Primer | Nucleotide Sequence (5' to 3') |
|---|---|
| HF | GCCGTGACGTTGGAC |
| HR | GAACCGCCTCCACCGGAGGAGACGATGACTTCGG* |
| LF | CGGTGGCGGATCGGCGCTGACTCAGCC |
| LR | ACCTAGGACGGTCAGGG* |
| Link1 | GGTGGAGGCGGTTCAGGCGGAGGTGGCTCT |
| Link2 | CGATCCGCCACCGCCAGAGCCACCTCCGCCTGA* |
| HF-Sfi | ATGTCTAT<u>GGCCCAGCCGGCC</u>GTGACGTTGGACG |
| LR-Not | AGTTACTGGA<u>GCGGCCGC</u>ACCTAGGACGGTCAGGG* |
| LF-Sal | GGCGGTGGCGG<u>GTCGAC</u>AGCGCTGACTCAGCCGTCC TCG |
| HR-Xba | GAACCGCCTCCACCA<u>TCTAGA</u>GAGGAGACGATGACTTCGG* |
| HF-Asc | TTAGCTG<u>GGCGCGCC</u>GTGACGTTGGACGAGTC |
| B94 | CGGCCATGGGGCGCGCCGTCTAGAGCTAAGATATCGC |
| B95 | GGCCGCGATATCTTAGCTCTAGACGGCGCGCCCCATGGCC GGCT* |
| B99 | CGCGCCACTGCAGCTCTAGATCCCGGGTCGACAGATATCAGTGC |
| B100 | GGCCGCACTGATATCTGTCGACCCGGGATCTAGAGCTGCA GTGG* |
| B107 | TAACTAATTCTAGATGGTGGAGGCGGTTCAGGCGGAGGTG GCTCT |
| B108 | TATAGATTATGTCGACCCGCCACCGCCAGAGCCACCTCCGCCT* |
| Seq 1 | GGTTCAGGCGGAGGTGGCTCTGG |
| Seq 2 | AGAGCCACCTCCGCCTGAACC* |

PCR Assembly of Single Chain Fv (scFv) Genes into PCANTAB 5E Vector

Purified VH and VL chains were connected via a synthetic linker (Gly$_4$Ser)$_3$ using overlap extension PCR. Purified VH and VL (100 ng each) were used in PCR as described above containing 2 μl (20 ng) of each linker primer, Link1 & Link2 (Table 1). After 7 rounds of amplification (94° C. for 1 min, 55° C. for 1 min and 72° C. for 2 min), 2 μl (200 ng) of each primer HF-Sfi and LR-Not were added (Table 1) and an additional 24 cycles was performed. Approximately 500 ng of the 750 bp scFv overlap extension product was gel purified and digested sequentially with SfiI and NotI according to the manufacturers instructions (NEB). The SfiI/NotI digested scFvs were further purified using a PCR purification kit (Qiagen).

Approximately 300 ng of the digested scFv fragments were ligated with 500 ng of SfiI/NotI digested pCANTAB 5E vector (Pharmacia) in a total volume 100 μl using the Rapid DNA Ligation Kit (Boehringer Mannheim). Contaminating salts were removed from the ligated DNA using the Rapid PCR purification kit (Boehringer Mannheim). DNA was electroporated into electrocompetent E. coli TG1 cells with a transformation effeciency of approximately $1 \times 10^9$/μg pUC19 DNA. An aliquot was taken to titrate the library size on SOB plates containing 100 μg/ml ampicillin and 2% glucose (SOB-AG) (Sambrook et al., Molecular Cloning: A Laboratoty Manual, Second Edition, Cold Spring Harbor Laboratory Press, Cold Spring Harbor, N.Y. (1989)). The remaining culture was plated out onto SOBAG plates and incubated overnight at 30° C. The resulting lawn of bacterial cells were scraped into 20 ml LB and a 1 ml aliquot diluted with 9 ml 2xYT containing 50 μg/ml ampicillin and 2% (w/v) glucose (2xYT-AG) (Sambrook et al., Molecular Cloning: A Laboratory Manual, Second Edition, Cold Spring Harbor Laboratory Press, Cold Spring Harbor, N.Y. (1989)) and infected with $6 \times 10^{10}$ pfu of M13KO7. After 2 hrs of shaking at 37° C. the cells were collected by centrifugation and resuspended in 10 ml 2xYT containing 100 μg/ml ampicillin and 50 μg/ml kanamycin. The culture was incubated overnight at 37° C. with shaking at 250 rpm. Cells were pelleted at 1400 g for 15 min and the supernatant, containing phage, was filtered through a 0.45 μm filter. Phage particles were concentrated from the supernatant by PEG precipitation (Griffiths et al., 1993, EMBO J. 12, 775-734). The concentration of infectious phage particles was determined by infecting log phase E. coli strain TG1 with serially diluted phage, incubating at 37° C. for 30 min and plating on SOB-AG plates.

Figure 6:
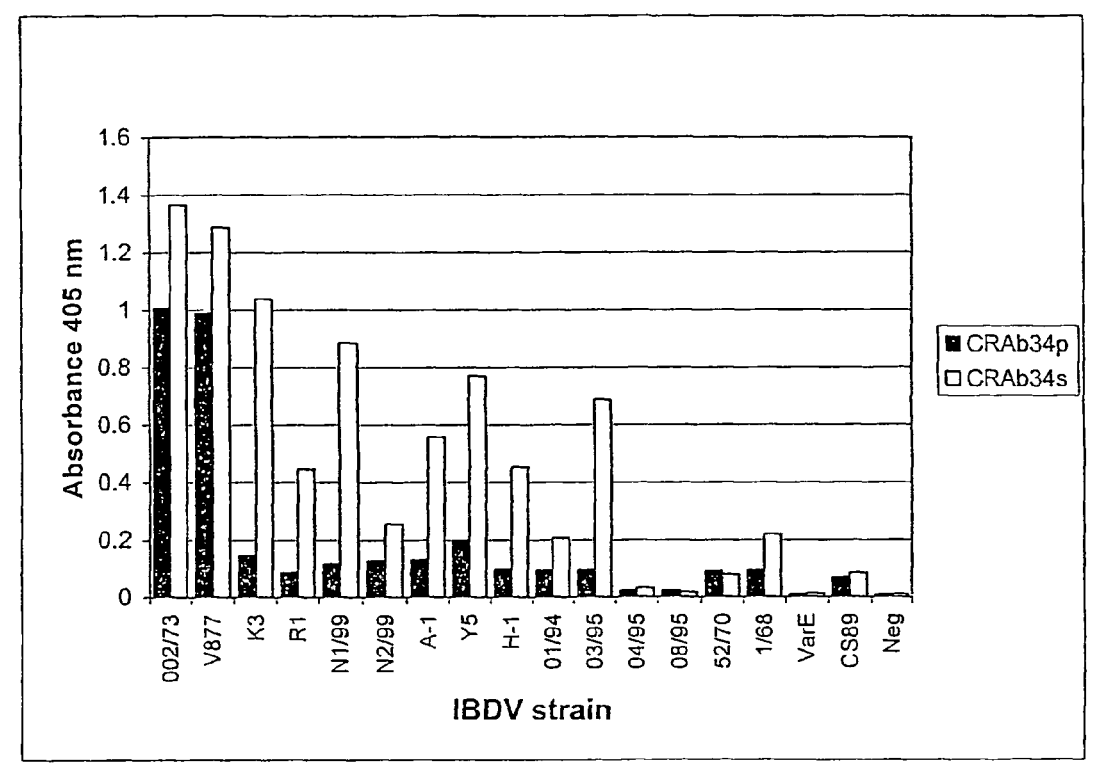
Figure 7:
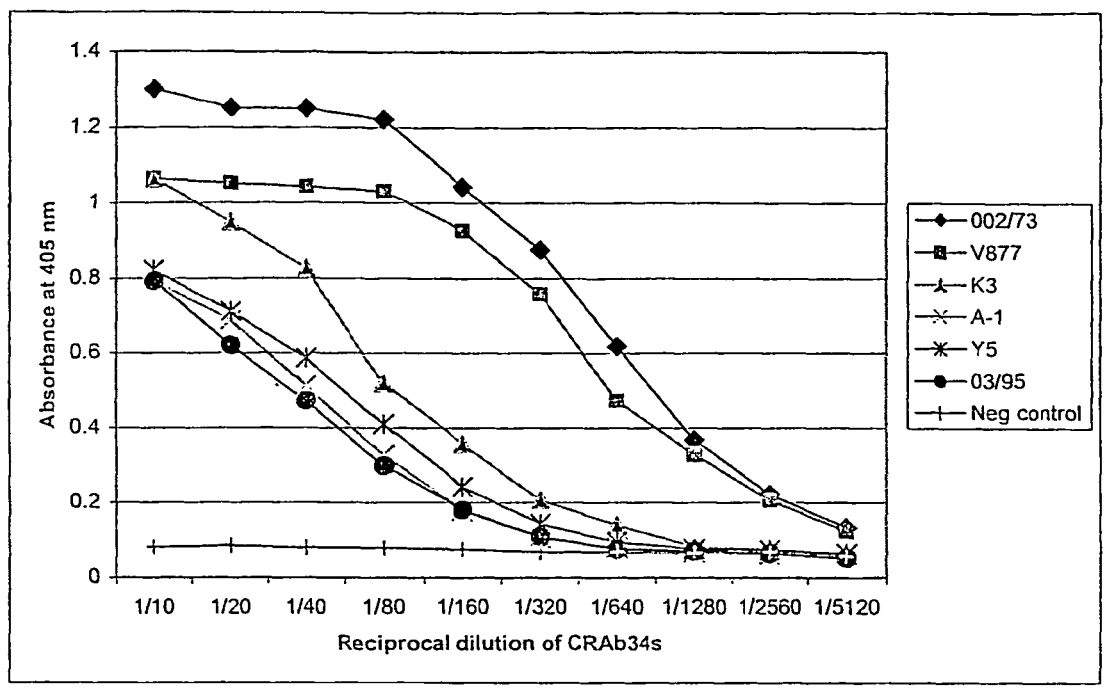
FIG. 7: Titration of CRAb34 soluble antibody against Australian IBDV strains. Various doses of soluble CRAb 34 were titrated against fixed concentrations of viral antigen coated on the microtitre plate.

Although high yields of chicken immunoglobulin $V_H$ and $V_L$ fragments were obtained by PCR amplification from spleen derived cDNA, the subsequent assembly of $V_H$ and $V_L$ into scFv fragments was highly inefficient, producing libraries containing only $1.5 \times 10^5$ clones. These libraries resulted in the identification of one unique CRAb (CRAb34) using the 002/73 library (FIGS. 6, 7). To improve upon the inefficient assembly and cloning steps, we developed a new vector that enabled the direct sequential ligation of $V_H$ and $V_L$ PCR fragments into a vector that already encoded a flexible linker region $(Gly_4Ser)_3$.

Construction of Phagemid Vectors for High Diversity scFv Libraries

The pCANTAB 5E vector was modified in order to acquire additional restriction enzyme sites for direct subcloning of individual $V_H$ and $V_L$ fragments, resulting in 3 different modifications (FIGS. 1, 2). Unique restriction sites (NcoI, AscI, XbaI and EcoRV) were inserted between the SfiI and NotI sites of the pCANTAB 5E vector by ligation of two partially overlapping oligonucleotides (B94 and B95) (Table 1). The resulting vector was named pCANTAB-AscI (FIG. 1). Two partially overlapping oligonucleotides (B99 and B100) (Table 1) were then inserted between the AscI and NotI sites of pCANTAB-AscI to introduce additional unique SmaI and PstI restriction enzyme sites. The resulting vector was named pCANTAB-SmaI (FIG. 1). An oligonucleotide encoding the polypeptide linker $(Gly_4Ser)_3$ was constructed by annealing two overlapping oligonucleotides (B107 and B108) (Table 1) and filling in with Klenow polymerase. The resulting linker fragment was digested with XbaI and SalI to generate the appropriate overhanging ends, and inserted between the XbaI and SalI restriction sites of pCANTAB-SmaI, yielding the phagemid pCANTAB-link (FIG. 1).

All modifications left the SfiI and NotI restriction sites and the reading frame of the parent vector pCANTAB 5E intact. The first modification, pCANTAB-AscI, introduced restriction sites AscI, NcoI, XbaI and EcoRV that could be used for subcloning of inserts. The second modification produced pCANTAB-SmaI, which contains additional unique SmaI and PstI restriction sites. The third vector, pCANTAB-link, encodes a flexible linker region $(Gly_4Ser)_3$, which allows construction of functional scFv antibodies by sequential insertion of $V_H$ and $V_L$ fragments on either side of the linker region. This eliminates the need to connect the VH and VL at the PCR level. All three modified vectors can still be used in the same way as pCANTAB 5E for subcloning of SfiI-NotI scFv fragments, but in addition they can also be used to sequentially ligate $V_H$ and $V_L$ fragments compatible with a range of different restriction sites.

Sequential Ligation of $V_H$ and $V_L$ Fragments into pCANTAB-link Vector

The vector pCANTAB-link was used for the direct sequential cloning of $V_H$ and $V_L$ PCR fragments into multiple cloning sites on either side of the flexible linker region $(Gly_4Ser)_3$ to generate functional scFv clones. The restriction fragments AscI-XbaI were chosen for the ligation of $V_H$ fragments upstream of the linker region and SalI-NotI downstream of the linker to generate scFv. This was achieved in the following manner.

$V_H$ and $V_L$ chains were amplified as described previously using modified primers HF-Sfi/HR-Xba and LF-Sal/LR-Not (Table 1). $V_H$ and $V_L$ fragments were gel purified and digested with AscI/XbaI and SalI/NotI, respectively (NEB). The pCANTAB-link vector was digested with either AscI/XbaI (for cloning of VH) or SalI/NotI (for cloning of $V_L$) and the $V_H$ and $V_L$ chains cloned respectively, creating 2 intermediate plasmids pCANTAB-link-H and pCANTAB-link-L. After propagation of these plasmids in E. coli DH5α cells, $V_L$ was cloned into the SalI/NotI site of pCANTAB-link-H and VH was cloned into the AscI/XbaI site of pCANTAB-link-L. The ligated DNA was electroporated into electrocompetent E. coli TG1 cells and recombinant phage produced as described above.

A range of published immunoglobulin variable regions from chicken and mouse were assessed for the absence of six-base cutter restriction enzyme sites that could be used for cloning. This assessment revealed the XbaI and SalI sites to be suitable for direct subcloning (of either SfiI-XbaI, AscI-XbaI or SalI-NotI fragments). If XbaI or SalI sites were present within the variable immunoglobulin fragments, different restriction enzymes that yield compatible ends for cloning could be incorporated in the ends of the PCR primers used for amplification of the immunoglobulin variable regions. Compatible ends for XbaI (T'CTAG,A) can be generated with NheI (G∝CTAG,C) and SpeI (A'CTAG,T), and compatible ends for SalI (G'TCGA,C) can be generated with XhoI (C'TCGA,G). A useful feature of the pCANTAB-link is the facility to easily replace different linkers (for example to generate diabodies or multimers) and to swap $V_H$ and $V_L$ domains for the construction of new combinatorial libraries from existing clones.

Selection Procedure for Phage Antibodies

Immunotubes (Maxisorb, Nunc) were coated overnight at room temperature with rabbit anti-IBDV sera (4 ml, diluted 1/500 in 50 mM sodium carbonate buffer, pH 9.6). After washing with PBS containing 0.1% Tween 20 (PBS-T), 002/73 virus (4 ml, diluted 1/200 in PBS containing 5% FCS) was captured at 37° C. for 1 hour. Tubes were blocked for 1 hr with PBS containing 5% skim milk and panning was carded out according to instructions provided with the pCANTAB 5E expression module (Pharmacia), with some modifications. Briefly, 8 ml of the PEG precipitated phage was mixed with 7 ml of 5% skim milk, and 3 ml was poured onto the blocked tubes. After a 2 hr incubation at 37° C. the tubes were washed 20 times with PBS, followed by 20 washes with PBS-T. Log phase E. coli TG1 cells (4 ml) were added to the tubes and incubated at 37° C. to allow infection by phage. Aliquots were plated onto SOB-AG to determine the titre of phage. The remaining culture was infected with helper phage M13K07 as described previously and subjected to an additional 3 rounds of panning. In later experiments the number of washes between rounds 1, 2, 3 and 4 of panning was reduced to 5, 10, 20 and 40 washes with PBS-T, respectively.

Construction and Selection of scFv Libraries from Immunised Chickens in pCANTAB 5E and the Modified pCANTAB-Link Vector The scFv recombinant antibody libraries in the pCANTAB 5E vector produced $1.5 \times 10^5$ clones with almost 100% of the clones carrying a scFv insert. The library was subjected to two different panning procedures. In the first procedure, phage were panned three times and washed 40 times after each adsorption. After each panning step, 88 clones were screened for binding in an ELISA against 002/73. After the first, second and third pan, 2%, 28% and 81% of clones respectively, were ELISA positive All clones isolated from the third round of panning appeared to be identical by DNA sequencing and were designated chicken recombinant antibody 34 (CRAb34). One ELISA negative scFv, designated CRAb0, was chosen from the original unpanned library to serve as a negative control. The second panning procedure consisted of 4 panning steps using less stringent conditions, with the number of washes between pannings being reduced to 5, 10, 20 and 40 after the first, second, third and fourth panning steps, respectively. Despite a reduction in the number of washing steps it was not possible to isolate additional antigen positive CRAbs other than those identical to CRAb34. To overcome the limited library diversity, new libraries were prepared using the modified vector pCANTAB-link as described above.

The same chicken lymphocyte mRNA used for construction of the pCANTAB 5E library was also used for the construction of the scFv library in the pCANTAB-link vector. The $V_H$ and $V_L$ genes were cloned sequentially into the pCANTAB-link vector. Two separate intermediate libraries were constructed, one containing the H chain the other containing the L chain. Cloning the H or L chain first made no difference to the diversity of the library. The final library containing both the H and L chains yielded approximately $7.5 \times 10^7$ clones and upon superinfection with helper phage gave rise to approximately $4.7 \times 10^{12}$ phage particles. Phage were subjected to three rounds of panning with 5, 10, 20 and 40 washes after each round, respectively. The binding capacity of (combined) phage was examined after each round of panning using ELISA. With each successive round of panning, an increase in the ELISA absorbance was observed indicating an enrichment of IBDV specific clones (results not shown).

Expression of scFvs (i) Expression of Phage Displayed Antibodies:

Individual colonies were inoculated into 500 µl of 2xYT-AG and grown at 30° C. overnight with shaking at 250 rpm. Aliquots of 50 µl were transferred to 500 µl of 2xYT-AG containing M13KO7 helper phage. Cultures were shaken at 37° C. for 2 hrs at 150 rpm and then centrifuged at 1000 g for 15 mins. The bacterial pellets were resuspended in 2xYT containing 100 µg/ml ampicillin and 50 µg/ml kanamycin grown at 30° C. overnight with shaking at 250 rpm. Cells were pelleted and the phage-containing supernatant (~400 µl) removed for analysis in ELISA. For large scale screening against IBDV strains cultures were scaled up to 10 ml.

(ii) Expression of Soluble Antibodies:

ELISA positive phage were used to infect a non-suppressor strain of E. coli (HB2151) according to the instructions provided by Pharmacia with some minor modifications. Briefly, 2 µl of phage supernatant was used to infect log phase E. coli HB2151 cells and the cultures were plated out onto SOB-AG containing 100 µg/ml Naladixic Acid (SOB-AGN). Single colonies were inoculated into 2xYT-AG and cultures were grown shaking overnight at 30° C. Aliquots of overnight culture were diluted 1/10 into fresh SB medium containing 100 µg/ml ampicillin and 2% (w/v) glucose (SB-AG) and incubated shaking at 30° C. for 2.5 hrs. Cells were pelleted and resuspended in fresh SB-A medium containing 1 mM IPTG and shaken for 6 hours at 30° C. to induce expression of soluble scFv protein (Sab). Cells were pelleted and the periplasm (containing soluble antibodies) extracted using mild osmotic shock (Alvi A Z, et al (1999) *Hybridoma* 18, 413-421). For neutralization studies, large-scale stocks of soluble antibodies were produced and dialysed extensively against PBS.

Characterisation of rec Ab Clones by ELISA

Phage ELISA: For detection of binding to IBDV, phage were subjected to ELISA in which IBDV was captured onto microtitre plates in the same manner as described for panning, but in 100 µl volumes. For the initial screening, IBDV was diluted 1/100, but a dilution of 1/20 was used for all subsequent experiments. Bound phage were detected using anti-M13 HRP conjugate (Pharmacia) and absorbances at 405 nm were recorded after the addition of ABTS [2, 2-azino-bis (3-ethylbenzthiazoline-6-sulfonicacid)diammonium salt].

ELISA with Sabs: ELISA plates were coated with rabbit-anti-IBDV IgG overnight at room temperature. IBDV antigen diluted in 2% skim milk was then added and incubated for 1 hr at room temperature. After washing Sabs, diluted 1/10 in 2% skim milk, were added and incubated for 1 hr at room temperature. Bound Sabs were detected using anti-E tag monoclonal antibody (Pharmacia), followed by addition of goat anti mouse IgG-HRP conjugate (Biorad). Absorbances were recorded as for the phage ELISA.

ELISA of Phage Against Different IBDV Strains

Approximately 1,000 individual clones obtained from the third and fourth rounds of panning were screened in ELISA for reactivity against 002/73 or CS88 virus. Of the 1,000 clones examined, 46% reacted positively in an ELISA. Around 290 ELISA positive clones were randomly chosen and examined for their reactivity against a panel of Australian and overseas IBDV strains, first as phage displayed antibodies and subsequently as soluble antibodies. In the initial screen, the viral antigen used for coating of ELISA plates was diluted 1/100. When antigen was diluted 1/20 in subsequent ELISAs, all phage showed higher levels of cross-reactivity, making it more difficult to differentiate clones on the basis of ELISA reactivity (Table 2). The majority of CRAbs were cross-reactive, both as phage and soluble antibodies and included CRAbs 24, 96, 83, 15, 5, 22, 12, 151, 18, 176, 174, 154, 66, 149, and 20. Other CRAbs such as CRAb11 and 34 appeared to be specific for Australian strains, while CRAb 88 appeared specific for vvIBDV. A number of interesting differences were observed when comparing the same CRAb expressed as either on the surface of phage or as soluble antibody, in particular CRAbs 33, 8 and 9. Depending on the expression system, these CRABs could differentiate between Australian and overseas strains, with CRAb33 and CRAb9 being specific for Australian strains when expressed as a soluble antibody, while the reverse situation was true for CRAb8.

DNA Sequence Determination and Analysis

Phagemid DNA was isolated using the Qiagen midi prep (low copy plasmid procedure). Each scFv construct was sequenced using the S4, S6 sequencing primers (Pharmacia), which were complementary to the vector sequence. Two additional primers Seq 1 and Seq 2 (Table 1) were used which were complementary to the linker sequence. Nucleotide sequences were determined using the Big Dye Terminator Ready Reaction Kit in conjunction with the 377 XL automated DNA sequencer (Applied Biosystems). Resulting sequences were aligned using the CLUSTAL-X multiple sequence alignment program version 1.81 (Thompson, J. D., et al (1997) *Nucleic Acids Research* 25, 4876-4882). DNA sequence analyses were performed using analysis programs on the Internet accessed via the Australian National Genomic Information Service (ANGIS) or PC based programs (DNASIS, PROSIS).

TABLE 2

ELISA reactivity pattern of different CRAbs (as phage displayed = p or as soluble antibodies = s) with a panel of IBDV strains. [++++, +++; ++, + = optical density greater than 1.1, 0.7-1.1, 0.3-0.7, and 0.1-0.3, respectively; − = optical density less than 0.1; NT = not tested]. Tested under saturating conditions; antigen (bursa homogenate 1/20), Sab 1/10, phage diluted 1/5 using 10% skim milk (final 2%).

| | | 002/73 | V877 | 06/95 | K3 | M4 | R1 | T4 | N1/99 | N2/99 | A-1 | Y5 | H-1 | 01/94 | 02/95 | 03/95 | 04/95 | 08/95 | 52/70 | 1/68 | Var E | Cs88 | Neg |
|---|---|---|---|---|---|---|---|---|---|---|---|---|---|---|---|---|---|---|---|---|---|---|---|
| 002/73 | CRAb 34p | +++ | +++ | ++ | + | − | − | + | + | + | + | + | − | − | − | − | − | − | − | − | − | − | − |
| derived | CRAb34s | ++++ | ++++ | +++ | +++ | ++ | ++ | +++ | +++ | + | ++ | +++ | ++ | + | ++ | ++ | − | − | − | + | − | − | − |
| | CRAb24p | ++++ | ++++ | +++ | +++ | +++ | ++ | +++ | +++ | +++ | +++ | +++ | +++ | +++ | ++ | ++ | − | − | +++ | ++ | − | ++ | − |
| | CRAb24s | ++++ | ++++ | ++++ | ++++ | +++ | +++ | ++++ | ++++ | +++ | ++++ | +++ | +++ | +++ | +++ | +++ | − | − | +++ | +++ | − | ++ | − |
| | CRAb3p | ++++ | ++++ | ++++ | ++++ | ++++ | ++++ | ++++ | ++++ | ++++ | ++++ | ++++ | ++++ | ++++ | ++++ | ++++ | − | − | ++++ | ++++ | − | ++++ | − |
| | CRAb3s | ++++ | ++++ | +++ | +++ | ++ | ++ | +++ | +++ | ++ | +++ | +++ | ++ | ++ | ++ | ++ | + | + | + | + | − | ++ | − |
| | CRAb33p | ++++ | ++++ | ++++ | +++ | ++++ | ++++ | +++ | ++++ | ++++ | +++ | ++++ | +++ | +++ | +++ | +++ | − | − | ++++ | +++ | − | ++++ | − |
| | CRAb33s | ++++ | ++++ | +++ | +++ | ++ | ++ | +++ | ++++ | +++ | +++ | +++ | +++ | ++ | ++ | +++ | − | − | − | − | − | − | − |
| | CRAb96p | +++ | +++ | +++ | ++++ | +++ | +++ | +++ | ++++ | ++++ | ++++ | ++++ | +++ | +++ | +++ | +++ | − | − | +++ | +++ | − | +++ | − |
| | CRAb96s | ++++ | ++++ | ++++ | ++++ | +++ | ++ | ++++ | ++++ | +++ | +++ | ++++ | +++ | ++ | ++ | +++ | − | − | ++ | +++ | − | ++ | − |
| | CRAb83p | ++++ | ++++ | ++++ | ++++ | ++++ | ++++ | ++++ | ++++ | ++++ | ++++ | ++++ | ++++ | ++++ | ++++ | ++++ | − | − | ++++ | ++++ | − | ++++ | − |
| | CRAb83s | ++++ | ++++ | ++++ | ++++ | +++ | +++ | ++++ | ++++ | +++ | +++ | ++++ | +++ | +++ | +++ | +++ | − | − | ++ | +++ | − | ++ | − |
| | CRAb15p | ++++ | ++++ | ++++ | ++++ | ++++ | ++++ | ++++ | ++++ | +++ | ++++ | ++++ | ++++ | ++++ | ++++ | ++++ | − | − | ++++ | ++++ | − | ++++ | − |
| | CRAb15s | ++++ | +++ | ++++ | ++++ | +++ | ++ | +++ | ++++ | +++ | +++ | ++++ | +++ | +++ | ++ | +++ | − | − | ++ | +++ | − | ++ | − |
| | CRAb5p | ++++ | +++ | +++ | ++++ | +++ | ++ | +++ | +++ | +++ | +++ | +++ | ++ | ++ | ++ | ++ | − | − | ++ | +++ | − | ++ | − |
| | CRAb5s | ++++ | ++++ | ++++ | ++++ | +++ | +++ | ++++ | ++++ | ++++ | ++++ | ++++ | ++++ | ++++ | +++ | +++ | + | − | +++ | ++++ | − | ++++ | − |
| | CRAb11p | ++++ | ++++ | ++++ | ++++ | ++++ | ++++ | ++++ | ++++ | ++++ | ++++ | ++++ | ++ | ++ | ++ | ++ | ++ | ++ | − | − | − | − | − |
| | CRAb11s | ++++ | ++++ | ++++ | ++++ | +++ | +++ | ++++ | ++++ | ++++ | ++++ | +++ | ++++ | ++ | +++ | ++++ | ++ | ++ | − | − | − | − | − |
| | CRAb21p | +++ | +++ | +++ | +++ | +++ | +++ | +++ | +++ | +++ | +++ | +++ | ++ | ++ | ++ | ++ | ++ | ++ | ++ | ++ | − | ++ | − |
| | CRAb21s | +++ | ++++ | ++++ | +++ | ++ | + | +++ | ++ | +++ | +++ | ++ | − | − | − | − | − | − | + | + | − | + | − |
| | CRAb23p | ++++ | +++ | ++++ | ++++ | +++ | ++++ | ++++ | ++++ | ++++ | ++++ | ++++ | ++++ | ++++ | +++ | ++++ | − | − | +++ | +++ | − | +++ | − |
| | CRAb23s | ++++ | ++++ | +++ | ++ | + | + | +++ | ++ | ++ | ++ | ++ | + | + | + | + | − | − | + | + | − | ++ | − |
| | CRAb22p | ++++ | ++++ | +++ | +++ | +++ | +++ | +++ | ++++ | ++++ | ++++ | ++++ | ++++ | +++ | +++ | +++ | − | − | +++ | ++++ | − | +++ | − |
| | CRAb22s | ++++ | +++ | ++++ | +++ | ++ | ++ | +++ | +++ | +++ | ++ | +++ | +++ | ++ | +++ | +++ | − | − | ++ | ++ | − | ++ | − |
| | CRAb52p | ++++ | ++++ | ++++ | ++++ | ++++ | ++++ | ++++ | ++++ | ++++ | ++++ | ++++ | ++++ | ++++ | ++++ | ++++ | − | − | ++ | ++ | − | ++ | − |
| | CRAb52s | ++++ | +++ | +++ | ++ | + | + | ++ | ++ | ++ | ++ | ++ | +++ | ++ | ++ | ++ | − | − | − | − | − | + | − |
| | CRAb8p | ++++ | ++++ | ++++ | ++ | ++ | ++ | +++ | ++ | +++ | +++ | +++ | ++++ | +++ | +++ | +++ | − | − | − | − | − | − | − |
| | CRAb8s | ++++ | ++++ | ++++ | ++++ | +++ | +++ | ++++ | ++++ | ++++ | ++++ | +++ | +++ | +++ | +++ | +++ | − | − | ++ | +++ | − | +++ | − |
| | CRAb7p | ++++ | ++++ | ++++ | ++++ | ++++ | ++++ | ++++ | ++++ | ++++ | ++++ | ++++ | − | − | − | − | | − | ++ | ++ | − | ++ | − |
| | CRAb7s | ++++ | ++++ | ++++ | +++ | +++ | +++ | +++ | ++++ | ++++ | ++++ | ++ | − | − | + | − | | − | − | − | − | + | − |
| | CRAb12p | ++++ | ++++ | ++++ | ++++ | ++++ | ++++ | ++++ | ++++ | ++++ | ++++ | ++++ | ++++ | ++++ | ++++ | ++++ | ++++ | ++++ | ++++ | ++++ | − | ++++ | − |
| | CRAb12s | ++++ | ++++ | ++++ | ++++ | ++ | ++ | +++ | ++++ | +++ | +++ | +++ | +++ | +++ | +++ | +++ | ++ | ++ | ++ | ++ | − | ++ | − |
| | CRAb20p | +++ | +++ | ++++ | +++ | +++ | ++ | +++ | +++ | ++ | ++ | +++ | ++ | ++ | +++ | ++ | + | ++ | ++++ | +++ | ++ | ++++ | − |
| | CRAb20s | ++++ | +++ | ++++ | ++++ | +++ | +++ | ++++ | + | + | + | + | + | + | +++ | +++ | + | − | +++ | ++++ | − | ++++ | − |
| | CRAb9p | +++ | +++ | ++++ | +++ | +++ | +++ | +++ | + | +++ | ++ | + | ++ | + | ++ | ++ | − | ++ | ++ | ++ | − | ++ | − |
| | CRAb9s | ++++ | ++++ | ++++ | ++++ | +++ | ++ | ++++ | +++ | +++ | ++++ | +++ | +++ | +++ | +++ | +++ | + | − | − | − | − | − | − |
| | CRAb0p | − | − | − | − | − | − | − | − | − | − | − | − | − | − | − | − | − | − | − | − | − | − |
| | CRAb0s | − | − | − | − | − | − | − | − | − | − | − | − | − | − | − | − | − | − | − | − | − | − |
| | Mab 9-6 | ++++ | ++++ | ++++ | ++++ | ++++ | ++++ | ++++ | ++++ | ++++ | ++++ | ++++ | ++++ | ++ | ++++ | ++++ | + | + | ++++ | ++++ | − | ++++ | − |
| CS88 | CRAb 151p | ++++ | ++++ | ++++ | ++++ | ++++ | ++++ | ++++ | NT | NT | NT | NT | NT | NT | +++ | +++ | NT | ++ | +++ | +++ | + | +++ | − |
| derived | CRAb 151s | ++++ | ++++ | ++++ | ++++ | ++++ | ++++ | ++++ | NT | NT | NT | NT | NT | NT | ++++ | ++++ | NT | ++++ | ++++ | ++++ | + | ++++ | − |
| | CRAb 28p | − | − | − | − | − | − | − | NT | NT | NT | NT | NT | NT | − | − | NT | − | ++++ | +++ | − | ++++ | − |
| | CRAb 28s | − | − | − | − | − | − | + | NT | NT | NT | NT | NT | NT | + | − | NT | − | ++++ | ++++ | − | ++++ | − |

TABLE 2-continued

Figure 5:
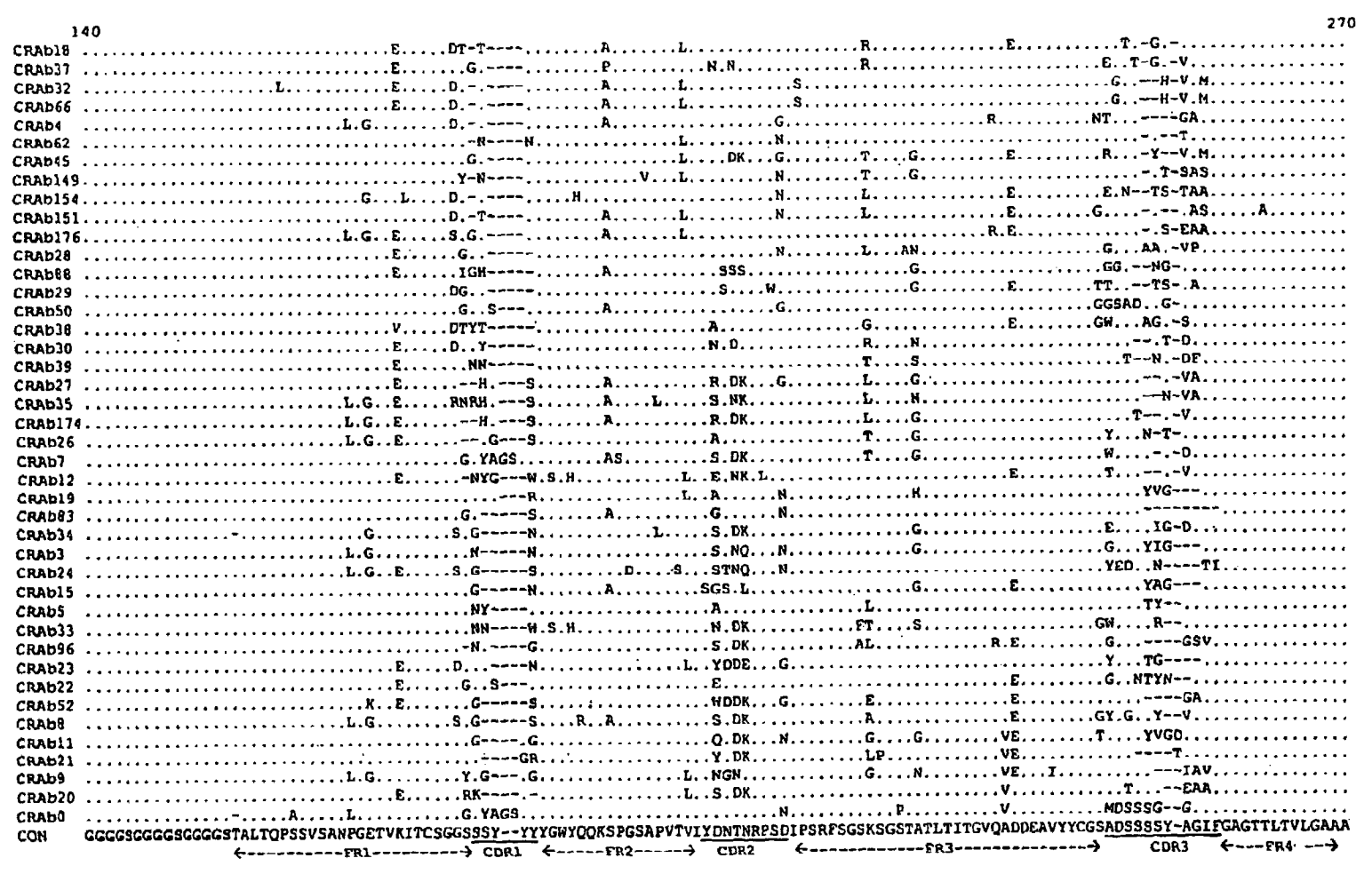

ELISA reactivity pattern of different CRAbs (as phage displayed = p or as soluble antibodies = s) with a panel of IBDV strains. [++++, +++, ++, + = optical density greater than 1.1, 0.7-1.1, 0.3-0.7, and 0.1-0.3, respectively; − = opt Nucleotide sequencing of 60 clones revealed 42 unique CRAbs. An alignment of the deduced amino acid sequences of the CRAbs is shown in FIG. 5 along with that of the negative control CRAb0. Three complementarity regions and four framework regions were identified in each of the H and L chains. Eight of the CRAbs (CRAb24, 3, 33, 96, 83, 15, 5, and 19) possessed an identical H chain, which was the same as that found in CRAb34 (except for two additional amino acids L & D which occur by virtue of the pCANTAB-link vector) but all varied in their L chain sequences. Despite having the same H chains, these 9 CRAbs show significant differences in reactivity against IBDV strains (Table 2). For example, CRAb24, 96, 83, 15 and 5 appeared to be reactive with most IBDV strains tested, whilst CRAb11 and 34 were specific for Australian strains. The nucleotide and amino acid sequence of 35 individual $V_H$ chains (1-35) and 42 individual $V_L$ chains (36-77) is shown in FIG. 3 and FIG. 4.

Binding Activity in ELISA

Antigen binding activity of CRAbs was determined in ELISA using homologous antigen e.g. either 002/73 or CS88 (Table 2). As shown in Table 2, some CRAbs reacted with all IBDV strains (CRAb151, 154, 66, 149 and 176). CRAbs 28, 29 and 50 recated only with classical IBDV strains from Europe and did not react with any of Australian IBDV strains, or the USA variants. CRAbs 9, 11, 33, 34 and 52, as soluble antibodies, reacted only with Australian IBDV strains. CRAb88 reacted only with very virulent strain CS88 and did not react with any classical or variant strains (Table 2). Additionally it was shown that CRAb88 reacted in ELISA only with all known very virulent IBDV strains, the results of which (with selected strains only) are shown in Table 3. This indicates that CRAb88 is specific for vvIBDV strains and can be used for differential diagnosis of vvIBDV. Some CRAbs showed differences in antigen specificity when expressesd as phage and soluble antibodies. Such differences are shown in FIG. 6 with CRAb34, as an example; CRAb34 as phage antibody binds only to 002/73 and V877 antigens, whereas as soluble antibody CRAb34 binds to all Australian IBDV strains, albeit to a lesser degree (FIG. 6 & FIG. 7). Binding titres of 29 CRAbs for 002/73 antigen are shown in Table 4.

TABLE 3

Specificity of CRAb88 for very virulent IBDV strains in ELISA

| Virus | Virus type | Mab 9-6 | CRAb154 | CRAb88 |
| --- | --- | --- | --- | --- |
| GLS | Variant | − | +++ | − |
| Ga | | + | +++ | − |
| VarE | | + | ++ | − |
| VarA | | − | ++ | − |
| DV86 | Classical | ++++ | ++++ | − |
| 52/70 | | ++++ | ++++ | − |
| 1/68 | | ++++ | ++++ | − |
| APHIS | | ++++ | ++++ | − |
| CuIM | Classical | NT* | ++ | − |
| TadForte | vaccines | NT | ++++ | − |
| 228E | | NT | ++ | − |
| D78 | | NT | +++ | − |
| Bursine | | NT | + | − |
| PBG98 | | NT | +++ | − |
| DV86 | Very virulent | +++ | ++++ | +++ |
| UK661 | | +++ | ++++ | +++ |
| CS88 | | ++++ | ++++ | +++ |
| VB849 | | +++ | ++++ | +++ |
| 99006 | | NT | ++++ | +++ |
| 89163 | | NT | ++++ | ++++ |
| 91168 | | NT | ++++ | ++++ |
| 94432 | | NT | ++++ | +++ |
| Tasik94 | | ++++ | ++++ | +++ |
| Indo1 | | ++++ | ++++ | +++ |

TABLE 3-continued

Specificity of CRAb88 for very virulent IBDV strains in ELISA

| Virus | Virus type | Mab 9-6 | CRAb154 | CRAb88 |
| --- | --- | --- | --- | --- |
| Indo6 | | ++++ | ++++ | +++ |
| Indo10 | | ++++ | ++++ | +++ |

Figure 8:
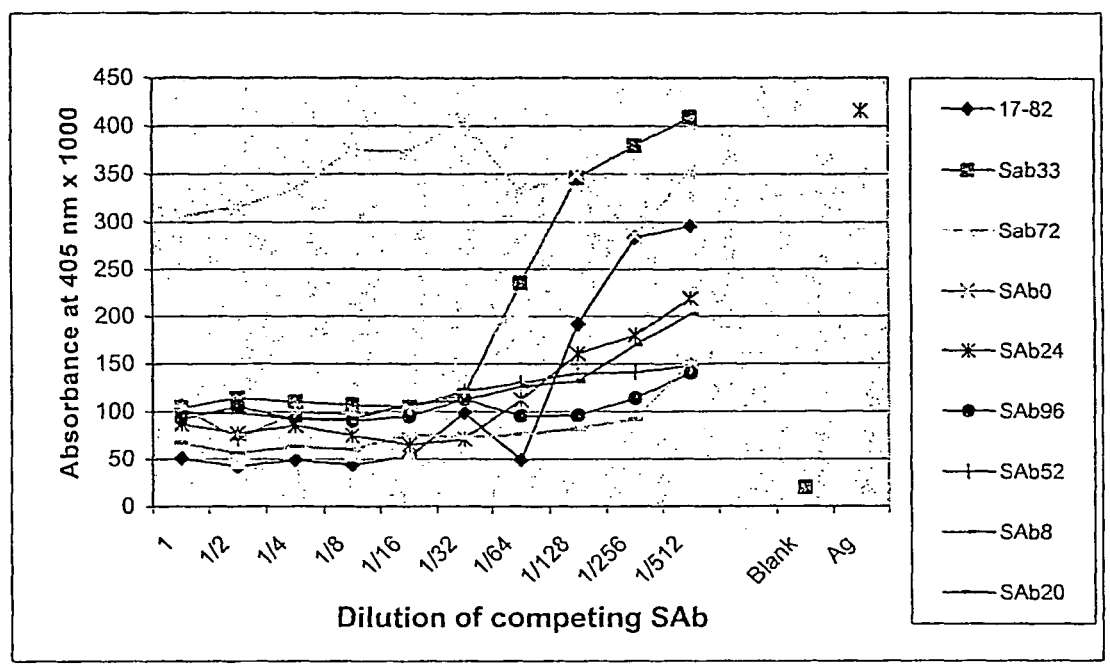
FIG. 8: CRAbs compete with immune ant-IBDV sera for binding to 002/73 antigen.

CRAbs Ability to Compete with Polyclonal Immune Chicken Sera for Binding to IBDV Antigen in ELISA Chicken immune IBDV sera was titrated first to determine the dilution that would give 80-90% of maximum binding in a capture ELISA. For competition ELISA, soluble CRAbs, in $\log_2$ dilution, were incubated with a constant amount of 002/73 or CS88 antigen. After one hour, 100 μl of this reaction mixture was added to ELISA plates coated with rabbit anti-IBDV sera. After incubation for 1 hour, a constant amount of chicken immune IBDV sera was added, followed by addition of goat-anti-chicken IgG-HRP. After incubation of 1 hour at room temperature, substrate was added and absorbance measured at 405 nm. As shown in FIG. 1, many CRAbs competed effectively against anti-002/73 antisera for binding to 002/73 antigen indicating that CRAbs and immune IBDV chick sera recognise the same epitopes on the IBDV antigen. Negative control CRAb0 did not compete with immune sera (FIG. 8).

Figure 9:
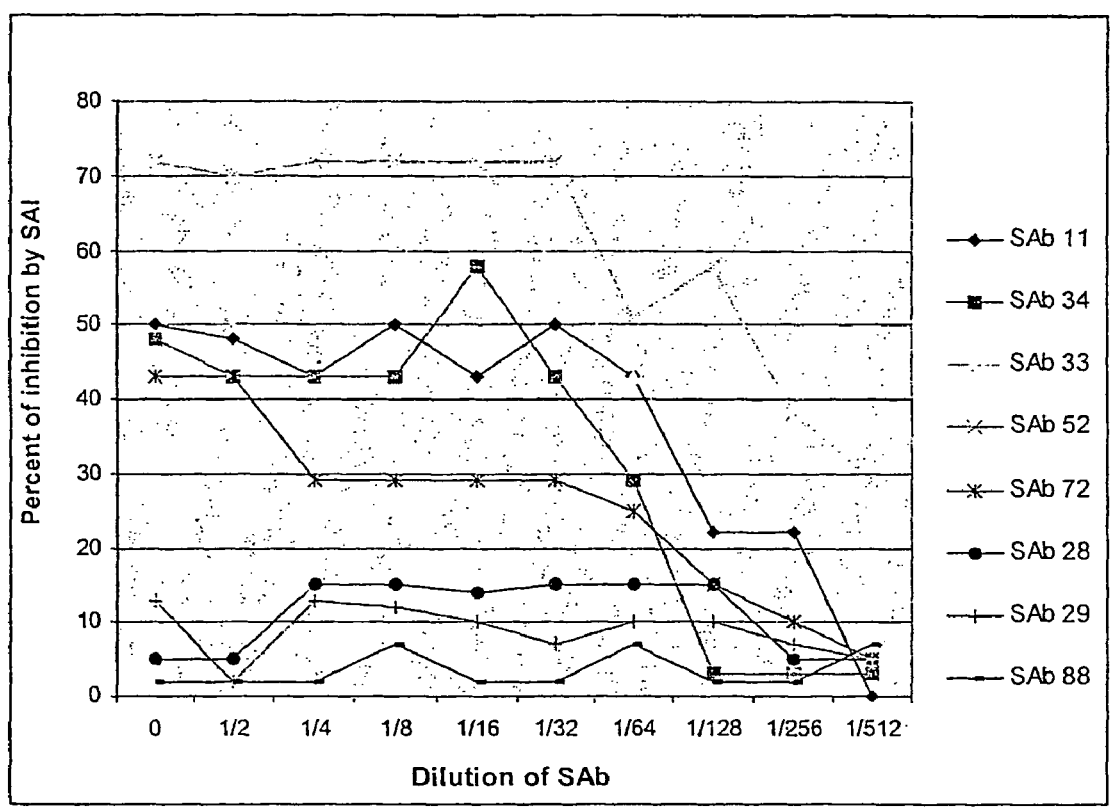
FIG. 9: Competition by SAbs specific for Australian (11, 34, 33, 52, 72) or overseas (28, 29, 88) IBDV strains with anti-002/73 sera for binding to 002/73 Australian IBDV antigen FIG. 10:. Competition by SAbs specific for Australian (11, 34, 33, 52, 72) or overseas (28, 29, 88) IBDV strains with anti-very virulent CS88 sera for binding to very virulent CS88 antigen
Figure 10:
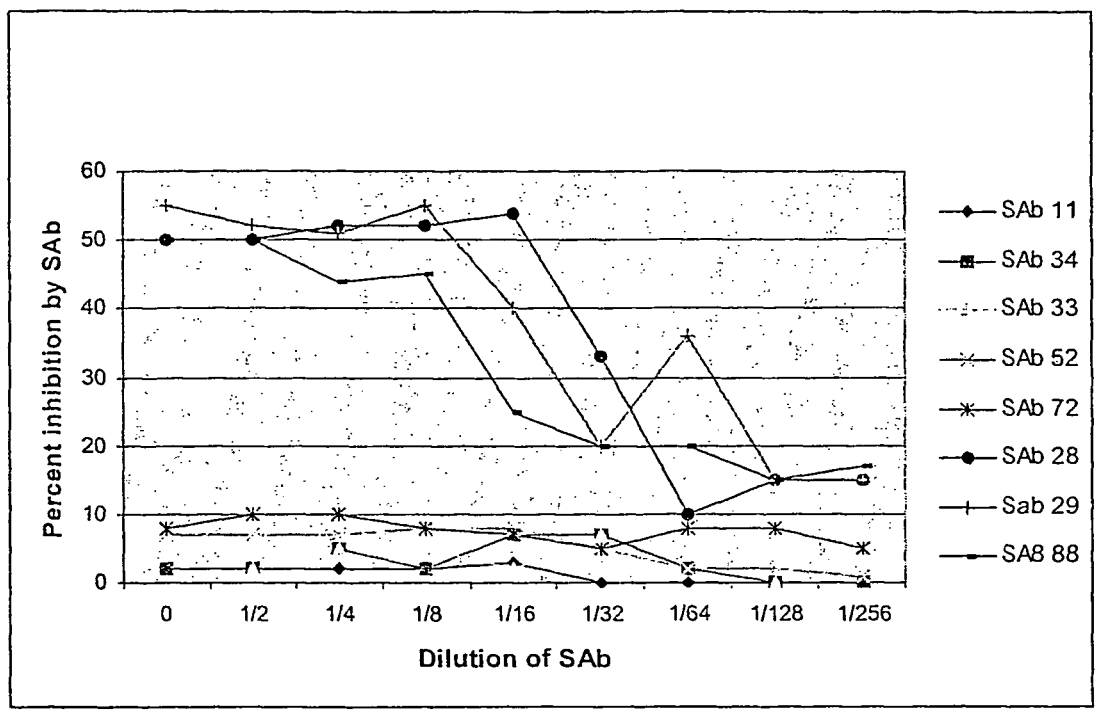

CRAbs were able to differentiate type of IBDV strains that chickens have been exposed to, using their immune sera (FIGS. 9 & 10). As shown in FIG. 9, only CRAbs specific for Australian IBDV strains (CRAb11, 34, 33 and 52) competed with anti-002/73 antisera for binding to 002/73 antigen, whereas CRAbs specific for overseas strains (CRAb28, 29 and 88) did not inhibit binding. Similarly in FIG. 10 is shown that CRAbs specific for Australian strains (CRAb11, 34, 33 and 52) did not compete with anti-CS88 antisera for binding to CS88 antigen, however, CRAbs 28, 29 and 88 did compete. Altogether these results indicate that CRAb88 can be used to differentiate expose of chickens to very virulent IBDV strains, after active infection has waned and when only immune sera is available. Furthermore that exposure to different types of IBDV, such as vaccinal and field exposure, can be differentiated in immune sera using selected CRAbs.

Virus Neutralizing Activity In Vitro

The neutralizing activity of all CRAbs was assessed in vitro using the following method. Antibody, in 1092 dilutions, was incubated with approximately 30-50 median tissue culture infective doses ($CID_{50}$) of GT101 IBDV strain [Fahey et al (1991) Avian Diseases 35, 365-373] for 1 hr at 37° C. The antibody/virus mixture was then added to the suspension of freshly prepared secondary chicken embryo fibroblasts and incubated at 37° C. in the presence of 3% $CO_2$. Four to 5 days later cell monolayers in wells of tissue culture plates were examined for cytopathic effect visually. Complete absence of a cytopathic effect in all replicates (quadruplicate for each CRAb dilution) was taken to indicate virus neutralization. The results in Table 4 show that 19 CRAbs were able to neutralize IBDV in vitro. Ten CRAbs had titres higher than 128 compared with a negative control scFv (CRAb0) which was not able to neutralize GT101 virus. Eight other antibodies showed lower neutralizing titres of between 8-64.

TABLE 4

ELISA and virus neutralisation (VN) titres of different CRAbs expressed as soluble antibodies, obtained in vitro, in ovo and in vivo

| CRAb Origin | CRAb | IBDV protein specificity* | ELISA binding titre with 002/73# | VN titre in CEFs with GT101# | % VN in ovo of 100 EID$_{50}$ of BursavacL | VN in vivo with 002/73 100 CID$_{50}$ | VN in vivo with BursavacL 10 CID$_{50}$ | VN in vivo with BursavacL 100 CID$_{50}$ |
|---|---|---|---|---|---|---|---|---|
| 002/73 library | 0 | None | 0 | 0 | 0 | | none | none |
| | 3 | VP3 | 10,000 | 0 | 71 | | | |
| | 5 | VP2 | 10,000 | 6,400 | 100 | partial | | none |
| | 7 | VP2 | 20,000 | 0 | 75 | | | none |
| | 8 | VP2 | 40,000 | 3200 | 75 | partial | | partial |
| | 9 | VP2 | 30,000 | >10,240 | 71 | none | | none |
| | 11 | VP2 | 40,000 | >10,400 | 50 | | | none |
| | 12 | VP2 | 16,000 | >128 | 0 | none | | none |
| | 15 | VP2 | 80,000 | 1,024 | 80 | partial | | partial |
| | 20 | VP3 | 10,000 | 12,800 | 67 | none | | none |
| | 21 | VP2 | 2,560 | 8 | 0 | | | |
| | 22 | VP2 | 40,000 | 160 | 100 | | | none |
| | 23 | VP2 | 80,000 | 160 | 80 | none | | none |
| | 24 | VP2 | 2,500 | 64 | 89 | none | complete | partial |
| | 33 | VP2 | 6,400 | 16 | 86 | partial | complete | none |
| | 34 | VP2 | 2,500 | 16 | 80 | partial | complete | partial |
| | 52 | VP2 | 10,000 | 32 | 100 | partial | | partial |
| | 83 | VP2 | 5,600 | 64 | 86 | partial | complete | partial |
| | 96 | VP2 | 10,000 | 64 | 100 | partial | complete | none |
| CS88 library | 18 | VP2 | >5,120 | 8 | 0 | | partial | |
| | 62 | VP3 | 2,560 | 0 | 0 | | | |
| | 66 | VP2 | >5,120 | 0 | 0 | | | |
| | 88 | VP2 | 512 | 0 | 0 | | | |
| | 149 | VP2 | >5,120 | 0 | 0 | | | |
| | 151 | VP2 | >5,120 | 0 | 0 | | none | |
| | 154 | VP2 | 5,120 | 0 | 83 | none | complete | none |
| | 174 | VP2 | >5120 | >128 | 0 | | partial | |
| | 176 | VP2 | >5,120 | 0 | 0 | | | |
| Mab | 9-6 | VP2 | 160 | 5,120 | 100 | | complete | complete |
| Chicken | anti-BV | VP2, VP3 | 100,000 | 64,000 | 100 | | complete | complete |

Virus Neutralizing Activity In Ovo

All CRAbs from Table 4 were incubated with 100 median egg infective doses (EID$_{50}$) of IBDV vaccine strain BursavacL and injected into the allantoic cavity of 10-day-old embryonating chicken eggs. Embryos were incubated for 7-8 days at 37° C. Embryos were inspected daily for deaths due to IBDV. At the end of incubation period the number of surviving embryos were counted and expressed as % of neutralisation in comparison to virus control where all embryos were dead. Results in Table 4 show that the majority of CRAbs neutralised IBDV in ovo.

Virus Neutralizing Activity In Vivo

Figure 11:
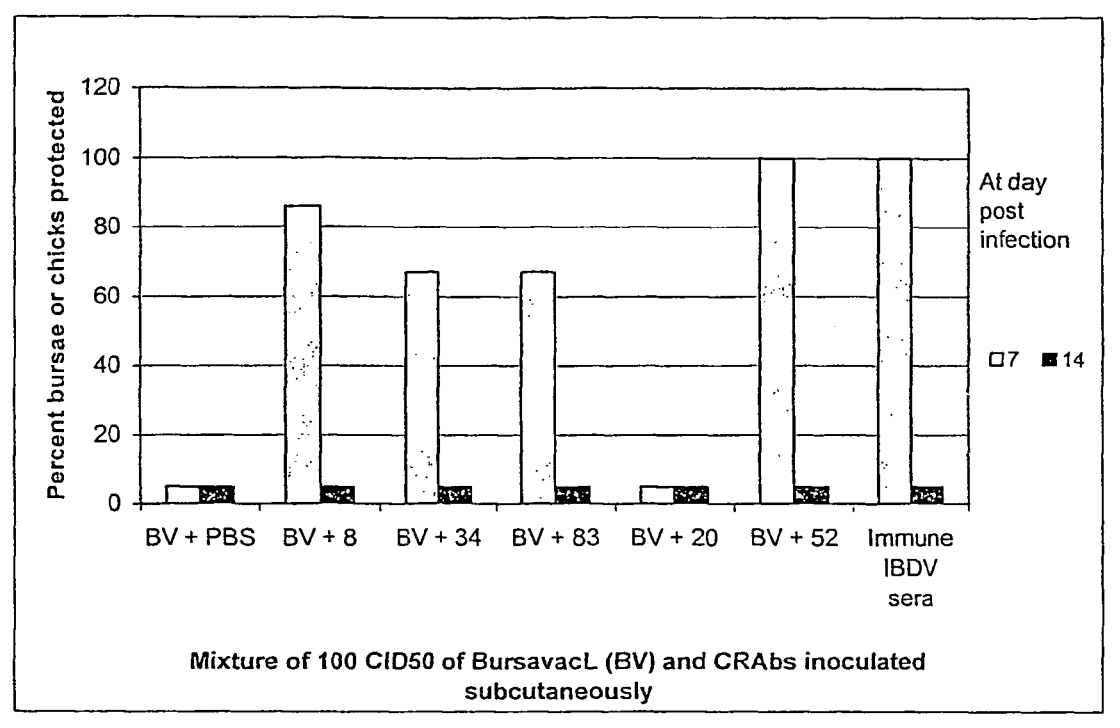
Figure 12:
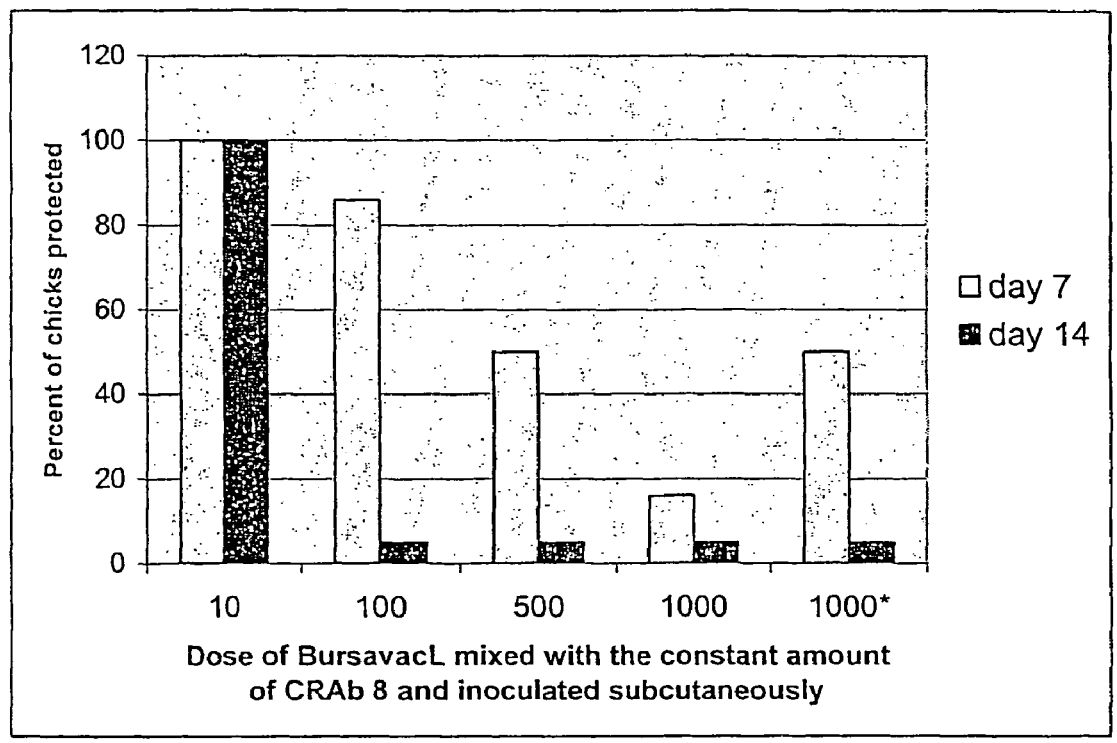
FIG. 12: Neutralization of various doses of BursvacL vaccine by CRAb8 in day-old or 2-week-old* chickens

CRAbs as well as polyclonal chicken anti-IBDV sera (anti-BV) and monoclonal antibody 9-6 specific for VP2 of IBDV (Mab 9-6) (Fahey K J, et al (1991) *Avian Diseases* 35, 365-373) were incubated with 10, 100 or 1000 median chick infective doses (CID$_{50}$) of BursavacL, or 100 CID$_{50}$ of 002/73 strain and injected subcutaneously into the nape of neck of day old or two-week-old specific pathogen-free (SPF) chickens to assess CRAbs ability to neutralise virus infectivity in vivo. At 7 and 14 days after injection bursa were collected from 6 chicks and bursa to body weight determined. If bursae were reduced in size in comparison to the non-infected controls (regressed) at both day 7 and day 14 after inoculation it was taken to mean that virus was not neutralised. If bursae were normal in size (not regressed) at both day 7 and day 14 after inoculation it was taken to mean that virus was completely neutralised. If bursae were normal size (not regressed) at day 7 and regressed at day 14 after inoculation it was taken to mean that neutralisation of virus was partial. The results obtained with CRAbs are shown in Table 4 and with selected CRAbs in FIG. 11. As shown in Table 4, some CRAbs (CRAb8, 15, 34, 52 and 83) were able to neutralise 100 CID$_{50}$ of both BursavacL and 002/73, whereas CRAb5, 33 and 96 were able to neutralise only 002/73 and CRAb24 to neutralise only BursavacL and not 002/73. In FIG. 11 is shown the time course of partial neutralisation of 100 CID$_{50}$ of BursavacL by CRAbs 8, 34 and 52; all three CRAbs neutralised BursavacL at day 7 post infection whereas virus was released from the complex and induced bursal regression at day 14 post infection as did the polygonal immune anti-IBDV sera (FIG. 11). Ability of CRAbs to neutralize IBDV was dependent on the amount of infectious virus used. As shown in Table 4, many CRAbs were able to neutralise completely a low dose of BursavacL, being 10 CID$_{50}$, however with higher dose of virus (100 CID$_{50}$) neutralisation was either partial or no neutralisation was achieved. In FIG. 12 is shown the ability of the constant amount of CRAb8 to neutralise various doses of BursavacL. Also in FIG. 12 is shown that in 2-week-old chickens higher doses of BursavacL can be neutralised with the same amount of CRAbs unlike in day-old chicks. Overall these results showed that CRAbs are able to holt the onset of IBDV infection in chickens by complexing the IBDV virus particle in a manner identical to that observed for polyclonal chicken sera (Whitfill et al., (1995) *Avian Diseases* 39, 687-699; Haddad et al., (1997), *Avian Diseases* 41, 882-889)

Figure 13:
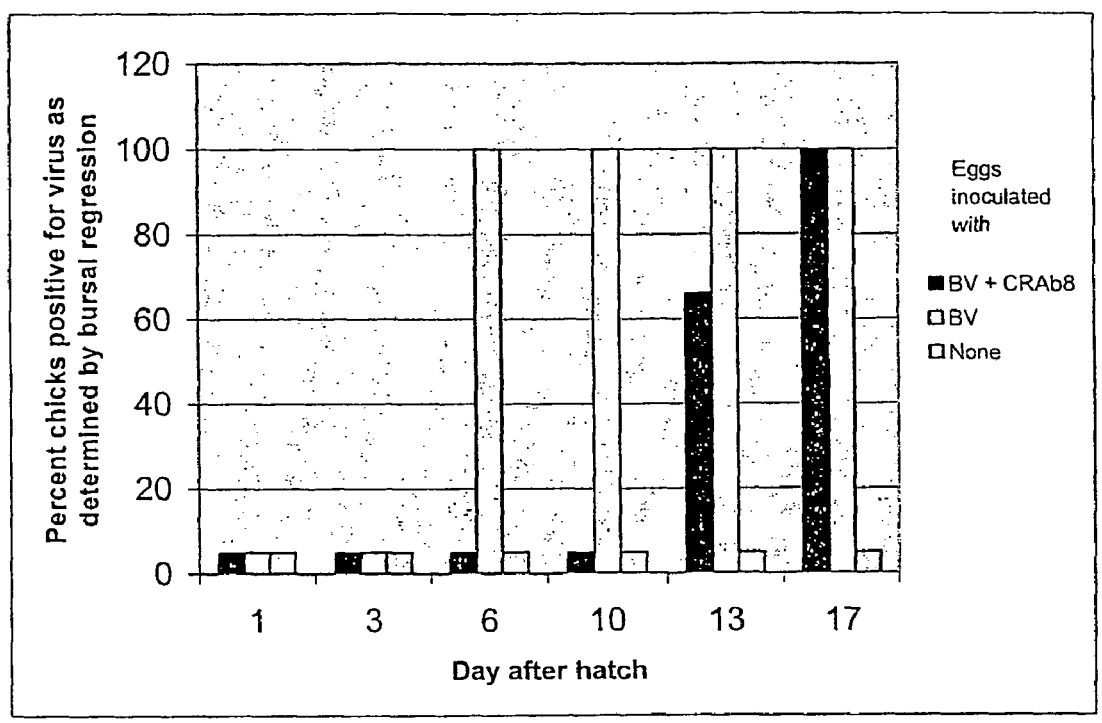
FIG. 13: Time course of BursavacL release from BursavacL.CRAb8 complex following inoculation into 18-day-old specific pathogen-free embryos Q

Virus Neutralizing Activity Following Inoculation of IBDV. CRAb Mixture into 18-Day-Old Embryonating Chicken Eggs Eighteen-day-old embryonated SPF chicken eggs were inoculated with either 100 $EID_{50}$ or BursvacL or 100 $EID_{50}$ of BursvacL mixed with CRAb8 or phosphate buffered saline. Chickens were hatched from these eggs, placed into positive pressure isolation units for containment of infection, and bursa collected at various times after infection. Bursa to body ratio was determined and bursal tissue frozen, sectioned and used in an immunofluorescence assay with Mab 9-6 to determine the presence of virus in tissue of these chickens. Only results of bursal regression observed in these chickens is shown in FIG. 13. Chicks that received only BursavacL all had regressed bursa at day 6 after hatch, whereas in those inoculated with Bursavacl.CRAb8 mixture first signs of regression was visible at day 13 after hatch. These results showed that CRAb8 was able to holt the onset of infection when given as a mixture with IBDV to 18-day-old embryonating eggs in a manner similar to that observed for polyclonal chicken sera (Jeurissen et al. (1998), *Immunology* 95, 494-500.

Mapping of Antibody Binding

Figure 14:
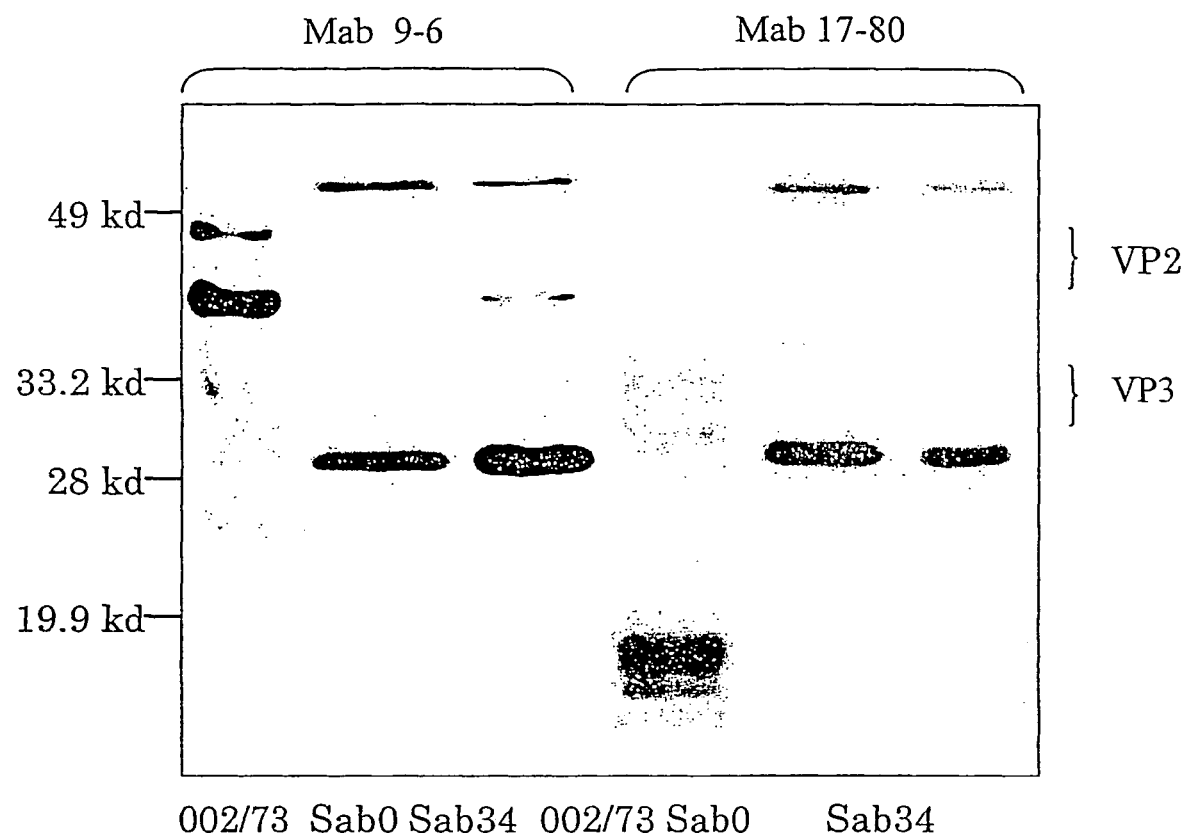
FIG. 14: Immunoprecipitation with Sab34 and Sab0 showing that CRAb34 recognises the VP2 protein of 002/73 strain of IBDV

Viral proteins of 002/73 or CS88 were solubilized with 2% n-octylglucoside and used in immunoprecipitation experiments to determine the antigenic target of all CRAbs. Each CRAb was incubated with either 002173 or CS88 solubilised antigen and the complex was immunoprecipitated using anti E-tag monoclonal antibody followed by Protein A-Sepharose. Immunoprecipitated proteins were detected by SDS-PAGE and Western blotting, using monoclonal antibodies 9-6 (for detection of VP2) and 17-80 (for detection of VP3) [Fahey et al., (1991) *Avian Diseases* 35, 365-373]. An example of this specific immunoprecipitation by CRAbs is shown in FIG. 14, in which CRAb34 was shown to be specific for VP2. As shown in Table 4 the majority of CRAbs were specific for VP2 protein, whereas only three CRAbs 3, 20 and 62 were specific for VP3. The negative control antibody, CRAb0 did not bind either VP2 or VP3 (Table 4 and FIG. 14).

It is to be understood that the above examples are included solely for the purposes of exemplifying the present invention. They should not be understood in any way as a restriction on the broad description of the invention as set out above.

The invention claimed is:

1. A recombinant antibody fragment having a binding specificity for an IBDV antigenic determinant, the recombinant antibody fragment comprising a variable region comprising:
   a) the heavy chain variable region of SEQ ID NO:92;
   b) the light chain variable region of SEQ ID NO:125; or
   c) CDR 1, 2, and 3 of a) and b); and
   wherein the recombinant antibody fragment binds vvIBDV strain CS88.

2. A recombinant antibody fragment comprising a $V_H$ region of SEQ ID NO:92 and a $V_L$ region of SEQ ID NO:125.

3. The recombinant antibody fragment according to claim 1 conjugated with, or attached to other antibodies or parts thereof.

4. The recombinant antibody fragment according to claim 1 which are multivalent monospecific and comprise at least two single chain antibody fragments bound to each other by a connecting structure which protein is not a natural immunoglobulin and wherein at least one of said recombinant antibody fragments has a specificity for an IBDV antigenic determinant.

5. The recombinant antibody fragment according to claim 1 wherein $V_H$ domains and the $V_L$ domains are linked.

6. The recombinant antibody fragment(s) according to claim 5 wherein the linker is $(Gly_4Ser)_3$.

7. The recombinant antibody fragment according to claim 1 wherein the fragment is capable of distinguishing at least two IBDV strains.

8. The recombinant antibody fragment according to claim 1 having a differential binding affinity capable of distinguishing at least two IBDV strains.

9. The recombinant antibody fragment according to claim 1 capable of binding one or more of the group of IBDV selected from: Australian IBDV strain 002/73; vaccine strain V877; classical field strains 06/95, K3, M4, R1, T4, N 1/99, N2/99, A-1 or Y-5; variant field strains 01/94, 02/95, 03/95, 04/95 or 08/95; classical overseas strains 52/70 and 1/68; variant strain E and vvIBDV strain CS88.

10. The recombinant antibody fragment according to claim 1 derived from a host that has been caused to produce antibodies against IBDV or an IBDV polypeptide or fragment thereof.

11. The recombinant antibody fragment according to claim 10 wherein the host is of avian origin.

12. The recombinant antibody fragment according to claim 10, wherein the host is a fowl.

13. A kit for diagnosis of IBDV strain comprising an antibody fragment or fragments according to claim 1.

14. The recombinant antibody fragments according to claim 1 initially derived from nucleotide sequences encoding heavy and light chain variable regions produced in B-lymphocytes from a host that has been caused to produce antibodies against at least IBDV or an IBDV polypeptide or a fragment thereof.

15. A therapeutic composition comprising at least a recombinant antibody fragment according to claim 1 and a pharmaceutically acceptable carrier.

16. A method of treating a IBDV disease comprising administering a functional recombinant antibody polypeptide of claim 1 to suppress IBDV proliferation in a host.

17. A recombinant antibody fragment comprising a heavy chain variable region of SEQ ID NO:92, wherein the antibody fragment binds vvIBDV strain CS88.

18. A recombinant antibody fragment comprising a light chain variable region of SEQ ID NO:125, wherein the antibody fragment binds vvIBDV strain CS88.

19. The recombinant antibody fragment according to claim 1, wherein the recombinant antibody fragment differentially binds one or more very virulent IBDV strains compared to classical IBDV strains or virulent IBDV strains.

20. The recombinant antibody fragment according to claim 17, wherein the recombinant antibody fragment differentially binds one or more very virulent IBDV strains compared to classical IBDV strains or virulent IBDV strains.

21. The recombinant antibody fragment according to claim 18, wherein the recombinant antibody fragment differentially binds one or more very virulent IBDV strains compared to classical IBDV strains or virulent IBDV strains.

22. A recombinant antibody fragment according to claim 10 wherein the fowl is a chicken, turkey, guinea fowl, duck, or goose.

* * * * *

SEQUENCE LISTING

```
<160> NUMBER OF SEQ ID NOS: 215

<210> SEQ ID NO 1
<211> LENGTH: 375
<212> TYPE: DNA
<213> ORGANISM: Gallus gallus
<220> FEATURE:
<221> NAME/KEY: misc_feature
<223> OTHER INFORMATION: VH Sequence 1

<400> SEQUENCE: 1
gccgtgacgt tggacgagtc cggggggcggc ctccagacgc ccggaggaac gctcagcctc      60
gtctgcaagg cctccgggtt caccttcagc agttatcaga tgaactggtt gcgccaggct     120
cccggcaagg ggctggagtg ggtcggtgtt attagcaccc gtggcagtag cacagcatac     180
ggggcggcgg tgaagggccg tgccaccatc tcgagggaca acgggcagag cacagtgagg     240
ctgcagctga acagcctcag gactgaggac accgccacct actactgcgc caaagctggt     300
tatgcttgtg gttggagtgt tggttgtatc gacgcatggg gccacgggac cgaagtcatc     360
gtctcctctc tagat                                                      375

<210> SEQ ID NO 2
<211> LENGTH: 369
<212> TYPE: DNA
<213> ORGANISM: Gallus gallus

<400> SEQUENCE: 2
gccgtgacgt tggacgagtc cggggggcggc ctccagacgc ccggaggaac gctcagcctc      60
gtctgcaagg cctccgggtt caccttcagc agttatcaga tgaactggtt gcgccaggct     120
cccggcaagg ggctggagtg ggtcggtgtt attagcaccc gtggcagtag cacagcatac     180
ggggcggcgg tgaagggccg tgccaccatc tcgagggaca acgggcagag cacagtgagg     240
ctgcagctga acagcctcag gactgaggac accgccacct actactgcgc caaagctggt     300
tatgcttgtg gttggagtgt tggttgtatc gacgcatggg gccacgggac cgaagtcatc     360
```

```
                                                       gtctcctcc                                       369

<210> SEQ ID NO 3
<211> LENGTH: 378
<212> TYPE: DNA
<213> ORGANISM: Gallus gallus

<400> SEQUENCE: 3
gccgtgacgt tggacgagtc cggggcggc   ctccagacgc  ccggaggagc  actcagcctc      60
gtctgcaagg gctccgggtt caccttcagc  agttacaaca  tgggttgggt  cgacaggcg      120 cccggcaagg ggctggaatt cgtcgcagct  attagcaaca  ctggtagata  cacaggctac     180
gggtcggcgg tgaagggccg tgccaccatc  tcgagggaca  acgggcagag  cacagtgagg     240
ctgcagctga caaccctcag ggctgaggac  accgccacct  actactgcgc  caaaactgct     300
ggttactatg gttggaatac tgctagtgat  atcgacgcat  ggggccacgg  gaccgaagtc     360
atcgtctcct ctctagat                                                      378

<210> SEQ ID NO 4
<211> LENGTH: 378
<212> TYPE: DNA
<213> ORGANISM: Gallus gallus

<400> SEQUENCE: 4
gccgtgacgt tggacgagtc cggggtggc   ctccagacgc  ccggaagagc  gctcagcctc      60
gtctgcaagg gctccgggtt caccctcagc  agttacaaca  tgggttgggt  cgacaggcg      120 cccggcaagg ggctggaatt cgtcgcagct  attagcaaca  ctggtagata  cacaggctac     180
gggtcggcgg tgaagggccg tgccaccatc  tcgagggaca  acgggcagag  cacagtgagg     240
ctgcagctga acaacctcag ggctgaggac  accggcacct  actactgcgc  caaaactgct     300
ggttactatg gttggaatac tgctagtgat  atcgacgcat  ggggccacgg  gaccgaagtc     360
atcgtctcct ctctagat                                                      378

<210> SEQ ID NO 5
<211> LENGTH: 393
<212> TYPE: DNA
<213> ORGANISM: Gallus gallus

<400> SEQUENCE: 5
gccgtgacgt tggacgagtc cggggcggc   ctccagacgc  ccggaagagc  gctcagcctc      60
gtctgcaagg cctccgggtt ctctatcagc  ggttacaaca  tgggttgggt  cgacaggcg      120 cccggcaagg ggctggagtt cgtcgctggt  attggcaaca  ctggtagata  cacaggatac     180
ggggcggcgg tgaagggccg tgccaccatc  tcgagggaca  acgggcagag  cacagtgagg     240
ctgcagctga acaacctcag ggctgaggac  accggcatct  actactgcgc  caaaggtgct     300
agtcattact gttgggatgt tggttgtagt  aatattgctg  gtagtatcga  cgcatggggc     360
cacgggaccg aagtcatcgt ctcctctcta  gat                                    393

<210> SEQ ID NO 6
<211> LENGTH: 387
<212> TYPE: DNA
<213> ORGANISM: Gallus gallus

<400> SEQUENCE: 6
gccgtgacgt tggacgagtc cggggcggc   ctccagacgc  ccggaagagc  gctcagcctc      60
gtctgcaagg cctccgggtt caccttcagg  agttacaaca  tggcctgggt  cgacaggcg      120
```

```
cccggcaagg ggctggagtt cgtcgctgaa attagcggca ctggtagtac cacaaactac      180
gcgccggcgg tgaagggccg tgccaccatc tcgagggaca acgggcagag cacagtgagg      240
ctgcagctga acaacctcag ggctgaggac accggcacct acttctgcgc caaagctgct      300
ggtgcttact gtgcttggag tggttgtact gctggtagca tcgacgcatg gggccacggg      360
accgaagtca tcgtctcctc tctagat                                         387

<210> SEQ ID NO 7
<211> LENGTH: 390
<212> TYPE: DNA
<213> ORGANISM: Gallus gallus

<400> SEQUENCE: 7
gccgtgacgt tggacgagtc cggggcggc ctccagacgc ccagaggacg gctccgcctc       60
gtctgcaagg cctccgggtt caccttcagc agttacgaga tgggttgggt gcgacaggcg     120
cccggcaagg ggctggagtg ggtcgctggt attggcggca gtggtagtgg ctcagcatac     180
gggtcggcgg tgaagggccg tgccaccatc tcgagggaca acgggcagag caccgtgagg     240
ctgcagctga acaacctcag ggctgaggac accggcacct actattgcgc caaaagtact     300
acaaaatgta gttactgctg gtatggtgct actgctggta gtatcgacgc atggggccac     360
ggggccgaag tcatcgtctc tctctagat                                       390

<210> SEQ ID NO 8
<211> LENGTH: 390
<212> TYPE: DNA
<213> ORGANISM: Gallus gallus

<400> SEQUENCE: 8
gccgtgacgt tggacgagtc cggggcggc ctccagacgc ccagaggacg gctccgcctc       60
gtctgcaagg cctccgggtt cgacttcagc agttacgaga tgggttgggt gcgacaggcg     120
cccggcaagg ggctggagtg ggtcgctggt attggcggca gtggtagtgg ctcagcatac     180
gggccggcgg tgaagggccg tgccaccatc acgagggaca atgggcagag cacagtgagg     240
ctgcagctga acaacctcag ggctgaggac accggcacct actactgcgc caaaagtact     300
acaagatgta gtttctgttg gtatggtgct actgctggta gcatcgacgc atggggccac     360
ggggccgaag tcatcgtctc tctctagat                                       390

<210> SEQ ID NO 9
<211> LENGTH: 390
<212> TYPE: DNA
<213> ORGANISM: Gallus gallus

<400> SEQUENCE: 9
gccgtgacgt tggacgagtc cggggcggc ctccagacgc ccagaggacg gctccgcctc       60
gtctgcaagg cctccgggtt caccttcagc agttacgaga tgggttgggt gcgacaggcg     120
cccggcaagg ggctggagtg ggtcgctggt attggcggca gcggtagtgg ctcagcatac     180
gggtcggcgg tgaagggccg tgccaccatc tcgagggaca acgggcagag caccgtgagg     240
ctgcagctga acaacctcag ggctgaggac accggcacct actattgcgc caaaagtact     300
acaaaatgta atcactgttg gtatggtgca actgctggta gcatcgacgc atggggccac     360
gggaccgaag tcatcgtctc tctctagat                                       390

<210> SEQ ID NO 10
```

```
<211> LENGTH: 384
<212> TYPE: DNA
<213> ORGANISM: Gallus gallus

<400> SEQUENCE: 10
gccgtgacgt tggacgagtc cgggggcggc ctccatacgc ccggaggagc gctcaggctc      60
gtctgcaagg cctccgggtt ctccatcagc agttatggca tgggttgggt gcgacaggcg     120
cccggcaagg ggctggagtg ggtcgctcgt attggcagtg gtgctagtgg cacagcatac     180
gggtcggcgg tgaagggccg tgccaccatc tcgagggaca cgggcagag cacagtgagg      240 ctgcagctga caacctcag ggctgacgac accggcacct actactgcgc caaaagtgct     300
ggtgcttact gttggtatgc tggttgtcct agtagcatcg acgcatgggg ccacggggcc     360
gaagtcatcg tctcctctct agat                                            384

<210> SEQ ID NO 11
<211> LENGTH: 384
<212> TYPE: DNA
<213> ORGANISM: Gallus gallus

<400> SEQUENCE: 11
gccgtgactc ttgacgagtc cgggggcgga ctccagacgc ccggaggagc gctcaggctt      60
gtatgcaagg catccgggtt ctccatcagc agttatggca tgggttgggt gcgacaggcg     120
cccggcaagg ggctggagtg ggtcgctcgt attggcagcg gtgctagtgg cacagcatac     180
gggtcgacgg tgaagggccg tgccaccatc tcgagggaca cggacagag cacagtgagg      240 ttgcagctga caacctcag gactgaggac accggcacct actactgcgc caaaactgct     300
ggtgcttact gctggtatgc tggttgtcct agtagcatcg acgcatgggg ccacgggacc     360
gaagtcatcg tctcctcttt agat                                            384

<210> SEQ ID NO 12
<211> LENGTH: 384
<212> TYPE: DNA
<213> ORGANISM: Gallus gallus

<400> SEQUENCE: 12
gccgtgacgt tggacgagtc cgggggcggc ctccagacgc ccggcaaggg gctcagcctc      60
gtctgcaagg cctccgggtt ctccctcaat agttatggta tgggttgggt gcgacaggcg     120
cccggcaagg ggctggagtg ggtcgctcgt attggcagcg gtgctagtgg cactgcctac     180
gggtcggcgg tgaagggccg tgccaccatc tcgagggaca cgggcagag tatagtgagg      240 ctgcagctga acgacctcag ggctgaggac accgccacct actactgcgc caaaactgct     300
ggtgcttact gttggtatgc tggttgtcct agtagcatcg acgcatgggg ccacgggacc     360
gaagtcatcg tctcctctct agat                                            384

<210> SEQ ID NO 13
<211> LENGTH: 384
<212> TYPE: DNA
<213> ORGANISM: Gallus gallus

<400> SEQUENCE: 13
gccgtgacgt tggacgagtc cgggggcggc ctccagacgc ccggcaaggg gctcagcctc      60
gtctgcaagg cctccgggtt taccttcact agttatggca tgggttgggt gcgacaggcg     120
cccggcaagg ggctggagtg ggtcgctcgt attggcagcg gtgctagtgg cactgcctac     180
gcgacagcgg tgaagggccg tgccaccatc tcgagggaca cgggcagag cacagtgagg      240
```

```
ctgcagctga acgacctcag ggctgaggac accgccacct actactgcgc caaaactgct    300
ggtgcttact gttggtatgc tggttgtcct agtagcatcg acgcatgggg ccacgggacc    360
gaagtcatcg tctcctctct agat                                           384

<210> SEQ ID NO 14
<211> LENGTH: 381
<212> TYPE: DNA
<213> ORGANISM: Gallus gallus

<400> SEQUENCE: 14
gccgtgacgt tggacgagtc cggggcggc ctccagacgc cggaagagc gctcagcctc       60 gtctgcaagg cctccgggtt caccttcagc agttacgcca tgaactgggt gcgacaggcg    120
cccggcaagg ggctggagtt cgtcgctgaa attagcggca gtggtagata cacatactac    180
gcgccggcgg tgaagggccg tgccaccatc tcgaggaca acgggcagag cacagtaagc    240
ctgcagctga acaacctcag ggctgaggac accgccacct actactgcgc caaaactgct    300
gatagctgtc gttacggttg tagtgctgat cgtatcgacg catggggcca cgggaccgaa    360
gtcatcgtct cctctctaga t                                              381

<210> SEQ ID NO 15
<211> LENGTH: 381
<212> TYPE: DNA
<213> ORGANISM: Gallus gallus

<400> SEQUENCE: 15
gccgtgacgt tggacgaatc cggggcggc ctccagacgc cggaggagc gctcagcctc       60 gtctgcaagg cctccgggtt caccttcagc agttacgcca taaactgggt gcgacaggcg    120
cccggcaagg ggctggagtt cgtcgctgaa attagcggca gtggtagata cgtatactac    180
gcgccggcgg tgcagggccg tgccaccatc tcgaggaca acgggcagag cacagtgagg    240
ctgcagctga acaacctcag ggctgaggac accggcacct actactgcgc caaaactgct    300
gatagttgta gatacggttg taatgctgat cgtatcgacg catggggccg cgggaccgaa    360
gtcatcgtct cctctctaga t                                              381

<210> SEQ ID NO 16
<211> LENGTH: 381
<212> TYPE: DNA
<213> ORGANISM: Gallus gallus

<400> SEQUENCE: 16
gccgtgacgt tggacgagtc cggggcggc ctccagacgc cggaggagc gctcagcctc       60 gtctgcaagg gctccgggtt caccttcagc agccatggca tgttctgggt gcgacaggcg    120
cccggcaagg ggctggaata cgtcgctcaa attagcggca gtggtagatt aacaaactac    180
gggccggcgg tgaagggccg tgccaccatc tcgaggaca acgggcagag cacagtgagg    240
ctgcagctga acaacctcag ggctgaggac accggcacct actactgcgc caaaactgcc    300
gttaattgta gatacggttg tgcaggtgat aatatcgacg catggggcca cgggaccgaa    360
gtcatcgtct cctctctaga t                                              381

<210> SEQ ID NO 17
<211> LENGTH: 387
<212> TYPE: DNA
<213> ORGANISM: Gallus gallus
```

<400> SEQUENCE: 17

```
gccgtgacgt tggacgagtc cggggcggc ctccagacgc ccggaggagg gctcagcctc    60
gtctgcaagg cctccgggtt caccttcagc agttacggca tgggttgggt gcgacaggcg   120
cccggcaaag ggctggaatg ggtcgctgag attagcggca gtggtcgata cacaggatat   180
gggccggcgg tgcagggccg tgccaccatc tcgaggaca acgggcagag cacagtgagg    240
ctgcagctga gcgacctcag ggctgaggac accggcacct actactgcgc caaagctaca   300
gctagctgta cttacggttg tactccttat actggtgaaa tcgacgcatg gggccacggg   360
accgaagtca tcgtctcctc tctagat                                       387
```

<210> SEQ ID NO 18
<211> LENGTH: 381
<212> TYPE: DNA
<213> ORGANISM: Gallus gallus

<400> SEQUENCE: 18

```
gccgtgacgt tggacgagtc cggggcggc ctccagacgc ccggaggagc gctcagcctc    60
gtctgcaagg cctccgggtt caccttcagc agttacggca tgcagtgggt gcgccaggcg   120
cccggcaagg ggctggagtg ggtcgcgggt attagtggta gtggtagagg cacatggtac   180
gcgccggcgg tgaagggccg tgccaccatc tcgaggaca acgggcagag cacagtgagg    240
ctgcagctga acaacctcag ggctgaggac accggcacct actactgcgc caaagctgct   300
ggtagtgata cttacggtag tactggtgat aatatcgacg catggggcca cgggaccgaa   360
gtcatcgtct cctctctaga t                                             381
```

<210> SEQ ID NO 19
<211> LENGTH: 381
<212> TYPE: DNA
<213> ORGANISM: Gallus gallus

<400> SEQUENCE: 19

```
gccgtgacgt tggacgagtc cggggcggc ctccagacgc ccggaggaac gctcagcctc    60
gtctgcaagg gctccgggtt caccttcagc gattatggca tgggttggat gcggcaggcg   120
cccggcaagg ggctggaata cgtcgctgaa atcagcagca gtggtagata cacaaactac   180
gggccggcgg tgaagggccg tgccaccatc tcgagggaca acgggcagag cacagtgagg   240
ctgcagctga acaacctcag ggctgaggac accggcacct actactgcgc caaagctgct   300
ggtaggggtt actatggttg gagtgctggt accatcgacg catggggcca cgggaccgaa   360
gtcatcgtct cctctctaga t                                             381
```

<210> SEQ ID NO 20
<211> LENGTH: 381
<212> TYPE: DNA
<213> ORGANISM: Gallus gallus

<400> SEQUENCE: 20

```
gccgtgacgt tggacgagtc cggggcggc ctccagacgc ccggaggaac gctcagcctc    60
gtctgcaagg cctccgggtt cacttcagc agttatggca tgggatggat gcgacaggcg   120
cccggcaagg ggctcgaata cgtcgctgaa agcagcagca gtggtagata cacaaactac   180
gggccggcgg tgaagggccg tgccaccatc tcgaggaca acgggcagag cacagtgagg    240
ctgcagctga acaacctcag ggctgaggac accggcacct actactgcgc caaagctgct   300
ggtagtggtt actatggttg gagtgctggt agcatcgacg catggggcca cgggaccgaa   360
```

```
gtcatcgtct cctctctaga t                                              381
```

<210> SEQ ID NO 21
<211> LENGTH: 396
<212> TYPE: DNA
<213> ORGANISM: Gallus gallus

<400> SEQUENCE: 21

```
gccgtgacgt tggacgagtc cgggggcggc ctccagacgc ccggaggaac gctcagcctc     60
gtctgcaagg cctccgggtt caccttcagc agcttcaaca tattctgggt gcgacaggcg    120
cccggcaagg ggctggaatt cgtcgcagct attaacaagg atggtagttt cacacactac    180
gggtcggcgg tgaagggccg tgccaccatc tcgaggaca acgggcagag cacattgagg     240
ctgcagctga acgacctcgg ggctgaggac gccggcacct acttctgcgc cagaagtcct    300
ggtggtttta gttgtgctgg tggttggtgc ggtgcttatg ctgatggcat cgacgcatgg    360
ggccacggga ccgaagtcat catctcctct ctagat                              396
```

<210> SEQ ID NO 22
<211> LENGTH: 396
<212> TYPE: DNA
<213> ORGANISM: Gallus gallus

<400> SEQUENCE: 22

```
gccgtgacgt tggacgagtc cgggggcggc ctccagacgc ccggaggagg gctcagcctc     60
gtctgcaagg gctccgggtt cgacttcagc agttacaaca tgttctgggt gcgacaggcg    120
cccggcaagg ggctggagtt cgtcgcagct attagcagca ctggtagtta cacacactac    180
gggccggcgg tgaagggccg tgccaccatc tcgaggaca acgggcagag cacagtgagg     240
ctgcagctga acaacctcag ggctgaggac accgccatct actactgcgc cagaagtcct    300
ggtggtttta gttgtgctgg tggttggtgt ggtggttatg ctgatagcat cgacgcatgg    360
ggccacggga ccgaagtcat cgtctcctct ctagat                              396
```

<210> SEQ ID NO 23
<211> LENGTH: 390
<212> TYPE: DNA
<213> ORGANISM: Gallus gallus

<400> SEQUENCE: 23

```
gccgtgacgt tggacgagtc cgggggcggc ctccagacgc ccggaggaac gctcagcctc     60
gtctgcaagg cctccgggtt caccttcagc agcttcaaca tgcagtgggt gcgacaggcg    120
cccggcaagg ggctggagtt cgtcgcgggt attgacaata ttggtagaaa aacatcatat    180
gggtcggcgg tgaagggccg tgccaccatc tcgagggaca acgggcagag cacagtgagg    240
ctgcagctga ataacctcag ggccgaggac accgccacct acttctgcgc caaaggtgct    300
gggagtagtg cttacagttg tgcttttttgt tatcctggtt ggatcgacgc atggggccac    360
gggaccgaag tcatcgtctc ctctctagat                                     390
```

<210> SEQ ID NO 24
<211> LENGTH: 375
<212> TYPE: DNA
<213> ORGANISM: Gallus gallus

<400> SEQUENCE: 24

```
gccgtgacgt tggacgagtc cgggggcggc ctccagacgc ccggaggagc gctcagcctc     60
```

```
gtctgcaagg cctccgggtt caccttcagc agccatggca tgggttgggt gcgacaggcg    120
cccggcaaag ggctggagtg ggtcgctggt attgagaatg atggtagtat aacaggctac    180
ggggcggcgg tgaagggccg tgccaccatc tcgaggaca acgggcagag cacagtgagg      240
ctgcagctga caacctcag ggctgaggac accggcacct acttctgcgc caaacgcagt     300
ggtagtggtt gttgtaatgc ttacgctatc gacgcatggg ccacgggac cgaagtcatc     360 gtctcctctc tagat                                                      375

<210> SEQ ID NO 25
<211> LENGTH: 393
<212> TYPE: DNA
<213> ORGANISM: Gallus gallus

<400> SEQUENCE: 25
gccgtgacgt tggacgagtc cggggcggc ctccagacgc ccggaggagg gctcagcctc      60
gtctgcaagg cctccgggtt caccttcagc agttacgcca tgtactgggt gcgacagacg    120
cccggcaagg ggctggagtt cgtcgccggt attgacagcg gtgatggtag atactcaaaa    180
tacgggccgg cggtggatgg ccgtgccacc atgtcgaggg acaacgggca gagcacagtg    240
aggctgcagc tgaacgacct cagggctgag gactccggca cctactactg cgccaagggt    300
gcagtaactg gttactgtgg ttggaatgct tgcactgttg ctaacatcga cacatggggc    360
cacgggaccg aagtcatcgt ctcctctcta gat                                  393

<210> SEQ ID NO 26
<211> LENGTH: 378
<212> TYPE: DNA
<213> ORGANISM: Gallus gallus

<400> SEQUENCE: 26
gccgtgacgt tggacgagtc cggggcggc ctccagacgc ccggaggagg gctcagcctc      60
gtctgcaagg cctccgggtt ctccttcagc agttattcca tgcagtgggt gcgacaggcg   120
cccggcaagg ggctggactg ggtcgctggt attagtggca ctggtagaca cagaaactac    180
gggtcggcgg tggagggccg tgccaccatc tcgagggaca acgggcagag tacagtgagg    240
ctgcagctgg acaacctcag ggctgaggac accggcacct actactgcgc cagagctcct    300
tgtactggtt gtggttggag tgccggtagc atcgacgcat ggggccacgg gaccgaagtc    360
atcgtctcct ctctagat                                                   378

<210> SEQ ID NO 27
<211> LENGTH: 375
<212> TYPE: DNA
<213> ORGANISM: Gallus gallus

<400> SEQUENCE: 27
gccgtgacgt tggacgagtc cggggcggc ctccagacgc ccggaggagg gctcagcctc      60
gtctgcaagg cctccgggtt caccttcagc agttatcaga tgcactggat acgacaggct   120
cccggcaagg ggctggagtg ggtcggtgtt attagcagca gaggtagtag cacaaactac    180
ggggctgcgg tgaagggccg tgccaccatc tcgagggaca acgggcagag cacagtgagg    240
ctgcaactga caacctcag ggctgaggac accgccacct actactgcgc caaaagtggt    300
tatgcttgtg gttggagtgg tggttgtatc gacgcatggg ccacgggac cgaagtcatc    360 gtctcctctc tagat                                                      375
```

<210> SEQ ID NO 28
<211> LENGTH: 381
<212> TYPE: DNA
<213> ORGANISM: Gallus gallus

<400> SEQUENCE: 28

| | | | | | |
|---|---|---|---|---|---|
| gccgtgacgt | tggacgagtc | cggggcggc | ctccaggcgc | cggaggagg | gctcagcctc | 60 |
| gtctgcaagg | cctccgggtt | caccttcagc | agccatggca | tgggctgggt | gcgacaggca | 120 |
| cccggcaagg | ggctggaata | cgtcgcgagt | attagcacca | gaggtagtag | cacatactac | 180 |
| ggggcggcgg | tgaagggccg | tgccaccatc | tcgaggaca | acgggcagag | cacagtgagg | 240 |
| ctgcagctga | caacctcag | ggctgaggac | accgccacct | actactgcgc | caaaactggt | 300 |
| tatgcatgta | gttatagtta | tcatactgcc | tgtatcgacg | catggggcca | cgggaccgaa | 360 |
| gtcatcgtct | cctctctaga | t | | | | 381 |

<210> SEQ ID NO 29
<211> LENGTH: 372
<212> TYPE: DNA
<213> ORGANISM: Gallus gallus

<400> SEQUENCE: 29

| | | | | | |
|---|---|---|---|---|---|
| gccgtgacgt | tggacgagtc | cggggcggc | ctccagacgc | ccggaggagc | gctcagcctc | 60 |
| gtctgcaagg | cctccgggtt | caccttcagg | agtcatcaga | tgttctgggt | gcgacaggct | 120 |
| cccggcaagg | ggctggaata | cgtcggtcaa | attaccacca | ggggtactac | tacatattac | 180 |
| ggggcggcgg | tgacgggccg | cgccaccatc | tcgaggaca | acgggcagaa | cacagtgagg | 240 |
| ctgcagctaa | caacctcag | ggctgaggac | accggcacct | acttctgcgc | caaagctgct | 300 |
| tacggttata | gttatgttag | taccatcgac | gcatggggcc | acgggaccga | agtcatcgtc | 360 |
| tcctctctag | at | | | | | 372 |

<210> SEQ ID NO 30
<211> LENGTH: 378
<212> TYPE: DNA
<213> ORGANISM: Gallus gallus

<400> SEQUENCE: 30

| | | | | | |
|---|---|---|---|---|---|
| gccgtgacgt | tggacgagtc | cggggcggc | ctccagacgc | ccggaggagg | gctcagcctc | 60 |
| gtctgcaggg | cctccgggtt | catcttcagc | agtcatccca | tggtgtgggt | gcgacaggcg | 120 |
| cccggcaagg | ggctggaatg | gtcgcagca | attaccacaa | gaggtactag | cgcatactac | 180 |
| gggccggcgg | tgaagggccg | tgccaccatc | tcgagggaca | acgggcagag | cacagtgagg | 240 |
| ctgcagctga | acagcctcag | ggctgaggac | accggcacct | actactgcgc | cagaagtggt | 300 |
| tatggttaca | ctggtagtga | tgctggtaac | atcgacacat | ggggccacgg | gaccgaagtc | 360 |
| atcgtctcct | ctctagat | | | | | 378 |

<210> SEQ ID NO 31
<211> LENGTH: 411
<212> TYPE: DNA
<213> ORGANISM: Gallus gallus

<400> SEQUENCE: 31

| | | | | | |
|---|---|---|---|---|---|
| gccgtgacgt | tggacgagtc | cggggcggc | ctccagacgc | ccggaggagc | gctcagcctc | 60 |
| gtctgcaagg | cctccgggtt | cgccttcagc | agatacgcca | tgaactgggt | gcgacaggcg | 120 |
| cccggcaagg | ggctggagtg | ggtcgcgggt | gtcagaaatg | ttgggagtag | cacaaactac | 180 |

```
gcgccggcag tgaagggccg tgccaccatc tcgagggaca acgggcagag cacactgagg    240
ctgcagctga acaacctcag ggctgaggac accggcatct actactgcgc caaagctgcc    300
ggtagtggtt actgtgcttg gtgggctgat gctttgactt gtggtggtta taagactcat    360
gacatcgacg catgggccca cgggaccgaa gtcatcgtct cctctctaga t             411
```

<210> SEQ ID NO 32
<211> LENGTH: 384
<212> TYPE: DNA
<213> ORGANISM: Gallus gallus

<400> SEQUENCE: 32

```
gccgtgacgt tggacgagtc cgggggcggc ctccagacgc ccggaggagc gctcagcctc     60
gtctgcaagg cctccgggtt caccttcagc agttatggca tgggctgggt gcgacaggcg    120
cctggcaaag ggctggaatg ggtcgctggt attgacaaca ttggtagata cacaaactac    180
gggccggcgg tgaagggccg tgccaccatc tcgagggaca cgggcagag cacagtgagg     240 ctgcagctga acaacctcag ggctgaggac accgccacct actactgcgc caaatctgct    300
gctagtggta gttggtccta ttacggtact ggttggatcg acggatgggg ccacgggacc    360
gaagtcatcg tctcctctct agat                                           384
```

<210> SEQ ID NO 33
<211> LENGTH: 384
<212> TYPE: DNA
<213> ORGANISM: Gallus gallus

<400> SEQUENCE: 33

```
gccgtgacgt tggacgagtc cgggggcggc ctccagacgc ccggaggagc gctcagcctc     60
gtctgcaagg cctccgggtt caccttcgcc atttatgcca tgcactgggt gcgacaggcg    120
cccgacaagg ggctggagtt cgtcgctggt attagcagtg atggtagtag gacgaaatac    180
ggggctgcgg tgaagggccg tgccaccatg tcgagggaca acgggcagag cacagtgagg    240
ctgcagctga acaacctcag gactgaggac accgccacct acttctgcgc caaaactgct    300
ggtagttgga gtcgctataa tggtcttcat tctaatatcg acacatgggg ccacgggacc    360
gaagtcatcg tctcctctct agat                                           384
```

<210> SEQ ID NO 34
<211> LENGTH: 381
<212> TYPE: DNA
<213> ORGANISM: Gallus gallus

<400> SEQUENCE: 34

```
gccgtgacgt tggacgagtc cgggggcggc ctccagacgc ccggaggagg gctcagcctc     60
gtctgcaagg cctccgggtt caccttcacc gattatggca tgggctggat gcgacaggca    120
cccgggaagg ggctggaata cgtcgttggt attagcaaca ctggtagata cacatactac    180
gggtcggcgg tgaagggccg tgccaccatc tcaagggaca cgggcagag cacagtgagg     240 ctgcagctga acaacctcag ggctgaggac accgccacct actactgcgc caaatctgct    300
gggagttggt ggcattatac tggtgctgat aatatcgacg catgggccca cgggaccgaa    360
gtcatcgtct cctctctaga t                                              381
```

<210> SEQ ID NO 35
<211> LENGTH: 384
<212> TYPE: DNA
<213> ORGANISM: Gallus gallus

<400> SEQUENCE: 35

```
gccgtgacgt tggacgagtc cggggcggc ctccagacgc ccggaggagg gctcagcctc    60
gtctgcaagg cctccgggtt caccttcagc agttacgcca tgaactgggt gcgacaggcg   120
cccggcaagg ggctggagtg ggtcgccagt attaacagtg ctggtagtta cacacactac   180
gggtcggcgg tgaagggccg tgccaccatc tcaaggaca acgggcagag cacagtgagg    240
ctgcagctga caacctcagg gctgaggac accggcacct actactgcgc cagaggaggt    300
ggtggttgtg gtatttggag ttgtggttct tatgctggtg aaatcgacgc atggggccac   360
gggaccgaag tcatcgtctc ctcc                                         384
```

<210> SEQ ID NO 36
<211> LENGTH: 327
<212> TYPE: DNA
<213> ORGANISM: Gallus gallus

<400> SEQUENCE: 36

```
acagcgctga ctcagccgtc ctcggtgtca gcgaacccgg gagaaaccgt cgagatcacc    60
tgctccgggg ataccaccta ctatggctgg taccagcaga aggcacctgg cagtgcccct   120
gtcactctga tctatgacaa caccaacaga ccctcggaca tcccttcacg attctccggt   180
tccagatccg gctccacagc cacattaacc atcactgggg tccaagccga ggacgaggct   240
gtctatttct gtgggagtgc agacaccagt ggttatgctg gtatatttgg ggccgggaca   300
accctgaccg tcctaggtgc ggccgca                                      327
```

<210> SEQ ID NO 37
<211> LENGTH: 330
<212> TYPE: DNA
<213> ORGANISM: Gallus gallus

<400> SEQUENCE: 37

```
acagcgctga ctcagccgtc ctcggtgtca gcgaacccgg gagaaaccgt cgagatcacc    60
tgctccgggg gtagtggcag ctactatggc tggtaccagc agaagccacc tggcagtgcc   120
cctgtcactg tgatctataa caacaacaac agaccctcgg acatcccttc acgattctcc   180
ggttccagat ccggctccac agccacatta accatcactg gggtccaagc cgacgacgag   240
gctgtctatt tctgtgggag tgaagacagc acaggatatg ttggtatatt tggggccggg   300
acaaccctga ccgtcctagg tgcggccgca                                   330
```

<210> SEQ ID NO 38
<211> LENGTH: 324
<212> TYPE: DNA
<213> ORGANISM: Gallus gallus

<400> SEQUENCE: 38

```
acagcgctga ctcagctgtc ctcggtgtca gcgaacccgg gagaaaccgt cgagatcacc    60
tgctccgggg atagcagcta ctatggctgg tatcagcaga aggcacctgg cagtgcccct   120
gtcactctga tctatgacaa caccaacaga ccctcggaca tctcttcacg attctccggt   180
tccaaatccg gctccacagc cacattaacc atcactgggg tccaagccga cgacgaggct   240
gtctattact gtgggagtgc aggcagcagc catgttggta tgtttggggc cgggacaacc   300
ctgaccgtcc taggtgcggc cgca                                         324
```

<210> SEQ ID NO 39

```
<211> LENGTH: 324
<212> TYPE: DNA
<213> ORGANISM: Gallus gallus

<400> SEQUENCE: 39
acagcgctga ctcagccgtc ctcggtgtca gcgaacccgg gagaaaccgt cgagatcacc      60
tgctccgggg atagcagcta ctatggctgg tatcagcaga aggcacctgg cagtgcccct     120
gtcactctga tctatgacaa caccaacaga ccctcggaca tctcttcacg attctccggt     180
tccaaatccg gctccacagc cacattaacc atcactgggg tccaagccga cgacgaggct     240
gtctattact gtgggagtgc aggcagcagc catgttggta tgtttggggc cgggacaacc     300
ctgaccgtcc taggtgcggc cgca                                            324

<210> SEQ ID NO 40
<211> LENGTH: 321
<212> TYPE: DNA
<213> ORGANISM: Gallus gallus

<400> SEQUENCE: 40
acagcgctga ctcagccgtc ctcggtgtcg gcaaacctgg gaggaaccgt caagatcacc      60
tgctccgggg atagcagcta ctatggttgg taccagcaga aggcacctgg cagtgcccct     120
gtcactgtaa tctatgacaa caccaacaga ccctcgggta tcccttcacg attctccggt     180
tccaaatccg gctccacagc cacattaacc atcactgggg tccgagccga cgacgaggct     240
gtctattact gtgggaatac agacagcagt ggtgctatat ttggggccgg acaaccctg     300 accgtcctag gtgcggccgc a                                              321

<210> SEQ ID NO 41
<211> LENGTH: 324
<212> TYPE: DNA
<213> ORGANISM: Gallus gallus

<400> SEQUENCE: 41
acagcgctga ctcagccgtc ctcggtgtca gcgaacccgg gagaaaccgt caagatcacc      60
tgctccgggg gtagcaacaa ctatggctgg taccagcaga agtctcctgg cagtgcccct     120
gtcactctga tctatgacaa caccaacaga ccctcgaaca tcccttcacg attttccggt     180
tccaaatccg gctccacagc cacattaacc atcactgggg tccaagccga cgacgaggct     240
gtctattact gtgggagtgc agacagcagt agtactggta tatttggggc cgggacaacc     300
ctgaccgtcc taggtgcggc cgca                                            324

<210> SEQ ID NO 42
<211> LENGTH: 327
<212> TYPE: DNA
<213> ORGANISM: Gallus gallus

<400> SEQUENCE: 42
acagcgctga ctcagccgtc ctcggtgtca gcaaacccgg gagaaaccgt caagatcacc      60
tgctccgggg gtagtggcag ctactatggc tggtaccagc agaagtctcc tggcagtgcc     120
cctgtcactc tgatctatga caacgacaag agaccctcgg gcatcccttc acgattctcc     180
ggttccacat ctggctccac gggcacatta accatcactg gggtccaagc cgaggacgag     240
gctgtctatt attgtgggag cagggacagc agctatgttg gtatgtttgg ggccgggaca     300
accctgaccg tcctaggtgc ggccgca                                         327
```

```
<210> SEQ ID NO 43
<211> LENGTH: 327
<212> TYPE: DNA
<213> ORGANISM: Gallus gallus

<400> SEQUENCE: 43
acagcgctga ctcagccgtc ctcggtgtca gcaaatccag agaaaccgt caagatcacc      60 tgctccgggg gttacaacta ctatggctgg taccagcaga agtcacctgg cagtgtccct    120
gtcactctga tctatgacaa caccaacaga ccctcgaaca tcccttcacg attctccggt    180
tccacatctg gctccacagg cacattaacc atcactgggg tccaagccga cgacgaggct    240
gtctatttct gtgggagtgc agacagcagc agcactagtg cttcatttgg ggccgggaca    300
accctgaccg tcctaggtgc ggccgca                                        327

<210> SEQ ID NO 44
<211> LENGTH: 324
<212> TYPE: DNA
<213> ORGANISM: Gallus gallus

<400> SEQUENCE: 44
acagcgctga ctcagccgtc ctcggtgtca gcgaacccgg gaggaaccgt caagctcacc     60
tgctccgggg atagcagcta ctatggctgg taccatcaga agtctcctgg cagtgccct    120 gtcactgtga tctatgacaa caccaacaga ccctcgaaca tcccttcacg attctccggt    180
tccctatccg gctccacagc cacattaacc atcactgggg tccaagccga ggacgaggct    240
gtctattact gtgggagtga agacaacacc agtactgctg catttggggc cgggacaacc    300
ctgaccgtcc taggtgcggc cgca                                           324

<210> SEQ ID NO 45
<211> LENGTH: 324
<212> TYPE: DNA
<213> ORGANISM: Gallus gallus

<400> SEQUENCE: 45
acagcgctga ctcagccgtc ctcggtgtca gcgaacccgg gagaaaccgt caagatcacc    60
tgctccgggg atagcaccta ctatggctgg taccagcaga aggcacctgg cagtgcccct   120
gtcactctga tctatgacaa caccaacaga ccctcgaaca tcccttcacg attctccggt   180
tccctatctg gctccacagc cacattaacc atcactgggg tccaagccga ggacgaggct   240
gtctatttct gtgggggtgc agacagcagc agtgctgctt catttggggc cgggacagcc   300
ctgaccgtcc taggtgcggc cgca                                          324

<210> SEQ ID NO 46
<211> LENGTH: 330
<212> TYPE: DNA
<213> ORGANISM: Gallus gallus

<400> SEQUENCE: 46
acagcgctga ctcaaccgtc ctcggtgtca gcaaacctgg gaggaaccgt cgagatcacc    60
tgctccggga gtagtggcag ctactatggc tggtaccagc agaaggcacc tggcagtgcc   120
cctgtcactc tgatctatga caacaccaac agacctcag acatcccttc acgattctcc   180
ggttccaaat ccggctccac agccacatta accatcactg gggtccgagc cgaggacgag   240
gctgtctatt actgtggaag tgccgacagc agcagtagtg aagctgcatt tggggccggg   300
acaaccctga ccgtcctagg tgcggccgca                                    330
```

<210> SEQ ID NO 47
<211> LENGTH: 330
<212> TYPE: DNA
<213> ORGANISM: Gallus gallus

<400> SEQUENCE: 47

```
acagcgctga ctcagccgtc ctcggtgtca gcgaacccgg gagaaaccgt cgagatcacc    60
tgctccgggg gtggcagcag ctatggctgg taccagcaga agtctcctgg cagtgcccct   120
gtcactgtga tctatgacaa caccaacaga ccctcgaaca tcccttcacg attctccggt   180
tccctatccg gctccgcaaa cacgttaacc atcactgggg tccaagccga cgacgaggct   240
gtctattact gtgggagtgg agacagcagt gctgcttatg ttcctatatt tggggccggg   300
acaacccctga ccgtcctagg tgcggccgca                                    330
```

<210> SEQ ID NO 48
<211> LENGTH: 324
<212> TYPE: DNA
<213> ORGANISM: Gallus gallus

<400> SEQUENCE: 48

```
acagcgctga ctcagccgtc ctcggtgtca gcaaacccgg gagaaaccgt cgagatcacc    60
tgcagtggag gtatcggcca ctatggctgg taccagcaga aggcacctgg cagtgcccct   120
gtcactgtga tttatgatag cagcagcaga ccctcggaca tcccttcacg attctccggt   180
tccaaatccg gctccacggg cacattaacc atcactgggg tccaagccga cgacgaggct   240
gtctattact gtgggagtgg aggcagcaat ggtgctggta tatttggggc cgggacaacc   300
ctgaccgtcc taggtgcggc cgca                                           324
```

<210> SEQ ID NO 49
<211> LENGTH: 324
<212> TYPE: DNA
<213> ORGANISM: Gallus gallus

<400> SEQUENCE: 49

```
acagcgctga ctcagccgtc ctcggtgtca gcaaacccag gagaaaccgt caagatcacc    60
tgctccgggg atgggagcag ctatggctgg tatcagcaga agtcacctgg cagtgcccct   120
gtcactgtga tctatgacag caccaacaga ccctgggaca tcccttcacg attctccggt   180
tccaaatccg gctccacggg cacattaacc atcactgggg tccaagccga ggacgaggct   240
gtctatttct gtgggactac agacagcacc agtgctgcta tatttggggc cgggacaacc   300
ctgaccgtcc taggtgcggc cgca                                           324
```

<210> SEQ ID NO 50
<211> LENGTH: 336
<212> TYPE: DNA
<213> ORGANISM: Gallus gallus

<400> SEQUENCE: 50

```
acagcgctga ctcagccgtc ctcggtgtca gcgaacccgg gagaaaccgt caagatcacc    60
tgctccgggg gtggtagcag cagctactat ggctggtacc agcagaaggc acctggcagt   120
gcccctgtca ctgtgatcta tgacaacacc aacagaccct cggcatccc ttcacgattt    180
tccggttcca aatccggctc cacagccaca ttaaccatca ctggggtcca agccgacgac   240
gaggctgtct attactgtgg tggtgggagt gcagacagca gtggtgctgg tatatttggg   300
gccgggacaa ccctgaccgt cctaggtgcg gccgca                              336
```

<210> SEQ ID NO 51
<211> LENGTH: 330
<212> TYPE: DNA
<213> ORGANISM: Gallus gallus

<400> SEQUENCE: 51

```
acagcgctga ctcagccgtc ctcggtgtca gcaaacccgg gagaaaccgt cgtgatcacc      60
tgctccgggg ataccttatac ttatggctgg tatcagcaga agtcacctgg cagtgcccct    120
gtcactgtga tctatgctaa caccaacaga ccctcggaca tcccttcacg attctccggt    180
tctggatccg gctccacagc cacattaacc atcactgggg tccaagccga ggacgaggct    240
gtctattact gtggtggctg ggacagcagt gctggttatt ctggtatatt tggggccggg    300
acaaccctga ccgtcctagg tgcggccgca                                      330
```

<210> SEQ ID NO 52
<211> LENGTH: 324
<212> TYPE: DNA
<213> ORGANISM: Gallus gallus

<400> SEQUENCE: 52

```
acagcgctga ctcagccgtc ctcggtgtca gcgaacccgg gagaaaccgt cgagatcacc      60
tgctccgggg atagcagcta ctatggctgg tatcagcaga agtcacctgg cagtgcccct    120
gtcactgtga tctataacaa cgacaacaga ccctcggaca tcccttcacg attctccggt    180
tccagatccg gctccacaaa cacattaacc atcactgggg tccaagccga cgacgaggct    240
gtctattact gtgggagtgc agacagcagt actgatggta tatttggggc cgggacaacc    300
ctgaccgtcc taggtgcggc cgca                                            324
```

<210> SEQ ID NO 53
<211> LENGTH: 324
<212> TYPE: DNA
<213> ORGANISM: Gallus gallus

<400> SEQUENCE: 53

```
acagcgctga ctcagccgtc ctcggtgtca gcgaacccgg gagaaaccgt cgagatcacc      60
tgctccgggg gtagcaacaa ctatggctgg ttccagcaga agtctcctgg cagtgcccct    120
gtcactgtga tctatgacaa caccaacaga ccctcggaca tcccttcacg attctccggt    180
tccacatccg gctccacaag cacattaacc atcactgggg tccaagccga cgacgaggct    240
gtctatttct gtgggagtgc agacaccaac tatgattta tatttggggc cgggacaacc    300
ctgaccgtcc taggtgcggc cgca                                            324
```

<210> SEQ ID NO 54
<211> LENGTH: 324
<212> TYPE: DNA
<213> ORGANISM: Gallus gallus

<400> SEQUENCE: 54

```
acagcgctga ctcagccgtc ctcggtgtca gcaaacccgg gagaaaccgt cgagatcacc      60
tgctctgggg gtcactatag ctacggctgg ttccagcaga aggcacctgg cagtgcccct    120
gtcactgtga tctataggaa cgacaagaga ccctcgggca tcccttcacg attctccggt    180
tccctatccg gctccacggg cacattaacc atcactgggg tccaagccga cgacgaggct    240
gtctactact gtgggagtgc agacagcagc tatgttgcta tatttggggc cgggacaacc    300
```
ctgaccgtcc taggtgcggc cgca                                              324

<210> SEQ ID NO 55
<211> LENGTH: 330
<212> TYPE: DNA
<213> ORGANISM: Gallus gallus

<400> SEQUENCE: 55
acagcgctga ctcagccgtc ctcggtgtca gcaaacctgg gaggaaccgt cgagatcacc        60
tgctctggga ggaaccgtca ctatagttac ggctggttcc agcagaaggc acctggcagt       120
gcccttgtca ctgtgatcta tagcaacaac aagagaccct cggacatccc ttcacgattc       180
tccggttccc tatccggctc cacaaacaca ttaaccatca ctgggtccaa gccgacgac        240 gaggctgtct attactgcgg gagtgcagac agcagcaatg ttgctatatt tggggccggg       300
acaaccctga ccgtcctagg tgcggccgca                                        330

<210> SEQ ID NO 56
<211> LENGTH: 324
<212> TYPE: DNA
<213> ORGANISM: Gallus gallus

<400> SEQUENCE: 56
acagcgctga ctcaaccgtc ctcggtgtca gcaaacctgg gaggaaccgt cgagatcacc        60
tgctccgggg gtcactattc ctacggctgg ttccagcaga aggcacctgg cagtgcccct       120
gtcactgtga tctataggaa cgacaagaga ccctcggaca tcccttcacg attctccggt       180
tccctatccg gctccacggg cacattaacc atcactgggg tccaagccga cgacgaggct       240
gtctatttct gtgggagtgc agacagcacc tatgttggta tatttggggc cgggacaacc       300
ctgaccgtcc taggtgcggc cgca                                              324

<210> SEQ ID NO 57
<211> LENGTH: 327
<212> TYPE: DNA
<213> ORGANISM: Gallus gallus

<400> SEQUENCE: 57
acagcgctga ctcagccgtc ctcggtgtca gcaaacctgg gaggaaccgt cgagatcacc        60
tgctccgggg gtagtggcag ctatggctgg tatcagcaga agtcacctgg cagtgcccct       120
gtcactgtga tctatgctaa caccaacaga ccctcggaca tcccttcacg attctccggt       180
tccacatctg gctccacggg cacattaacc atcactgggg tccaagccga cgacgaggct       240
gtctatttct gtgggagcta cgacagcagt aatactgctg gtatatttgg ggccgggaca       300
accctgaccg tcctaggtgc ggccgca                                           327

<210> SEQ ID NO 58
<211> LENGTH: 342
<212> TYPE: DNA
<213> ORGANISM: Gallus gallus

<400> SEQUENCE: 58
acagcgctga ctcagccgtc ctcggtgtca gcaaacccgg gagaaaccgt caagatcacc        60
tgctccgggg gtggcagcta tgctggaagt tactattatg ctggtatcag caaaaggcca      120
tctggcagtg cccctgtcac tgtgatctat agcaacgaca agagaccctc ggacatcct       180 tcacgattct ccggttccac atccggctcc acgggcacat taaccatcac tggggtccaa      240
gccgacgacg aggctgtcta ttactgtggg agctgggaca gcagcagtta tgatggtata      300

```
tttggagccg aacaaccct gaccgtccta ggtgcggccg ca                        342

<210> SEQ ID NO 59
<211> LENGTH: 327
<212> TYPE: DNA
<213> ORGANISM: Gallus gallus

<400> SEQUENCE: 59
acagcgctga ctcagccgtc ctcggtgtca gcgaacccgg agaaaccgt cgagatcacc     60 tgctccgggg gcaactatgg ctggtatagc tggcaccagc agaagtctcc tggcagtgcc   120
cctgtcactc tgatctatga aaacaacaag agactctcgg acatcccttc acgattctcc   180
ggttccaaat ccggctccac agccacatta accatcactg gggtccaagc cgaggacgag   240
gctgtctatt tctgtgggag tacagacagc agctatgttg gtatatttgg ggccgggaca   300
accctgaccg tcctaggtgc ggccgca                                       327

<210> SEQ ID NO 60
<211> LENGTH: 330
<212> TYPE: DNA
<213> ORGANISM: Gallus gallus

<400> SEQUENCE: 60
acagcgctga ctcagccgtc ctcggtgtca gcaaacccgg agaaaccgt caagatcacc     60 tgctccgggg gtagcagcag ctataggtat ggctggtacc agcagaagtc tcctggcagt   120 gccccctgtca ctctgatcta tgctaacacc aacagaccct caaacatccc ttcacgattc   180
tccggttcca atctggctc cacacacaca ttaaccatca ctgggggtcca agccgacgac   240 gaggctgtct attactgtgg gagtgcagac agcagctatg ttggtatatt tggggccggg   300
acaaccctga ccgtcctagg tgcggccgca                                    330

<210> SEQ ID NO 61
<211> LENGTH: 309
<212> TYPE: DNA
<213> ORGANISM: Gallus gallus

<400> SEQUENCE: 61
acagcgctga ctcagccgtc ctcggtgtca gcgaacccgg agaaaccgt caagatcacc     60 tgctccgggg gtggcagcag ctatggctgg taccagcaga aggcacctgg cagtgcccct   120
gtcactgtga tctatggtaa caccaacaga ccctcgaaca tcccttcacg attttccggt   180
tccaaatccg gctccacagc cacattaacc atcactgggg tccaagccga cgacgaggct   240
gtctatttct gtgggagtgc agacagcagc ggggccggga caaccctgac cgtcctaggt   300
gcggccgca                                                           309

<210> SEQ ID NO 62
<211> LENGTH: 327
<212> TYPE: DNA
<213> ORGANISM: Gallus gallus

<400> SEQUENCE: 62
gcgctgactc agccgtcctc ggtgtcagca aacccgggag gaaccgtcaa gatcacctgc     60
tccgggagta gtggcaacta tggctggtat cagcagaagt ctcctggtag tgcccttgtc   120
actgtgatct atagcaacga caagagaccc tcagacatcc cttcacgatt ctccggttcc   180
aaatccggct ccacgggcac attaaccatc actgggggtcc aagccgacga cgaggctgtc   240
```

```
tatttctgtg ggagtgaaga cagcagcagt attggtgatg gtatatttgg ggccgggaca    300
accctgaccg tcctaggtgc ggccgca                                        327

<210> SEQ ID NO 63
<211> LENGTH: 324
<212> TYPE: DNA
<213> ORGANISM: Gallus gallus

<400> SEQUENCE: 63
acagcgctga ctcagccgtc ctcggtgtca gcaaacctgg gaggaaccgt caagatcacc    60
tgctccgggg gtagcaacaa ctatggctgg ttccagcaga agtcacctgg cagtgcccct    120
gtcactgtga tctatagcaa caaccagaga ccctcgaaca tcccttcacg attctccggt    180
tccaaatccg gctccacggg cacattaacc atcactgggg tccaagccga cgacgaggct    240
gtctattact gtgggagtgg agacagcagc tatattggta tatttggggc cgggacaacc    300
ctgaccgtcc taggtgcggc cgca                                           324

<210> SEQ ID NO 64
<211> LENGTH: 321
<212> TYPE: DNA
<213> ORGANISM: Gallus gallus

<400> SEQUENCE: 64
acagcgctga ctcagccgtc ctcggtgtca gcaaacctgg gaggaaccgt cgagatcacc    60
tgctccggga gtagtggcag ctatggctgg tatcagcaga agtctcctga cagtgcccct    120
gtcagtgtga tctatagcac caaccagaga ccctcgaaca tcccttcacg attctccggt    180
tccaaatccg gctccacagc cacattaacc atcactgggg tccaagccga cgacgaggct    240
gtctattact gtgggagcta cgaagacagt agcaatacta ttggggccgg gacaaccctg    300
accgtcctag gtgcggccgc a                                              321

<210> SEQ ID NO 65
<211> LENGTH: 324
<212> TYPE: DNA
<213> ORGANISM: Gallus gallus

<400> SEQUENCE: 65
acagcgctga ctcagccgtc ctcggtgtca gcgaacccgg gagaaaccgt caagatcacc    60
tgctccgggg gtagtggcaa ctatggctgg tatcagcaga aggcacctgg cagtgcccct    120
gtcactgtga tctctggtag taccctgaga ccctcggaca tcccttcacg attctccggt    180
tccaaatccg gctccacggg cacattaacc atcactgggg tccaagccga ggacgaggct    240
gtttatttct gtgggagtgc agacagcagc tatgctggta tatttggggc cgggacaacc    300
ctgaccgtcc taggtgcggc cgca                                           324

<210> SEQ ID NO 66
<211> LENGTH: 330
<212> TYPE: DNA
<213> ORGANISM: Gallus gallus

<400> SEQUENCE: 66
acagcgctga ctcagccgtc ctcggtgtca gcaaacccgg gagaaaccgt caagatcacc    60
tgctccgggg gtagcaatta ctactatggc tggtaccagc agaagtctcc tggcagtgcc    120
cctgtcactg tgatctatgc taacaccaac agaccctcgg acatcccttc acgattctcc    180
ggttccctat ccggctccac agccacatta accatcactg ggtccaagc cgacgacgag    240
```

```
gctgtctact actgtgggag tgcagacagc agcacttatg ctggtatatt tggggccggg      300
acaaccctga ccgtcctagg tgcggccgca                                       330

<210> SEQ ID NO 67
<211> LENGTH: 330
<212> TYPE: DNA
<213> ORGANISM: Gallus gallus

<400> SEQUENCE: 67
acagcgctga ctcagccgtc ctcggtgtca gcaaacccgg gagaaaccgt caagatcacc       60
tgttccgggg gaagcaacaa ctggtatagc tggcaccagc agaagtctcc tggcagtgcc      120
cctgtcactg tgatctataa caacgacaag agaccctcgg acatcccttc acgattctcc      180
ggtttcacat ctggctccac aagcacatta accatcactg gggtccaagc cgacgacgag      240
gctgtctatt tctgtggtgg ctgggacagt agtagtcgtg ccggtatatt tggggccggg      300
acaaccctga ccgtcctagg tgcggccgca                                       330

<210> SEQ ID NO 68
<211> LENGTH: 321
<212> TYPE: DNA
<213> ORGANISM: Gallus gallus

<400> SEQUENCE: 68
acagcgctga ctcaaccgtc ctcggtgtca gcaaacccgg gagaaaccgt caagatcacc       60
tgctccgggg gcaacagcgg ctatggctgg taccagcaga agtcacctgg cagtgcccct      120
gtcactgtga tctatagcaa cgacaagaga ccctcggaca tcccttcacg attctccggt      180
gccctatccg gctccacagc cacattaacc atcactgggg tccagccgag gacgaggct      240 gtctattact gtgggagtgg agacagcagt ggttctgtat ttggggccgg gacaaccctg      300
accgtcctag gtgcggccgc a                                                321

<210> SEQ ID NO 69
<211> LENGTH: 324
<212> TYPE: DNA
<213> ORGANISM: Gallus gallus

<400> SEQUENCE: 69
acagcgctga ctcagccgtc ctcggtgtca gcgaacccgg gagaaaccgt cgagatcacc       60
tgctccgggg atagcagcag caactatggc tggtaccagc agaagtctcc tggcagtgcc      120
cctgtcactc tgatctacta tgatgatgag agaccctcgg gcatcccttc acgattctcc      180
ggttccaaat ccggctccac agccacatta accattactg gggtccaagc cgacgacgag      240
gctgtctatt actgtgggag ctacgacagc agtactggta tatttggggc cgggacaacc      300
ctgaccgtcc taggtgcggc cgca                                             324

<210> SEQ ID NO 70
<211> LENGTH: 333
<212> TYPE: DNA
<213> ORGANISM: Gallus gallus

<400> SEQUENCE: 70
acagcgctga ctcagccgtc ctcggtgtca gcaaacccag gagaaaccgt cgagatcacc       60
tgctccgggg gtggtagcag cagctactat ggctggtacc agcagaagtc tcctggcagt      120
gcccctgtca ctgtaatcta tgagaacacc aacagaccct cggacatccc ttcacgattc      180
```

```
tccggttcca aatccggctc cacagccaca ttaaccatca ctggagtcca agccgaggac    240
gaggctgtct attactgtgg gagtggagac agcaacactt ataatggtat atttggggcc    300
gggacaaccc tgaccgtcct aggtgcggcc gca                                333
```

<210> SEQ ID NO 71
<211> LENGTH: 321
<212> TYPE: DNA
<213> ORGANISM: Gallus gallus

<400> SEQUENCE: 71

```
acagcgctga ctcaaccgtc ctcggtgtca gcaaacccgg gaaaaaccgt cgagatcacc     60
tgctccgggg gtagtggcag ctacggctgg tatcagcaga agtcacctgg cagtgcccct    120
gtcactgtga tctactggga tgacaagaga ccctcgggca tcccttcacg attctccggt    180
tccgagtccg gctccacagc cacattaacc atcactgggg tccaagccga ggacgaggct    240
gtctattact gtgggagtgc agacagcagt ggtgctatat ttggggccgg gacaaccctg    300
accgtcctag gtgcggccgc a                                              321
```

<210> SEQ ID NO 72
<211> LENGTH: 327
<212> TYPE: DNA
<213> ORGANISM: Gallus gallus

<400> SEQUENCE: 72

```
acagcgctga ctcagccgtc ctcggtgtca gcaaacctgg gaggaaccgt caagatcacc     60
tgctccggga gtagtggcag ctatggctgg taccggcaga aggcacctgg cagtgcccct    120
gtcactgtga tctatagcaa cgacaagaga ccctcgggaca tcccttcacg attctccggt   180
tccgcatccg gctccacagc cacattaacc atcactgggg tccaagccga ggacgaggct    240
gtctatttct gtggtggcta cgacggcagc agttatgttg gtatatttgg ggccgggaca    300
accctgaccg tcctaggtgc ggccgca                                        327
```

<210> SEQ ID NO 73
<211> LENGTH: 336
<212> TYPE: DNA
<213> ORGANISM: Gallus gallus

<400> SEQUENCE: 73

```
acagcgctga ctcagccgtc ctcggtgtca gcaaacccgg gagaaaccgt caagatcacc     60
tgctctgggg gtagtggcta tggttatggc tggtatcagc agaagtctcc tggcagtgcc    120
cctgtcactg tgatctatca gaacgacaag agaccctcga acatcccttc acgattctcc    180
ggttctggat ccggctccac aggcacatta accatcactg ggtccaagt cgaggacgag    240 gctgtctatt actgtgggac tgcagacagc agctatgttg gtgatgctgg tatatttggg    300
gccgggacaa ccctgaccgt cctaggtgcg gccgca                              336
```

<210> SEQ ID NO 74
<211> LENGTH: 324
<212> TYPE: DNA
<213> ORGANISM: Gallus gallus

<400> SEQUENCE: 74

```
acagcgctga ctcagccgtc ctcggtgtca gcaaacccag gagaaaccgt caagatcacc     60
tgctccgggg gtagcagtgg caggtatggc tggtatcagc agaagtcacc tggcagtgcc    120
cctgtcactg tgatctatta caacgacaag agacctcgg acatcccttc acgattctcc    180
```

-continued

```
ggctccctac ccggctccac agccacatta accatcactg gggtccaagt cgaagacgag    240
gctgtctatt tctgtgggag tgcagacagc actgctggta tatttggggc cgggacaacc    300
ctgaccgtcc taggtgcggc cgca                                            324

<210> SEQ ID NO 75
<211> LENGTH: 330
<212> TYPE: DNA
<213> ORGANISM: Gallus gallus

<400> SEQUENCE: 75
acagcgctga ctcagccgtc ctcggtgtca gcaaacctgg aggaaccgt caagatcacc      60 tgctccgggg gttacagtgg ctatggttat ggctggtatc agcagaagtc acctggcagt    120
gcccctgtca ctttgatcta taatggcaat aacagaccct cggacatccc ttcacgattc    180
tccggttctg gatctggctc acaaacaca ttaaccatca ctggggtcca agtcgaggac     240
gaggctatct atttctgtgg gagtgcagac agcagcagta ttgctgtatt tggggccggg    300
acaaccctga ccgtcctagg tgcggccgca                                     330

<210> SEQ ID NO 76
<211> LENGTH: 327
<212> TYPE: DNA
<213> ORGANISM: Gallus gallus

<400> SEQUENCE: 76
acagcgctga ctcagccgtc ctcggtgtca gcgaacccgg gagaaaccgt cgagatcacc     60
tgctccgggg gtaggaagta ctatggctgg taccagcaga agtctcctgg cagtgcccct    120
gtcactctga tctatagcaa cgacaagaga ccctcggaca tcccttcacg attctccggt    180
tccaaatccg gctccacagc cacattaacc atcactgggg tccaagtcga cgacgaggct    240
gtctattact gtgggagtgc agacaccagc agcagtgaag ctgcatttgg ggccgggaca   300
accctgaccg tcctaggtgc ggccgca                                        327

<210> SEQ ID NO 77
<211> LENGTH: 339
<212> TYPE: DNA
<213> ORGANISM: Gallus gallus

<400> SEQUENCE: 77
gcgctgactc agccggcctc ggtgtcagca aacctgggag aaaccgtcaa gatcacctgc     60
tccgggggtg gtagctatgc tggaagttac tattatggct ggtatcagca gaagtctcct    120
ggcagtgccc ctgtcactgt gatctatgac aacaccaaca gccctcgaa catcccttca    180 cgattctccg gttccaaatc cggccccaca gccacattaa ccatcactgg ggtccaagtc    240
gacgacgagg ctgtctatta ttgtgggagc atggacagca gtagtggtgg cggtatattt    300
ggggccggga caaccctgac cgtcctaggt gcggccgca                            339

<210> SEQ ID NO 78
<211> LENGTH: 125
<212> TYPE: PRT
<213> ORGANISM: Gallus gallus

<400> SEQUENCE: 78

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Tyr
            20                  25                  30
```

Gln Met Asn Trp Leu Arg Gln Ala Pro Gly Lys Gly Leu Glu Trp Val
            35                  40                  45

Gly Val Ile Ser Thr Arg Gly Ser Ser Thr Ala Tyr Gly Ala Ala Val
        50                  55                  60

Lys Gly Arg Ala Thr Ile Ser Arg Asp Asn Gly Arg Ser Thr Val Arg
65                  70                  75                  80

Leu Gln Leu Asn Ser Leu Arg Thr Glu Asp Thr Ala Thr Tyr Tyr Cys
                85                  90                  95

Ala Lys Ala Gly Tyr Ala Cys Gly Trp Ser Val Gly Cys Ile Asp Ala
                100                 105                 110

Trp Gly His Gly Thr Glu Val Ile Val Ser Ser Leu Asp
            115                 120                 125

<210> SEQ ID NO 79
<211> LENGTH: 123
<212> TYPE: PRT
<213> ORGANISM: Gallus gallus

<400> SEQUENCE: 79

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Tyr
            20                  25                  30

Gln Met Asn Trp Leu Arg Gln Ala Pro Gly Lys Gly Leu Glu Trp Val
            35                  40                  45

Gly Val Ile Ser Thr Arg Gly Ser Ser Thr Ala Tyr Gly Ala Ala Val
        50                  55                  60

Lys Gly Arg Ala Thr Ile Ser Arg Asp Asn Gly Gln Ser Thr Val Arg
65                  70                  75                  80

Leu Gln Leu Asn Ser Leu Arg Thr Glu Asp Thr Ala Thr Tyr Tyr Cys
                85                  90                  95

Ala Lys Ala Gly Tyr Ala Cys Gly Trp Ser Val Gly Cys Ile Asp Ala
                100                 105                 110

Trp Gly His Gly Thr Glu Val Ile Val Ser Ser
            115                 120

<210> SEQ ID NO 80
<211> LENGTH: 126
<212> TYPE: PRT
<213> ORGANISM: Gallus gallus

<400> SEQUENCE: 80

Ala Val Thr Leu Asp Glu Ser Gly Gly Gly Leu Gln Thr Pro Gly Gly
1               5                   10                  15

Ala Leu Ser Leu Val Cys Lys Gly Ser Gly Phe Thr Phe Ser Ser Tyr
            20                  25                  30

Asn Met Gly Trp Val Arg Gln Ala Pro Gly Lys Gly Leu Glu Phe Val
            35                  40                  45

Ala Ala Ile Ser Asn Thr Gly Arg Tyr Thr Gly Tyr Gly Ser Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Thr Ala Gly Tyr Tyr Gly Trp Asn Thr Ala Ser Asp Ile Asp
                100                 105                 110

```
Ala Trp Gly His Gly Thr Glu Val Ile Val Ser Ser Leu Asp
        115                 120                 125
```

<210> SEQ ID NO 81
<211> LENGTH: 126
<212> TYPE: PRT
<213> ORGANISM: Gallus gallus

<400> SEQUENCE: 81

```
Ala Val Thr Leu Asp Glu Ser Gly Gly Leu Gln Thr Pro Gly Arg
1               5                   10                  15

Ala Leu Ser Leu Val Cys Lys Gly Ser Gly Phe Thr Leu Ser Ser Tyr
                20                  25                  30

Asn Met Gly Trp Val Arg Gln Ala Pro Gly Lys Gly Leu Glu Phe Val
            35                  40                  45

Ala Ala Ile Ser Asn Thr Gly Arg Tyr Thr Gly Tyr Gly Ser Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Tyr Tyr Cys
                85                  90                  95

Ala Lys Thr Ala Gly Tyr Tyr Gly Trp Asn Thr Ala Ser Asp Ile Asp
            100                 105                 110

Ala Trp Gly His Gly Thr Glu Val Ile Val Ser Ser Leu Asp
        115                 120                 125
```

<210> SEQ ID NO 82
<211> LENGTH: 131
<212> TYPE: PRT
<213> ORGANISM: Gallus gallus

<400> SEQUENCE: 82

```
Ala Val Thr Leu Asp Glu Ser Gly Gly Leu Gln Thr Pro Gly Arg
1               5                   10                  15

Ala Leu Ser Leu Val Cys Lys Ala Ser Gly Phe Ser Ile Ser Gly Tyr
                20                  25                  30

Asn Met Gly Trp Val Arg Gln Ala Pro Gly Lys Gly Leu Glu Phe Val
            35                  40                  45

Ala Gly Ile Gly Asn Thr Gly Arg Tyr Thr Gly Tyr Gly Ala Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Ile Tyr Tyr Cys
                85                  90                  95

Ala Lys Gly Ala Ser His Tyr Cys Trp Asp Val Gly Cys Ser Asn Ile
            100                 105                 110

Ala Gly Ser Ile Asp Ala Trp Gly His Gly Thr Glu Val Ile Val Ser
        115                 120                 125

Ser Leu Asp
    130
```

<210> SEQ ID NO 83
<211> LENGTH: 129
<212> TYPE: PRT
<213> ORGANISM: Gallus gallus

<400> SEQUENCE: 83

Ala Val Thr Leu Asp Glu Ser Gly Gly Gly Leu Gln Thr Pro Gly Arg
1               5                   10                  15

Ala Leu Ser Leu Val Cys Lys Ala Ser Gly Phe Thr Phe Arg Ser Tyr
            20                  25                  30

Asn Met Ala Trp Val Arg Gln Ala Pro Gly Lys Gly Leu Glu Phe Val
        35                  40                  45

Ala Glu Ile Ser Gly Thr Gly Ser Thr Thr Asn Tyr Ala Pro Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Lys Ala Ala Gly Ala Tyr Cys Ala Trp Ser Gly Cys Thr Ala Gly
            100                 105                 110

Ser Ile Asp Ala Trp Gly His Gly Thr Glu Val Ile Val Ser Ser Leu
            115                 120                 125

Asp

<210> SEQ ID NO 84
<211> LENGTH: 130
<212> TYPE: PRT
<213> ORGANISM: Gallus gallus

<400> SEQUENCE: 84

Ala Val Thr Leu Asp Glu Ser Gly Gly Gly Leu Gln Thr Pro Arg Gly
1               5                   10                  15

Arg Leu Arg Leu Val Cys Lys Ala Ser Gly Phe Thr Phe Ser Ser Tyr
            20                  25                  30

Glu Met Gly Trp Val Arg Gln Ala Pro Gly Lys Gly Leu Glu Trp Val
        35                  40                  45

Ala Gly Ile Gly Gly Ser Gly Ser Gly Ser Ala Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ser Thr Thr Lys Cys Ser Tyr Cys Trp Tyr Gly Ala Thr Ala
            100                 105                 110

Gly Ser Ile Asp Ala Trp Gly His Gly Ala Glu Val Ile Val Ser Ser
            115                 120                 125

Leu Asp
    130

<210> SEQ ID NO 85
<211> LENGTH: 130
<212> TYPE: PRT
<213> ORGANISM: Gallus gallus

<400> SEQUENCE: 85

Ala Val Thr Leu Asp Glu Ser Gly Gly Gly Leu Gln Thr Pro Arg Gly
1               5                   10                  15

Arg Leu Arg Leu Val Cys Lys Ala Ser Gly Phe Asp Phe Ser Ser Tyr
            20                  25                  30

Glu Met Gly Trp Val Arg Gln Ala Pro Gly Lys Gly Leu Glu Trp Val
        35                  40                  45

Ala Gly Ile Gly Gly Ser Gly Ser Gly Ser Ala Tyr Gly Pro Ala Val

```
                50                   55                 60
Lys Gly Arg Ala Thr Ile Thr Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                 85                  90                  95

Ala Lys Ser Thr Thr Arg Cys Ser Phe Cys Trp Tyr Gly Ala Thr Ala
                100                 105                 110

Gly Ser Ile Asp Ala Trp Gly His Gly Ala Glu Val Ile Val Ser Ser
                115                 120                 125

Leu Asp
    130

<210> SEQ ID NO 86
<211> LENGTH: 130
<212> TYPE: PRT
<213> ORGANISM: Gallus gallus

<400> SEQUENCE: 86

Ala Val Thr Leu Asp Glu Ser Gly Gly Leu Gln Thr Pro Arg Gly
 1               5                  10                  15

Arg Leu Arg Leu Val Cys Lys Ala Ser Gly Phe Thr Phe Ser Ser Tyr
                 20                  25                  30

Glu Met Gly Trp Val Arg Gln Ala Pro Gly Lys Gly Leu Glu Trp Val
                 35                  40                  45

Ala Gly Ile Gly Gly Ser Gly Ser Gly Ser Ala Tyr Gly Ser Ala Val
                 50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                 85                  90                  95

Ala Lys Ser Thr Thr Lys Cys Asn His Cys Trp Tyr Gly Ala Thr Ala
                100                 105                 110

Gly Ser Ile Asp Ala Trp Gly His Gly Thr Glu Val Ile Val Ser Ser
                115                 120                 125

Leu Asp
    130

<210> SEQ ID NO 87
<211> LENGTH: 128
<212> TYPE: PRT
<213> ORGANISM: Gallus gallus

<400> SEQUENCE: 87

Ala Val Thr Leu Asp Glu Ser Gly Gly Leu His Thr Pro Gly Gly
 1               5                  10                  15

Ala Leu Arg Leu Val Cys Lys Ala Ser Gly Phe Ser Ile Ser Ser Tyr
                 20                  25                  30

Gly Met Gly Trp Val Arg Gln Ala Pro Gly Lys Gly Leu Glu Trp Val
                 35                  40                  45

Ala Arg Ile Gly Ser Gly Ala Ser Gly Thr Ala Tyr Gly Ser Ala Val
                 50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Asp Thr Gly Thr Tyr Tyr Cys
                 85                  90                  95

Ala Lys Ser Ala Gly Ala Tyr Cys Trp Tyr Ala Gly Cys Pro Ser Ser
```

```
                    100                 105                 110
Ile Asp Ala Trp Gly His Gly Ala Glu Val Ile Val Ser Ser Leu Asp
        115                 120                 125

<210> SEQ ID NO 88
<211> LENGTH: 128
<212> TYPE: PRT
<213> ORGANISM: Gallus gallus

<400> SEQUENCE: 88

Ala Val Thr Leu Asp Glu Ser Gly Gly Leu Gln Thr Pro Gly Gly
1               5                  10                  15

Ala Leu Arg Leu Val Cys Lys Ala Ser Gly Phe Ser Ile Ser Ser Tyr
            20                  25                  30

Gly Met Gly Trp Val Arg Gln Ala Pro Gly Lys Gly Leu Glu Trp Val
        35                  40                  45

Ala Arg Ile Gly Ser Gly Ala Ser Gly Thr Ala Tyr Gly Ser Thr Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Thr Glu Asp Thr Gly Thr Tyr Tyr Cys
                85                  90                  95

Ala Lys Thr Ala Gly Ala Tyr Cys Trp Tyr Ala Gly Cys Pro Ser Ser
            100                 105                 110

Ile Asp Ala Trp Gly His Gly Thr Glu Val Ile Val Ser Ser Leu Asp
        115                 120                 125

<210> SEQ ID NO 89
<211> LENGTH: 128
<212> TYPE: PRT
<213> ORGANISM: Gallus gallus

<400> SEQUENCE: 89

Ala Val Thr Leu Asp Glu Ser Gly Gly Gly Leu Gln Thr Pro Gly Lys
1               5                  10                  15

Gly Leu Ser Leu Val Cys Lys Ala Ser Gly Phe Ser Leu Asn Ser Tyr
            20                  25                  30

Gly Met Gly Trp Val Arg Gln Ala Pro Gly Lys Gly Leu Glu Trp Val
        35                  40                  45

Ala Arg Ile Gly Ser Gly Ala Ser Gly Thr Ala Tyr Gly Ser Ala Val
    50                  55                  60

Lys Gly Arg Ala Thr Ile Ser Arg Asp Asn Gly Gln Ser Ile Val Arg
65                  70                  75                  80

Leu Gln Leu Asn Asp Leu Arg Ala Glu Asp Thr Ala Thr Tyr Tyr Cys
                85                  90                  95

Ala Lys Thr Ala Gly Ala Tyr Cys Trp Tyr Ala Gly Cys Pro Ser Ser
            100                 105                 110

Ile Asp Ala Trp Gly His Gly Thr Glu Val Ile Val Ser Ser Leu Asp
        115                 120                 125

<210> SEQ ID NO 90
<211> LENGTH: 128
<212> TYPE: PRT
<213> ORGANISM: Gallus gallus

<400> SEQUENCE: 90

Ala Val Thr Leu Asp Glu Ser Gly Gly Gly Leu Gln Thr Pro Gly Lys
1               5                  10                  15
```

```
Gly Leu Ser Leu Val Cys Lys Ala Ser Gly Phe Thr Phe Thr Ser Tyr
            20                  25                  30

Gly Met Gly Trp Val Arg Gln Ala Pro Gly Lys Gly Leu Glu Trp Val
        35                  40                  45

Ala Arg Ile Gly Ser Gly Ala Ser Gly Thr Ala Tyr Ala Thr Ala Val
    50                  55                  60

Lys Gly Arg Ala Thr Ile Ser Arg Asp Asn Gly Gln Ser Thr Val Arg
65                  70                  75                  80

Leu Gln Leu Asn Asp Leu Arg Ala Glu Asp Thr Ala Thr Tyr Tyr Cys
                85                  90                  95

Ala Lys Thr Ala Gly Ala Tyr Cys Trp Tyr Ala Gly Cys Pro Ser Ser
            100                 105                 110

Ile Asp Ala Trp Gly His Gly Thr Glu Val Ile Val Ser Ser Leu Asp
            115                 120                 125
```

<210> SEQ ID NO 91
<211> LENGTH: 127
<212> TYPE: PRT
<213> ORGANISM: Gallus gallus

<400> SEQUENCE: 91

```
Ala Val Thr Leu Asp Glu Ser Gly Gly Leu Gln Thr Pro Gly Arg
1               5                   10                  15

Ala Leu Ser Leu Val Cys Lys Ala Ser Gly Phe Thr Phe Ser Ser Tyr
            20                  25                  30

Ala Met Asn Trp Val Arg Gln Ala Pro Gly Lys Gly Leu Glu Phe Val
        35                  40                  45

Ala Glu Ile Ser Gly Ser Gly Arg Tyr Thr Tyr Tyr Ala Pro Ala Val
    50                  55                  60

Lys Gly Arg Ala Thr Ile Ser Arg Asp Asn Gly Gln Ser Thr Val Ser
65                  70                  75                  80

Leu Gln Leu Asn Asn Leu Arg Ala Glu Asp Thr Ala Thr Tyr Tyr Cys
                85                  90                  95

Ala Lys Thr Ala Asp Ser Cys Arg Tyr Gly Cys Ser Ala Asp Arg Ile
            100                 105                 110

Asp Ala Trp Gly His Gly Thr Glu Val Ile Val Ser Ser Leu Asp
            115                 120                 125
```

<210> SEQ ID NO 92
<211> LENGTH: 127
<212> TYPE: PRT
<213> ORGANISM: Gallus gallus

<400> SEQUENCE: 92

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Ala Ile Asn Trp Val Arg Gln Ala Pro Gly Lys Gly Leu Glu Phe Val
        35                  40                  45

Ala Glu Ile Ser Gly Ser Gly Arg Tyr Val Tyr Tyr Ala Pro Ala Val
    50                  55                  60

Gln Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Tyr Tyr Tyr Cys
                85                  90                  95
```

```
Ala Lys Thr Ala Asp Ser Cys Arg Tyr Gly Cys Asn Ala Asp Arg Ile
            100                 105                 110

Asp Ala Trp Gly Arg Gly Thr Glu Val Ile Val Ser Ser Leu Asp
            115                 120                 125

<210> SEQ ID NO 93
<211> LENGTH: 127
<212> TYPE: PRT
<213> ORGANISM: Gallus gallus

<400> SEQUENCE: 93

Ala Val Thr Leu Asp Glu Ser Gly Gly Leu Gln Thr Pro Gly Gly
1               5                   10                  15

Ala Leu Ser Leu Val Cys Lys Gly Ser Gly Phe Thr Phe Ser Ser His
            20                  25                  30

Gly Met Phe Trp Val Arg Gln Ala Pro Gly Lys Gly Leu Glu Tyr Val
            35                  40                  45

Ala Gln Ile Ser Gly Ser Gly Arg Leu Thr Asn Tyr Gly Pro Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Thr Ala Val Asn Cys Arg Tyr Gly Cys Ala Gly Asp Asn Ile
            100                 105                 110

Asp Ala Trp Gly His Gly Thr Glu Val Ile Val Ser Ser Leu Asp
            115                 120                 125

<210> SEQ ID NO 94
<211> LENGTH: 129
<212> TYPE: PRT
<213> ORGANISM: Gallus gallus

<400> SEQUENCE: 94

Ala Val Thr Leu Asp Glu Ser Gly Gly Leu Gln Thr Pro Gly Gly
1               5                   10                  15

Gly Leu Ser Leu Val Cys Lys Ala Ser Gly Phe Thr Phe Ser Ser Tyr
            20                  25                  30

Gly Met Gly Trp Val Arg Gln Ala Pro Gly Lys Gly Leu Glu Trp Val
            35                  40                  45

Ala Glu Ile Ser Gly Ser Gly Arg Tyr Thr Gly Tyr Gly Pro Ala Val
        50                  55                  60

Gln Gly Arg Ala Thr Ile Ser Arg Asp Asn Gly Gln Ser Thr Val Arg
65                  70                  75                  80

Leu Gln Leu Ser Asp Leu Arg Ala Glu Asp Thr Gly Thr Tyr Tyr Cys
                85                  90                  95

Ala Lys Ala Thr Ala Ser Cys Thr Tyr Gly Cys Thr Pro Tyr Thr Gly
            100                 105                 110

Glu Ile Asp Ala Trp Gly His Gly Thr Glu Val Ile Val Ser Ser Leu
            115                 120                 125

Asp

<210> SEQ ID NO 95
<211> LENGTH: 127
<212> TYPE: PRT
<213> ORGANISM: Gallus gallus
```

<400> SEQUENCE: 95

```
Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Gly Met Gln Trp Val Arg Gln Ala Pro Gly Lys Gly Leu Glu Trp Val
            35                  40                  45

Ala Gly Ile Ser Gly Ser Gly Arg Gly Thr Trp Tyr Ala Pro Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ala Ala Gly Ser Asp Thr Tyr Gly Ser Thr Gly Asp Asn Ile
            100                 105                 110

Asp Ala Trp Gly His Gly Thr Glu Val Ile Val Ser Ser Leu Asp
            115                 120                 125
```

<210> SEQ ID NO 96
<211> LENGTH: 127
<212> TYPE: PRT
<213> ORGANISM: Gallus gallus

<400> SEQUENCE: 96

```
Ala Val Thr Leu Asp Glu Ser Gly Gly Leu Gln Thr Pro Gly Gly
1               5                   10                  15

Thr Leu Ser Leu Val Cys Lys Gly Ser Gly Phe Thr Phe Ser Asp Tyr
            20                  25                  30

Gly Met Gly Trp Met Arg Gln Ala Pro Gly Lys Gly Leu Glu Tyr Val
            35                  40                  45

Ala Glu Ile Ser Ser Ser Gly Arg Tyr Thr Asn Tyr Gly Pro Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ala Ala Gly Arg Gly Tyr Tyr Gly Trp Ser Ala Gly Thr Ile
            100                 105                 110

Asp Ala Trp Gly His Gly Thr Glu Val Ile Val Ser Ser Leu Asp
            115                 120                 125
```

<210> SEQ ID NO 97
<211> LENGTH: 127
<212> TYPE: PRT
<213> ORGANISM: Gallus gallus

<400> SEQUENCE: 97

```
Ala Val Thr Leu Asp Glu Ser Gly Gly Leu Gln Thr Pro Gly Gly
1               5                   10                  15

Thr Leu Ser Leu Val Cys Lys Ala Ser Gly Phe Thr Phe Ser Ser Tyr
            20                  25                  30

Gly Met Gly Trp Met Arg Gln Ala Pro Gly Lys Gly Leu Glu Tyr Val
            35                  40                  45

Ala Glu Ser Ser Ser Gly Arg Tyr Thr Asn Tyr Gly Pro Ala Val
        50                  55                  60

Lys Gly Arg Ala Thr Ile Ser Arg Asp Asn Gly Gln Ser Thr Val Arg
```

```
                65                  70                  75                  80
Leu Gln Leu Asn Asn Leu Arg Ala Glu Asp Thr Gly Thr Tyr Tyr Cys
                    85                  90                  95

Ala Lys Ala Ala Gly Ser Gly Tyr Tyr Gly Trp Ser Ala Gly Ser Ile
                100                 105                 110

Asp Ala Trp Gly His Gly Thr Glu Val Ile Val Ser Ser Leu Asp
            115                 120                 125
```

<210> SEQ ID NO 98
<211> LENGTH: 132
<212> TYPE: PRT
<213> ORGANISM: Gallus gallus

<400> SEQUENCE: 98

```
Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Phe
            20                  25                  30

Asn Ile Phe Trp Val Arg Gln Ala Pro Gly Lys Gly Leu Glu Phe Val
        35                  40                  45

Ala Ala Ile Asn Lys Asp Gly Ser Phe Thr His Tyr Gly Ser Ala Val
    50                  55                  60

Lys Gly Arg Ala Thr Ile Ser Arg Asp Asn Gly Gln Ser Thr Leu Arg
65                  70                  75                  80

Leu Gln Leu Asn Asp Leu Gly Ala Glu Asp Ala Gly Thr Tyr Phe Cys
                85                  90                  95

Ala Arg Ser Pro Gly Gly Phe Ser Cys Ala Gly Gly Trp Cys Gly Ala
                100                 105                 110

Tyr Ala Asp Gly Ile Asp Ala Trp Gly His Gly Thr Glu Val Ile Ile
            115                 120                 125

Ser Ser Leu Asp
        130
```

<210> SEQ ID NO 99
<211> LENGTH: 132
<212> TYPE: PRT
<213> ORGANISM: Gallus gallus

<400> SEQUENCE: 99

```
Ala Val Thr Leu Asp Glu Ser Gly Gly Gly Leu Gln Thr Pro Gly Gly
1               5                   10                  15

Gly Leu Ser Leu Val Cys Lys Gly Ser Gly Phe Asp Phe Ser Ser Tyr
            20                  25                  30

Asn Met Phe Trp Val Arg Gln Ala Pro Gly Lys Gly Leu Glu Phe Val
        35                  40                  45

Ala Ala Ile Ser Ser Thr Gly Ser Tyr Thr His Tyr Gly Pro Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Ile Tyr Tyr Cys
                85                  90                  95

Ala Arg Ser Pro Gly Gly Phe Ser Cys Ala Gly Gly Trp Cys Gly Gly
                100                 105                 110

Tyr Ala Asp Ser Ile Asp Ala Trp Gly His Gly Thr Glu Val Ile Val
            115                 120                 125

Ser Ser Leu Asp
```

130

<210> SEQ ID NO 100
<211> LENGTH: 130
<212> TYPE: PRT
<213> ORGANISM: Gallus gallus

<400> SEQUENCE: 100

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Phe
            20                  25                  30

Asn Met Gln Trp Val Arg Gln Ala Pro Gly Lys Gly Leu Glu Phe Val
        35                  40                  45

Ala Gly Ile Asp Asn Ile Gly Arg Lys Thr Ser Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Phe Cys
                85                  90                  95

Ala Lys Gly Ala Gly Ser Ser Ala Tyr Ser Cys Ala Phe Cys Tyr Pro
            100                 105                 110

Gly Trp Ile Asp Ala Trp Gly His Gly Thr Glu Val Ile Val Ser Ser
        115                 120                 125

Leu Asp
    130

<210> SEQ ID NO 101
<211> LENGTH: 125
<212> TYPE: PRT
<213> ORGANISM: Gallus gallus

<400> SEQUENCE: 101

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser His
            20                  25                  30

Gly Met Gly Trp Val Arg Gln Ala Pro Gly Lys Gly Leu Glu Trp Val
        35                  40                  45

Ala Gly Ile Glu Asn Asp Gly Ser Ile Thr Gly Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Lys Arg Ser Gly Ser Gly Cys Cys Asn Ala Tyr Ala Ile Asp Ala
            100                 105                 110

Trp Gly His Gly Thr Glu Val Ile Val Ser Ser Leu Asp
        115                 120                 125

<210> SEQ ID NO 102
<211> LENGTH: 131
<212> TYPE: PRT
<213> ORGANISM: Gallus gallus

<400> SEQUENCE: 102

Ala Val Thr Leu Asp Glu Ser Gly Gly Gly Leu Gln Thr Pro Gly Gly
1               5                   10                  15

```
Gly Leu Ser Leu Val Cys Lys Ala Ser Gly Phe Thr Phe Ser Ser Tyr
            20                  25                  30

Ala Met Tyr Trp Val Arg Gln Thr Pro Gly Lys Gly Leu Glu Phe Val
        35                  40                  45

Ala Gly Ile Asp Ser Gly Asp Gly Arg Tyr Ser Lys Tyr Gly Pro Ala
    50                  55                  60

Val Asp Gly Arg Ala Thr Met Ser Arg Asp Asn Gly Gln Ser Thr Val
65                  70                  75                  80

Arg Leu Gln Leu Asn Asp Leu Arg Ala Glu Asp Ser Gly Thr Tyr Tyr
                85                  90                  95

Cys Ala Lys Gly Ala Val Thr Gly Tyr Cys Gly Trp Asn Ala Cys Thr
                100                 105                 110

Val Ala Asn Ile Asp Thr Trp Gly His Gly Thr Glu Val Ile Val Ser
            115                 120                 125

Ser Leu Asp
    130

<210> SEQ ID NO 103
<211> LENGTH: 126
<212> TYPE: PRT
<213> ORGANISM: Gallus gallus

<400> SEQUENCE: 103

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Ser Phe Ser Ser Tyr
            20                  25                  30

Ser Met Gln Trp Val Arg Gln Ala Pro Gly Lys Gly Leu Asp Trp Val
        35                  40                  45

Ala Gly Ile Ser Gly Thr Gly Arg His Arg Asn Tyr Gly Ser Ala Val
    50                  55                  60

Glu Gly Arg Ala Thr Ile Ser Arg Asp Asn Gly Gln Ser Thr Val Arg
65                  70                  75                  80

Leu Gln Leu Asp Asn Leu Arg Ala Glu Asp Thr Gly Thr Tyr Tyr Cys
                85                  90                  95

Ala Arg Ala Pro Cys Thr Gly Cys Gly Trp Ser Ala Gly Ser Ile Asp
                100                 105                 110

Ala Trp Gly His Gly Thr Glu Val Ile Val Ser Ser Leu Asp
            115                 120                 125

<210> SEQ ID NO 104
<211> LENGTH: 125
<212> TYPE: PRT
<213> ORGANISM: Gallus gallus

<400> SEQUENCE: 104

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Tyr
            20                  25                  30

Gln Met His Trp Ile Arg Gln Ala Pro Gly Lys Gly Leu Glu Trp Val
        35                  40                  45

Gly Val Ile Ser Ser Arg Gly Ser Ser Thr Asn Tyr Gly Ala Ala Val
    50                  55                  60

Lys Gly Arg Ala Thr Ile Ser Arg Asp Asn Gly Gln Ser Thr Val Arg
65                  70                  75                  80
```

```
Leu Gln Leu Asn Asn Leu Arg Ala Glu Asp Thr Ala Thr Tyr Tyr Cys
                85                  90                  95

Ala Lys Ser Gly Tyr Ala Cys Gly Trp Ser Gly Gly Cys Ile Asp Ala
            100                 105                 110

Trp Gly His Gly Thr Glu Val Ile Val Ser Ser Leu Asp
        115                 120                 125

<210> SEQ ID NO 105
<211> LENGTH: 127
<212> TYPE: PRT
<213> ORGANISM: Gallus gallus

<400> SEQUENCE: 105

Ala Val Thr Leu Asp Glu Ser Gly Gly Leu Gln Ala Pro Gly Gly
1               5                   10                  15

Gly Leu Ser Leu Val Cys Lys Ala Ser Gly Phe Thr Phe Ser Ser His
            20                  25                  30

Gly Met Gly Trp Val Arg Gln Ala Pro Gly Lys Gly Leu Glu Tyr Val
        35                  40                  45

Ala Ser Ile Ser Thr Arg Gly Ser Ser Thr Tyr Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Thr Gly Tyr Ala Cys Ser Tyr Ser Tyr His Thr Ala Cys Ile
            100                 105                 110

Asp Ala Trp Gly His Gly Thr Glu Val Ile Val Ser Ser Leu Asp
        115                 120                 125

<210> SEQ ID NO 106
<211> LENGTH: 124
<212> TYPE: PRT
<213> ORGANISM: Gallus gallus

<400> SEQUENCE: 106

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Arg Ser His
            20                  25                  30

Gln Met Phe Trp Val Arg Gln Ala Pro Gly Lys Gly Leu Glu Tyr Val
        35                  40                  45

Gly Gln Ile Thr Thr Arg Gly Thr Thr Tyr Tyr Gly Ala Ala Val
    50                  55                  60

Thr Gly Arg Ala Thr Ile Ser Arg Asp Asn Gly Gln Asn Thr Val Arg
65                  70                  75                  80

Leu Gln Leu Asn Asn Leu Arg Ala Glu Asp Thr Gly Thr Tyr Phe Cys
                85                  90                  95

Ala Lys Ala Ala Tyr Gly Tyr Ser Tyr Val Ser Thr Ile Asp Ala Trp
            100                 105                 110

Gly His Gly Thr Glu Val Ile Val Ser Ser Leu Asp
        115                 120

<210> SEQ ID NO 107
<211> LENGTH: 126
<212> TYPE: PRT
<213> ORGANISM: Gallus gallus
```

```
<400> SEQUENCE: 107

Ala Val Thr Leu Asp Glu Ser Gly Gly Gly Leu Gln Thr Pro Gly Gly
1               5                   10                  15

Gly Leu Ser Leu Val Cys Arg Ala Ser Gly Phe Ile Phe Ser Ser His
            20                  25                  30

Pro Met Val Trp Val Arg Gln Ala Pro Gly Lys Gly Leu Glu Trp Val
        35                  40                  45

Ala Ala Ile Thr Thr Arg Gly Thr Ser Ala Tyr Tyr Gly Pro Ala Val
    50                  55                  60

Lys Gly Arg Ala Thr Ile Ser Arg Asp Asn Gly Gln Ser Thr Val Arg
65                  70                  75                  80

Leu Gln Leu Asn Ser Leu Arg Ala Glu Asp Thr Gly Thr Tyr Tyr Cys
                85                  90                  95

Ala Arg Ser Gly Tyr Gly Tyr Thr Gly Ser Asp Ala Gly Asn Ile Asp
            100                 105                 110

Thr Trp Gly His Gly Thr Glu Val Ile Val Ser Ser Leu Asp
        115                 120                 125

<210> SEQ ID NO 108
<211> LENGTH: 137
<212> TYPE: PRT
<213> ORGANISM: Gallus gallus

<400> SEQUENCE: 108

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Ala Phe Ser Arg Tyr
            20                  25                  30

Ala Met Asn Trp Val Arg Gln Ala Pro Gly Lys Gly Leu Glu Trp Val
        35                  40                  45

Ala Gly Val Arg Asn Val Gly Ser Ser Thr Asn Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Ile Tyr Tyr Cys
                85                  90                  95

Ala Lys Ala Ala Gly Ser Gly Tyr Cys Ala Trp Trp Ala Asp Ala Leu
            100                 105                 110

Thr Cys Gly Gly Tyr Lys Thr His Asp Ile Asp Ala Trp Gly His Gly
        115                 120                 125

Thr Glu Val Ile Val Ser Ser Leu Asp
    130                 135

<210> SEQ ID NO 109
<211> LENGTH: 128
<212> TYPE: PRT
<213> ORGANISM: Gallus gallus

<400> SEQUENCE: 109

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Gly Met Gly Trp Val Arg Gln Ala Pro Gly Lys Gly Leu Glu Trp Val
        35                  40                  45
```

```
Ala Gly Ile Asp Asn Ile Gly Arg Tyr Thr Asn Tyr Gly Pro Ala Val
     50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Ala Thr Tyr Tyr Cys
                 85                  90                  95

Ala Lys Ser Ala Ala Ser Gly Ser Trp Ser Tyr Tyr Gly Thr Gly Trp
                100                 105                 110

Ile Asp Gly Trp Gly His Gly Thr Glu Val Ile Val Ser Ser Leu Asp
                115                 120                 125

<210> SEQ ID NO 110
<211> LENGTH: 128
<212> TYPE: PRT
<213> ORGANISM: Gallus gallus

<400> SEQUENCE: 110

Ala Val Thr Leu Asp Glu Ser Gly Gly Leu Gln Thr Pro Gly Gly
 1               5                  10                  15

Ala Leu Ser Leu Val Cys Lys Ala Ser Gly Phe Thr Phe Ala Ile Tyr
                 20                  25                  30

Ala Met His Trp Val Arg Gln Ala Pro Asp Lys Gly Leu Glu Phe Val
                 35                  40                  45

Ala Gly Ile Ser Ser Asp Gly Ser Arg Thr Lys Tyr Gly Ala Ala Val
     50                  55                  60

Lys Gly Arg Ala Thr Met Ser Arg Asp Asn Gly Gln Ser Thr Val Arg
 65                  70                  75                  80

Leu Gln Leu Asn Asn Leu Arg Thr Glu Asp Thr Ala Thr Tyr Phe Cys
                 85                  90                  95

Ala Lys Thr Ala Gly Ser Trp Ser Arg Tyr Asn Gly Leu His Ser Asn
                100                 105                 110

Ile Asp Thr Trp Gly His Gly Thr Glu Val Ile Val Ser Ser Leu Asp
                115                 120                 125

<210> SEQ ID NO 111
<211> LENGTH: 127
<212> TYPE: PRT
<213> ORGANISM: Gallus gallus

<400> SEQUENCE: 111

Ala Val Thr Leu Asp Glu Ser Gly Gly Leu Gln Thr Pro Gly Gly
 1               5                  10                  15

Gly Leu Ser Leu Val Cys Lys Ala Ser Gly Phe Thr Phe Thr Asp Tyr
                 20                  25                  30

Gly Met Gly Trp Met Arg Gln Ala Pro Gly Lys Gly Leu Glu Tyr Val
                 35                  40                  45

Val Gly Ile Ser Asn Thr Gly Arg Tyr Thr Tyr Tyr Gly Ser Ala Val
     50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Ala Thr Tyr Tyr Cys
                 85                  90                  95

Ala Lys Ser Ala Gly Ser Trp Trp His Tyr Thr Gly Ala Asp Asn Ile
                100                 105                 110

Asp Ala Trp Gly His Gly Thr Glu Val Ile Val Ser Ser Leu Asp
                115                 120                 125
```

<210> SEQ ID NO 112
<211> LENGTH: 128
<212> TYPE: PRT
<213> ORGANISM: Gallus gallus

<400> SEQUENCE: 112

Ala Val Thr Leu Asp Glu Ser Gly Gly Leu Gln Thr Pro Gly Gly
1               5                   10                  15

Gly Leu Ser Leu Val Cys Lys Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ala Ser Ile Asn Ser Ala Gly Ser Tyr Thr His Tyr Gly Ser Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Arg Gly Gly Gly Gly Cys Gly Ile Trp Ser Cys Gly Ser Tyr Ala
            100                 105                 110

Gly Glu Ile Asp Ala Trp Gly His Gly Thr Glu Val Ile Val Ser Ser
        115                 120                 125

<210> SEQ ID NO 113
<211> LENGTH: 109
<212> TYPE: PRT
<213> ORGANISM: Gallus gallus

<400> SEQUENCE: 113

Thr Ala Leu Thr Gln Pro Ser Ser Val Ser Ala Asn Pro Gly Glu Thr
1               5                   10                  15

Val Glu Ile Thr Cys Ser Gly Asp Thr Thr Tyr Tyr Gly Trp Tyr Gln
                20                  25                  30

Gln Lys Ala Pro Gly Ser Ala Pro Val Thr Leu Ile Tyr Asp Asn Thr
            35                  40                  45

Asn Arg Pro Ser Asp Ile Pro Ser Arg Phe Ser Gly Ser Arg Ser Gly
        50                  55                  60

Ser Thr Ala Thr Leu Thr Ile Thr Gly Val Gln Ala Glu Asp Glu Ala
65                  70                  75                  80

Val Tyr Phe Cys Gly Ser Ala Asp Thr Ser Gly Tyr Ala Gly Ile Phe
                85                  90                  95

Gly Ala Gly Thr Thr Leu Thr Val Leu Gly Ala Ala Ala
            100                 105

<210> SEQ ID NO 114
<211> LENGTH: 110
<212> TYPE: PRT
<213> ORGANISM: Gallus gallus

<400> SEQUENCE: 114

Thr Ala Leu Thr Gln Pro Ser Ser Val Ser Ala Asn Pro Gly Glu Thr
1               5                   10                  15

Val Glu Ile Thr Cys Ser Gly Gly Ser Gly Ser Tyr Tyr Gly Trp Tyr
                20                  25                  30

Gln Gln Lys Pro Pro Gly Ser Ala Pro Val Thr Val Ile Tyr Asn Asn
            35                  40                  45

Asn Asn Arg Pro Ser Asp Ile Pro Ser Arg Phe Ser Gly Ser Arg Ser

```
                 50                  55                  60
Gly Ser Thr Ala Thr Leu Thr Ile Thr Gly Val Gln Ala Asp Asp Glu
 65                  70                  75                  80

Ala Val Tyr Phe Cys Gly Ser Glu Asp Ser Thr Gly Tyr Val Gly Ile
                 85                  90                  95

Phe Gly Ala Gly Thr Thr Leu Thr Val Leu Gly Ala Ala Ala
                100                 105                 110

<210> SEQ ID NO 115
<211> LENGTH: 108
<212> TYPE: PRT
<213> ORGANISM: Gallus gallus

<400> SEQUENCE: 115

Thr Ala Leu Thr Gln Leu Ser Ser Val Ser Ala Asn Pro Gly Glu Thr
  1               5                  10                  15

Val Glu Ile Thr Cys Ser Gly Asp Ser Ser Tyr Tyr Gly Trp Tyr Gln
                 20                  25                  30

Gln Lys Ala Pro Gly Ser Ala Pro Val Thr Leu Ile Tyr Asp Asn Thr
                 35                  40                  45

Asn Arg Pro Ser Asp Ile Ser Ser Arg Phe Ser Gly Ser Lys Ser Gly
             50                  55                  60

Ser Thr Ala Thr Leu Thr Ile Thr Gly Val Gln Ala Asp Asp Glu Ala
 65                  70                  75                  80

Val Tyr Tyr Cys Gly Ser Ala Gly Ser Ser His Val Gly Met Phe Gly
                 85                  90                  95

Ala Gly Thr Thr Leu Thr Val Leu Gly Ala Ala Ala
                100                 105

<210> SEQ ID NO 116
<211> LENGTH: 108
<212> TYPE: PRT
<213> ORGANISM: Gallus gallus

<400> SEQUENCE: 116

Thr Ala Leu Thr Gln Pro Ser Ser Val Ser Ala Asn Pro Gly Glu Thr
  1               5                  10                  15

Val Glu Ile Thr Cys Ser Gly Asp Ser Ser Tyr Tyr Gly Trp Tyr Gln
                 20                  25                  30

Gln Lys Ala Pro Gly Ser Ala Pro Val Thr Leu Ile Tyr Asp Asn Thr
                 35                  40                  45

Asn Arg Pro Ser Asp Ile Ser Ser Arg Phe Ser Gly Ser Lys Ser Gly
             50                  55                  60

Ser Thr Ala Thr Leu Thr Ile Thr Gly Val Gln Ala Asp Asp Glu Ala
 65                  70                  75                  80

Val Tyr Tyr Cys Gly Ser Ala Gly Ser Ser His Val Gly Met Phe Gly
                 85                  90                  95

Ala Gly Thr Thr Leu Thr Val Leu Gly Ala Ala Ala
                100                 105

<210> SEQ ID NO 117
<211> LENGTH: 107
<212> TYPE: PRT
<213> ORGANISM: Gallus gallus

<400> SEQUENCE: 117

Thr Ala Leu Thr Gln Pro Ser Ser Val Ser Ala Asn Leu Gly Gly Thr
  1               5                  10                  15
```

```
Val Lys Ile Thr Cys Ser Gly Asp Ser Ser Tyr Tyr Gly Trp Tyr Gln
            20                  25                  30

Gln Lys Ala Pro Gly Ser Ala Pro Val Thr Val Ile Tyr Asp Asn Thr
            35                  40                  45

Asn Arg Pro Ser Gly Ile Pro Ser Arg Phe Ser Gly Ser Lys Ser Gly
            50                  55                  60

Ser Thr Ala Thr Leu Thr Ile Thr Gly Val Arg Ala Asp Asp Glu Ala
 65                  70                  75                  80

Val Tyr Tyr Cys Gly Asn Thr Asp Ser Ser Gly Ala Ile Phe Gly Ala
                85                  90                  95

Gly Thr Thr Leu Thr Val Leu Gly Ala Ala Ala
            100                 105

<210> SEQ ID NO 118
<211> LENGTH: 108
<212> TYPE: PRT
<213> ORGANISM: Gallus gallus

<400> SEQUENCE: 118

Thr Ala Leu Thr Gln Pro Ser Ser Val Ser Ala Asn Pro Gly Glu Thr
 1               5                  10                  15

Val Lys Ile Thr Cys Ser Gly Gly Ser Asn Asn Tyr Gly Trp Tyr Gln
            20                  25                  30

Gln Lys Ser Pro Gly Ser Ala Pro Val Thr Leu Ile Tyr Asp Asn Thr
            35                  40                  45

Asn Arg Pro Ser Asn Ile Pro Ser Arg Phe Ser Gly Ser Lys Ser Gly
            50                  55                  60

Ser Thr Ala Thr Leu Thr Ile Thr Gly Val Gln Ala Asp Asp Glu Ala
 65                  70                  75                  80

Val Tyr Tyr Cys Gly Ser Ala Asp Ser Ser Ser Thr Gly Ile Phe Gly
                85                  90                  95

Ala Gly Thr Thr Leu Thr Val Leu Gly Ala Ala Ala
            100                 105

<210> SEQ ID NO 119
<211> LENGTH: 109
<212> TYPE: PRT
<213> ORGANISM: Gallus gallus

<400> SEQUENCE: 119

Thr Ala Leu Thr Gln Pro Ser Ser Val Ser Ala Asn Pro Gly Glu Thr
 1               5                  10                  15

Val Lys Ile Thr Cys Ser Gly Gly Ser Gly Ser Tyr Tyr Gly Trp Tyr
            20                  25                  30

Gln Gln Lys Ser Pro Gly Ser Ala Pro Val Thr Leu Ile Tyr Asp Asn
            35                  40                  45

Asp Lys Arg Pro Ser Gly Ile Pro Ser Arg Phe Ser Gly Ser Thr Ser
            50                  55                  60

Gly Ser Thr Gly Thr Leu Thr Ile Thr Gly Val Gln Ala Glu Asp Glu
 65                  70                  75                  80

Ala Val Tyr Tyr Cys Gly Ser Arg Asp Ser Ser Tyr Val Gly Met Phe
                85                  90                  95

Gly Ala Gly Thr Thr Leu Thr Val Leu Gly Ala Ala Ala
            100                 105

<210> SEQ ID NO 120
```

```
<211> LENGTH: 109
<212> TYPE: PRT
<213> ORGANISM: Gallus gallus

<400> SEQUENCE: 120

Thr Ala Leu Thr Gln Pro Ser Ser Val Ser Ala Asn Pro Gly Glu Thr
1               5                   10                  15

Val Lys Ile Thr Cys Ser Gly Gly Tyr Asn Tyr Tyr Gly Trp Tyr Gln
            20                  25                  30

Gln Lys Ser Pro Gly Ser Val Pro Val Thr Leu Ile Tyr Asp Asn Thr
        35                  40                  45

Asn Arg Pro Ser Asn Ile Pro Ser Arg Phe Ser Gly Ser Thr Ser Gly
    50                  55                  60

Ser Thr Gly Thr Leu Thr Ile Thr Gly Val Gln Ala Asp Asp Glu Ala
65                  70                  75                  80

Val Tyr Phe Cys Gly Ser Ala Asp Ser Ser Thr Ser Ala Ser Phe
                85                  90                  95

Gly Ala Gly Thr Thr Leu Thr Val Leu Gly Ala Ala Ala
                100                 105

<210> SEQ ID NO 121
<211> LENGTH: 108
<212> TYPE: PRT
<213> ORGANISM: Gallus gallus

<400> SEQUENCE: 121

Thr Ala Leu Thr Gln Pro Ser Ser Val Ser Ala Asn Pro Gly Gly Thr
1               5                   10                  15

Val Lys Leu Thr Cys Ser Gly Asp Ser Ser Tyr Tyr Gly Trp Tyr His
            20                  25                  30

Gln Lys Ser Pro Gly Ser Ala Pro Val Thr Val Ile Tyr Asp Asn Thr
        35                  40                  45

Asn Arg Pro Ser Asn Ile Pro Ser Arg Phe Ser Gly Ser Leu Ser Gly
    50                  55                  60

Ser Thr Ala Thr Leu Thr Ile Thr Gly Val Gln Ala Glu Asp Glu Ala
65                  70                  75                  80

Val Tyr Tyr Cys Gly Ser Glu Asp Asn Thr Ser Thr Ala Ala Phe Gly
                85                  90                  95

Ala Gly Thr Thr Leu Thr Val Leu Gly Ala Ala Ala
                100                 105

<210> SEQ ID NO 122
<211> LENGTH: 108
<212> TYPE: PRT
<213> ORGANISM: Gallus gallus

<400> SEQUENCE: 122

Thr Ala Leu Thr Gln Pro Ser Ser Val Ser Ala Asn Pro Gly Glu Thr
1               5                   10                  15

Val Lys Ile Thr Cys Ser Gly Asp Ser Thr Tyr Tyr Gly Trp Tyr Gln
            20                  25                  30

Gln Lys Ala Pro Gly Ser Ala Pro Val Thr Leu Ile Tyr Asp Asn Thr
        35                  40                  45

Asn Arg Pro Ser Asn Ile Pro Ser Arg Phe Ser Gly Ser Leu Ser Gly
    50                  55                  60

Ser Thr Ala Thr Leu Thr Ile Thr Gly Val Gln Ala Glu Asp Glu Ala
65                  70                  75                  80
```

```
Val Tyr Phe Cys Gly Gly Ala Asp Ser Ser Ser Ala Ala Ser Phe Gly
                85                  90                  95

Ala Gly Thr Ala Leu Thr Val Leu Gly Ala Ala Ala
            100                 105
```

<210> SEQ ID NO 123
<211> LENGTH: 110
<212> TYPE: PRT
<213> ORGANISM: Gallus gallus

<400> SEQUENCE: 123

```
Thr Ala Leu Thr Gln Pro Ser Ser Val Ser Ala Asn Leu Gly Gly Thr
1               5                   10                  15

Val Glu Ile Thr Cys Ser Gly Ser Gly Ser Tyr Tyr Gly Trp Tyr
                20                  25                  30

Gln Gln Lys Ala Pro Gly Ser Ala Pro Val Thr Leu Ile Tyr Asp Asn
            35                  40                  45

Thr Asn Arg Pro Ser Asp Ile Pro Ser Arg Phe Ser Gly Ser Lys Ser
50                  55                  60

Gly Ser Thr Ala Thr Leu Thr Ile Thr Gly Val Arg Ala Glu Asp Glu
65                  70                  75                  80

Ala Val Tyr Tyr Cys Gly Ser Ala Asp Ser Ser Ser Glu Ala Ala
                85                  90                  95

Phe Gly Ala Gly Thr Thr Leu Thr Val Leu Gly Ala Ala Ala
            100                 105                 110
```

<210> SEQ ID NO 124
<211> LENGTH: 110
<212> TYPE: PRT
<213> ORGANISM: Gallus gallus

<400> SEQUENCE: 124

```
Thr Ala Leu Thr Gln Pro Ser Ser Val Ser Ala Asn Pro Gly Glu Thr
1               5                   10                  15

Val Glu Ile Thr Cys Ser Gly Gly Gly Ser Ser Tyr Gly Trp Tyr Gln
                20                  25                  30

Gln Lys Ser Pro Gly Ser Ala Pro Val Thr Val Ile Tyr Asp Asn Thr
            35                  40                  45

Asn Arg Pro Ser Asn Ile Pro Ser Arg Phe Ser Gly Ser Leu Ser Gly
50                  55                  60

Ser Ala Asn Thr Leu Thr Ile Thr Gly Val Gln Ala Asp Asp Glu Ala
65                  70                  75                  80

Val Tyr Tyr Cys Gly Ser Gly Asp Ser Ser Ala Ala Tyr Val Pro Ile
                85                  90                  95

Phe Gly Ala Gly Thr Thr Leu Thr Val Leu Gly Ala Ala Ala
            100                 105                 110
```

<210> SEQ ID NO 125
<211> LENGTH: 108
<212> TYPE: PRT
<213> ORGANISM: Gallus gallus

<400> SEQUENCE: 125

```
Thr Ala Leu Thr Gln Pro Ser Ser Val Ser Ala Asn Pro Gly Glu Thr
1               5                   10                  15

Val Glu Ile Thr Cys Ser Gly Gly Ile Gly His Tyr Gly Trp Tyr Gln
                20                  25                  30

Gln Lys Ala Pro Gly Ser Ala Pro Val Thr Val Ile Tyr Asp Ser Ser
```

-continued

```
                35                  40                  45
Ser Arg Pro Ser Asp Ile Pro Ser Arg Phe Ser Gly Ser Lys Ser Gly
 50                  55                  60

Ser Thr Gly Thr Leu Thr Ile Thr Gly Val Gln Ala Asp Asp Glu Ala
 65                  70                  75                  80

Val Tyr Tyr Cys Gly Ser Gly Ser Asn Gly Ala Gly Ile Phe Gly
                 85                  90                  95

Ala Gly Thr Thr Leu Thr Val Leu Gly Ala Ala Ala
            100                 105
```

<210> SEQ ID NO 126
<211> LENGTH: 108
<212> TYPE: PRT
<213> ORGANISM: Gallus gallus

<400> SEQUENCE: 126

```
Thr Ala Leu Thr Gln Pro Ser Ser Val Ser Ala Asn Pro Gly Glu Thr
  1               5                  10                  15

Val Lys Ile Thr Cys Ser Gly Asp Gly Ser Ser Tyr Gly Trp Tyr Gln
                 20                  25                  30

Gln Lys Ser Pro Gly Ser Ala Pro Val Thr Val Ile Tyr Asp Ser Thr
             35                  40                  45

Asn Arg Pro Trp Asp Ile Pro Ser Arg Phe Ser Gly Ser Lys Ser Gly
 50                  55                  60

Ser Thr Gly Thr Leu Thr Ile Thr Gly Val Gln Ala Glu Asp Glu Ala
 65                  70                  75                  80

Val Tyr Phe Cys Gly Thr Thr Asp Ser Thr Ser Ala Ala Ile Phe Gly
                 85                  90                  95

Ala Gly Thr Thr Leu Thr Val Leu Gly Ala Ala Ala
            100                 105
```

<210> SEQ ID NO 127
<211> LENGTH: 112
<212> TYPE: PRT
<213> ORGANISM: Gallus gallus

<400> SEQUENCE: 127

```
Thr Ala Leu Thr Gln Pro Ser Ser Val Ser Ala Asn Pro Gly Glu Thr
  1               5                  10                  15

Val Lys Ile Thr Cys Ser Gly Gly Ser Ser Ser Tyr Tyr Gly Trp
                 20                  25                  30

Tyr Gln Gln Lys Ala Pro Gly Ser Ala Pro Val Thr Val Ile Tyr Asp
             35                  40                  45

Asn Thr Asn Arg Pro Ser Gly Ile Pro Ser Arg Phe Ser Gly Ser Lys
         50                  55                  60

Ser Gly Ser Thr Ala Thr Leu Thr Ile Thr Gly Val Gln Ala Asp Asp
 65                  70                  75                  80

Glu Ala Val Tyr Tyr Cys Gly Gly Gly Ser Ala Asp Ser Ser Gly Ala
                 85                  90                  95

Gly Ile Phe Gly Ala Gly Thr Thr Leu Thr Val Leu Gly Ala Ala Ala
            100                 105                 110
```

<210> SEQ ID NO 128
<211> LENGTH: 110
<212> TYPE: PRT
<213> ORGANISM: Gallus gallus

<400> SEQUENCE: 128

Thr Ala Leu Thr Gln Pro Ser Ser Val Ser Ala Asn Pro Gly Glu Thr
1               5                   10                  15

Val Val Ile Thr Cys Ser Gly Asp Thr Tyr Thr Tyr Gly Trp Tyr Gln
            20                  25                  30

Gln Lys Ser Pro Gly Ser Ala Pro Val Thr Val Ile Tyr Ala Asn Thr
        35                  40                  45

Asn Arg Pro Ser Asp Ile Pro Ser Arg Phe Ser Gly Ser Gly Ser Gly
    50                  55                  60

Ser Thr Ala Thr Leu Thr Ile Thr Gly Val Gln Ala Glu Asp Glu Ala
65                  70                  75                  80

Val Tyr Tyr Cys Gly Gly Trp Asp Ser Ser Ala Gly Tyr Ser Gly Ile
                85                  90                  95

Phe Gly Ala Gly Thr Thr Leu Thr Val Leu Gly Ala Ala Ala
                100                 105                 110

<210> SEQ ID NO 129
<211> LENGTH: 108
<212> TYPE: PRT
<213> ORGANISM: Gallus gallus

<400> SEQUENCE: 129

Thr Ala Leu Thr Gln Pro Ser Ser Val Ser Ala Asn Pro Gly Glu Thr
1               5                   10                  15

Val Glu Ile Thr Cys Ser Gly Asp Ser Ser Tyr Tyr Gly Trp Tyr Gln
            20                  25                  30

Gln Lys Ser Pro Gly Ser Ala Pro Val Thr Val Ile Tyr Asn Asn Asp
        35                  40                  45

Asn Arg Pro Ser Asp Ile Pro Ser Arg Phe Ser Gly Ser Arg Ser Gly
    50                  55                  60

Ser Thr Asn Thr Leu Thr Ile Thr Gly Val Gln Ala Asp Asp Glu Ala
65                  70                  75                  80

Val Tyr Tyr Cys Gly Ser Ala Asp Ser Ser Thr Asp Gly Ile Phe Gly
                85                  90                  95

Ala Gly Thr Thr Leu Thr Val Leu Gly Ala Ala Ala
                100                 105

<210> SEQ ID NO 130
<211> LENGTH: 108
<212> TYPE: PRT
<213> ORGANISM: Gallus gallus

<400> SEQUENCE: 130

Thr Ala Leu Thr Gln Pro Ser Ser Val Ser Ala Asn Pro Gly Glu Thr
1               5                   10                  15

Val Glu Ile Thr Cys Ser Gly Gly Ser Asn Asn Tyr Gly Trp Phe Gln
            20                  25                  30

Gln Lys Ser Pro Gly Ser Ala Pro Val Thr Val Ile Tyr Asp Asn Thr
        35                  40                  45

Asn Arg Pro Ser Asp Ile Pro Ser Arg Phe Ser Gly Ser Thr Ser Gly
    50                  55                  60

Ser Thr Ser Thr Leu Thr Ile Thr Gly Val Gln Ala Asp Asp Glu Ala
65                  70                  75                  80

Val Tyr Phe Cys Gly Ser Ala Asp Thr Asn Tyr Asp Phe Ile Phe Gly
                85                  90                  95

Ala Gly Thr Thr Leu Thr Val Leu Gly Ala Ala Ala
                100                 105

<210> SEQ ID NO 131
<211> LENGTH: 108
<212> TYPE: PRT
<213> ORGANISM: Gallus gallus

<400> SEQUENCE: 131

Thr Ala Leu Thr Gln Pro Ser Ser Val Ser Ala Asn Pro Gly Glu Thr
1               5                   10                  15

Val Glu Ile Thr Cys Ser Gly Gly His Tyr Ser Tyr Gly Trp Phe Gln
            20                  25                  30

Gln Lys Ala Pro Gly Ser Ala Pro Val Thr Val Ile Tyr Arg Asn Asp
        35                  40                  45

Lys Arg Pro Ser Gly Ile Pro Ser Arg Phe Ser Gly Ser Leu Ser Gly
    50                  55                  60

Ser Thr Gly Thr Leu Thr Ile Thr Gly Val Gln Ala Asp Asp Glu Ala
65                  70                  75                  80

Val Tyr Tyr Cys Gly Ser Ala Asp Ser Ser Tyr Val Ala Ile Phe Gly
                85                  90                  95

Ala Gly Thr Thr Leu Thr Val Leu Gly Ala Ala Ala
            100                 105

<210> SEQ ID NO 132
<211> LENGTH: 110
<212> TYPE: PRT
<213> ORGANISM: Gallus gallus

<400> SEQUENCE: 132

Thr Ala Leu Thr Gln Pro Ser Ser Val Ser Ala Asn Leu Gly Gly Thr
1               5                   10                  15

Val Glu Ile Thr Cys Ser Gly Arg Asn Arg His Tyr Ser Tyr Gly Trp
            20                  25                  30

Phe Gln Gln Lys Ala Pro Gly Ser Ala Leu Val Thr Val Ile Tyr Ser
        35                  40                  45

Asn Asn Lys Arg Pro Ser Asp Ile Pro Ser Arg Phe Ser Gly Ser Leu
    50                  55                  60

Ser Gly Ser Thr Asn Thr Leu Thr Ile Thr Gly Val Gln Ala Asp Asp
65                  70                  75                  80

Glu Ala Val Tyr Tyr Cys Gly Ser Ala Asp Ser Ser Asn Val Ala Ile
                85                  90                  95

Phe Gly Ala Gly Thr Thr Leu Thr Val Leu Gly Ala Ala Ala
            100                 105                 110

<210> SEQ ID NO 133
<211> LENGTH: 108
<212> TYPE: PRT
<213> ORGANISM: Gallus gallus

<400> SEQUENCE: 133

Thr Ala Leu Thr Gln Pro Ser Ser Val Ser Ala Asn Leu Gly Gly Thr
1               5                   10                  15

Val Glu Ile Thr Cys Ser Gly Gly His Tyr Ser Tyr Gly Trp Phe Gln
            20                  25                  30

Gln Lys Ala Pro Gly Ser Ala Pro Val Thr Val Ile Tyr Arg Asn Asp
        35                  40                  45

Lys Arg Pro Ser Asp Ile Pro Ser Arg Phe Ser Gly Ser Leu Ser Gly
    50                  55                  60

```
Ser Thr Gly Thr Leu Thr Ile Thr Gly Val Gln Ala Asp Asp Glu Ala
 65                  70                  75                  80

Val Tyr Phe Cys Gly Ser Ala Asp Ser Thr Tyr Val Gly Ile Phe Gly
                 85                  90                  95

Ala Gly Thr Thr Leu Thr Val Leu Gly Ala Ala Ala
            100                 105

<210> SEQ ID NO 134
<211> LENGTH: 109
<212> TYPE: PRT
<213> ORGANISM: Gallus gallus

<400> SEQUENCE: 134

Thr Ala Leu Thr Gln Pro Ser Ser Val Ser Ala Asn Pro Gly Gly Thr
 1               5                  10                  15

Val Glu Ile Thr Cys Ser Gly Gly Ser Tyr Gly Trp Tyr Gln
            20                  25                  30

Gln Lys Ser Pro Gly Ser Ala Pro Val Thr Val Ile Tyr Ala Asn Thr
             35                  40                  45

Asn Arg Pro Ser Asp Ile Pro Ser Arg Phe Ser Gly Ser Thr Ser Gly
         50                  55                  60

Ser Thr Gly Thr Leu Thr Ile Thr Gly Val Gln Ala Asp Asp Glu Ala
 65                  70                  75                  80

Val Tyr Phe Cys Gly Ser Tyr Asp Ser Ser Asn Thr Ala Gly Ile Phe
                 85                  90                  95

Gly Ala Gly Thr Thr Leu Thr Val Leu Gly Ala Ala Ala
            100                 105

<210> SEQ ID NO 135
<211> LENGTH: 114
<212> TYPE: PRT
<213> ORGANISM: Gallus gallus

<400> SEQUENCE: 135

Thr Ala Leu Thr Gln Pro Ser Ser Val Ser Ala Asn Pro Gly Glu Thr
 1               5                  10                  15

Val Lys Ile Thr Cys Ser Gly Gly Gly Ser Tyr Ala Gly Ser Tyr Tyr
            20                  25                  30

Tyr Gly Trp Tyr Gln Gln Lys Ala Ser Gly Ser Ala Pro Val Thr Val
             35                  40                  45

Ile Tyr Ser Asn Asp Lys Arg Pro Ser Asp Ile Pro Ser Arg Phe Ser
         50                  55                  60

Gly Ser Thr Ser Gly Ser Thr Gly Thr Leu Thr Ile Thr Gly Val Gln
 65                  70                  75                  80

Ala Asp Asp Glu Ala Val Tyr Tyr Cys Gly Ser Trp Asp Ser Ser Ser
                 85                  90                  95

Tyr Asp Gly Ile Phe Gly Ala Gly Thr Thr Leu Thr Val Leu Gly Ala
            100                 105                 110

Ala Ala

<210> SEQ ID NO 136
<211> LENGTH: 109
<212> TYPE: PRT
<213> ORGANISM: Gallus gallus

<400> SEQUENCE: 136

Thr Ala Leu Thr Gln Pro Ser Ser Val Ser Ala Asn Pro Gly Glu Thr
 1               5                  10                  15
```

```
Val Glu Ile Thr Cys Ser Gly Gly Asn Tyr Gly Trp Tyr Ser Trp His
            20                  25                  30

Gln Gln Lys Ser Pro Gly Ser Ala Pro Val Thr Leu Ile Tyr Glu Asn
        35                  40                  45

Asn Lys Arg Leu Ser Asp Ile Pro Ser Arg Phe Ser Gly Ser Lys Ser
    50                  55                  60

Gly Ser Thr Ala Thr Leu Thr Ile Thr Gly Val Gln Ala Glu Asp Glu
65                  70                  75                  80

Ala Val Tyr Phe Cys Gly Ser Thr Asp Ser Ser Tyr Val Gly Ile Phe
                85                  90                  95

Gly Ala Gly Thr Thr Leu Thr Val Leu Gly Ala Ala Ala
            100                 105
```

<210> SEQ ID NO 137
<211> LENGTH: 110
<212> TYPE: PRT
<213> ORGANISM: Gallus gallus

<400> SEQUENCE: 137

```
Thr Ala Leu Thr Gln Pro Ser Ser Val Ser Ala Asn Pro Gly Glu Thr
1               5                   10                  15

Val Lys Asn Thr Cys Ser Gly Gly Ser Ser Ser Tyr Arg Tyr Gly Trp
            20                  25                  30

Tyr Gln Gln Lys Ser Pro Gly Ser Ala Pro Val Thr Leu Ile Tyr Ala
        35                  40                  45

Asn Thr Asn Arg Pro Ser Asn Ile Pro Ser Arg Phe Ser Gly Ser Lys
    50                  55                  60

Ser Gly Ser Thr His Thr Leu Thr Ile Thr Gly Val Gln Ala Asp Asp
65                  70                  75                  80

Glu Ala Val Tyr Tyr Cys Gly Ser Ala Asp Ser Ser Tyr Val Gly Ile
                85                  90                  95

Phe Gly Ala Gly Thr Thr Leu Thr Val Leu Gly Ala Ala Ala
            100                 105                 110
```

<210> SEQ ID NO 138
<211> LENGTH: 103
<212> TYPE: PRT
<213> ORGANISM: Gallus gallus

<400> SEQUENCE: 138

```
Thr Ala Leu Thr Gln Pro Ser Ser Val Ser Ala Asn Pro Gly Glu Thr
1               5                   10                  15

Val Lys Ile Thr Cys Ser Gly Gly Gly Ser Ser Tyr Gly Trp Tyr Gln
            20                  25                  30

Gln Lys Ala Pro Gly Ser Ala Pro Val Thr Val Ile Tyr Gly Asn Thr
        35                  40                  45

Asn Arg Pro Ser Asn Ile Pro Ser Arg Phe Ser Gly Ser Lys Ser Gly
    50                  55                  60

Ser Thr Ala Thr Leu Thr Ile Thr Gly Val Gln Ala Asp Asp Glu Ala
65                  70                  75                  80

Val Tyr Phe Cys Gly Ser Ala Asp Ser Ser Gly Ala Gly Thr Thr Leu
                85                  90                  95

Thr Val Leu Gly Ala Ala Ala
            100
```

<210> SEQ ID NO 139

<211> LENGTH: 109
<212> TYPE: PRT
<213> ORGANISM: Gallus gallus

<400> SEQUENCE: 139

Ala Leu Thr Gln Pro Ser Ser Val Ser Ala Asn Pro Gly Gly Thr Val
1               5                   10                  15

Lys Ile Thr Cys Ser Gly Ser Gly Asn Tyr Gly Trp Tyr Gln Gln
            20                  25                  30

Lys Ser Pro Gly Ser Ala Leu Val Thr Val Ile Tyr Ser Asn Asp Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Gln Ala Asp Asp Glu Ala Val
65                  70                  75                  80

Tyr Phe Cys Gly Ser Glu Asp Ser Ser Ile Gly Asp Gly Ile Phe
                85                  90                  95

Gly Ala Gly Thr Thr Leu Thr Val Leu Gly Ala Ala Ala
            100                 105

<210> SEQ ID NO 140
<211> LENGTH: 108
<212> TYPE: PRT
<213> ORGANISM: Gallus gallus

<400> SEQUENCE: 140

Thr Ala Leu Thr Gln Pro Ser Ser Val Ser Ala Asn Leu Gly Gly Thr
1               5                   10                  15

Val Lys Ile Thr Cys Ser Gly Gly Ser Asn Asn Tyr Gly Trp Phe Gln
            20                  25                  30

Gln Lys Ser Pro Gly Ser Ala Pro Val Thr Val Ile Tyr Ser Asn Asn
        35                  40                  45

Gln Arg Pro Ser Asn Ile Pro Ser Arg Phe Ser Gly Ser Lys Ser Gly
    50                  55                  60

Ser Thr Gly Thr Leu Thr Ile Thr Gly Val Gln Ala Asp Asp Glu Ala
65                  70                  75                  80

Val Tyr Tyr Cys Gly Ser Gly Asp Ser Ser Tyr Ile Gly Ile Phe Gly
                85                  90                  95

Ala Gly Thr Thr Leu Thr Val Leu Gly Ala Ala Ala
            100                 105

<210> SEQ ID NO 141
<211> LENGTH: 107
<212> TYPE: PRT
<213> ORGANISM: Gallus gallus

<400> SEQUENCE: 141

Thr Ala Leu Thr Gln Pro Ser Ser Val Ser Ala Asn Leu Gly Gly Thr
1               5                   10                  15

Val Glu Ile Thr Cys Ser Gly Ser Ser Gly Ser Tyr Gly Trp Tyr Gln
            20                  25                  30

Gln Lys Ser Pro Asp Ser Ala Pro Val Ser Val Ile Tyr Ser Thr Asn
        35                  40                  45

Gln Arg Pro Ser Asn Ile Pro Ser Arg Phe Ser Gly Ser Lys Ser Gly
    50                  55                  60

Ser Thr Ala Thr Leu Thr Ile Thr Gly Val Gln Ala Asp Asp Glu Ala
65                  70                  75                  80

```
Val Tyr Tyr Cys Gly Ser Tyr Glu Asp Ser Ser Asn Thr Ile Gly Ala
                85                  90                  95

Gly Thr Thr Leu Thr Val Leu Gly Ala Ala Ala
            100                 105
```

<210> SEQ ID NO 142
<211> LENGTH: 108
<212> TYPE: PRT
<213> ORGANISM: Gallus gallus

<400> SEQUENCE: 142

```
Thr Ala Leu Thr Gln Pro Ser Ser Val Ser Ala Asn Pro Gly Glu Thr
1               5                   10                  15

Val Lys Ile Thr Cys Ser Gly Gly Ser Gly Asn Tyr Gly Trp Tyr Gln
                20                  25                  30

Gln Lys Ala Pro Gly Ser Ala Pro Val Thr Val Ile Ser Gly Ser Thr
            35                  40                  45

Leu Arg Pro Ser Asp Ile Pro Ser Arg Phe Ser Gly Ser Lys Ser Gly
        50                  55                  60

Ser Thr Gly Thr Leu Thr Ile Thr Gly Val Gln Ala Glu Asp Glu Ala
65                  70                  75                  80

Val Tyr Phe Cys Gly Ser Ala Asp Ser Ser Tyr Ala Gly Ile Phe Gly
                85                  90                  95

Ala Gly Thr Thr Leu Thr Val Leu Gly Ala Ala Ala
            100                 105
```

<210> SEQ ID NO 143
<211> LENGTH: 110
<212> TYPE: PRT
<213> ORGANISM: Gallus gallus

<400> SEQUENCE: 143

```
Thr Ala Leu Thr Gln Pro Ser Ser Val Ser Ala Asn Pro Gly Glu Thr
1               5                   10                  15

Val Lys Ile Thr Cys Ser Gly Gly Ser Asn Tyr Tyr Tyr Gly Trp Tyr
                20                  25                  30

Gln Gln Lys Ser Pro Gly Ser Ala Pro Val Thr Val Ile Tyr Ala Asn
            35                  40                  45

Thr Asn Arg Pro Ser Asp Ile Pro Ser Arg Phe Ser Gly Ser Leu Ser
        50                  55                  60

Gly Ser Thr Ala Thr Leu Thr Ile Thr Gly Val Gln Ala Asp Asp Glu
65                  70                  75                  80

Ala Val Tyr Tyr Cys Gly Ser Ala Asp Ser Ser Thr Tyr Ala Gly Ile
                85                  90                  95

Phe Gly Ala Gly Thr Thr Leu Thr Val Leu Gly Ala Ala Ala
            100                 105                 110
```

<210> SEQ ID NO 144
<211> LENGTH: 110
<212> TYPE: PRT
<213> ORGANISM: Gallus gallus

<400> SEQUENCE: 144

```
Thr Ala Leu Thr Gln Pro Ser Ser Val Ser Ala Asn Pro Gly Glu Thr
1               5                   10                  15

Val Lys Ile Thr Cys Ser Gly Gly Ser Asn Asn Trp Tyr Ser Trp His
                20                  25                  30

Gln Gln Lys Ser Pro Gly Ser Ala Pro Val Thr Val Ile Tyr Asn Asn
```

-continued

```
                35                  40                  45
Asp Lys Arg Pro Ser Asp Ile Pro Ser Arg Phe Ser Gly Phe Thr Ser
 50                  55                  60

Gly Ser Thr Ser Thr Leu Thr Ile Thr Gly Val Gln Ala Asp Asp Glu
 65                  70                  75                  80

Ala Val Tyr Phe Cys Gly Gly Trp Asp Ser Ser Arg Ala Gly Ile
                 85                  90                  95

Phe Gly Ala Gly Thr Thr Leu Thr Val Leu Gly Ala Ala Ala
            100                 105                 110
```

<210> SEQ ID NO 145
<211> LENGTH: 107
<212> TYPE: PRT
<213> ORGANISM: Gallus gallus

<400> SEQUENCE: 145

```
Thr Ala Leu Thr Gln Pro Ser Ser Val Ser Ala Asn Pro Gly Glu Thr
 1               5                  10                  15

Val Lys Ile Thr Cys Ser Gly Gly Asn Ser Gly Tyr Gly Trp Tyr Gln
                20                  25                  30

Gln Lys Ser Pro Gly Ser Ala Pro Val Thr Val Ile Tyr Ser Asn Asp
            35                  40                  45

Lys Arg Pro Ser Asp Ile Pro Ser Arg Phe Ser Gly Ala Leu Ser Gly
 50                  55                  60

Ser Thr Ala Thr Leu Thr Ile Thr Gly Val Arg Ala Glu Asp Glu Ala
 65                  70                  75                  80

Val Tyr Tyr Cys Gly Ser Gly Asp Ser Ser Gly Ser Val Phe Gly Ala
                85                  90                  95

Gly Thr Thr Leu Thr Val Leu Gly Ala Ala Ala
            100                 105
```

<210> SEQ ID NO 146
<211> LENGTH: 108
<212> TYPE: PRT
<213> ORGANISM: Gallus gallus

<400> SEQUENCE: 146

```
Thr Ala Leu Thr Gln Pro Ser Ser Val Ser Ala Asn Pro Gly Glu Thr
 1               5                  10                  15

Val Glu Ile Thr Cys Ser Gly Asp Ser Ser Asn Tyr Gly Trp Tyr
                20                  25                  30

Gln Gln Lys Ser Pro Gly Ser Ala Pro Val Thr Leu Ile Tyr Tyr Asp
            35                  40                  45

Asp Glu Arg Pro Ser Gly Ile Pro Ser Arg Phe Ser Gly Ser Lys Ser
 50                  55                  60

Gly Ser Thr Ala Thr Leu Thr Ile Thr Gly Val Gln Ala Asp Asp Glu
 65                  70                  75                  80

Ala Val Tyr Tyr Cys Gly Ser Tyr Asp Ser Ser Thr Gly Ile Phe Gly
                85                  90                  95

Ala Gly Thr Thr Leu Thr Val Leu Gly Ala Ala Ala
            100                 105
```

<210> SEQ ID NO 147
<211> LENGTH: 111
<212> TYPE: PRT
<213> ORGANISM: Gallus gallus

<400> SEQUENCE: 147

```
Thr Ala Leu Thr Gln Pro Ser Ser Val Ser Ala Asn Pro Gly Glu Thr
1               5                   10                  15

Val Glu Ile Thr Cys Ser Gly Gly Ser Ser Tyr Tyr Gly Trp
            20                  25                  30

Tyr Gln Gln Lys Ser Pro Gly Ser Ala Pro Val Thr Val Ile Tyr Glu
                35                  40                  45

Asn Thr Asn Arg Pro Ser Asp Ile Pro Ser Arg Phe Ser Gly Ser Lys
        50                  55                  60

Ser Gly Ser Thr Ala Thr Leu Thr Ile Thr Gly Val Gln Ala Glu Asp
65                  70                  75                  80

Glu Ala Val Tyr Tyr Cys Gly Ser Gly Asp Ser Asn Thr Tyr Asn Gly
                85                  90                  95

Ile Phe Gly Ala Gly Thr Thr Leu Thr Val Leu Gly Ala Ala Ala
            100                 105                 110

<210> SEQ ID NO 148
<211> LENGTH: 107
<212> TYPE: PRT
<213> ORGANISM: Gallus gallus

<400> SEQUENCE: 148

Thr Ala Leu Thr Gln Pro Ser Ser Val Ser Ala Asn Pro Gly Lys Thr
1               5                   10                  15

Val Glu Ile Thr Cys Ser Gly Gly Ser Gly Ser Tyr Gly Trp Tyr Gln
            20                  25                  30

Gln Lys Ser Pro Gly Ser Ala Pro Val Thr Val Ile Tyr Trp Asp Asp
        35                  40                  45

Lys Arg Pro Ser Gly Ile Pro Ser Arg Phe Ser Gly Ser Glu Ser Gly
    50                  55                  60

Ser Thr Ala Thr Leu Thr Ile Thr Gly Val Gln Ala Glu Asp Glu Ala
65                  70                  75                  80

Val Tyr Tyr Cys Gly Ser Ala Asp Ser Ser Gly Ala Ile Phe Gly Ala
                85                  90                  95

Gly Thr Thr Leu Thr Val Leu Gly Ala Ala Ala
            100                 105

<210> SEQ ID NO 149
<211> LENGTH: 109
<212> TYPE: PRT
<213> ORGANISM: Gallus gallus

<400> SEQUENCE: 149

Thr Ala Leu Thr Gln Pro Ser Ser Val Ser Ala Asn Leu Gly Gly Thr
1               5                   10                  15

Val Lys Ile Thr Cys Ser Gly Ser Ser Gly Ser Tyr Gly Trp Tyr Arg
            20                  25                  30

Gln Lys Ala Pro Gly Ser Ala Pro Val Thr Val Ile Tyr Ser Asn Asp
        35                  40                  45

Lys Arg Pro Ser Asp Ile Pro Ser Arg Phe Ser Gly Ser Ala Ser Gly
    50                  55                  60

Ser Thr Ala Thr Leu Thr Ile Thr Gly Val Gln Ala Glu Asp Glu Ala
65                  70                  75                  80

Val Tyr Phe Cys Gly Gly Tyr Asp Gly Ser Ser Tyr Val Gly Ile Phe
                85                  90                  95

Gly Ala Gly Thr Thr Leu Thr Val Leu Gly Ala Ala Ala
            100                 105
```

<210> SEQ ID NO 150
<211> LENGTH: 112
<212> TYPE: PRT
<213> ORGANISM: Gallus gallus

<400> SEQUENCE: 150

Thr Ala Leu Thr Gln Pro Ser Ser Val Ser Ala Asn Pro Gly Glu Thr
1               5                   10                  15

Val Lys Ile Thr Cys Ser Gly Gly Ser Gly Tyr Gly Tyr Gly Trp Tyr
            20                  25                  30

Gln Gln Lys Ser Pro Gly Ser Ala Pro Val Thr Val Ile Tyr Gln Asn
        35                  40                  45

Asp Lys Arg Pro Ser Asn Ile Pro Ser Arg Phe Ser Gly Ser Gly Ser
    50                  55                  60

Gly Ser Thr Gly Thr Leu Thr Ile Thr Gly Val Gln Val Glu Asp Glu
65                  70                  75                  80

Ala Val Tyr Tyr Cys Gly Thr Ala Asp Ser Ser Tyr Val Gly Asp Ala
                85                  90                  95

Gly Ile Phe Gly Ala Gly Thr Thr Leu Thr Val Leu Gly Ala Ala Ala
            100                 105                 110

<210> SEQ ID NO 151
<211> LENGTH: 108
<212> TYPE: PRT
<213> ORGANISM: Gallus gallus

<400> SEQUENCE: 151

Thr Ala Leu Thr Gln Pro Ser Ser Val Ser Ala Asn Pro Gly Glu Thr
1               5                   10                  15

Val Lys Ile Thr Cys Ser Gly Gly Ser Ser Gly Arg Tyr Gly Trp Tyr
            20                  25                  30

Gln Gln Lys Ser Pro Gly Ser Ala Pro Val Thr Val Ile Tyr Tyr Asn
        35                  40                  45

Asp Lys Arg Pro Ser Asp Ile Pro Ser Arg Phe Ser Gly Ser Leu Pro
    50                  55                  60

Gly Ser Thr Ala Thr Leu Thr Ile Thr Gly Val Gln Val Glu Asp Glu
65                  70                  75                  80

Ala Val Tyr Phe Cys Gly Ser Ala Asp Ser Thr Ala Gly Ile Phe Gly
                85                  90                  95

Ala Gly Thr Thr Leu Thr Val Leu Gly Ala Ala Ala
            100                 105

<210> SEQ ID NO 152
<211> LENGTH: 110
<212> TYPE: PRT
<213> ORGANISM: Gallus gallus

<400> SEQUENCE: 152

Thr Ala Leu Thr Gln Pro Ser Ser Val Ser Ala Asn Leu Gly Gly Thr
1               5                   10                  15

Val Lys Ile Thr Cys Ser Gly Gly Tyr Ser Gly Tyr Gly Tyr Gly Trp
            20                  25                  30

Tyr Gln Gln Lys Ser Pro Gly Ser Ala Pro Val Thr Leu Ile Tyr Asn
        35                  40                  45

Gly Asn Asn Arg Pro Ser Asp Ile Pro Ser Arg Phe Ser Gly Ser Gly
    50                  55                  60

-continued

Ser Gly Ser Thr Asn Thr Leu Thr Ile Thr Gly Val Gln Val Glu Asp
65                  70                  75                  80

Glu Ala Ile Tyr Phe Cys Gly Ser Ala Asp Ser Ser Ile Ala Val
            85                  90                  95

Phe Gly Ala Gly Thr Thr Leu Thr Val Leu Gly Ala Ala Ala
            100                 105                 110

<210> SEQ ID NO 153
<211> LENGTH: 109
<212> TYPE: PRT
<213> ORGANISM: Gallus gallus

<400> SEQUENCE: 153

Thr Ala Leu Thr Gln Pro Ser Ser Val Ser Ala Asn Pro Gly Glu Thr
1               5                   10                  15

Val Glu Ile Thr Cys Ser Gly Gly Arg Lys Tyr Tyr Gly Trp Tyr Gln
            20                  25                  30

Gln Lys Ser Pro Gly Ser Ala Pro Val Thr Leu Ile Tyr Ser Asn Asp
            35                  40                  45

Lys Arg Pro Ser Asp Ile Pro Ser Arg Phe Ser Gly Ser Lys Ser Gly
        50                  55                  60

Ser Thr Ala Thr Leu Thr Ile Thr Gly Val Gln Val Asp Asp Glu Ala
65                  70                  75                  80

Val Tyr Tyr Cys Gly Ser Ala Asp Thr Ser Ser Glu Ala Ala Phe
            85                  90                  95

Gly Ala Gly Thr Thr Leu Thr Val Leu Gly Ala Ala Ala
            100                 105

<210> SEQ ID NO 154
<211> LENGTH: 113
<212> TYPE: PRT
<213> ORGANISM: Gallus gallus

<400> SEQUENCE: 154

Ala Leu Thr Gln Pro Ala Ser Val Ser Ala Asn Leu Gly Glu Thr Val
1               5                   10                  15

Lys Ile Thr Cys Ser Gly Gly Ser Tyr Ala Gly Ser Tyr Tyr Tyr
            20                  25                  30

Gly Trp Tyr Gln Gln Lys Ser Pro Gly Ser Ala Pro Val Thr Val Ile
            35                  40                  45

Tyr Asp Asn Thr Asn Arg Pro Ser Asn Ile Pro Ser Arg Phe Ser Gly
        50                  55                  60

Ser Lys Ser Gly Pro Thr Ala Thr Leu Thr Ile Thr Gly Val Gln Val
65                  70                  75                  80

Asp Asp Glu Ala Val Tyr Tyr Cys Gly Ser Met Asp Ser Ser Ser Gly
            85                  90                  95

Gly Gly Ile Phe Gly Ala Gly Thr Thr Leu Thr Val Leu Gly Ala Ala
            100                 105                 110

Ala

<210> SEQ ID NO 155
<211> LENGTH: 250
<212> TYPE: PRT
<213> ORGANISM: Gallus gallus

<400> SEQUENCE: 155

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Tyr
            20                  25                  30

Gln Met Asn Trp Leu Arg Gln Ala Pro Gly Lys Gly Leu Glu Trp Val
            35                  40                  45

Gly Val Ile Ser Thr Arg Gly Ser Ser Thr Ala Tyr Gly Ala Ala Val
        50                  55                  60

Lys Gly Arg Ala Thr Ile Ser Arg Asp Asn Gly Arg Ser Thr Val Arg
65                  70                  75                  80

Leu Gln Leu Asn Ser Leu Arg Thr Glu Asp Thr Ala Thr Tyr Tyr Cys
                85                  90                  95

Ala Lys Ala Gly Tyr Ala Cys Gly Trp Ser Val Gly Cys Ile Asp Ala
            100                 105                 110

Trp Gly His Gly Thr Glu Val Ile Val Ser Ser Leu Asp Gly Gly Gly
            115                 120                 125

Gly Ser Gly Gly Gly Gly Ser Gly Gly Gly Gly Ser Thr Ala Leu Thr
        130                 135                 140

Gln Pro Ser Ser Val Ser Ala Asn Pro Gly Glu Thr Val Lys Asn Thr
145                 150                 155                 160

Cys Ser Gly Gly Ser Ser Tyr Arg Tyr Gly Trp Tyr Gln Gln Lys
                165                 170                 175

Ser Pro Gly Ser Ala Pro Val Thr Leu Ile Tyr Ala Asn Thr Asn Arg
            180                 185                 190

Pro Ser Asn Ile Pro Ser Arg Phe Ser Gly Ser Lys Ser Gly Ser Thr
        195                 200                 205

His Thr Leu Thr Ile Thr Gly Val Gln Ala Asp Asp Glu Ala Val Tyr
    210                 215                 220

Tyr Cys Gly Ser Ala Asp Ser Ser Tyr Val Gly Ile Phe Gly Ala Gly
225                 230                 235                 240

Thr Thr Leu Thr Val Leu Gly Ala Ala Ala
            245                 250

<210> SEQ ID NO 156
<211> LENGTH: 243
<212> TYPE: PRT
<213> ORGANISM: Gallus gallus

<400> SEQUENCE: 156

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Tyr
            20                  25                  30

Gln Met Asn Trp Leu Arg Gln Ala Pro Gly Lys Gly Leu Glu Trp Val
            35                  40                  45

Gly Val Ile Ser Thr Arg Gly Ser Ser Thr Ala Tyr Gly Ala Ala Val
        50                  55                  60

Lys Gly Arg Ala Thr Ile Ser Arg Asp Asn Gly Arg Ser Thr Val Arg
65                  70                  75                  80

Leu Gln Leu Asn Ser Leu Arg Thr Glu Asp Thr Ala Thr Tyr Tyr Cys
                85                  90                  95

Ala Lys Ala Gly Tyr Ala Cys Gly Trp Ser Val Gly Cys Ile Asp Ala
            100                 105                 110

Trp Gly His Gly Thr Glu Val Ile Val Ser Ser Leu Asp Gly Gly Gly
            115                 120                 125

Gly Ser Gly Gly Gly Gly Ser Gly Gly Gly Gly Ser Thr Ala Leu Thr

```
                130                 135                 140
Gln Pro Ser Ser Val Ser Ala Asn Pro Gly Glu Thr Val Lys Ile Thr
145                 150                 155                 160

Cys Ser Gly Gly Ser Ser Tyr Gly Trp Tyr Gln Gln Lys Ala Pro
                165                 170                 175

Gly Ser Ala Pro Val Thr Val Ile Tyr Gly Asn Thr Asn Arg Pro Ser
                180                 185                 190

Asn Ile Pro Ser Arg Phe Ser Gly Ser Lys Ser Gly Ser Thr Ala Thr
                195                 200                 205

Leu Thr Ile Thr Gly Val Gln Ala Asp Asp Glu Ala Val Tyr Phe Cys
                210                 215                 220

Gly Ser Ala Asp Ser Ser Gly Ala Gly Thr Thr Leu Thr Val Leu Gly
225                 230                 235                 240

Ala Ala Ala

<210> SEQ ID NO 157
<211> LENGTH: 248
<212> TYPE: PRT
<213> ORGANISM: Gallus gallus

<400> SEQUENCE: 157

Ala Val Thr Leu Asp Glu Ser Gly Gly Leu Gln Thr Pro Gly Gly
1               5                   10                  15

Thr Leu Ser Leu Val Cys Lys Ala Ser Gly Phe Thr Phe Ser Ser Tyr
                20                  25                  30

Gln Met Asn Trp Leu Arg Gln Ala Pro Gly Lys Gly Leu Glu Trp Val
                35                  40                  45

Gly Val Ile Ser Thr Arg Gly Ser Ser Thr Ala Tyr Gly Ala Ala Val
        50                  55                  60

Lys Gly Arg Ala Thr Ile Ser Arg Asp Asn Gly Arg Ser Thr Val Arg
65                  70                  75                  80

Leu Gln Leu Asn Ser Leu Arg Thr Glu Asp Thr Ala Thr Tyr Tyr Cys
                85                  90                  95

Ala Lys Ala Gly Tyr Ala Cys Gly Trp Ser Val Gly Cys Ile Asp Ala
                100                 105                 110

Trp Gly His Gly Thr Glu Val Ile Val Ser Ser Leu Asp Gly Gly Gly
                115                 120                 125

Gly Ser Gly Gly Gly Gly Ser Gly Gly Gly Ser Thr Ala Leu Thr
130                 135                 140

Gln Pro Ser Ser Val Ser Ala Asn Leu Gly Gly Thr Val Lys Ile Thr
145                 150                 155                 160

Cys Ser Gly Gly Ser Asn Asn Tyr Gly Trp Phe Gln Gln Lys Ser Pro
                165                 170                 175

Gly Ser Ala Pro Val Thr Val Ile Tyr Ser Asn Asn Gln Arg Pro Ser
                180                 185                 190

Asn Ile Pro Ser Arg Phe Ser Gly Ser Lys Ser Gly Ser Thr Gly Thr
                195                 200                 205

Leu Thr Ile Thr Gly Val Gln Ala Asp Asp Glu Ala Val Tyr Tyr Cys
                210                 215                 220

Gly Ser Gly Asp Ser Ser Tyr Ile Gly Ile Phe Gly Ala Gly Thr Thr
225                 230                 235                 240

Leu Thr Val Leu Gly Ala Ala Ala
                245
```

<210> SEQ ID NO 158
<211> LENGTH: 247
<212> TYPE: PRT
<213> ORGANISM: Gallus gallus

<400> SEQUENCE: 158

```
Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Tyr
            20                  25                  30

Gln Met Asn Trp Leu Arg Gln Ala Pro Gly Lys Gly Leu Glu Trp Val
        35                  40                  45

Gly Val Ile Ser Thr Arg Gly Ser Ser Thr Ala Tyr Gly Ala Ala Val
    50                  55                  60

Lys Gly Arg Ala Thr Ile Ser Arg Asp Asn Gly Arg Ser Thr Val Arg
65                  70                  75                  80

Leu Gln Leu Asn Ser Leu Arg Thr Glu Asp Thr Ala Thr Tyr Tyr Cys
                85                  90                  95

Ala Lys Ala Gly Tyr Ala Cys Gly Trp Ser Val Gly Cys Ile Asp Ala
            100                 105                 110

Trp Gly His Gly Thr Glu Val Ile Val Ser Ser Leu Asp Gly Gly Gly
        115                 120                 125

Gly Ser Gly Gly Gly Gly Ser Gly Gly Gly Gly Ser Thr Ala Leu Thr
    130                 135                 140

Gln Pro Ser Ser Val Ser Ala Asn Leu Gly Gly Thr Val Glu Ile Thr
145                 150                 155                 160

Cys Ser Gly Ser Ser Gly Ser Tyr Gly Trp Tyr Gln Gln Lys Ser Pro
                165                 170                 175

Asp Ser Ala Pro Val Ser Val Ile Tyr Ser Thr Asn Gln Arg Pro Ser
            180                 185                 190

Asn Ile Pro Ser Arg Phe Ser Gly Ser Lys Ser Gly Ser Thr Ala Thr
        195                 200                 205

Leu Thr Ile Thr Gly Val Gln Ala Asp Asp Glu Ala Val Tyr Tyr Cys
    210                 215                 220

Gly Ser Tyr Glu Asp Ser Ser Asn Thr Ile Gly Ala Gly Thr Thr Leu
225                 230                 235                 240

Thr Val Leu Gly Ala Ala Ala
                245
```

<210> SEQ ID NO 159
<211> LENGTH: 248
<212> TYPE: PRT
<213> ORGANISM: Gallus gallus

<400> SEQUENCE: 159

```
Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Tyr
            20                  25                  30

Gln Met Asn Trp Leu Arg Gln Ala Pro Gly Lys Gly Leu Glu Trp Val
        35                  40                  45

Gly Val Ile Ser Thr Arg Gly Ser Ser Thr Ala Tyr Gly Ala Ala Val
    50                  55                  60

Lys Gly Arg Ala Thr Ile Ser Arg Asp Asn Gly Arg Ser Thr Val Arg
65                  70                  75                  80

Leu Gln Leu Asn Ser Leu Arg Thr Glu Asp Thr Ala Thr Tyr Tyr Cys
```

```
                85                  90                  95
Ala Lys Ala Gly Tyr Ala Cys Gly Trp Ser Val Gly Cys Ile Asp Ala
            100                 105                 110
Trp Gly His Gly Thr Glu Val Ile Val Ser Ser Leu Asp Gly Gly Gly
            115                 120                 125
Gly Ser Gly Gly Gly Ser Gly Gly Gly Ser Thr Ala Leu Thr
            130                 135                 140
Gln Pro Ser Ser Val Ser Ala Asn Pro Gly Glu Thr Val Lys Ile Thr
145                 150                 155                 160
Cys Ser Gly Gly Ser Gly Asn Tyr Gly Trp Tyr Gln Gln Lys Ala Pro
                165                 170                 175
Gly Ser Ala Pro Val Thr Val Ile Ser Gly Ser Thr Leu Arg Pro Ser
            180                 185                 190
Asp Ile Pro Ser Arg Phe Ser Gly Ser Lys Ser Gly Ser Thr Gly Thr
            195                 200                 205
Leu Thr Ile Thr Gly Val Gln Ala Glu Asp Glu Ala Val Tyr Phe Cys
            210                 215                 220
Gly Ser Ala Asp Ser Ser Tyr Ala Gly Ile Phe Gly Ala Gly Thr Thr
225                 230                 235                 240
Leu Thr Val Leu Gly Ala Ala Ala
                245

<210> SEQ ID NO 160
<211> LENGTH: 250
<212> TYPE: PRT
<213> ORGANISM: Gallus gallus

<400> SEQUENCE: 160

Ala Val Thr Leu Asp Glu Ser Gly Gly Gly Leu Gln Thr Pro Gly Gly
1               5                   10                  15
Thr Leu Ser Leu Val Cys Lys Ala Ser Gly Phe Thr Phe Ser Ser Tyr
            20                  25                  30
Gln Met Asn Trp Leu Arg Gln Ala Pro Gly Lys Gly Leu Glu Trp Val
        35                  40                  45
Gly Val Ile Ser Thr Arg Gly Ser Ser Thr Ala Tyr Gly Ala Ala Val
    50                  55                  60
Lys Gly Arg Ala Thr Ile Ser Arg Asp Asn Gly Arg Ser Thr Val Arg
65                  70                  75                  80
Leu Gln Leu Asn Ser Leu Arg Thr Glu Asp Thr Ala Thr Tyr Tyr Cys
                85                  90                  95
Ala Lys Ala Gly Tyr Ala Cys Gly Trp Ser Val Gly Cys Ile Asp Ala
            100                 105                 110
Trp Gly His Gly Thr Glu Val Ile Val Ser Ser Leu Asp Gly Gly Gly
            115                 120                 125
Gly Ser Gly Gly Gly Ser Gly Gly Gly Ser Thr Ala Leu Thr
            130                 135                 140
Gln Pro Ser Ser Val Ser Ala Asn Pro Gly Glu Thr Val Lys Ile Thr
145                 150                 155                 160
Cys Ser Gly Gly Ser Asn Tyr Tyr Tyr Gly Trp Tyr Gln Gln Lys Ser
                165                 170                 175
Pro Gly Ser Ala Pro Val Thr Val Ile Tyr Ala Asn Thr Asn Arg Pro
            180                 185                 190
Ser Asp Ile Pro Ser Arg Phe Ser Gly Ser Leu Ser Gly Ser Thr Ala
            195                 200                 205
```

```
Thr Leu Thr Ile Thr Gly Val Gln Ala Asp Asp Glu Ala Val Tyr Tyr
    210                 215                 220

Cys Gly Ser Ala Asp Ser Ser Thr Tyr Ala Gly Ile Phe Gly Ala Gly
225                 230                 235                 240

Thr Thr Leu Thr Val Leu Gly Ala Ala Ala
                245                 250

<210> SEQ ID NO 161
<211> LENGTH: 250
<212> TYPE: PRT
<213> ORGANISM: Gallus gallus

<400> SEQUENCE: 161

Ala Val Thr Leu Asp Glu Ser Gly Gly Leu Gln Thr Pro Gly Gly
1               5                   10                  15

Thr Leu Ser Leu Val Cys Lys Ala Ser Gly Phe Thr Phe Ser Ser Tyr
            20                  25                  30

Gln Met Asn Trp Leu Arg Gln Ala Pro Gly Lys Gly Leu Glu Trp Val
        35                  40                  45

Gly Val Ile Ser Thr Arg Gly Ser Ser Thr Ala Tyr Gly Ala Ala Val
    50                  55                  60

Lys Gly Arg Ala Thr Ile Ser Arg Asp Asn Gly Arg Ser Thr Val Arg
65              70                  75                  80

Leu Gln Leu Asn Ser Leu Arg Thr Glu Asp Thr Ala Thr Tyr Tyr Cys
                85                  90                  95

Ala Lys Ala Gly Tyr Ala Cys Gly Trp Ser Val Gly Cys Ile Asp Ala
            100                 105                 110

Trp Gly His Gly Thr Glu Val Ile Val Ser Ser Leu Asp Gly Gly Gly
        115                 120                 125

Gly Ser Gly Gly Gly Gly Ser Gly Gly Gly Gly Ser Thr Ala Leu Thr
    130                 135                 140

Gln Pro Ser Ser Val Ser Ala Asn Pro Gly Glu Thr Val Lys Ile Thr
145                 150                 155                 160

Cys Ser Gly Gly Ser Asn Asn Trp Tyr Ser Trp His Gln Gln Lys Ser
                165                 170                 175

Pro Gly Ser Ala Pro Val Thr Val Ile Tyr Asn Asn Asp Lys Arg Pro
            180                 185                 190

Ser Asp Ile Pro Ser Arg Phe Ser Gly Phe Thr Ser Gly Ser Thr Ser
        195                 200                 205

Thr Leu Thr Ile Thr Gly Val Gln Ala Asp Asp Glu Ala Val Tyr Phe
    210                 215                 220

Cys Gly Gly Trp Asp Ser Ser Ser Arg Ala Gly Ile Phe Gly Ala Gly
225                 230                 235                 240

Thr Thr Leu Thr Val Leu Gly Ala Ala Ala
                245                 250

<210> SEQ ID NO 162
<211> LENGTH: 247
<212> TYPE: PRT
<213> ORGANISM: Gallus gallus

<400> SEQUENCE: 162

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Tyr
            20                  25                  30
```

```
Gln Met Asn Trp Leu Arg Gln Ala Pro Gly Lys Gly Leu Glu Trp Val
            35                  40                  45
Gly Val Ile Ser Thr Arg Gly Ser Ser Thr Ala Tyr Gly Ala Ala Val
 50                  55                  60
Lys Gly Arg Ala Thr Ile Ser Arg Asp Asn Gly Arg Ser Thr Val Arg
 65                  70                  75                  80
Leu Gln Leu Asn Ser Leu Arg Thr Glu Asp Thr Ala Thr Tyr Tyr Cys
                 85                  90                  95
Ala Lys Ala Gly Tyr Ala Cys Gly Trp Ser Val Gly Cys Ile Asp Ala
                100                 105                 110
Trp Gly His Gly Thr Glu Val Ile Val Ser Ser Leu Asp Gly Gly Gly
            115                 120                 125
Gly Ser Gly Gly Gly Ser Gly Gly Gly Ser Thr Ala Leu Thr
        130                 135                 140
Gln Pro Ser Ser Val Ser Ala Asn Pro Gly Glu Thr Val Lys Ile Thr
145                 150                 155                 160
Cys Ser Gly Gly Asn Ser Gly Tyr Gly Trp Tyr Gln Gln Lys Ser Pro
                165                 170                 175
Gly Ser Ala Pro Val Thr Val Ile Tyr Ser Asn Asp Lys Arg Pro Ser
                180                 185                 190
Asp Ile Pro Ser Arg Phe Ser Gly Ala Leu Ser Gly Ser Thr Ala Thr
                195                 200                 205
Leu Thr Ile Thr Gly Val Arg Ala Glu Asp Glu Ala Val Tyr Tyr Cys
            210                 215                 220
Gly Ser Gly Asp Ser Ser Gly Ser Val Phe Gly Ala Gly Thr Thr Leu
225                 230                 235                 240
Thr Val Leu Gly Ala Ala Ala
                245

<210> SEQ ID NO 163
<211> LENGTH: 247
<212> TYPE: PRT
<213> ORGANISM: Gallus gallus

<400> SEQUENCE: 163

Ala Val Thr Leu Asp Glu Ser Gly Gly Gly Leu Gln Thr Pro Gly Gly
  1               5                  10                  15
Thr Leu Ser Leu Val Cys Lys Ala Ser Gly Phe Thr Phe Ser Ser Tyr
                 20                  25                  30
Gln Met Asn Trp Leu Arg Gln Ala Pro Gly Lys Gly Leu Glu Trp Val
            35                  40                  45
Gly Val Ile Ser Thr Arg Gly Ser Ser Thr Ala Tyr Gly Ala Ala Val
 50                  55                  60
Lys Gly Arg Ala Thr Ile Ser Arg Asp Asn Gly Gln Ser Thr Val Arg
 65                  70                  75                  80
Leu Gln Leu Asn Ser Leu Arg Thr Glu Asp Thr Ala Thr Tyr Tyr Cys
                 85                  90                  95
Ala Lys Ala Gly Tyr Ala Cys Gly Trp Ser Val Gly Cys Ile Asp Ala
                100                 105                 110
Trp Gly His Gly Thr Glu Val Ile Val Ser Ser Gly Gly Gly Ser
            115                 120                 125
Gly Gly Gly Gly Ser Gly Gly Gly Ser Ala Leu Thr Gln Pro Ser
        130                 135                 140
Ser Val Ser Ala Asn Pro Gly Gly Thr Val Lys Ile Thr Cys Ser Gly
145                 150                 155                 160
```

-continued

```
Ser Ser Gly Asn Tyr Gly Trp Tyr Gln Gln Lys Ser Pro Gly Ser Ala
            165                 170                 175

Leu Val Thr Val Ile Tyr Ser Asn Asp Lys Arg Pro Ser Asp Ile Pro
        180                 185                 190

Ser Arg Phe Ser Gly Ser Lys Ser Gly Ser Thr Gly Thr Leu Thr Ile
    195                 200                 205

Thr Gly Val Gln Ala Asp Asp Glu Ala Val Tyr Phe Cys Gly Ser Glu
210                 215                 220

Asp Ser Ser Ser Ile Gly Asp Gly Ile Phe Gly Ala Gly Thr Thr Leu
225                 230                 235                 240

Thr Val Leu Gly Ala Ala Ala
                245

<210> SEQ ID NO 164
<211> LENGTH: 250
<212> TYPE: PRT
<213> ORGANISM: Gallus gallus

<400> SEQUENCE: 164

Ala Val Thr Leu Asp Glu Ser Gly Gly Gly Leu Gln Thr Pro Gly Gly
1               5                   10                  15

Ala Leu Ser Leu Val Cys Lys Gly Ser Gly Phe Thr Phe Ser Ser Tyr
            20                  25                  30

Asn Met Gly Trp Val Arg Gln Ala Pro Gly Lys Gly Leu Glu Phe Val
        35                  40                  45

Ala Ala Ile Ser Asn Thr Gly Arg Tyr Thr Gly Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Thr Ala Gly Tyr Tyr Gly Trp Asn Thr Ala Ser Asp Ile Asp
            100                 105                 110

Ala Trp Gly His Gly Thr Glu Val Ile Val Ser Ser Leu Asp Gly Gly
        115                 120                 125

Gly Gly Ser Gly Gly Gly Gly Ser Gly Gly Gly Gly Ser Thr Ala Leu
    130                 135                 140

Thr Gln Pro Ser Ser Val Ser Ala Asn Pro Gly Glu Thr Val Glu Ile
145                 150                 155                 160

Thr Cys Ser Gly Asp Thr Thr Tyr Tyr Gly Trp Tyr Gln Gln Lys Ala
                165                 170                 175

Pro Gly Ser Ala Pro Val Thr Leu Ile Tyr Asp Asn Thr Asn Arg Pro
            180                 185                 190

Ser Asp Ile Pro Ser Arg Phe Ser Gly Ser Arg Ser Gly Ser Thr Ala
        195                 200                 205

Thr Leu Thr Ile Thr Gly Val Gln Ala Glu Asp Glu Ala Val Tyr Phe
    210                 215                 220

Cys Gly Ser Ala Asp Thr Ser Gly Tyr Ala Gly Ile Phe Gly Ala Gly
225                 230                 235                 240

Thr Thr Leu Thr Val Leu Gly Ala Ala Ala
                245                 250

<210> SEQ ID NO 165
<211> LENGTH: 251
<212> TYPE: PRT
```

<213> ORGANISM: Gallus gallus

<400> SEQUENCE: 165

```
Ala Val Thr Leu Asp Glu Ser Gly Gly Leu Gln Thr Pro Gly Arg
1               5                   10                  15

Ala Leu Ser Leu Val Cys Lys Gly Ser Gly Phe Thr Leu Ser Ser Tyr
            20                  25                  30

Asn Met Gly Trp Val Arg Gln Ala Pro Gly Lys Gly Leu Glu Phe Val
        35                  40                  45

Ala Ala Ile Ser Asn Thr Gly Arg Tyr Thr Gly Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Thr Ala Gly Tyr Tyr Gly Trp Asn Thr Ala Ser Asp Ile Asp
            100                 105                 110

Ala Trp Gly His Gly Thr Glu Val Ile Val Ser Ser Leu Asp Gly Gly
        115                 120                 125

Gly Gly Ser Gly Gly Gly Ser Gly Gly Gly Ser Thr Ala Leu
    130                 135                 140

Thr Gln Pro Ser Ser Val Ser Ala Asn Pro Gly Glu Thr Val Glu Ile
145                 150                 155                 160

Thr Cys Ser Gly Gly Ser Gly Ser Tyr Tyr Gly Trp Tyr Gln Gln Lys
                165                 170                 175

Pro Pro Gly Ser Ala Pro Val Thr Val Ile Tyr Asn Asn Asn Arg
            180                 185                 190

Pro Ser Asp Ile Pro Ser Arg Phe Ser Gly Ser Arg Ser Gly Ser Thr
        195                 200                 205

Ala Thr Leu Thr Ile Thr Gly Val Gln Ala Asp Asp Glu Ala Val Tyr
    210                 215                 220

Phe Cys Gly Ser Glu Asp Ser Thr Gly Tyr Val Gly Ile Phe Gly Ala
225                 230                 235                 240

Gly Thr Thr Leu Thr Val Leu Gly Ala Ala Ala
                245                 250
```

<210> SEQ ID NO 166
<211> LENGTH: 254
<212> TYPE: PRT
<213> ORGANISM: Gallus gallus

<400> SEQUENCE: 166

```
Ala Val Thr Leu Asp Glu Ser Gly Gly Gly Leu Gln Thr Pro Gly Arg
1               5                   10                  15

Ala Leu Ser Leu Val Cys Lys Ala Ser Gly Phe Ser Ile Ser Gly Tyr
            20                  25                  30

Asn Met Gly Trp Val Arg Gln Ala Pro Gly Lys Gly Leu Glu Phe Val
        35                  40                  45

Ala Gly Ile Gly Asn Thr Gly Arg Tyr Thr Gly Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Ile Tyr Tyr Cys
                85                  90                  95

Ala Lys Gly Ala Ser His Tyr Cys Trp Asp Val Gly Cys Ser Asn Ile
```

```
                100             105              110
Ala Gly Ser Ile Asp Ala Trp Gly His Gly Thr Glu Val Ile Val Ser
        115                 120                 125

Ser Leu Asp Gly Gly Gly Ser Gly Gly Gly Ser Gly Gly Gly
    130                 135                 140

Gly Ser Thr Ala Leu Thr Gln Leu Ser Ser Val Ser Ala Asn Pro Gly
145                 150                 155                 160

Glu Thr Val Glu Ile Thr Cys Ser Gly Asp Ser Ser Tyr Tyr Gly Trp
                165                 170                 175

Tyr Gln Gln Lys Ala Pro Gly Ser Ala Pro Val Thr Leu Ile Tyr Asp
            180                 185                 190

Asn Thr Asn Arg Pro Ser Asp Ile Ser Ser Arg Phe Ser Gly Ser Lys
        195                 200                 205

Ser Gly Ser Thr Ala Thr Leu Thr Ile Thr Gly Val Gln Ala Asp Asp
    210                 215                 220

Glu Ala Val Tyr Tyr Cys Gly Ser Ala Gly Ser Ser His Val Gly Met
225                 230                 235                 240

Phe Gly Ala Gly Thr Thr Leu Thr Val Leu Gly Ala Ala Ala
                245                 250

<210> SEQ ID NO 167
<211> LENGTH: 252
<212> TYPE: PRT
<213> ORGANISM: Gallus gallus

<400> SEQUENCE: 167

Ala Val Thr Leu Asp Glu Ser Gly Gly Gly Leu Gln Thr Pro Gly Arg
1               5                   10                  15

Ala Leu Ser Leu Val Cys Lys Ala Ser Gly Phe Thr Phe Arg Ser Tyr
            20                  25                  30

Asn Met Ala Trp Val Arg Gln Ala Pro Gly Lys Gly Leu Glu Phe Val
        35                  40                  45

Ala Glu Ile Ser Gly Thr Gly Ser Thr Thr Asn Tyr Ala Pro Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Lys Ala Ala Gly Ala Tyr Cys Ala Trp Ser Gly Cys Thr Ala Gly
            100                 105                 110

Ser Ile Asp Ala Trp Gly His Gly Thr Glu Val Ile Val Ser Ser Leu
        115                 120                 125

Asp Gly Gly Gly Ser Gly Gly Gly Ser Gly Gly Gly Ser
    130                 135                 140

Thr Ala Leu Thr Gln Pro Ser Ser Val Ser Ala Asn Pro Gly Glu Thr
145                 150                 155                 160

Val Glu Ile Thr Cys Ser Gly Asp Ser Ser Tyr Tyr Gly Trp Tyr Gln
                165                 170                 175

Gln Lys Ala Pro Gly Ser Ala Pro Val Thr Leu Ile Tyr Asp Asn Thr
            180                 185                 190

Asn Arg Pro Ser Asp Ile Ser Ser Arg Phe Ser Gly Ser Lys Ser Gly
        195                 200                 205

Ser Thr Ala Thr Leu Thr Ile Thr Gly Val Gln Ala Asp Asp Glu Ala
    210                 215                 220
```

-continued

```
Val Tyr Tyr Cys Gly Ser Ala Gly Ser His Val Gly Met Phe Gly
225                 230                 235                 240

Ala Gly Thr Thr Leu Thr Val Leu Gly Ala Ala Ala
            245                 250

<210> SEQ ID NO 168
<211> LENGTH: 252
<212> TYPE: PRT
<213> ORGANISM: Gallus gallus

<400> SEQUENCE: 168

Ala Val Thr Leu Asp Glu Ser Gly Gly Leu Gln Thr Pro Arg Gly
1               5                   10                  15

Arg Leu Arg Leu Val Cys Lys Ala Ser Gly Phe Thr Phe Ser Ser Tyr
                20                  25                  30

Glu Met Gly Trp Val Arg Gln Ala Pro Gly Lys Gly Leu Glu Trp Val
            35                  40                  45

Ala Gly Ile Gly Gly Ser Gly Ser Ala Tyr Gly Ser Ala Val
50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ser Thr Thr Lys Cys Ser Tyr Cys Trp Tyr Gly Ala Thr Ala
                100                 105                 110

Gly Ser Ile Asp Ala Trp Gly His Gly Ala Glu Val Ile Val Ser Ser
            115                 120                 125

Leu Asp Gly Gly Gly Gly Ser Gly Gly Gly Ser Gly Gly Gly Gly
130                 135                 140

Ser Thr Ala Leu Thr Gln Pro Ser Ser Val Ser Ala Asn Leu Gly Gly
145                 150                 155                 160

Thr Val Lys Ile Thr Cys Ser Gly Asp Ser Ser Tyr Tyr Gly Trp Tyr
                165                 170                 175

Gln Gln Lys Ala Pro Gly Ser Ala Pro Val Thr Val Ile Tyr Asp Asn
            180                 185                 190

Thr Asn Arg Pro Ser Gly Ile Pro Ser Arg Phe Ser Gly Ser Lys Ser
        195                 200                 205

Gly Ser Thr Ala Thr Leu Thr Ile Thr Gly Val Arg Ala Asp Asp Glu
210                 215                 220

Ala Val Tyr Tyr Cys Gly Asn Thr Asp Ser Ser Gly Ala Ile Phe Gly
225                 230                 235                 240

Ala Gly Thr Thr Leu Thr Val Leu Gly Ala Ala Ala
            245                 250

<210> SEQ ID NO 169
<211> LENGTH: 253
<212> TYPE: PRT
<213> ORGANISM: Gallus gallus

<400> SEQUENCE: 169

Ala Val Thr Leu Asp Glu Ser Gly Gly Leu Gln Thr Pro Arg Gly
1               5                   10                  15

Arg Leu Arg Leu Val Cys Lys Ala Ser Gly Phe Asp Phe Ser Ser Tyr
                20                  25                  30

Glu Met Gly Trp Val Arg Gln Ala Pro Gly Lys Gly Leu Glu Trp Val
            35                  40                  45
```

```
Ala Gly Ile Gly Gly Ser Gly Ser Gly Ser Ala Tyr Gly Pro Ala Val
    50                  55                  60

Lys Gly Arg Ala Thr Ile Thr Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                 85                  90                  95

Ala Lys Ser Thr Thr Arg Cys Ser Phe Cys Trp Tyr Gly Ala Thr Ala
                100                 105                 110

Gly Ser Ile Asp Ala Trp Gly His Gly Ala Glu Val Ile Val Ser Ser
            115                 120                 125

Leu Asp Gly Gly Gly Gly Ser Gly Gly Gly Gly Ser Gly Gly Gly Gly
130                 135                 140

Ser Thr Ala Leu Thr Gln Pro Ser Ser Val Ser Ala Asn Pro Gly Glu
145                 150                 155                 160

Thr Val Lys Ile Thr Cys Ser Gly Gly Ser Asn Asn Tyr Gly Trp Tyr
                165                 170                 175

Gln Gln Lys Ser Pro Gly Ser Ala Pro Val Thr Leu Ile Tyr Asp Asn
                180                 185                 190

Thr Asn Arg Pro Ser Asn Ile Pro Ser Arg Phe Ser Gly Ser Lys Ser
            195                 200                 205

Gly Ser Thr Ala Thr Leu Thr Ile Thr Gly Val Gln Ala Asp Asp Glu
210                 215                 220

Ala Val Tyr Tyr Cys Gly Ser Ala Asp Ser Ser Ser Thr Gly Ile Phe
225                 230                 235                 240

Gly Ala Gly Thr Thr Leu Thr Val Leu Gly Ala Ala Ala
                245                 250

<210> SEQ ID NO 170
<211> LENGTH: 254
<212> TYPE: PRT
<213> ORGANISM: Gallus gallus

<400> SEQUENCE: 170

Ala Val Thr Leu Asp Glu Ser Gly Gly Gly Leu Gln Thr Pro Arg Gly
 1               5                  10                  15

Arg Leu Arg Leu Val Cys Lys Ala Ser Gly Phe Thr Phe Ser Ser Tyr
                20                  25                  30

Glu Met Gly Trp Val Arg Gln Ala Pro Gly Lys Gly Leu Glu Trp Val
            35                  40                  45

Ala Gly Ile Gly Gly Ser Gly Ser Gly Ser Ala Tyr Gly Ser Ala Val
    50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                 85                  90                  95

Ala Lys Ser Thr Thr Lys Cys Asn His Cys Trp Tyr Gly Ala Thr Ala
                100                 105                 110

Gly Ser Ile Asp Ala Trp Gly His Gly Thr Glu Val Ile Val Ser Ser
            115                 120                 125

Leu Asp Gly Gly Gly Gly Ser Gly Gly Gly Gly Ser Gly Gly Gly Gly
130                 135                 140

Ser Thr Ala Leu Thr Gln Pro Ser Ser Val Ser Ala Asn Pro Gly Glu
145                 150                 155                 160

Thr Val Lys Ile Thr Cys Ser Gly Gly Ser Gly Ser Tyr Tyr Gly Trp
                165                 170                 175
```

-continued

Tyr Gln Gln Lys Ser Pro Gly Ser Ala Pro Val Thr Leu Ile Tyr Asp
            180                 185                 190

Asn Asp Lys Arg Pro Ser Gly Ile Pro Ser Arg Phe Ser Gly Ser Thr
            195                 200                 205

Ser Gly Ser Thr Gly Thr Leu Thr Ile Thr Gly Val Gln Ala Glu Asp
    210                 215                 220

Glu Ala Val Tyr Tyr Cys Gly Ser Arg Asp Ser Ser Tyr Val Gly Met
225                 230                 235                 240

Phe Gly Ala Gly Thr Thr Leu Thr Val Leu Gly Ala Ala Ala
                245                 250

<210> SEQ ID NO 171
<211> LENGTH: 252
<212> TYPE: PRT
<213> ORGANISM: Gallus gallus

<400> SEQUENCE: 171

Ala Val Thr Leu Asp Glu Ser Gly Gly Gly Leu His Thr Pro Gly Gly
1               5                   10                  15

Ala Leu Arg Leu Val Cys Lys Ala Ser Gly Phe Ser Ile Ser Ser Tyr
            20                  25                  30

Gly Met Gly Trp Val Arg Gln Ala Pro Gly Lys Gly Leu Glu Trp Val
        35                  40                  45

Ala Arg Ile Gly Ser Gly Ala Ser Gly Thr Ala Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Asp Asp Thr Gly Thr Tyr Tyr Cys
                85                  90                  95

Ala Lys Ser Ala Gly Ala Tyr Cys Trp Tyr Ala Gly Cys Pro Ser Ser
            100                 105                 110

Ile Asp Ala Trp Gly His Gly Ala Glu Val Ile Val Ser Ser Leu Asp
        115                 120                 125

Gly Gly Gly Gly Ser Gly Gly Gly Ser Gly Gly Gly Gly Ser Thr
    130                 135                 140

Ala Leu Thr Gln Pro Ser Ser Val Ser Ala Asn Pro Gly Glu Thr Val
145                 150                 155                 160

Lys Ile Thr Cys Ser Gly Gly Tyr Asn Tyr Tyr Gly Trp Tyr Gln Gln
                165                 170                 175

Lys Ser Pro Gly Ser Val Pro Val Thr Leu Ile Tyr Asp Asn Thr Asn
            180                 185                 190

Arg Pro Ser Asn Ile Pro Ser Arg Phe Ser Gly Ser Thr Ser Gly Ser
        195                 200                 205

Thr Gly Thr Leu Thr Ile Thr Gly Val Gln Ala Asp Asp Glu Ala Val
    210                 215                 220

Tyr Phe Cys Gly Ser Ala Asp Ser Ser Thr Ser Ala Ser Phe Gly
225                 230                 235                 240

Ala Gly Thr Thr Leu Thr Val Leu Gly Ala Ala Ala
                245                 250

<210> SEQ ID NO 172
<211> LENGTH: 251
<212> TYPE: PRT
<213> ORGANISM: Gallus gallus

<400> SEQUENCE: 172

```
Ala Val Thr Leu Asp Glu Ser Gly Gly Gly Leu Gln Thr Pro Gly Gly
1               5                   10                  15

Ala Leu Arg Leu Val Cys Lys Ala Ser Gly Phe Ser Ile Ser Ser Tyr
            20                  25                  30

Gly Met Gly Trp Val Arg Gln Ala Pro Gly Lys Gly Leu Glu Trp Val
        35                  40                  45

Ala Arg Ile Gly Ser Gly Ala Ser Gly Thr Ala Tyr Gly Ser Thr Val
50                  55                  60

Lys Gly Arg Ala Thr Ile Ser Arg Asp Asn Gly Gln Ser Thr Val Arg
65                  70                  75                  80

Leu Gln Leu Asn Asn Leu Arg Thr Glu Asp Thr Gly Thr Tyr Tyr Cys
                85                  90                  95

Ala Lys Thr Ala Gly Ala Tyr Cys Trp Tyr Ala Gly Cys Pro Ser Ser
            100                 105                 110

Ile Asp Ala Trp Gly His Gly Thr Glu Val Ile Val Ser Ser Leu Asp
            115                 120                 125

Gly Gly Gly Gly Ser Gly Gly Gly Ser Gly Gly Gly Gly Ser Thr
            130                 135                 140

Ala Leu Thr Gln Pro Ser Ser Val Ser Ala Asn Pro Gly Gly Thr Val
145                 150                 155                 160

Lys Leu Thr Cys Ser Gly Asp Ser Ser Tyr Tyr Gly Trp Tyr His Gln
            165                 170                 175

Lys Ser Pro Gly Ser Ala Pro Val Thr Val Ile Tyr Asp Asn Thr Asn
            180                 185                 190

Arg Pro Ser Asn Ile Pro Ser Arg Phe Ser Gly Ser Leu Ser Gly Ser
            195                 200                 205

Thr Ala Thr Leu Thr Ile Thr Gly Val Gln Ala Glu Asp Glu Ala Val
            210                 215                 220

Tyr Tyr Cys Gly Ser Glu Asp Asn Thr Ser Thr Ala Ala Phe Gly Ala
225                 230                 235                 240

Gly Thr Thr Leu Thr Val Leu Gly Ala Ala Ala
            245                 250

<210> SEQ ID NO 173
<211> LENGTH: 251
<212> TYPE: PRT
<213> ORGANISM: Gallus gallus

<400> SEQUENCE: 173

Ala Val Thr Leu Asp Glu Ser Gly Gly Gly Leu Gln Thr Pro Gly Gly
1               5                   10                  15

Ala Leu Arg Leu Val Cys Lys Ala Ser Gly Phe Ser Ile Ser Ser Tyr
            20                  25                  30

Gly Met Gly Trp Val Arg Gln Ala Pro Gly Lys Gly Leu Glu Trp Val
        35                  40                  45

Ala Arg Ile Gly Ser Gly Ala Ser Gly Thr Ala Tyr Gly Ser Thr Val
50                  55                  60

Lys Gly Arg Ala Thr Ile Ser Arg Asp Asn Gly Gln Ser Thr Val Arg
65                  70                  75                  80

Leu Gln Leu Asn Asn Leu Arg Thr Glu Asp Thr Gly Thr Tyr Tyr Cys
                85                  90                  95

Ala Lys Thr Ala Gly Ala Tyr Cys Trp Tyr Ala Gly Cys Pro Ser Ser
            100                 105                 110

Ile Asp Ala Trp Gly His Gly Thr Glu Val Ile Val Ser Ser Leu Asp
```

```
                115                 120                 125
Gly Gly Gly Gly Ser Gly Gly Gly Ser Gly Gly Gly Ser Thr
            130                 135                 140

Ala Leu Thr Gln Pro Ser Ser Val Ser Ala Asn Pro Gly Glu Thr Val
145                 150                 155                 160

Lys Ile Thr Cys Ser Gly Asp Ser Thr Tyr Tyr Gly Trp Tyr Gln Gln
                165                 170                 175

Lys Ala Pro Gly Ser Ala Pro Val Thr Leu Ile Tyr Asp Asn Thr Asn
            180                 185                 190

Arg Pro Ser Asn Ile Pro Ser Arg Phe Ser Gly Ser Leu Ser Gly Ser
            195                 200                 205

Thr Ala Thr Leu Thr Ile Thr Gly Val Gln Ala Glu Asp Glu Ala Val
210                 215                 220

Tyr Phe Cys Gly Gly Ala Asp Ser Ser Ala Ala Ser Phe Gly Ala
225                 230                 235                 240

Gly Thr Ala Leu Thr Val Leu Gly Ala Ala Ala
            245                 250

<210> SEQ ID NO 174
<211> LENGTH: 253
<212> TYPE: PRT
<213> ORGANISM: Gallus gallus

<400> SEQUENCE: 174

Ala Val Thr Leu Asp Glu Ser Gly Gly Leu Gln Thr Pro Gly Lys
1               5                   10                  15

Gly Leu Ser Leu Val Cys Lys Ala Ser Gly Phe Thr Phe Thr Ser Tyr
                20                  25                  30

Gly Met Gly Trp Val Arg Gln Ala Pro Gly Lys Gly Leu Glu Trp Val
            35                  40                  45

Ala Arg Ile Gly Ser Gly Ala Ser Gly Thr Ala Tyr Ala Thr Ala Val
    50                  55                  60

Lys Gly Arg Ala Thr Ile Ser Arg Asp Asn Gly Gln Ser Thr Val Arg
65                  70                  75                  80

Leu Gln Leu Asn Asp Leu Arg Ala Glu Asp Thr Ala Thr Tyr Tyr Cys
                85                  90                  95

Ala Lys Thr Ala Gly Ala Tyr Cys Trp Tyr Ala Gly Cys Pro Ser Ser
            100                 105                 110

Ile Asp Ala Trp Gly His Gly Thr Glu Val Ile Val Ser Ser Leu Asp
        115                 120                 125

Gly Gly Gly Gly Ser Gly Gly Gly Ser Gly Gly Gly Ser Thr
            130                 135                 140

Ala Leu Thr Gln Pro Ser Ser Val Ser Ala Asn Leu Gly Gly Thr Val
145                 150                 155                 160

Glu Ile Thr Cys Ser Gly Ser Ser Gly Ser Tyr Tyr Gly Trp Tyr Gln
                165                 170                 175

Gln Lys Ala Pro Gly Ser Ala Pro Val Thr Leu Ile Tyr Asp Asn Thr
            180                 185                 190

Asn Arg Pro Ser Asp Ile Pro Ser Arg Phe Ser Gly Ser Lys Ser Gly
            195                 200                 205

Ser Thr Ala Thr Leu Thr Ile Thr Gly Val Arg Ala Glu Asp Glu Ala
210                 215                 220

Val Tyr Tyr Cys Gly Ser Ala Asp Ser Ser Ser Glu Ala Ala Phe
225                 230                 235                 240
```

```
Gly Ala Gly Thr Thr Leu Thr Val Leu Gly Ala Ala Ala
            245                 250
```

<210> SEQ ID NO 175
<211> LENGTH: 252
<212> TYPE: PRT
<213> ORGANISM: Gallus gallus

<400> SEQUENCE: 175

```
Ala Val Thr Leu Asp Glu Ser Gly Gly Leu Gln Thr Pro Gly Arg
1               5                   10                  15

Ala Leu Ser Leu Val Cys Lys Ala Ser Gly Phe Thr Phe Ser Ser Tyr
            20                  25                  30

Ala Met Asn Trp Val Arg Gln Ala Pro Gly Lys Gly Leu Glu Phe Val
            35                  40                  45

Ala Glu Ile Ser Gly Ser Gly Arg Tyr Thr Tyr Tyr Ala Pro Ala Val
        50                  55                  60

Lys Gly Arg Ala Thr Ile Ser Arg Asp Asn Gly Gln Ser Thr Val Ser
65                  70                  75                  80

Leu Gln Leu Asn Asn Leu Arg Ala Glu Asp Thr Ala Thr Tyr Tyr Cys
                85                  90                  95

Ala Lys Thr Ala Asp Ser Cys Arg Tyr Gly Cys Ser Ala Asp Arg Ile
            100                 105                 110

Asp Ala Trp Gly His Gly Thr Glu Val Ile Val Ser Ser Leu Asp Gly
            115                 120                 125

Gly Gly Gly Ser Gly Gly Gly Ser Gly Gly Gly Ser Thr Ala
        130                 135                 140

Leu Thr Gln Pro Ser Ser Val Ser Ala Asn Pro Gly Glu Thr Val Glu
145                 150                 155                 160

Ile Thr Cys Ser Gly Gly Gly Ser Ser Tyr Gly Trp Tyr Gln Gln Lys
                165                 170                 175

Ser Pro Gly Ser Ala Pro Val Thr Val Ile Tyr Asp Asn Thr Asn Arg
            180                 185                 190

Pro Ser Asn Ile Pro Ser Arg Phe Ser Gly Ser Leu Ser Gly Ser Ala
        195                 200                 205

Asn Thr Leu Thr Ile Thr Gly Val Gln Ala Asp Asp Glu Ala Val Tyr
210                 215                 220

Tyr Cys Gly Ser Gly Asp Ser Ser Ala Ala Tyr Val Pro Ile Phe Gly
225                 230                 235                 240

Ala Gly Thr Thr Leu Thr Val Leu Gly Ala Ala Ala
            245                 250
```

<210> SEQ ID NO 176
<211> LENGTH: 250
<212> TYPE: PRT
<213> ORGANISM: Gallus gallus

<400> SEQUENCE: 176

```
Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Ala Ile Asn Trp Val Arg Gln Ala Pro Gly Lys Gly Leu Glu Phe Val
            35                  40                  45

Ala Glu Ile Ser Gly Ser Gly Arg Tyr Val Tyr Tyr Ala Pro Ala Val
        50                  55                  60
```

Gln Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Thr Ala Asp Ser Cys Arg Tyr Gly Cys Asn Ala Asp Arg Ile
            100                 105                 110

Asp Ala Trp Gly Arg Gly Thr Glu Val Ile Val Ser Ser Leu Asp Gly
        115                 120                 125

Gly Gly Gly Ser Gly Gly Gly Ser Gly Gly Gly Ser Thr Ala
    130                 135                 140

Leu Thr Gln Pro Ser Ser Val Ser Ala Asn Pro Gly Glu Thr Val Glu
145                 150                 155                 160

Ile Thr Cys Ser Gly Gly Ile Gly His Tyr Gly Trp Tyr Gln Gln Lys
                165                 170                 175

Ala Pro Gly Ser Ala Pro Val Thr Val Ile Tyr Asp Ser Ser Ser Arg
            180                 185                 190

Pro Ser Asp Ile Pro Ser Arg Phe Ser Gly Ser Lys Ser Gly Ser Thr
        195                 200                 205

Gly Thr Leu Thr Ile Thr Gly Val Gln Ala Asp Glu Ala Val Tyr
    210                 215                 220

Tyr Cys Gly Ser Gly Gly Ser Asn Gly Ala Gly Ile Phe Gly Ala Gly
225                 230                 235                 240

Thr Thr Leu Thr Val Leu Gly Ala Ala Ala
                245                 250

<210> SEQ ID NO 177
<211> LENGTH: 250
<212> TYPE: PRT
<213> ORGANISM: Gallus gallus

<400> SEQUENCE: 177

Ala Val Thr Leu Asp Glu Ser Gly Gly Gly Leu Gln Thr Pro Gly Gly
1               5                   10                  15

Ala Leu Ser Leu Val Cys Lys Gly Ser Gly Phe Thr Phe Ser Ser His
                20                  25                  30

Gly Met Phe Trp Val Arg Gln Ala Pro Gly Lys Gly Leu Glu Tyr Val
            35                  40                  45

Ala Gln Ile Ser Gly Ser Gly Arg Leu Thr Asn Tyr Gly Pro Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Thr Ala Val Asn Cys Arg Tyr Gly Cys Ala Gly Asp Asn Ile
            100                 105                 110

Asp Ala Trp Gly His Gly Thr Glu Val Ile Val Ser Ser Leu Asp Gly
        115                 120                 125

Gly Gly Gly Ser Gly Gly Gly Ser Gly Gly Gly Ser Thr Ala
    130                 135                 140

Leu Thr Gln Pro Ser Ser Val Ser Ala Asn Pro Gly Glu Thr Val Lys
145                 150                 155                 160

Ile Thr Cys Ser Gly Asp Gly Ser Ser Tyr Gly Trp Tyr Gln Gln Lys
                165                 170                 175

Ser Pro Gly Ser Ala Pro Val Thr Val Ile Tyr Asp Ser Thr Asn Arg
            180                 185                 190

```
Pro Trp Asp Ile Pro Ser Arg Phe Ser Gly Ser Lys Ser Gly Ser Thr
            195                 200                 205

Gly Thr Leu Thr Ile Thr Gly Val Gln Ala Glu Asp Glu Ala Val Tyr
        210                 215                 220

Phe Cys Gly Thr Thr Asp Ser Thr Ser Ala Ala Ile Phe Gly Ala Gly
225                 230                 235                 240

Thr Thr Leu Thr Val Leu Gly Ala Ala Ala
                245                 250

<210> SEQ ID NO 178
<211> LENGTH: 256
<212> TYPE: PRT
<213> ORGANISM: Gallus gallus

<400> SEQUENCE: 178

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Tyr
            20                  25                  30

Gly Met Gly Trp Val Arg Gln Ala Pro Gly Lys Gly Leu Glu Trp Val
        35                  40                  45

Ala Glu Ile Ser Gly Ser Gly Arg Tyr Thr Tyr Gly Pro Ala Val
    50                  55                  60

Gln Gly Arg Ala Thr Ile Ser Arg Asp Asn Gly Gln Ser Thr Val Arg
65                  70                  75                  80

Leu Gln Leu Ser Asp Leu Arg Ala Glu Asp Thr Gly Thr Tyr Tyr Cys
                85                  90                  95

Ala Lys Ala Thr Ala Ser Cys Thr Tyr Gly Cys Thr Pro Tyr Thr Gly
            100                 105                 110

Glu Ile Asp Ala Trp Gly His Gly Thr Glu Val Ile Val Ser Ser Leu
        115                 120                 125

Asp Gly Gly Gly Gly Ser Gly Gly Gly Gly Ser Gly Gly Gly Gly Ser
    130                 135                 140

Thr Ala Leu Thr Gln Pro Ser Ser Val Ser Ala Asn Pro Gly Glu Thr
145                 150                 155                 160

Val Lys Ile Thr Cys Ser Gly Gly Gly Ser Ser Ser Tyr Tyr Gly Trp
                165                 170                 175

Tyr Gln Gln Lys Ala Pro Gly Ser Ala Pro Val Thr Val Ile Tyr Asp
            180                 185                 190

Asn Thr Asn Arg Pro Ser Gly Ile Pro Ser Arg Phe Ser Gly Ser Lys
        195                 200                 205

Ser Gly Ser Thr Ala Thr Leu Thr Ile Thr Gly Val Gln Ala Asp Asp
    210                 215                 220

Glu Ala Val Tyr Tyr Cys Gly Gly Ser Ala Asp Ser Ser Gly Ala
225                 230                 235                 240

Gly Ile Phe Gly Ala Gly Thr Thr Leu Thr Val Leu Gly Ala Ala Ala
                245                 250                 255

<210> SEQ ID NO 179
<211> LENGTH: 252
<212> TYPE: PRT
<213> ORGANISM: Gallus gallus

<400> SEQUENCE: 179

Ala Val Thr Leu Asp Glu Ser Gly Gly Gly Leu Gln Thr Pro Gly Gly
1               5                   10                  15
```

```
Ala Leu Ser Leu Val Cys Lys Ala Ser Gly Phe Thr Phe Ser Ser Tyr
             20                  25                  30

Gly Met Gln Trp Val Arg Gln Ala Pro Gly Lys Gly Leu Glu Trp Val
         35                  40                  45

Ala Gly Ile Ser Gly Ser Gly Arg Gly Thr Trp Tyr Ala Pro Ala Val
     50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                 85                  90                  95

Ala Lys Ala Ala Gly Ser Asp Thr Tyr Gly Ser Thr Gly Asp Asn Ile
            100                 105                 110

Asp Ala Trp Gly His Gly Thr Glu Val Ile Val Ser Ser Leu Asp Gly
        115                 120                 125

Gly Gly Gly Ser Gly Gly Gly Ser Gly Gly Gly Ser Thr Ala
            130                 135                 140

Leu Thr Gln Pro Ser Ser Val Ser Ala Asn Pro Gly Glu Thr Val Val
145                 150                 155                 160

Ile Thr Cys Ser Gly Asp Thr Tyr Thr Tyr Gly Trp Tyr Gln Gln Lys
                165                 170                 175

Ser Pro Gly Ser Ala Pro Val Thr Val Ile Tyr Ala Asn Thr Asn Arg
            180                 185                 190

Pro Ser Asp Ile Pro Ser Arg Phe Ser Gly Ser Gly Ser Gly Ser Thr
        195                 200                 205

Ala Thr Leu Thr Ile Thr Gly Val Gln Ala Glu Asp Glu Ala Val Tyr
    210                 215                 220

Tyr Cys Gly Gly Trp Asp Ser Ser Ala Gly Tyr Ser Gly Ile Phe Gly
225                 230                 235                 240

Ala Gly Thr Thr Leu Thr Val Leu Gly Ala Ala Ala
            245                 250

<210> SEQ ID NO 180
<211> LENGTH: 250
<212> TYPE: PRT
<213> ORGANISM: Gallus gallus

<400> SEQUENCE: 180

Ala Val Thr Leu Asp Glu Ser Gly Gly Gly Leu Gln Thr Pro Gly Gly
 1               5                  10                  15

Thr Leu Ser Leu Val Cys Lys Gly Ser Gly Phe Thr Phe Ser Asp Tyr
             20                  25                  30

Gly Met Gly Trp Met Arg Gln Ala Pro Gly Lys Gly Leu Glu Tyr Val
         35                  40                  45

Ala Glu Ile Ser Ser Ser Gly Arg Tyr Thr Asn Tyr Gly Pro Ala Val
     50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                 85                  90                  95

Ala Lys Ala Ala Gly Arg Gly Tyr Tyr Gly Trp Ser Ala Gly Thr Ile
            100                 105                 110

Asp Ala Trp Gly His Gly Thr Glu Val Ile Val Ser Ser Leu Asp Gly
        115                 120                 125

Gly Gly Gly Ser Gly Gly Gly Gly Ser Gly Gly Gly Ser Thr Ala
```

```
            130                 135                 140
Leu Thr Gln Pro Ser Ser Val Ser Ala Asn Pro Gly Glu Thr Val Glu
145                 150                 155                 160

Ile Thr Cys Ser Gly Asp Ser Ser Tyr Tyr Gly Trp Tyr Gln Gln Lys
                165                 170                 175

Ser Pro Gly Ser Ala Pro Val Thr Val Ile Tyr Asn Asn Asp Asn Arg
            180                 185                 190

Pro Ser Asp Ile Pro Ser Arg Phe Ser Gly Ser Arg Ser Gly Ser Thr
            195                 200                 205

Asn Thr Leu Thr Ile Thr Gly Val Gln Ala Asp Asp Glu Ala Val Tyr
210                 215                 220

Tyr Cys Gly Ser Ala Asp Ser Ser Thr Asp Gly Ile Phe Gly Ala Gly
225                 230                 235                 240

Thr Thr Leu Thr Val Leu Gly Ala Ala Ala
                245                 250

<210> SEQ ID NO 181
<211> LENGTH: 250
<212> TYPE: PRT
<213> ORGANISM: Gallus gallus

<400> SEQUENCE: 181

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Tyr
                20                  25                  30

Gly Met Gly Trp Met Arg Gln Ala Pro Gly Lys Gly Leu Glu Tyr Val
            35                  40                  45

Ala Glu Ser Ser Ser Ser Gly Arg Tyr Thr Asn Tyr Gly Pro Ala Val
50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ala Ala Gly Ser Gly Tyr Tyr Gly Trp Ser Ala Gly Ser Ile
            100                 105                 110

Asp Ala Trp Gly His Gly Thr Glu Val Ile Val Ser Ser Leu Asp Gly
            115                 120                 125

Gly Gly Gly Ser Gly Gly Gly Gly Ser Gly Gly Gly Gly Ser Thr Ala
130                 135                 140

Leu Thr Gln Pro Ser Ser Val Ser Ala Asn Pro Gly Glu Thr Val Glu
145                 150                 155                 160

Ile Thr Cys Ser Gly Gly Ser Asn Asn Tyr Gly Trp Phe Gln Gln Lys
                165                 170                 175

Ser Pro Gly Ser Ala Pro Val Thr Val Ile Tyr Asp Asn Thr Asn Arg
            180                 185                 190

Pro Ser Asp Ile Pro Ser Arg Phe Ser Gly Ser Thr Ser Gly Ser Thr
            195                 200                 205

Ser Thr Leu Thr Ile Thr Gly Val Gln Ala Asp Asp Glu Ala Val Tyr
210                 215                 220

Phe Cys Gly Ser Ala Asp Thr Asn Tyr Asp Phe Ile Phe Gly Ala Gly
225                 230                 235                 240

Thr Thr Leu Thr Val Leu Gly Ala Ala Ala
                245                 250
```

<210> SEQ ID NO 182
<211> LENGTH: 255
<212> TYPE: PRT
<213> ORGANISM: Gallus gallus

<400> SEQUENCE: 182

Ala Val Thr Leu Asp Glu Ser Gly Gly Leu Gln Thr Pro Gly Gly
1               5                   10                  15

Thr Leu Ser Leu Val Cys Lys Ala Ser Gly Phe Thr Phe Ser Ser Phe
            20                  25                  30

Asn Ile Phe Trp Val Arg Gln Ala Pro Gly Lys Gly Leu Glu Phe Val
        35                  40                  45

Ala Ala Ile Asn Lys Asp Gly Ser Phe Thr His Tyr Gly Ser Ala Val
    50                  55                  60

Lys Gly Arg Ala Thr Ile Ser Arg Asp Asn Gly Gln Ser Thr Leu Arg
65                  70                  75                  80

Leu Gln Leu Asn Asp Leu Gly Ala Glu Asp Ala Gly Thr Tyr Phe Cys
                85                  90                  95

Ala Arg Ser Pro Gly Gly Phe Ser Cys Ala Gly Gly Trp Cys Gly Ala
            100                 105                 110

Tyr Ala Asp Gly Ile Asp Ala Trp Gly His Gly Thr Glu Val Ile Ile
        115                 120                 125

Ser Ser Leu Asp Gly Gly Gly Ser Gly Gly Gly Ser Gly Gly
    130                 135                 140

Gly Gly Ser Thr Ala Leu Thr Gln Pro Ser Ser Val Ser Ala Asn Pro
145                 150                 155                 160

Gly Glu Thr Val Glu Ile Thr Cys Ser Gly Gly His Ser Tyr Gly
            165                 170                 175

Trp Phe Gln Gln Lys Ala Pro Gly Ser Ala Pro Val Thr Val Ile Tyr
        180                 185                 190

Arg Asn Asp Lys Arg Pro Ser Gly Ile Pro Ser Arg Phe Ser Gly Ser
    195                 200                 205

Leu Ser Gly Ser Thr Gly Thr Leu Thr Ile Thr Gly Val Gln Ala Asp
    210                 215                 220

Asp Glu Ala Val Tyr Tyr Cys Gly Ser Ala Asp Ser Ser Tyr Val Ala
225                 230                 235                 240

Ile Phe Gly Ala Gly Thr Thr Leu Thr Val Leu Gly Ala Ala Ala
                245                 250                 255

<210> SEQ ID NO 183
<211> LENGTH: 257
<212> TYPE: PRT
<213> ORGANISM: Gallus gallus

<400> SEQUENCE: 183

Ala Val Thr Leu Asp Glu Ser Gly Gly Gly Leu Gln Thr Pro Gly Gly
1               5                   10                  15

Gly Leu Ser Leu Val Cys Lys Gly Ser Gly Phe Asp Phe Ser Ser Tyr
            20                  25                  30

Asn Met Phe Trp Val Arg Gln Ala Pro Gly Lys Gly Leu Glu Phe Val
        35                  40                  45

Ala Ala Ile Ser Ser Thr Gly Ser Tyr Thr His Tyr Gly Pro Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Ile Tyr Tyr Cys
                85                  90                  95

Ala Arg Ser Pro Gly Gly Phe Ser Cys Ala Gly Gly Trp Cys Gly Gly
            100                 105                 110

Tyr Ala Asp Ser Ile Asp Ala Trp Gly His Gly Thr Glu Val Ile Val
            115                 120                 125

Ser Ser Leu Asp Gly Gly Gly Ser Gly Gly Gly Ser Gly Gly
130                 135                 140

Gly Gly Ser Thr Ala Leu Thr Gln Pro Ser Ser Val Ser Ala Asn Leu
145                 150                 155                 160

Gly Gly Thr Val Glu Ile Thr Cys Ser Gly Arg Asn His Tyr Ser
                165                 170                 175

Tyr Gly Trp Phe Gln Gln Lys Ala Pro Gly Ser Ala Leu Val Thr Val
            180                 185                 190

Ile Tyr Ser Asn Asn Lys Arg Pro Ser Asp Ile Pro Ser Arg Phe Ser
            195                 200                 205

Gly Ser Leu Ser Gly Ser Thr Asn Thr Leu Thr Ile Thr Gly Val Gln
            210                 215                 220

Ala Asp Asp Glu Ala Val Tyr Tyr Cys Gly Ser Ala Asp Ser Ser Asn
225                 230                 235                 240

Val Ala Ile Phe Gly Ala Gly Thr Thr Leu Thr Val Leu Gly Ala Ala
                245                 250                 255

Ala

<210> SEQ ID NO 184
<211> LENGTH: 253
<212> TYPE: PRT
<213> ORGANISM: Gallus gallus

<400> SEQUENCE: 184

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Phe
            20                  25                  30

Asn Met Gln Trp Val Arg Gln Ala Pro Gly Lys Gly Leu Glu Phe Val
            35                  40                  45

Ala Gly Ile Asp Asn Ile Gly Arg Lys Thr Ser Tyr Gly Ser Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Phe Cys
                85                  90                  95

Ala Lys Gly Ala Gly Ser Ser Ala Tyr Ser Cys Ala Phe Cys Tyr Pro
            100                 105                 110

Gly Trp Ile Asp Ala Trp Gly His Gly Thr Glu Val Ile Val Ser Ser
            115                 120                 125

Leu Asp Gly Gly Gly Gly Ser Gly Gly Gly Ser Gly Gly Gly Gly
130                 135                 140

Ser Thr Ala Leu Thr Gln Pro Ser Ser Val Ser Ala Asn Leu Gly Gly
145                 150                 155                 160

Thr Val Glu Ile Thr Cys Ser Gly Gly His Tyr Ser Tyr Gly Trp Phe
            165                 170                 175

Gln Gln Lys Ala Pro Gly Ser Ala Pro Val Thr Val Ile Tyr Arg Asn
            180                 185                 190

```
Asp Lys Arg Pro Ser Asp Ile Pro Ser Arg Phe Ser Gly Ser Leu Ser
        195                 200                 205

Gly Ser Thr Gly Thr Leu Thr Ile Thr Gly Val Gln Ala Asp Asp Glu
    210                 215                 220

Ala Val Tyr Phe Cys Gly Ser Ala Asp Ser Thr Tyr Val Gly Ile Phe
225                 230                 235                 240

Gly Ala Gly Thr Thr Leu Thr Val Leu Gly Ala Ala Ala
                245                 250

<210> SEQ ID NO 185
<211> LENGTH: 249
<212> TYPE: PRT
<213> ORGANISM: Gallus gallus

<400> SEQUENCE: 185

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser His
            20                  25                  30

Gly Met Gly Trp Val Arg Gln Ala Pro Gly Lys Gly Leu Glu Trp Val
        35                  40                  45

Ala Gly Ile Glu Asn Asp Gly Ser Ile Thr Gly Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Lys Arg Ser Gly Ser Gly Cys Cys Asn Ala Tyr Ala Ile Asp Ala
            100                 105                 110

Trp Gly His Gly Thr Glu Val Ile Val Ser Ser Leu Asp Gly Gly Gly
        115                 120                 125

Gly Ser Gly Gly Gly Gly Ser Gly Gly Gly Gly Ser Thr Ala Leu Thr
    130                 135                 140

Gln Pro Ser Ser Val Ser Ala Asn Pro Gly Gly Thr Val Glu Ile Thr
145                 150                 155                 160

Cys Ser Gly Gly Ser Gly Ser Tyr Gly Trp Tyr Gln Gln Lys Ser Pro
                165                 170                 175

Gly Ser Ala Pro Val Thr Val Ile Tyr Ala Asn Thr Asn Arg Pro Ser
            180                 185                 190

Asp Ile Pro Ser Arg Phe Ser Gly Ser Thr Ser Gly Ser Thr Gly Thr
        195                 200                 205

Leu Thr Ile Thr Gly Val Gln Ala Asp Asp Glu Ala Val Tyr Phe Cys
    210                 215                 220

Gly Ser Tyr Asp Ser Ser Asn Thr Ala Gly Ile Phe Gly Ala Gly Thr
225                 230                 235                 240

Thr Leu Thr Val Leu Gly Ala Ala Ala
                245

<210> SEQ ID NO 186
<211> LENGTH: 260
<212> TYPE: PRT
<213> ORGANISM: Gallus gallus

<400> SEQUENCE: 186

Ala Val Thr Leu Asp Glu Ser Gly Gly Gly Leu Gln Thr Pro Gly Gly
1               5                   10                  15
```

```
Gly Leu Ser Leu Val Cys Lys Ala Ser Gly Phe Thr Phe Ser Ser Tyr
            20                  25                  30

Ala Met Tyr Trp Val Arg Gln Thr Pro Gly Lys Gly Leu Glu Phe Val
            35                  40                  45

Ala Gly Ile Asp Ser Gly Asp Gly Arg Tyr Ser Lys Tyr Gly Pro Ala
 50                  55                  60

Val Asp Gly Arg Ala Thr Met Ser Arg Asp Asn Gly Gln Ser Thr Val
 65                  70                  75                  80

Arg Leu Gln Leu Asn Asp Leu Arg Ala Glu Asp Ser Gly Thr Tyr Tyr
                85                  90                  95

Cys Ala Lys Gly Ala Val Thr Gly Tyr Cys Gly Trp Asn Ala Cys Thr
            100                 105                 110

Val Ala Asn Ile Asp Thr Trp Gly His Gly Thr Glu Val Ile Val Ser
            115                 120                 125

Ser Leu Asp Gly Gly Gly Ser Gly Gly Gly Ser Gly Gly Gly
            130                 135                 140

Gly Ser Thr Ala Leu Thr Gln Pro Ser Ser Val Ser Ala Asn Pro Gly
145                 150                 155                 160

Glu Thr Val Lys Ile Thr Cys Ser Gly Gly Ser Tyr Ala Gly Ser
                165                 170                 175

Tyr Tyr Tyr Gly Trp Tyr Gln Gln Lys Ala Ser Gly Ser Ala Pro Val
            180                 185                 190

Thr Val Ile Tyr Ser Asn Asp Lys Arg Pro Ser Asp Ile Pro Ser Arg
            195                 200                 205

Phe Ser Gly Ser Thr Ser Gly Ser Thr Gly Thr Leu Thr Ile Thr Gly
            210                 215                 220

Val Gln Ala Asp Asp Glu Ala Val Tyr Tyr Cys Gly Ser Trp Asp Ser
225                 230                 235                 240

Ser Ser Tyr Asp Gly Ile Phe Gly Ala Gly Thr Thr Leu Thr Val Leu
                245                 250                 255

Gly Ala Ala Ala
            260

<210> SEQ ID NO 187
<211> LENGTH: 250
<212> TYPE: PRT
<213> ORGANISM: Gallus gallus

<400> SEQUENCE: 187

Ala Val Thr Leu Asp Glu Ser Gly Gly Gly Leu Gln Thr Pro Gly Gly
 1               5                  10                  15

Gly Leu Ser Leu Val Cys Lys Ala Ser Gly Phe Ser Phe Ser Ser Tyr
            20                  25                  30

Ser Met Gln Trp Val Arg Gln Ala Pro Gly Lys Gly Leu Asp Trp Val
            35                  40                  45

Ala Gly Ile Ser Gly Thr Gly Arg His Arg Asn Tyr Gly Ser Ala Val
 50                  55                  60

Glu Gly Arg Ala Thr Ile Ser Arg Asp Asn Gly Gln Ser Thr Val Arg
 65                  70                  75                  80

Leu Gln Leu Asp Asn Leu Arg Ala Glu Asp Thr Gly Thr Tyr Tyr Cys
                85                  90                  95

Ala Arg Ala Pro Cys Thr Gly Cys Gly Trp Ser Ala Gly Ser Ile Asp
            100                 105                 110

Ala Trp Gly His Gly Thr Glu Val Ile Val Ser Ser Leu Asp Gly Gly
            115                 120                 125
```

```
Gly Gly Ser Gly Gly Gly Ser Gly Gly Gly Ser Thr Ala Leu
        130                 135                 140

Thr Gln Pro Ser Ser Val Ser Ala Asn Pro Gly Glu Thr Val Glu Ile
145                 150                 155                 160

Thr Cys Ser Gly Gly Asn Tyr Gly Trp Tyr Ser Trp His Gln Gln Lys
                165                 170                 175

Ser Pro Gly Ser Ala Pro Val Thr Leu Ile Tyr Glu Asn Asn Lys Arg
                180                 185                 190

Leu Ser Asp Ile Pro Ser Arg Phe Ser Gly Ser Lys Ser Gly Ser Thr
                195                 200                 205

Ala Thr Leu Thr Ile Thr Gly Val Gln Ala Glu Asp Glu Ala Val Tyr
        210                 215                 220

Phe Cys Gly Ser Thr Asp Ser Ser Tyr Val Gly Ile Phe Gly Ala Gly
225                 230                 235                 240

Thr Thr Leu Thr Val Leu Gly Ala Ala Ala
                245                 250

<210> SEQ ID NO 188
<211> LENGTH: 248
<212> TYPE: PRT
<213> ORGANISM: Gallus gallus

<400> SEQUENCE: 188

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Tyr
                20                  25                  30

Gln Met His Trp Ile Arg Gln Ala Pro Gly Lys Gly Leu Glu Trp Val
            35                  40                  45

Gly Val Ile Ser Ser Arg Gly Ser Ser Thr Asn Tyr Gly Ala Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Ser Gly Tyr Ala Cys Gly Trp Ser Gly Gly Cys Ile Asp Ala
                100                 105                 110

Trp Gly His Gly Thr Glu Val Ile Val Ser Ser Leu Asp Gly Gly Gly
            115                 120                 125

Gly Ser Gly Gly Gly Ser Gly Gly Gly Ser Thr Ala Leu Thr
        130                 135                 140

Gln Pro Ser Ser Val Ser Ala Asn Pro Gly Glu Thr Val Glu Ile Thr
145                 150                 155                 160

Cys Ser Gly Asp Ser Ser Asn Tyr Gly Trp Tyr Gln Gln Lys Ser
                165                 170                 175

Pro Gly Ser Ala Pro Val Thr Leu Ile Tyr Tyr Asp Asp Glu Arg Pro
                180                 185                 190

Ser Gly Ile Pro Ser Arg Phe Ser Gly Ser Lys Ser Gly Ser Thr Ala
                195                 200                 205

Thr Leu Thr Ile Thr Gly Val Gln Ala Asp Asp Glu Ala Val Tyr Tyr
        210                 215                 220

Cys Gly Ser Tyr Asp Ser Ser Thr Gly Ile Phe Gly Ala Gly Thr Thr
225                 230                 235                 240

Leu Thr Val Leu Gly Ala Ala Ala
```

<210> SEQ ID NO 189
<211> LENGTH: 253
<212> TYPE: PRT
<213> ORGANISM: Gallus gallus

<400> SEQUENCE: 189

Ala Val Thr Leu Asp Glu Ser Gly Gly Leu Gln Ala Pro Gly Gly
1               5                   10                  15

Gly Leu Ser Leu Val Cys Lys Ala Ser Gly Phe Thr Phe Ser Ser His
            20                  25                  30

Gly Met Gly Trp Val Arg Gln Ala Pro Gly Lys Gly Leu Glu Tyr Val
        35                  40                  45

Ala Ser Ile Ser Thr Arg Gly Ser Ser Thr Tyr Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Thr Gly Tyr Ala Cys Ser Tyr Ser Tyr His Thr Ala Cys Ile
            100                 105                 110

Asp Ala Trp Gly His Gly Thr Glu Val Ile Val Ser Ser Leu Asp Gly
        115                 120                 125

Gly Gly Gly Ser Gly Gly Gly Ser Gly Gly Gly Ser Thr Ala
    130                 135                 140

Leu Thr Gln Pro Ser Ser Val Ser Ala Asn Pro Gly Glu Thr Val Glu
145                 150                 155                 160

Ile Thr Cys Ser Gly Gly Ser Ser Ser Tyr Tyr Gly Trp Tyr Gln
                165                 170                 175

Gln Lys Ser Pro Gly Ser Ala Pro Val Thr Val Ile Tyr Glu Asn Thr
            180                 185                 190

Asn Arg Pro Ser Asp Ile Pro Ser Arg Phe Ser Gly Ser Lys Ser Gly
        195                 200                 205

Ser Thr Ala Thr Leu Thr Ile Thr Gly Val Gln Ala Glu Asp Glu Ala
    210                 215                 220

Val Tyr Tyr Cys Gly Ser Gly Asp Ser Asn Thr Tyr Asn Gly Ile Phe
225                 230                 235                 240

Gly Ala Gly Thr Thr Leu Thr Val Leu Gly Ala Ala Ala
                245                 250

<210> SEQ ID NO 190
<211> LENGTH: 246
<212> TYPE: PRT
<213> ORGANISM: Gallus gallus

<400> SEQUENCE: 190

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Arg Ser His
            20                  25                  30

Gln Met Phe Trp Val Arg Gln Ala Pro Gly Lys Gly Leu Glu Tyr Val
        35                  40                  45

Gly Gln Ile Thr Thr Arg Gly Thr Thr Thr Tyr Tyr Gly Ala Ala Val
    50                  55                  60

Thr Gly Arg Ala Thr Ile Ser Arg Asp Asn Gly Gln Asn Thr Val Arg

```
                65                  70                  75                  80
Leu Gln Leu Asn Asn Leu Arg Ala Glu Asp Thr Gly Thr Tyr Phe Cys
                    85                  90                  95

Ala Lys Ala Ala Tyr Gly Tyr Ser Tyr Val Ser Thr Ile Asp Ala Trp
                100                 105                 110

Gly His Gly Thr Glu Val Ile Val Ser Ser Leu Asp Gly Gly Gly Gly
                115                 120                 125

Ser Gly Gly Gly Gly Ser Gly Gly Gly Ser Thr Ala Leu Thr Gln
        130                 135                 140

Pro Ser Val Ser Ala Asn Pro Gly Lys Thr Val Glu Ile Thr Cys
145                 150                 155                 160

Ser Gly Gly Ser Gly Ser Tyr Gly Trp Tyr Gln Gln Lys Ser Pro Gly
                165                 170                 175

Ser Ala Pro Val Thr Val Ile Tyr Trp Asp Asp Lys Arg Pro Ser Gly
                180                 185                 190

Ile Pro Ser Arg Phe Ser Gly Ser Glu Ser Gly Ser Thr Ala Thr Leu
                195                 200                 205

Thr Ile Thr Gly Val Gln Ala Glu Asp Glu Ala Val Tyr Tyr Cys Gly
        210                 215                 220

Ser Ala Asp Ser Ser Gly Ala Ile Phe Gly Ala Gly Thr Thr Leu Thr
225                 230                 235                 240

Val Leu Gly Ala Ala Ala
                245

<210> SEQ ID NO 191
<211> LENGTH: 250
<212> TYPE: PRT
<213> ORGANISM: Gallus gallus

<400> SEQUENCE: 191

Ala Val Thr Leu Asp Glu Ser Gly Gly Leu Gln Thr Pro Gly Gly
1               5                   10                  15

Gly Leu Ser Leu Val Cys Arg Ala Ser Gly Phe Ile Phe Ser Ser His
                20                  25                  30

Pro Met Val Trp Val Arg Gln Ala Pro Gly Lys Gly Leu Glu Trp Val
                35                  40                  45

Ala Ala Ile Thr Thr Arg Gly Thr Ser Ala Tyr Tyr Gly Pro Ala Val
                50                  55                  60

Lys Gly Arg Ala Thr Ile Ser Arg Asp Asn Gly Gln Ser Thr Val Arg
65                  70                  75                  80

Leu Gln Leu Asn Ser Leu Arg Ala Glu Asp Thr Gly Thr Tyr Tyr Cys
                    85                  90                  95

Ala Arg Ser Gly Tyr Gly Tyr Thr Gly Ser Asp Ala Gly Asn Ile Asp
                100                 105                 110

Thr Trp Gly His Gly Thr Glu Val Ile Val Ser Ser Leu Asp Gly Gly
                115                 120                 125

Gly Gly Ser Gly Gly Gly Gly Ser Gly Gly Gly Gly Ser Thr Ala Leu
        130                 135                 140

Thr Gln Pro Ser Ser Val Ser Ala Asn Leu Gly Gly Thr Val Lys Ile
145                 150                 155                 160

Thr Cys Ser Gly Ser Ser Gly Ser Tyr Gly Trp Tyr Arg Gln Lys Ala
                165                 170                 175

Pro Gly Ser Ala Pro Val Thr Val Ile Tyr Ser Asn Asp Lys Arg Pro
                180                 185                 190
```

```
Ser Asp Ile Pro Ser Arg Phe Ser Gly Ser Ala Ser Gly Ser Thr Ala
        195                 200                 205

Thr Leu Thr Ile Thr Gly Val Gln Ala Glu Asp Glu Ala Val Tyr Phe
    210                 215                 220

Cys Gly Gly Tyr Asp Gly Ser Ser Tyr Val Gly Ile Phe Gly Ala Gly
225                 230                 235                 240

Thr Thr Leu Thr Val Leu Gly Ala Ala Ala
            245                 250

<210> SEQ ID NO 192
<211> LENGTH: 264
<212> TYPE: PRT
<213> ORGANISM: Gallus gallus

<400> SEQUENCE: 192

Ala Val Thr Leu Asp Glu Ser Gly Gly Leu Gln Thr Pro Gly Gly
1               5                   10                  15

Ala Leu Ser Leu Val Cys Lys Ala Ser Gly Phe Ala Phe Ser Arg Tyr
            20                  25                  30

Ala Met Asn Trp Val Arg Gln Ala Pro Gly Lys Gly Leu Glu Trp Val
            35                  40                  45

Ala Gly Val Arg Asn Val Gly Ser Ser Thr Asn Tyr Ala Pro Ala Val
        50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Ile Tyr Tyr Cys
                85                  90                  95

Ala Lys Ala Ala Gly Ser Gly Tyr Cys Ala Trp Trp Ala Asp Ala Leu
            100                 105                 110

Thr Cys Gly Gly Tyr Lys Thr His Asp Ile Asp Ala Trp Gly His Gly
        115                 120                 125

Thr Glu Val Ile Val Ser Ser Leu Asp Gly Gly Gly Ser Gly Gly
    130                 135                 140

Gly Gly Ser Gly Gly Gly Ser Thr Ala Leu Thr Gln Pro Ser Ser
145                 150                 155                 160

Val Ser Ala Asn Pro Gly Glu Thr Val Lys Ile Thr Cys Ser Gly Gly
                165                 170                 175

Ser Gly Tyr Gly Tyr Gly Trp Tyr Gln Gln Lys Ser Pro Gly Ser Ala
            180                 185                 190

Pro Val Thr Val Ile Tyr Gln Asn Asp Lys Arg Pro Ser Asn Ile Pro
            195                 200                 205

Ser Arg Phe Ser Gly Ser Gly Ser Gly Ser Thr Gly Thr Leu Thr Ile
        210                 215                 220

Thr Gly Val Gln Val Glu Asp Glu Ala Val Tyr Tyr Cys Gly Thr Ala
225                 230                 235                 240

Asp Ser Ser Tyr Val Gly Asp Ala Gly Ile Phe Gly Ala Gly Thr Thr
            245                 250                 255

Leu Thr Val Leu Gly Ala Ala Ala
            260

<210> SEQ ID NO 193
<211> LENGTH: 251
<212> TYPE: PRT
<213> ORGANISM: Gallus gallus

<400> SEQUENCE: 193
```

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Gly Met Gly Trp Val Arg Gln Ala Pro Gly Lys Gly Leu Glu Trp Val
        35                  40                  45

Ala Gly Ile Asp Asn Ile Gly Arg Tyr Thr Asn Tyr Gly Pro Ala Val
50                      55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Ser Ala Ala Ser Gly Ser Trp Ser Tyr Tyr Gly Thr Gly Trp
            100                 105                 110

Ile Asp Gly Trp Gly His Gly Thr Glu Val Ile Val Ser Ser Leu Asp
        115                 120                 125

Gly Gly Gly Gly Ser Gly Gly Gly Ser Gly Gly Gly Gly Ser Thr
130                 135                 140

Ala Leu Thr Gln Pro Ser Ser Val Ser Ala Asn Pro Gly Glu Thr Val
145                 150                 155                 160

Lys Ile Thr Cys Ser Gly Gly Ser Gly Arg Tyr Gly Trp Tyr Gln
                165                 170                 175

Gln Lys Ser Pro Gly Ser Ala Pro Val Thr Val Ile Tyr Tyr Asn Asp
            180                 185                 190

Lys Arg Pro Ser Asp Ile Pro Ser Arg Phe Ser Gly Ser Leu Pro Gly
        195                 200                 205

Ser Thr Ala Thr Leu Thr Ile Thr Gly Val Gln Val Glu Asp Glu Ala
        210                 215                 220

Val Tyr Phe Cys Gly Ser Ala Asp Ser Thr Ala Gly Ile Phe Gly Ala
225                 230                 235                 240

Gly Thr Thr Leu Thr Val Leu Gly Ala Ala Ala
                245                 250

<210> SEQ ID NO 194
<211> LENGTH: 253
<212> TYPE: PRT
<213> ORGANISM: Gallus gallus

<400> SEQUENCE: 194

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ala Ile Tyr
            20                  25                  30

Ala Met His Trp Val Arg Gln Ala Pro Asp Lys Gly Leu Glu Phe Val
        35                  40                  45

Ala Gly Ile Ser Ser Asp Gly Ser Arg Thr Lys Tyr Gly Ala Ala Val
50                      55                  60

Lys Gly Arg Ala Thr Met Ser Arg Asp Asn Gly Gln Ser Thr Val Arg
65                  70                  75                  80

Leu Gln Leu Asn Asn Leu Arg Thr Glu Asp Thr Ala Thr Tyr Phe Cys
                85                  90                  95

Ala Lys Thr Ala Gly Ser Trp Ser Arg Tyr Asn Gly Leu His Ser Asn
            100                 105                 110

Ile Asp Thr Trp Gly His Gly Thr Glu Val Ile Val Ser Ser Leu Asp
        115                 120                 125
```

-continued

Gly Gly Gly Gly Ser Gly Gly Gly Ser Gly Gly Gly Ser Thr
        130                 135                 140

Ala Leu Thr Gln Pro Ser Ser Val Ser Ala Asn Leu Gly Gly Thr Val
145                 150                 155                 160

Lys Ile Thr Cys Ser Gly Gly Tyr Ser Gly Tyr Gly Tyr Trp Tyr
                165                 170                 175

Gln Gln Lys Ser Pro Gly Ser Ala Pro Val Thr Leu Ile Tyr Asn Gly
                180                 185                 190

Asn Asn Arg Pro Ser Asp Ile Pro Ser Arg Phe Ser Gly Ser Gly Ser
                195                 200                 205

Gly Ser Thr Asn Thr Leu Thr Ile Thr Gly Val Gln Val Glu Asp Glu
        210                 215                 220

Ala Ile Tyr Phe Cys Gly Ser Ala Asp Ser Ser Ile Ala Val Phe
225                 230                 235                 240

Gly Ala Gly Thr Thr Leu Thr Val Leu Gly Ala Ala Ala
                245                 250

<210> SEQ ID NO 195
<211> LENGTH: 251
<212> TYPE: PRT
<213> ORGANISM: Gallus gallus

<400> SEQUENCE: 195

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Thr Asp Tyr
                20                  25                  30

Gly Met Gly Trp Met Arg Gln Ala Pro Gly Lys Gly Leu Glu Tyr Val
            35                  40                  45

Val Gly Ile Ser Asn Thr Gly Arg Tyr Thr Tyr Tyr Gly Ser Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Ser Ala Gly Ser Trp Trp His Tyr Thr Gly Ala Asp Asn Ile
            100                 105                 110

Asp Ala Trp Gly His Gly Thr Glu Val Ile Val Ser Ser Leu Asp Gly
        115                 120                 125

Gly Gly Gly Ser Gly Gly Gly Ser Gly Gly Gly Ser Thr Ala
        130                 135                 140

Leu Thr Gln Pro Ser Ser Val Ser Ala Asn Pro Gly Glu Thr Val Glu
145                 150                 155                 160

Ile Thr Cys Ser Gly Gly Arg Lys Tyr Tyr Gly Trp Tyr Gln Gln Lys
                165                 170                 175

Ser Pro Gly Ser Ala Pro Val Thr Leu Ile Tyr Ser Asn Asp Lys Arg
                180                 185                 190

Pro Ser Asp Ile Pro Ser Arg Phe Ser Gly Ser Lys Ser Gly Ser Thr
                195                 200                 205

Ala Thr Leu Thr Ile Thr Gly Val Gln Val Asp Asp Glu Ala Val Tyr
        210                 215                 220

Tyr Cys Gly Ser Ala Asp Thr Ser Ser Ser Glu Ala Ala Phe Gly Ala
225                 230                 235                 240

Gly Thr Thr Leu Thr Val Leu Gly Ala Ala Ala

```
                        245                 250

<210> SEQ ID NO 196
<211> LENGTH: 256
<212> TYPE: PRT
<213> ORGANISM: Gallus gallus

<400> SEQUENCE: 196

Ala Val Thr Leu Asp Glu Ser Gly Gly Leu Gln Thr Pro Gly Gly
1               5                   10                  15

Gly Leu Ser Leu Val Cys Lys Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Ser Ile Asn Ser Ala Gly Ser Tyr Thr His Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Arg Gly Gly Gly Gly Cys Gly Ile Trp Ser Cys Gly Ser Tyr Ala
            100                 105                 110

Gly Glu Ile Asp Ala Trp Gly His Gly Thr Glu Val Ile Val Ser Ser
        115                 120                 125

Gly Gly Gly Gly Ser Gly Gly Gly Ser Gly Gly Gly Gly Ser Ala
    130                 135                 140

Leu Thr Gln Pro Ala Ser Val Ser Ala Asn Leu Gly Glu Thr Val Lys
145                 150                 155                 160

Ile Thr Cys Ser Gly Gly Ser Tyr Ala Gly Ser Tyr Tyr Tyr Gly
                165                 170                 175

Trp Tyr Gln Gln Lys Ser Pro Gly Ser Ala Pro Val Thr Val Ile Tyr
            180                 185                 190

Asp Asn Thr Asn Arg Pro Ser Asn Ile Pro Ser Arg Phe Ser Gly Ser
        195                 200                 205

Lys Ser Gly Pro Thr Ala Thr Leu Thr Ile Thr Gly Val Gln Val Asp
210                 215                 220

Asp Glu Ala Val Tyr Tyr Cys Gly Ser Met Asp Ser Ser Ser Gly Gly
225                 230                 235                 240

Gly Ile Phe Gly Ala Gly Thr Thr Leu Thr Val Leu Gly Ala Ala Ala
                245                 250                 255

<210> SEQ ID NO 197
<211> LENGTH: 15
<212> TYPE: DNA
<213> ORGANISM: Gallus gallus

<400> SEQUENCE: 197
gccgtgacgt tggac                                                          15

<210> SEQ ID NO 198
<211> LENGTH: 34
<212> TYPE: DNA
<213> ORGANISM: Gallus gallus

<400> SEQUENCE: 198
gaaccgcctc caccggagga gacgatgact tcgg                                     34
```

```
<210> SEQ ID NO 199
<211> LENGTH: 27
<212> TYPE: DNA
<213> ORGANISM: Gallus gallus

<400> SEQUENCE: 199
cggtggcgga tcggcgctga ctcagcc                                        27

<210> SEQ ID NO 200
<211> LENGTH: 17
<212> TYPE: DNA
<213> ORGANISM: Gallus gallus

<400> SEQUENCE: 200
acctaggacg gtcaggg                                                   17

<210> SEQ ID NO 201
<211> LENGTH: 30
<212> TYPE: DNA
<213> ORGANISM: Gallus gallus

<400> SEQUENCE: 201
ggtggaggcg gttcaggcgg aggtggctct                                     30

<210> SEQ ID NO 202
<211> LENGTH: 33
<212> TYPE: DNA
<213> ORGANISM: Gallus gallus

<400> SEQUENCE: 202
cgatccgcca ccgccagagc cacctccgcc tga                                 33

<210> SEQ ID NO 203
<211> LENGTH: 34
<212> TYPE: DNA
<213> ORGANISM: Gallus gallus

<400> SEQUENCE: 203
atgtctatgg cccagccggc cgtgacgttg gacg                                34

<210> SEQ ID NO 204
<211> LENGTH: 35
<212> TYPE: DNA
<213> ORGANISM: Gallus gallus

<400> SEQUENCE: 204
agttactgga gcggccgcac ctaggacggt caggg                               35

<210> SEQ ID NO 205
<211> LENGTH: 39
<212> TYPE: DNA
<213> ORGANISM: Gallus gallus

<400> SEQUENCE: 205
ggcggtggcg ggtcgacagc gctgactcag ccgtcctcg                           39

<210> SEQ ID NO 206
<211> LENGTH: 40
<212> TYPE: DNA
<213> ORGANISM: Gallus gallus

<400> SEQUENCE: 206
gaaccgcctc caccatctag agaggagacg atgacttcgg                          40
```

```
<210> SEQ ID NO 207
<211> LENGTH: 32
<212> TYPE: DNA
<213> ORGANISM: Gallus gallus

<400> SEQUENCE: 207
ttagctgggc gcgccgtgac gttggacgag tc                           32

<210> SEQ ID NO 208
<211> LENGTH: 37
<212> TYPE: DNA
<213> ORGANISM: Gallus gallus

<400> SEQUENCE: 208
cggccatggg gcgcgccgtc tagagctaag atatcgc                      37

<210> SEQ ID NO 209
<211> LENGTH: 44
<212> TYPE: DNA
<213> ORGANISM: Gallus gallus

<400> SEQUENCE: 209
ggccgcgata tcttagctct agacggcgcg ccccatggcc ggct              44

<210> SEQ ID NO 210
<211> LENGTH: 44
<212> TYPE: DNA
<213> ORGANISM: Gallus gallus

<400> SEQUENCE: 210
cgcgccactg cagctctaga tcccgggtcg acagatatca gtgc              44

<210> SEQ ID NO 211
<211> LENGTH: 44
<212> TYPE: DNA
<213> ORGANISM: Gallus gallus

<400> SEQUENCE: 211
ggccgcactg atatctgtcg acccgggatc tagagctgca gtgg              44

<210> SEQ ID NO 212
<211> LENGTH: 45
<212> TYPE: DNA
<213> ORGANISM: Gallus gallus

<400> SEQUENCE: 212
taactaattc tagatggtgg aggcggttca ggcggaggtg gctct             45

<210> SEQ ID NO 213
<211> LENGTH: 43
<212> TYPE: DNA
<213> ORGANISM: Gallus gallus

<400> SEQUENCE: 213
tatagattat gtcgacccgc caccgccaga gccacctccg cct               43

<210> SEQ ID NO 214
<211> LENGTH: 23
<212> TYPE: DNA
<213> ORGANISM: Gallus gallus

<400> SEQUENCE: 214
ggttcaggcg gaggtggctc tgg                                     23
```

```
<210> SEQ ID NO 215
<211> LENGTH: 21
<212> TYPE: DNA
<213> ORGANISM: Gallus gallus

<400> SEQUENCE: 215
agagccacct ccgcctgaac c                                                    21
```